(12) United States Patent
McBrine et al.

(10) Patent No.: US 10,202,610 B2
(45) Date of Patent: Feb. 12, 2019

(54) RECOMBINANT K1-5 BACTERIOPHAGES AND USES THEREOF

(71) Applicant: The Charles Stark Draper Laboratory, Inc., Cambridge, MA (US)

(72) Inventors: Connor McBrine, Somerville, MA (US); Jason Holder, Swampscott, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 15/893,094

(22) Filed: Feb. 9, 2018

(65) Prior Publication Data

US 2018/0223262 A1 Aug. 9, 2018

Related U.S. Application Data

(60) Provisional application No. 62/456,783, filed on Feb. 9, 2017, provisional application No. 62/515,223, filed on Jun. 5, 2017.

(51) Int. Cl.

| | |
|---|---|
| *C12N 7/00* | (2006.01) |
| *C12N 15/70* | (2006.01) |
| *C12N 15/11* | (2006.01) |
| *C12N 9/96* | (2006.01) |
| *C12N 9/22* | (2006.01) |
| *C12N 9/02* | (2006.01) |
| *C07K 14/005* | (2006.01) |
| *C12Q 1/70* | (2006.01) |
| *C12N 15/113* | (2010.01) |
| *C12N 15/86* | (2006.01) |
| *C12N 15/90* | (2006.01) |

(52) U.S. Cl.
CPC ............ *C12N 15/70* (2013.01); *C07K 14/005* (2013.01); *C12N 7/00* (2013.01); *C12N 9/0069* (2013.01); *C12N 9/22* (2013.01); *C12N 9/96* (2013.01); *C12N 15/11* (2013.01); *C12N 15/1131* (2013.01); *C12N 15/86* (2013.01); *C12Q 1/70* (2013.01); *C12N 15/902* (2013.01); *C12N 2310/20* (2017.05); *C12N 2795/10221* (2013.01); *C12N 2795/10243* (2013.01); *C12N 2800/80* (2013.01)

(58) Field of Classification Search
None
See application file for complete search history.

(56) References Cited

U.S. PATENT DOCUMENTS

2017/0283779 A1* 10/2017 Holder ..................... C12N 7/00

FOREIGN PATENT DOCUMENTS

WO WO-2016/100389 A1 6/2016

OTHER PUBLICATIONS

Box et al., "Functional Analysis of Bacteriophage Immunity through a Type 1-E CRISPR-Cas System in Vibrio cholerae and Its Application in Bacteriophage Genome Engineering", Journal of Bacteriology, vol. 198, No. 3, Nov. 23, 2015 (Nov. 23, 2015), pp. 578-590, XP055385261.
Bryson et al, "Covalent Modification of Bacteriophage T4 DNA Inhibits CRISPR-Cas9", mBio, vol. 6, No. 3, Jun. 16, 2015 (Jun. 16, 2015), pp. e00648-15, XP055323622.
International Search Report and Written Opinion for PCT/US2018/017425 dated May 9, 2018.
International Search Report and Written Opinion for PCT/US2018/017429 dated May 9, 2018.
Kiro et al., "Efficient engineering of a bacteriophage genome using the type 1-E CRISPR-Cas system", RNA Biology, vol. 11, No. 1, Jan. 22, 2014 (Jan. 22, 2014), pp. 42-44, XP055385263.
Martel et al., "CRISPR-Cas: an efficient tool for genome engineering of virulent bacteriophages", Nucleic Acids Research, vol. 42, No. 14, Jul. 24, 2014 (Jul. 24, 2014), pp. 9504-9513, XP055311115.
Office Action on U.S. Appl. No. 15/893,104 dated May 29, 2018.
Sagona et al, "Genetically modified bacteriophages", Integrative Biology, vol. 8, No. 4, Feb. 15, 2016 (Feb. 15, 2016), pp. 465-474, XP055334383.
Schmelcher et al, "Application of bacteriophages for detection of foodborne pathogens", Bacteriophage, vol. 4, No. 2, Feb. 7, 2014 (Feb. 7, 2014), p. e28137, XP055323023.
Wang et al., BioTechniques vol. 58, 2015, pp. 161-170, 2015.
Yaung et al., "CRISPR/Cas9-Mediated Phage Resistance Is Not Impeded by the DNA Modifications of Phage T4", PLoS ONE, vol. 9, No. 6, Jun. 2, 2014 (Jun. 2, 2014), p. e98811, XP055323625.

* cited by examiner

*Primary Examiner* — Michelle S Horning
(74) *Attorney, Agent, or Firm* — Christopher J. McKenna; Foley & Lardner LLP

(57) ABSTRACT

The present disclosure provides compositions including recombinant K1-5 bacteriophages, methods for making the same, and uses thereof. The recombinant K1-5 bacteriophages disclosed herein are useful for the identification and/or antibiotic susceptibility profiling of specific bacterial strains/species present in a sample.

25 Claims, 48 Drawing Sheets
Specification includes a Sequence Listing.

Figure 1A

>AY370674.1 Enterobacteria phage K1-5, complete genome (SEQ ID NO:1)
TCGCCCTCGCCCTCGCCGGGTTGTCCCCATAGGGTGGCCTGAGGGAATCCGTCTTCGACGGGCAGGGCTG
ATGTACTCCTTGTCTAGTACAAGGGAGGCGGAGGGAACGCCTAGGGAGGCCTAGGAATGGCTTAGTGGTG
GACAAGGTGATTACCTTAGTGAAGCCTCTTAGTGCATTCCTGAGGCCATTCAGGGCGTTTATGAGGGATT
GACAGGGTGTGAGGGCGTGGGCTATCTGTTCCTTTGCTCCTCACTTCGTTCGTCGCTGCGGTAGCCTGAT
GTGTACCTTAGGTTATTCCTTGATGGATAGCTTAGGTTAGCCTTAGTGGATTACCTTAGTTAAAGCCTTA
GTGCTTCACTTAGTATCAGCTTAGTAGTGTACCTTAGTAAGTCTTAGTGTCTTCTCTTAGTGATTGCACA
TGCAAGCATGTAAGATGCTAATAGGTCGCGGTCGGCAGACCGCTAAAGAAAGAGAATGGTAATAAGATGC
AGTAGGAGGAACACCAGAAGCCTAGCCAACCTAAGCTATCCTAGCTCTATATCTATTGCTTTTCCTTAGT
CTAACACGTTAGACAACCTATCTTATTCTTAGTGATGGTAACTTAGTGTTGACAAGATAATCTTAGTGTA
ATACTATGCATCACGTAGGCGGTGCTGAGGCACCTAGTAGCCAGCTAGTAAGGCATACGAAGAGACTAGC
GCTTACATTGCTCTTTAACAATTTGCTTAGTGTAACCTATGTATGCCGTGGTTAACTACTTATTGAATGA
GGTATTAACTATGACATTAAATAACCGTGAACTGTCCGTTCTCTTCACTCTGTTGTGCTACATGATTCGT
AACAACGAATTACTTACAGATGATGAGTTAGCCTTGTATCACCGCTTTCTTAACGAAGGTTGGACCGATA
CAGTTAATCAATACCGTAACATGATAGATGAGTTGAGGGAGGGTAAATAATGTATCAACATGAGGTATTC
TTTGAATCAGCTAGCGAAGCTATTCGCTTCCGTGATGATATGATGCAAGCTGGTGTAGGCGTTGATGTGT
ATCACTATTTGATAGATTACGACACTGAATATCACCGAGTTACCTTAGTATCTGAGTATGACAACCAAGT
CATTACTGAGTATCTAGGCAGTGAAGATTACGATTACGATGAAGTAATCACGACAAATCTCTAAATTAAC
TGTTGACAGCCACGGCATACAAGGTTACATTAAGCATCAAGACGGCGACGTCTTTAAACATCCCGCTCTT
TAACAATACGGTTTGTGTCTTGATAGGCTAACTAACTAACTAAGGTAATTATCATGAAAGGGTTAATTTG
TGTAGAACGTATGGTCAATGGTAAACTTGAAATATTACCACTGGAAAACCAATCTAGCTTCAAAGAGTGG
TATGGCTGTTTCTCACTGATTTAAGGTAAAGGCTGGCACTAGTCAGCCTATCAAGGCGCAAACCAAGCTC
TTTAACAATTTGGATGGTAGCTTCTTAGTCTGGATAGGTTAAACCTAGGAGATTCTCTTGAGTCTCCTAT
AATGTAACCTAACTAACTAAATGAGGATTAAATCATGGAACGCAATGCTAACGCTTACTACAACCTTCTG
GCTGCAACTGTTGAAGCATTCAACGAGCGTATTCAGTTTGATGAGATTCGCGAAGGTGATGATTACTCTG
ATGCACTACATGAGGTTGTAGACAGCAATGTTCCAGTTTATTACAGCGAAATCTTTACAGTGATGGCTGC
TGATGGTATTGATGTTGATTTTGAGGATGCTGGTTTGATTCCTGACACGAAGGATGTAACCAAGATTCTA
CAAGCTCGCATCTATGAAGCTCTTTATAATGATGTACCAAATGACAGCGATGTAGTTTGGTGTGAAGGCG
AAGAAGAGGAAGAATAAGGATGGAAAAGCAATATAACTTTATCTTTTCAGACGGTGTAACCCTGAAGTGT
TCCCTACGATTCGCACAAATTCGTGAGGAAGTACTAGGCACTACATACAAACTATTTAGCTGACACTATA
AGAGAAGGCTTAACAAGGCGTTACTAAGGTAGCGCCTGATTAAACTTTCACTTACTAGGAGTTGAGATTA
TGAAAACCTTGATTGGATGCTTCTTGTTGGCTTCTCTTGCTCTGGCATTTACCGCTAAAGCTGGTTATGA
CGCTTATAAAGTAGAACAAGCCCAGCAAGACTGGGCCAAAAAAAGTTCAACTTGTGCAGCAAGAGCAAC
ACCTACGAGTACTGCAACAAAACACTAAGACACTTATGGAAAGAGTAACTAGCCTATAGCCCACCTGAGT
GGGCTATGTGATATTTACTTAACACTATATAAGGTGATTACTATGACTACTGAAAACACCCTCGTGTCTG
TCCGTGAAGCTGCAACCGCTGAAATCAAGCAACATTTAGACAATATCGGCACTTCTTACATCAAAGTAGG
GGCTTGTCTGAATGAGTTACGCGGAGACTTTGAAGGTCAAAAAGAGTTTTTAGCCTATGTTGAAGCAGAG
TTTGCCATTAAGAAGGCACAATGTTACAAGCTGATGAGTGTAGCCCGTGTCTTTGAAGGCGATGATCGCT
TTAAAGGCGTGGCGATGCGTGTAATGCTGGCGCTTGTTCCTTTCGCTGATGAAAATATAATCATGGAGAA
GGCCGGAACTCGCCGCAAATGGCAAGCTGGACACTAATGCCGTAAACGCCCTGATTGAACCTAAGAAA
GAGTCAAAGGCCGAAACGGTACAATCTAAGGCTGAGACAGTAAAACCGCAGGAGAACGCGACTGAGTCCG
CAGAATCACATGAAATGCAAGCGCCGCAGGTAGTGCCACCCGCGAGCGAGCAGGAGTCCGACGAATCAGC
ACCTTGGGAAGAGGAAAGCAAACCGGAAGCGCCAAAGGCAGCTCCGATGGATAACACGGCTAATACTGAG
AATGCCGCTATTGCTGGTCTGCTGGCACAAATTAAAGCACTGACTGAGCAATTACAGGCAGCCAATGACC
GCATCGCCTCCTTAAGTAGCGCACGCGAAAGCAAGAAGGCATCCGCACCTATGCTGCCGCAGTTCAAATC
TTCCTGCTTCTACGCTCGCTTAGGCTTGAGCGCGGAGGAGGCAACGAAGAAAACAGCAGTTAACAAGGCA
CGCCGCGAACTGGTTAAGCTGGGATACGGTGAAGGCCATGAGGCATGGCCCTTAATCTCTGAGGCAGTAG
AAGAGTTGACTAAGTAACCTTATCGGTGGCATCTTCTTAGGTGTCACCTATTAAGGTTTCTTTCACTAGG
AGTAAACAAGATGCAAGGCCTACACGCTATTCAACTTCAACTTGAAGAAGAAATGTTTAACGGCGGTATC
CGTCGCTTTGAAGCGGACCAACAACGCCAGATTGCATCCGGTAATGAATCAGACACGGCATGGAATCGCC
GCTTATTGTCCGAGTTAATCGCGCCAATGGCTGAAGGTATTCAGGCATACAAGGAAGAGTATGAAGGTAA

Figure 1B

```
AAGAGGCCGTGCACCGCGTGCATTAGCTTTCATTAACTGCGTAGAAAACGAAGTGGCAGCATATATCACG
ATGAAAATCGTTATGGATATGCTGAACACGGATGTAACCTTGCAGGCTATAGCCATGAATGTAGCTGACC
GCATTGAGGACCAAGTACGTTTTAGCAAGCTGGAAGGTCACGCCGCCAAATACTTTGAAAAAGTTAAGAA
GTCACTTAAGGCAAGTAAGACTAAATCATATCGCCATGCGCACAACGTAGCGGTAGTGGCTGAGAAGTCA
GTAGCTGACCGTGACGCTGATTTCTCCCGCTGGGAGGCATGGCCTAAAGACACCTTGCTGCAAATTGGGA
TGACCTTGCTTGAAATCTTAGAGAATAGCGTATTCTTCAACGGGCAACCTGTCTTCCTCCGCACCTTGCG
CACTAATGGCGGCAAACATGGTGTTTACTACCTACAGACTAGTGAACACGTAGGTGAGTGGATAACTGCA
TTCAAAGAGCACGTAGCGCAACTGAGTCCTGCCTATGCTCCTTGCGTCATCCCTCCGCGTCCGTGGGTAT
CACCTTTTAACGGCGGTTTCCACACTGAGAAAGTAGCAAGCCGTATTCGTCTGGTAAAAGGAAACCGCGA
ACACGTCCGCAAGCTGACCAAAAAGCAAATGCCAGAGGTTTACAAGGCTGTTAACGCGTTGCAGGCGACT
AAATGGCAGGTTAACAAGGAAGTTTTACAGGTTGTGGAAGACGTCATCCGTCTAGACCTAGGTTATGGTG
TACCTTCCTTTAAACCACTCATTGACCGCGAGAACAAGCCAGCTAATCCAGTGCCGCTAGAATTTCAGCA
CCTACGGGCCGTGAACTGAAAGAAATGCTTACGCCGGAACAATGGCAAGCCTTTATCAACTGGAAAGGT
GAATGTACTAAGCTGTACACCGCTGAAACTAAGCGCGGAAGCAAATCGGCGGCAACCGTTCGCATGGTTG
GTCAGGCCCGTAAATATAGCCAGTTCGACGCAATCTACTTCGTGTATGCACTGGACAGCCGCAGCCGCGT
CTACGCGCAATCTAGCACACTCTCACCGCAATCAAATGACTTGGGCAAGGCCTTGCTCCGTTTTACCGAA
GGGCAGCGTCTTGATAGCGCTGAGGCGCTTAAGTGGTTTTTGGTGAACGGGGCTAATAACTGGGGTTGGG
ATAAGAAAACTTTTGACGTGCGCACCGCTAACGTGCTGGATAGTGAATTTCAAGACATGTGCCGCGACAT
TGCAGCGGATCCGCTGACCTTCACTCAATGGGTAAATGCCGACTCCCCTTACGGCTTCCTTGCATGGTGC
TTTGAATATGCGCGTTATCTGGATGCACTGGATGAAGGCACGCAAGACCAATTCATGACGCACCTCCCAG
TCCATCAAGATGGTAGTTGTTCTGGTATCCAGCACTACAGTGCTATGCTACGCGATGCAGTAGGTGCGAA
AGCAGTAAACCTTAAGCCCTCTGACTCTCCTCAAGATATTTATGGTGCCGTTGCGCAGGTAGTAATTCAG
AAGAATTATGCATACATGAATGCAGAGGATGCGGAAACCTTCACTTCTGGCAGCGTGACTTTAACAGGTG
CGGAGCTGCGTAGTATGGCTAGTGCGTGGGATATGATAGGAATCACTCGCGGCCTGACCAAAAAGCCCGT
AATGACACTACCTTATGGCAGCACACGTCTAACCTGCCGTGAGTCAGTGATTGATTATATCGTTGATTTA
GAAGAAAAAGAGGCCCAACGGGCTATTGCGGAAGGGCGTACCGCCAATCCTGTACACCCTTTTGATAATG
ACCGTAAAGACAGCCTGACACCTAGCGCAGCTTATAACTATATGACAGCTTTAATCTGGCCTTCTATTTC
GGAAGTGGTTAAAGCCCCTATAGTGGCAATGAAAATGATTCGTCAGCTTGCCCGTTTCGCAGCTAAAAGG
AATGAAGGCTTAGAGTATACCCTGCCTACTGGCTTCATCTTGCAACAAAGATTATGGCTACTGATATGC
TCCGCGTATCTACTTGCTTGATGGGAGAAATCAAGATGAGTCTACAGATTGAAACAGACGTAGTGGATGA
AACGGCAATGATGGGCGCTGCTGCTCCTAACTTTGTGCATGGTCATGATGCCAGCCACCTTATCTTAACA
GTCTGCGACCTTGTTGATAAAGGGATTACATCTATCGCAGTTATTCATGACTCTTTTGGCACTCATGCAG
GCCGTACAGCCGACCTTCGTGATAGCTTAAGGGCAGAAATGGTGAAGATGTATCAAGGCCGTAATGCACT
GCAAAGCCTGCTAGATGAGCACGAAGAACGCTGGTTAGTTGATACCGGAATACAAGTACCAGAGCAAGGG
GAGTTTGACCTTAACGAAATCTTAGTTTCAGACTATTGCTTCGCATAATATTAATAGGCCATTCCTTCGG
GAGTGGCCTTTCTTTTACCTACTACCTGTAACATTTCATTAACATAAAGTGTCTCACATGTGAGACTTA
TTTACCGGACACTATAGGATAGCCGTCGGAGACGGGAAAGAAAGGGAAGATAAAGGATATAAGGAAGTA
ATAGGTATTAAAGGTTATATAGGTTATCTAGGAATACCTATTACCTTCTTCCTTCCTCTTATTACCACTC
AGAGGAAGGGCAGACCTAGGTTGTCTCACATGTGAGACTTCGTATTTACCGGACAGTATAGATAAGATTA
ACTCACTTTGGAGATTTAACCATGCGCAACTTTGAGAAGATGGCCCGTAAAGCTAACCGTTTTGACATGG
AAGAGGGGCAGAAGAAAGGCAAGAAGCTGAATAAGCCTGTCCGTGACCGTGCATCTAAACGCGCTGCGTG
GGAGTTCTAAGTTATGGCTATTATTCAGAATGTACCGTGTCCTGCCTGTCAAAAGAATGGACATGATATT
ACTGGCAACCATCTCATGATATTTGATGATGGTGCCGGCTACTGTAATCGTGGACACTTTCATGATAATG
GTAGACCTTACTATCACAAGCCGGAAGGTGGCATCGAGATAACCGAGTTATCTATTACTGGCAATATCAA
ATATACACCTTCTCAATTCAAAGAAATGGAGAAGGAAGGGAAGATAAGCGACCCTAAATTACGTGCCATC
GCACTTGGTGGTATGCGTATGAAAGACCGTTGGGAGGTCATGAATGAACAAGAAAGGGCAGAGCAAGAAG
CAGAGTGGAAACTTGATGTTGAATGGTTCCTCACGCTTAAGCGTAAGAACCTTGTTTCCAGGCACATTCG
CGGCGACATTTGCGCATTGTATGATGTACGTGTTGGGCACGATGAAGAGGGTAGAGTCTCACGGCATTAC
TATCCGCGCTTCGAAAAGGTGAGCTAGTAGGCGCTAAGTGTCGCACATTACCTAAAGATTTTAAGTTTG
GTCATTTAGGTAAACTCTTTGGTATGCAAGATCTTTTCGGTATGAATACTTTGTCTCACGTGTTAGACAA
GGGAAGACGAAAGGATTGCTTGCTCATTGTCGGCGGCGAACTGGATGCACTAGCAGCGCAGCAGATGCTC
CTTGATTCTGCCAAGGGTACTAAGTGGGAAGGCCAGCCATACCATGTATGGTCTGTCAACAAAGGCGAGT
CTTGCCTTGAAGAGATAGTGCAGAACCGTGAGCATATCGCCCAATTCAAGAAGATTATATGGGGTTTTGA
TGGAGATGAGGTAGGGCAGAAGCAGAATCAGCAAGCGGCTCGCCTGTTTCCTGGTAAATCCTATATCCTT
```

Figure 1C

```
GAATACCCCTCTGGTTGCAAAGATGCTAACAAGGCATTGATGGCTGGCAAGGCTAAAGAATTTGTAGATG
CATGGTTTAATGCCAAGTCATCTGATGAAGTCTTTGGTAGCCAGATTAAATCTATCGCATCTCAAAGGGA
TAAGCTCAAGGCTGCACGTCCAGAGCAAGGACTGTCATGGCCTTGGCCTAAGCTGAACAAGGTAACGCTA
GGTATTCGTAAGAACCAGCTTATCATTGTAGGTGCAGGGTCTGGTGTAGGTAAGACTGAGTTCCTTCGTG
AAGTAGTTAAGCACCTCATTGAAGAACACGGTGAATCTGTAGGCATCATTTCTACAGAAGACCCGATGGT
CAAGGTGTCCCGTGCTTTTATCGGCAAGTGGATTGATAAGCGTATTGAGTTACCTCCAACCAACGACCCG
AAAGAAGACGGATACCGTGAGGTGTTCGACTATACCGAGGAAGAAGCTAACGCCGCCATTGATTATGTAG
CTGATACAGGTAAGCTGTTTGTAGCTGACCTAGAGGGTGACTATTCGATGGAAAAGGTAGAGCAAACTTG
CCTAGAGTTTGAGGCTATGGGTATTTCTAATATCATCATTGATAACTTAACGGGGATTAAATTAGATGAG
CGTGCTTTTGGTGGGAAGGTTGGTGCACTTGATGAATGCGTCAAGCGGATTGGTACTATCAAAGACCGAC
ACCCGGTTACTATATTCCTTGTATCACACCTTACACGTCCTCCGGCAAACCGTACCCAACACGAAGAAGG
TGGCGAAGTTATCCTTTCTGACTTCCGAGGCTCAGGCGCTATCGGATTCTGGGCATCTTACGCCTTGGGG
ATTGAGCGTAATACAAGAGCTGAAACGCTTGACGAAAGGACTACCACGTACATCTCATGTGTCAAAGACC
GCGACCAAGGTATCTACACTGGAACCAAGGTCATGCTTAAGGGTGACATTCAAACCGGACGTTTAATGGA
ACCACAAGCCCGTACTAAGTCATTTGATACAGGTGAAGCAAGGCAACAAGAAGTACCAGATTTACCGGAT
ACTATAGAAGAGACTACCTTCGATGAAGAAAGTGAGTTCTGATTAGTGTATTTATCAGGCTTGTCTCACA
TGTGAGACAGGCTCTTATTAAGTACATTAAATAACTGGAGATTGATTATGTATAACTTAGTGTTGAATGT
AGGTGACTTTGTACGCAACATCAAGAAAGATTCAAGTCGCTATCTTTGCCGTGGTGTTGTAACCTTTGTA
GGTGAGAACCTGTATTATGTAGAATATCGCAGTGGTGTTAAGCAATATTACCACAAGAAGACAGCACATA
AATATCTTGAAAAGATTGTAGAGATAAACAATCAATGTAAGTGCATACATGATGAGGTTTGCGATAAATG
TGCTCGCCAGATGCTTAAGAATTTCCTAGCTCCTCTTTATTATGGTGCTGGTCCTCAAACACTAGCAGAG
TGCATGGCAGAAAAGAAAACCACACTCAAGAAAGAGCGTCGCAATGTAATCACTGGTAAGACTCAAAGTG
AGATGATTAAGCAATGTGGCACTGCATTAGGTGTTACACAGTTTAATACTCGTGCATTGGGTAAATCCAC
AGGACAAGCTATGGTAAAGATTGGAGAAGCCATGATGCATCCAAATGTACCTGTGCGAATCATGGATGTT
GACCATGCAATCACAGAACAAGGTACGCAACGACGTGTAATTAATAAGCATTTTGCCGACACTATAGAAG
GCATTATTCGTAAGCAAGGGTTGAAAGGTCTTCACATCTTAAATGGTGAAGAATTACTGTACCTACCTAT
CGTTACTGAAGAAACATACGTGAATATCTAAGGAGTTAATCATGACTAAGGTATTAATTTATATGCGTGG
ACCTCATAAATGCTATGCAGTTGTAGCACCAAATGGTGTTAAGCCTTATCGTACTTCAAAAAGATTGGCA
TTAATAGGTGCTAGTAGTAGTGCAAGTTTCCAAATGGAACTTTTTGGTCATTGGACTGAAAGGCAATTCC
GTGAGGATTTTAAAGTCATTGGCAGCTTCATGGTGAAATATGCAGAATAAACATAGTCTTAGAATGTTCG
ATGGTCATGAAAACCTGCAAGCCAAGATTACTAACCAAGCCTTCCTGTTCGCACAGTTAACTATGGCTGA
GGCTAAGAAGAATAGTCTCACTCGTGAACAGGTTATCAAGGAGGCCACTTGGGAACCACACCAAGGTAAA
TATATGGGCCACAAATTAACTGTAACACGCAGTCGATAAGTCAAGGGTTGTCCAACGTGTTGGACAGCCT
TTCATCATATTGATTGGGAGGTATTAAATGACTAAGTTTACTATGCAAGACCTCATTAAATTACGTGATG
AAATAGAATCACCGGAAGTTAATACAGAGTTTCACTACATTGATCCACGAGATAAACGAGAGATTCCTGA
TTATCAGATTGAGACGGAGTTAATGTATGAAGATTATTGATTGGAAGAAGGAAGCAGAAGGCCGTATCCT
AGTGATGGATGCGGAGGCTAAAGGCCTGCTGGGTGCTATCCGCTACGGTCATCGTGAAGATGTACACATT
ATTTGCTGCATGGACTTGCTCACCACTGAGGAGTTCCTCTTCTTCGACCCATATGAGATGCGTGACCCTG
AAGCAAGGGAACACTTGAAAGAGTGGGAAGGCCATCAAGATGGGACCTTGGTTGATGGTGTTAACTTCCT
AAAGCACTGTGAAGCCATCGTCTCACAGAACTTCCTAGGCTATGACGGGCTTCTCTTTGAGAAAGCCTTC
CCTGACATCTGGAAGGGATTTAACTACACCGAGAGGCGCGCGGCAAGGGCAGACTACGTGCTGACTTGTGTC
CGGTACGCGTCATGGATACGCTGGTCATGAGTCGCCTGTTAAACCCAGATAGACGCCTTCCTCCGCAAGC
ATATGCCAAAGGTATGGGTAACGTTGCCCCTCACTCAATTGAGGCGCACGGCATTCGTATAGGCCGTTAT
AAGCCGGAGAACGAGGATTGGTCTAAACTAACTGACCACATGGTACATCGTGTACGCGAGGACGTGGCGA
TAGGCCGTGACCTATTCCTCTGGCTATTTAACGGAGAATGGACGGAGCACAAACGCCGTGGCGTGAATAA
ACGCACTGGCCTAGGTATTGAGACAGCCTTCCACATGGAGTCCATTGTGACGCTGGAGATGAGCCGTCAG
GCCGAGCGTGGATTCCGTCTGGATATAGATAAAGCATTAGCACGATGCGAGGAATTGGACGCTAAGATTG
ATGAGACAGTCGCAGCGTTCCGTCCGCACATGCCTATGCGTATCAAGTCTAAACCTTTTAAACCGGAAGA
AAAGAATGAAGTATGCCAACGCGCAAATGAGTATGGAGCTAGCAACAATATACCTACTGTCCTTGACCCC
TCTCACTTTCTTCACGCAGAGAGACGAGGAGATCGCAAGACAGTATGGAGTGTCACTACTAAGTCTGGTG
ATTGGTCGGCTAGCGTCAAGAAAGACTTTCCTCACCTTAGAGGAAACCGTAATGACACGCCAAGTGTCAA
GTGGATTGGCGCTTACTCGCCTGTTACTTTCGAAGAGATTCCCTTGGGTAACAGGGATACAGTTAAGCAA
GTGCTCTATGATTATGGATGGAAAGGTGTTGAATTTAACGATACCGAGCAAGCGCATCTCGATGAGCATG
GCGTATTACCCAAGCCTTGGAGTGGGAAGATAAATGAAAAGTCCCTTACTTTATGGCAAGAGAGAGCCGC
```

Figure 1D

```
ACGTGAAGGTAAAACAGTCCCTGATTGGTGCTTGGGTATCGCTGCATGGTACATACTCGTATCCCGTCGT
GGTCAGATCCTCAACCGTGGTGACGTTGAAGCCTTCGACCAGAAGGGGGTGTGGCCTTCGCAAGCTGGTA
TACGAAAGTGTCGCGGCCTTGTACCTGTAGCATTTAACAAGGAGTTAGGAATCAATGCGCAGCAATACTA
CGAAAGGTACGGATGCTGGCCTACGTCAGACAAGGATGACGGAGAATGGCGTGTGCCAGCTATTGCTATT
AGTATTGGAACTTCTACGTTCCGTATGCGTCATCGTAACGTGGTTAATATTCCTGCCCGTGGCTTGTATC
CTTTACGTGATTTATTCATAGCAGGGAAAGGCAAGCTAATCCTTGGTTGTGACGGTGCAGGTCTTGAACT
GCGTGTCCTGTCTCACTTCATGAATGACCCTGAGTACCAAGAGATTGTACTGCACGGTGATATTCATACG
CATAACCAGATGAAGGCTGGTCTTCCTAAGCGTGATATGGCGAAGACATTTATATATGCCTTCCTATATG
GGTCTGGTATAGCTAACCTTGCAGCAGTATGTGGTGTTACTGAGGAAGAAATGGAGGAAGTTGTGGCAAG
ATTTGAGGTTGAACTACCATCTCTTGCACGTCTTCGTGAGAATGTTATCGCACAAGGTAACAAGTTTGGC
TACCTACAAGCACCTGATGGTCATTGGGGTCGCATCCGTATGTCTGGTGGTGAACTTAAAGAACACACTA
TGCTTAACGTACTACTCCAGATGACTGGTTCTCTGTGTATGAAATACGCATTGGTCAGAGCGTTTGCAGT
GATGCGCAAGGAAGGTGTGGCCTTAGATAGCATGGGAAACCCTTGCGGTATAGCTAACGTGCACGATGAA
ATCCAGATGGAAGTCCCTGAAGATGAGGTCTTGTATCTCAACTACGACTTGCCTTTCACCTTAGAAGGGT
TCGAAACAGAGAAGGCTGCTGTGAAAGCAGTGTTCGATGCAGAGGAGAAACGTGTTCATGTGGATTCTGA
AGGACGTATGTGGTCTGCTGCAAATCTCGTTAGTGTTGATGCTGGTGTACTTCATTGCCAGCGTCGTTAT
CACCGTGCAGGGCATATCATTGCCGACGCAATGACCTGGGCGGGTCAGTACCTGAAGATGCGTTGTCCGA
TGGCAGGTGAGTATAAGATTGGTGCAAGTTGGAAGGAAACACACTGATGGACAGGTTTGATATTGTTTGC
CTATTCTCTACCTTCTTTCTTATATTCCTTATGCTTGCTTGCTATGGAAGTATGCGATTAGATATACCTG
ATGAAGAGGAGGGTTACGATTGATGCAGGCATCTTTTATTATTCTTGGAGTCATATTATTTATGGTAGTA
TTCTGGGCTTTCTCTGGCATTGACCCAGATTGTGATGGTAACTACGACTGAGTTATACTCAAGGTCACTT
ACGAGTGGCCTTTATGAATAACTTATTCCTACTTATTTTGTCTAACATGATTTACTGGACACTATAGAAG
GAAAGCATAGGTAATCTAGGTTTATAAGGTAGTATAGGTAATTAAGTAAATATAGGAGATATAAATATGT
CTATGGTAACTACTCTGGTATTCGTGGCTCAATACTTTCGTGGTCTTGCTAATAAGTTCAAGTCCAAGGC
TATCAAAGCTATTGAGGCTCGCATCGAAGCAGTACAGGCAGAGCAAGTTAAAGTTGAAGAACATCGTAGT
TCTCAAATGATTGACTGTCATAACCGCTACTATGCATCTCGTGATGAACTAAATGCACGTCAAGTCAAAG
AGGTAGAAGATATGCTGGCACGTCACCAGCAAGAGCGTGACAGCCTGAAAGCTGAATTTGAAGAGAACAA
GGCATCAATTGCTCTTGTACATCAAGCTGCATCTGACAGTCTGAAGAAAGAGATTGTTATGCTGGAAATC
GAACTGGATAACCTGACCAAATAAGGGGGGGTTATGATGGAAGAAGTAATTCAAGCTAAACATGTAGGTA
TTATCTTTCGCGATCTAGAGCAGCGTAAAGTTGCAGGTCATACTCGTCTGGCTAAAGAGGAAGACACCGC
AATCACTACTGTAGAACAAGCAGATGCCTATCGTGGACCAGAGTTCACTCAAGGTGAAACTTGTCACCAA
TTGAGCCTATCAATTTGTGACACTATGGCTATTGTAAATGTGCAAGAAGTCGAAGAGGGTGAGTGTGTCA
GTTACATCTACCCTTTAGATACTATTGCACGCATTAAGGTAATCCATAAGTAATTACTAGACACTATAGA
ACAATAGGTCGGCTTAGTTCGGCCTATGATTGTAAAGTGTTGTTGATGTTGAACCATTGTGCATCTTGCA
CAACCCGATACCGTATAGGGCTTTCTAGTGAGTACATGCTTGTGCTCAGTACAAAGCTAACTGACAATAG
GAGACTAAATAAATGGCACGTGGTGATTTTGATTTTGGTGCTCAGGTTACTAAATCTGAAGGTAAAGTCT
TTAAGAATCCAGAAGTAGGTGATCATGAAGCAGTAATCTCTGGCATCATTCATGTTGGTTCCTTCCAAGA
CATCTTTAAGAAAGGTAATACCACTGAAGTTAAGAAGCCAGCAAACTTTGTTCTGGTTAAGATTGTCCTG
ATGGGTGACGATGACAAGAACGAAGATGGTTCTCGCATGGAACAATGGATGGCTGTGCCTCTGAAGTCTG
GTGATAAGGCAACACTGACTAAGTTCCTGAATGCAGTTGACCCTAAAGAGTTGCTGGGTGGCTTCGATGA
TTTCATTGGTGAATGCCTGACTGCAACGATGGTCGGTTCTGGTGATAAGAATGACGATGGCTCATTCAAG
TATGTTAACTGGAAGGGATTTGGTGGTATGCCGGACAAGCTGAAGAAACTGGTCATTGCTCAGGTTGAAG
AGGAAGGTCTGTCTATGACAGGTCACATTACCTTCGACAAGCTGACCAAAGAAATCCTTGATGACATCCC
AGCCAACTTGGTGCGTCAATACTTCCTGAACGAGACGCCTCGTGGTAAGAACCTGTCTGTTGCTGGTTCT
CACGTAGAAGCAATCATTAAAGCTGCTCGTGAAGAAGACCCAGAATGGAAGAAGGCTAAGAAGAAAGACG
AGGAAGATGCTACCCCAGCTAATCGTAAATCTCTGGATACTGGTGAGTCTGTTCCACAGGAAGTACCTGA
AGCAGAAGATACTCCTGCACCGGAGATGGATGAGGACGCGGAATATTAAGGAGAAAGGATGAAAGTACAA
ATCGTAACCCTGCACTGCAAGAAAGGAATTACAACTCTTGGCGGCAACACTTTTCACTCCTTCTCTGAAG
GGGACACATATGCCGACCTGCACTACATCTGGCGCGACGGACAGCACGTGGTGAACTACAGCGACCCAGC
TACGGGGAAACGCCACGGCGTATCGCTTCCGGCGCATGACATTGCTCAGGTGAACACAGTTTTATAAAGT
CTCACGTGTGAGACAAATCGGTGTCCGGTATTTACTGGACACTATAGAAGAGAAGAATTTTAATCGGCGA
TAATGCCATAACCAACAAAAGGAGAATTTAATATGTTCAAGATTGAAACTATCGTAAACCGTGTTGTTAA
AGGTGCTGCTCTGGTATCCGTTGAGTCTTTCATTATCGTCGATGAAACTGATCAACTGGTAGCTGGTACT
AAGGCTTACGATACCCGTGAAGAAGCTCAGGCTAAGATTGACAGCATGGGTAACTTCGCTGCTGGTCTGG
```

Figure 1E

```
AGTTCGCTCGTGCTTGCTTCCCTGAGCAGGCTGACAAAGCTCAGATTGGTAAGGCTAATATCGTAGCTGA
ATATCTGGATTGGGTTGCTGCTGGTAAACCAGTGAAAGAAGTTAAGGCTGCTGAAGAAGCTGAAGCTCCA
GCAGAAGAAGTAGCTGCACCGGAAACTCCGGTAAGTGAAGAGGAAGAATTTTGATAATAGCAGGTGTTGC
CTCTGTTAGTCCTAGCTGACTATCACGCTCACCTCATCTAATGCCCTGTCTGCCTTAGTGTAGGCAGGGT
CTTTTGCGTAATAGTTATTGGAGAATGAATTATGCCGACTATTGAATCTCGAATTGAACTGGACATTAGC
TACAATGCAATCACCAGACAGTATATTGGGGTTGCCTATGATTACAAAACTGGTGAGAAGCTAGTGGAGG
TGAGACAATGGGATGACTATTGGTTAAGACAGAACCTCCATGATGCGGTGTCCTCCTTCCTGAAGGAGTG
GCCTACATGCGACCAAACTTCGACTTCGGAGCTACAGTATCGGAAGACAATAACCTGTTGCTGTGGCCAA
CTGAAGGTAATCGAATCGCTTTAATAGATGCTGATATGTTACCTTACATCATAGGGTATACAATCAGTGA
TATGACTTATGTACGAGCCACAACTCGTGTTAAGTCAGGGCAAGTCCCCTCAATCAAAGATACACCTGAG
TGTAAGCAAGCGTGTGACCGTGTGAACTCCTTGCTTAACTCTTGGGTGTATGCAGCAGAATGTGATGCAG
CTAAGTTGTTCATGACGAAATCAGAAGCTAACTTCCGTGTCCGCCTAGCATTCACCAAGCCTTATAAAGG
TCAACGTAAGACCGAGAAGCCTCCATTCTTCTATGAATTGCGAGAGCATCTCTTAGAGGTTCACGGTGCA
ATCTTGGCAGATGGAGAGGAAGCAGATGACCTCATGAGTATCGCACAATGGGACAGCCACCGCCGCTTCC
AGCAAGATACAGGTAACGAGTTCCCTATCGGTAGTCCAGAGCATAAAGCATTCTCTGATACTTGCATCGT
TTCCTTGGATAAGGATTTGATGATTGTTCCCGGTTGGCATCTACAGCCGGGTCAAGAGAAGAAATGGGTA
GAGCCTATGGGTTGGCTTGAGCTACGCCGTAAGGCTAATGGGCAAGTCAAAGATCTAAAAGGTGCTGGCC
TCATGTTCCACTATGCACAGATGATTATCGGTGATGATATTGATAACTATGCTGGCATACCAGGTCGTGG
TGCTAAATATGCCTATGATCTTCTCAAAGATTGTAAGACAGAGAAAGAGTTGTACATGGCAGTGCTGGGT
GCTTACAAGGCTAAGTTCGGGCATGGACAAGTTAAAATTAAGAATTACCGAGGTGGTTATCGTATCGGCA
AAGCCTTTGACCTAATGCTTGAGTGTGGTCGCTTATCTCACATGGCAAGATTCAAGGGTGATATATGGCG
AGCCGATAAGAACCCAATCTTGTGGGGAGATGATGCGGAATGGTTAGCAAATTAAAATCATCGGAGGTGG
CAGCTTATAAGAAGGAATTGCTAGATAAGCAAGGATGGAAATGCCCTCTGTGTGGCGGCAGTCTCAAAGC
TGTCACACCTGTAAACCGTGTACTTGACCATGACCATGAGACAGGATTCTGCCGCGCTGTTGTATGCCGA
GGCTGCAATGGTGCGGAAGGGAAGATTAAGGGTGTTATCTCTGGTTATGGTAAGGCTGGTAACAACCGTT
ACTTCCAGCTTCAATGGTTAGAGCGACTATATGAATACTGGAAGTTACATAGTACGCCTCAGACAGATAA
GTTATATCACAAACATCAAACGGAGGCAGAGAAGCGCGAGGCTAAGAACCGTAAGGCACGCCTTGCTTAT
GCAAGAAAGAAGGAGGTTAAAGTTGGGTAAGCTGCGCAGCTTGTACAAAGACTCCGAGGTACTTGATGCA
ATCGAGCAAGCTACCGACGAGAAAGGTAATGTTAACTACAATGAGATGGCACGTGTATTATCGTGTCATA
CTGTGGGTAAGAAGATTACCCGCCAGTTGGCTCGATACTGGCATGGTCAATTCAAGAAGACCAAGAAGAA
TGGTGATTACTACCAGACCCTTCTGCAAGAAGATAAGCGTATCAAAGAAGAGCGTAAGCTCAGGACTCCT
GACCGCTACGAGGATTTGGCTATTGTGCCATTGCCTGACTCGCCTCATCGAAGTGTACTGGTGATCCCTG
ATACTCATGCACCTTATGAGCACCCAGATACCCTAGAGTTCCTTGCAGCCGTGGCAGCACGTTACCGTCC
AGACACAGTGGTACACCTAGGAGATGAGGCAGACAAACATGCCCTGTCATTCCACGATTCGGACCCAAAT
CTGGATAGTGCTGGCATGGAGTTAGAGAAGGCTCGTATCTTCATGCACAAATTGCACAAGATGTTCCCTG
TGATGCGCCTGTGTCACTCTAACCACGGCTCTATGCACTTCCGTAAGGCAAGCGCCAAAGGCATCCCTGT
GCAATACCTGCGCACCTATCGTGAAGTCTTCTTCCCGCAGGGAGGTGGCGACCAGTGGGATTGGCAACAT
ACGCACGTCCTTGAGTTGCCGAATGGTGAACAAGTGGCATTCAAGCATCAACCTGCTGGCTCTGTCCTAG
CAGATGCAGCGCATGAGCGTATGAACCTTGTGTGTGGTCACTTGCACGGTAAGATGTCTGTGGAGTACGC
ACGTAATACACATGAACAGTATTGGGCTGTGCAAGGTGGCTGCTTAATTGATGAGTCATCCCGTGCATTT
GCCTATGGTCGTGAGTCTAAATACAAGCCAGCATTAGGTTGTGTGGTCATTCTGGAGGGTGTGCCTCACA
TTGTCCCGATGCAAACCAATAGCGACAACCGTTGGATTGGCAAGATTTAGTTGACACTATAGAACAAAGG
GCTAGGTAAGACTTTATCGGCTGGCGTATCCAAATGATATTGCACTAGCCCTTGATTGTATAGTGAATGG
AGGATTCAATATGTCACACTATGAATGTAAGAAGTGTCATAAGCGTTATGATTACTGTACTTGTGGTCAA
GAGAAAACATCTTTTAAAGTTGGAGACAAGGTATTTCGTAATGAAAAGATTCGATTCCTTGGAATCAAT
ACTGCAAAGAAGCTGGTATTGACCCTGATAGCCCTGTAACCATAGATGATATTGATGGCATTAACTTGTG
CTTTCGTGAGGTGAGGGGTACAGGTTGGGATTCCAAAAAATTCAAACTTGCATCTGATAAGTTAGACAAC
AATATGGTAATTAAGCCTAAGCACTACGAGTTCTTTGATGGCGTAGAGGCAATCACTATCATTGCCCGCA
GTATGACCGAGAAGCAATTCGCTGGCTATTGCATGGGTAATGCTTTGAAGTACCGTCTACGTGCAGGTAA
GAAGTTCAACACTGAAGAAGACCTGAAGAAAGCAGATTACTACAAAGAGTTATTCCAGAAGCATCGTCAC
GAATGTATTGATGAGGATATTTGATATGAATATCTTTGAGTTCCTAGGTCTTCCAGAAGACCACCGCAAT
CACCCATTCATGCTGGTGAAGCATCGCGGTGAAGTTCCTGAGAAGAAATTAACTTTTCCATGTTATGCAC
AGGTGAAACGAGATGGTATCTTTTCTGCTGTTGTTGTTCGCACTGATGGTGTCGTTGGCATTTTTGGTCG
CACTGGTAAGAAATTGGCAAACACTGAAGGACTCGAACAAGCCTTTGCTACCTTTCCGGTTGGCATTTAT
```

Figure 1F

```
CTTGGTGAGCTTCAGTCTATGGCCATTGATATCTACCTTGAGGCAATCTCTGGGGTTGTGAACCCCAATC
GCACTGAGCCACTTGATTTCATAGGCCAGCAGATTAAAGACAACCTGTATATCGACTTCTTCGATATGTT
AACTATTAAGGCATTCCATGATGGATTCACTGATGTTTCTTATCTCAAACGTTACGATGCTTTACATCGT
CGTATCGGCGCTCATCTTAGCGGGTGCAACGCTATCCTTCCTATCACTCCTTGCCATAATGAGCGAGAAG
TTGAAGCGTTTGCGCAAGAGCAAATAGATGCAGGACGTGAGGGTGCTGTATTCAAACTGGACTGCGATTA
TGAAGCAGGACACAAAGGTTATCGTCAGACTAAAGAAGTCCGTAAGGTAACCTATGACCTTACTTGTATT
GGCTTTGAAGAAGGTAAAGGCAAATACAAAGGTAAGGTAGCTAACCTCATTTTCAAATGGAAAGGAGGCA
AGACAATCAAAGCTATGTTAGGTAAGGGGTGGACTCATGCAGATGCAGAGCAGATGTTCCACGACATTAA
ACATGGTGGACGATTGAATGTCATTGGTAAAATCTTTGAAGTCAAAGGTCTTCAGGATTCAAGCAAGGGC
AACATTCGTCTGCCCAAAGCGGGAGAATTAAGACATGACAAAGATGAACCAGATTTCTTTTGATAGCATG
AAGGCAACTCGTGCAGTTGAGGTAGCAGAAGCTATCTTCGAAACTTTATCCTGTGGCATGGAAGTGCCAT
ATACTTTACTTGCTGATGCAGAAGAACTTGGTCTTTCTGTAGAAGCTATCCAAGAGAAGGTTGACGAATT
ATATGGTACAGACGAAGAAGAAACCGACGATTTCATTTGAAGGAATGGAGATGCTTGAGATGATTCTCAA
GCCTTCTTCTCCTAAGGTGACTAAGACTCATGAAGAGTTAATCGTTGATGAAGTTAAGCGTTACATCATG
GATTGTGTCAGAGCACAACTGGTGGTCCAATGATACGTCCAGCCTCCTTCCTAGATATTCCTGAGATTAT
AAACCTTGGGAATAAATATGTGGAAGAGGAAGTCAAGGTTGTAGCCCACCACTCAGCCTCATGGAATGCA
GAACAAAGTGCCATAACCTTTGTGCATCTCTTAATAGAGACCCACCACTCAGCCTCATGGAATGCAGAAC
AAAGTGCACATAACCTTTGTGCATCTCTTAGTAGAAGATTTATCCCTATGGGTTGCTGTAGATGAAGG
GCAGATTGTAGGGTTCCTGTGGGCTGGCTATCACGAGTTGGCCCCTTGGACACCTGTAAGAGTTGCCTCT
GACATTCTCTTTTATATTATACCAGAGAGGCGAGGAACACTACTTGGTATGCGTCTCATCAAAGCCCTAA
AGCAATGGGCTAGTGATAATGAATGCTCTGAGGTTCGCCTGTCTATCGCCTCTGGTATTAATGAAGAACG
TGTCGGACGTATGTATAAGCGACTTGGCTTTGAACCGTTTGGCACTGTGTATAACCTGAAGTTCTAAGGA
GATAACATGGGTGTTGTAAAGAAAGCATTTAAGGCTATCGGTCTTGCTCAAGATGCACCACGTATTGAAG
CCAAAGTCCCAGCACAGCAGCTTGAGCGTAAGCCTGAGACTGAAGCTGAAGATATTCAAATTGGTGCAGG
GGATGATGCTACTGCATCTGCAAAAGGTAAGCGTGGCCTTGTCCGTCCGGTAGCTTCTAGCTTGAAGGTG
TAATATGAAACAGAGCATAGATTTGGAGTATGGAGGTAAGCGGTCTAAGATACCTAAGCTATGGGAGAAG
TTCTCCAATAAACGTAGCTCTTTCCTTGATAGGGCGAAGCATTACTCCAAATTAACCTTGCCCTATCTGA
TGAATGACAAAGGTGATAACGAGACTTCGCAGAATGGATGGCAAGGTGTAGGTGCTCAGGCAACCAACCA
TCTAGCCAACAAGCTAGCGCAAGTACTATTCCCTGCACAGCGTTCCTTCTTCCGTGTAGACTTAACTGCA
CAAGGTGAGAAGGTTCTTAATCAGCGTGGCCTGAAGAAGACAGAGCTAGCTACCATCTTCGCTCAAGTGG
AAACACGGGCAATGAAAGAGTTAGAGCAACGTCAATTCCGGCCTGCTGTAGTAGAAGCATTTAAGCATCT
TATTGTTGCTGGCAGCTGTATGCTATACAAGCCGAGCAAAGGTGCAATCAGTGCTATCCCAATGCATCAC
TACGTAGTTAACCGTGATACCAATGGCGACCTGTTAGACATTATCTTGCTACAAGAGAAAGCCTTACGTA
CCTTTGACCCAGCTACACGTGCGGTAGTAGAGGTTGGCCTGAAAGGTAAGAAGTGCAAGGAAGATGACAG
CGTTAAGCTGTACACACATGCTAAGTATCTTGGTGATGGATTTTGGGAACTCAAGCAATCTGCTGATGAT
ATCCCTGTGGGTAAGGTGAGTAAAATCAAATCAGAAAAGCTACCTTTCATCCCATTAACTTGGAAGCGAA
GCTATGGTGAGGATTGGGGTCGACCTCTTGCAGAGGATTACTCCGGTGATTTATTCGTTATCCAATTCTT
ATCTGAAGCGGTTGCCCGTGGTGCTGCGCTGATGGCAGATATCAAGTACCTGATTCGTCCTGGTGCTCAA
ACTGATGTTGACCACTTTGTTAACTCTGGCACTGGTGAGGTTGTCACTGGTGTAGAAGAAGACATCCATA
TTGTACAGTTAGGTAAGTACGCAGACCTCACACCTATTAGCGCGGTTCTAGAGGTATACACTCGCCGTAT
CGGTGTTGTCTTCATGATGGAGACAATGACACGCCGTGACGCCGAACGTGTTACTGCTGTAGAAATCCAG
CGAGATGCGTTAGAGATTGAGCAGAACATGGGTGGTGTATACTCCCTCTTTGCTACTACTATGCAATCGC
CAGTAGCGATGTGGGGTCTGCTGGAGGCAGGGGAGTCCTTCACTAGTGACTTAGTGGACCCTGTGATTAT
CACAGGTATTGAAGCTTTAGGACGCATGGCTGAGTTGGATAAACTGGCTAACTTTGCTCAGTATATGTCA
CTGCCATTACAATGGCCTGAGCCTGTCCTAGCTGCTGTGAAATGGCCTGACTATATGGATTGGGTGCGTG
GTCAAATCTCTGCTGAACTGCCGTTCCTTAAATCGGCTGAAGAGATGGCACAAGAACAGGAAGCACAGAT
GCAAGCACAGCAAGCACAGATGCTTGAAGAAGGTGTGGCTAAGGCCGTGCCGGGTGTAATTCAACAAGAA
CTTAAGGAGGCGTAATGTCTTTCTCATTTACTGAACCGTCAACCACTCACCCTACTGCTGAAGAGGGTCC
GGTAGAAACCAAGGAGGTAACAACTGATGCTGCTACTACTGATGCTCCTGCTGACGCTGGCACTTCTGTA
CAAGATGACAATGCTGGTGCACAACCTACTGAAGACACCGGAGGAGAAGCTTCTGGACAGCCTTCAGAAA
AAGGAGACAATGGCGGAGAGAATGGTGAACCTAAGCCAGATGATACCGCGACCGACACTGAGGAAGTGCA
ATACTTCTTCGGAGAACATGAAGTAACAGTAGACATCCCACAGGATGTAACTGACAGCCTTAAAGAGAAA
GGCATTGATGCCAAGCAGGTTGCCAAGGAACTCTATTCCAAAGGTGGCAAGTTTGAACTGTCAGATGCAA
CCAAGCAGAAATTGTATGATGCTTTTGGCAAGTTTGCGGTAGATGCTTACCTATCAGGTCTAAAGGCTCA
```

Figure 1G

```
AAATGAAGCCTTCTTCCTGAAAGAAGCCAACGCAGCTAAAGAGTTGGAAGCAGCTAACACCCAACGCTTC
TCTGATGTTTCTAAGGAAATTGGTGGCGAAGAAGGTTGGTCCCGTCTTGAGGAGTGGGCACTTGAAGCGC
TGTCTGATGACGAACTAATGGCATTCAATGCGGTGATGGAATCTGGCAACCAGTACCTGCAACAATATGC
TGTTCGTGAACTGGAGGGTCGTCGTAAGCAGGCACAGGGGGATGATAAGCCATCCCTGATTGAGCCATCA
GCACCTGCTAAGGCTAATGAAGAGAATGGCCCACTGACGCGAGATCAGTACGTTCAAGCAATCGCAACTC
TTAGCCAGAAGTACGGCAATGACCGTAAAGCTATGGCAGAAGCTCAGGCTAAACTGGACGCCCGTCGCCG
TGCTGGCATGGCTCGCGGTATCTAATTCAGTATTTACTGGACACTATAGAAGGGAGAAAAGTTCTCCCTA
GTTATCAATTTGATTTATAAGGAGATTATAATACATGTCTACACCGAATACTCTGACTAACGTTGCTGTA
TCTGCGTCCGGTGAGGTTGACAGCCTTCTCATTGAGAAGTTTAATGGTAAGGTCAATGAGCAGTACCTGA
AAGGTGAGAACATTCTGTCCTACTTTGATGTACAAACTGTTACTGGCACTAACACAGTGAGCAACAAATA
TTTGGGCGAAACTGAGTTGCAGGTGCTAGCACCGGGTCAGTCCCCTAATGCCACCCCTACTCAGGCGGAT
AAAAACCAGTTGGTAATTGATACCACTGTCATTGCTCGTAACACTGTGGCTCACATCCACGATGTACAAG
GTGACATCGATAGCCTGAAACCAAAACTGGCTATGAACCAAGCCAAGCAACTGAAACGTCTGGAAGACCA
GATGGCAATTCAGCAGATGCTGTTAGGCGGTATTGCTAACACCAAGGCCGAACGTAACAAGCCGCGTGTT
AAAGGGCATGGCTTCTCTATCAACGTTAACGTAACTGAGAGTGAAGCACTGGCTAACCCTCAGTATGTTA
TGGCTGCGGTAGAGTATGCTCTGGAGCAACAGCTTGAGCAGGAAGTGGACATCTCTGATGTAGCTATCAT
GATGCCGTGGAAGTTCTTCAATGCTTTGCGTGATGCAGACCGAATTGTAGATAAGACTTACACTATCAGC
CAGTCTGGTGCAACCATTAATGGCTTCGTTCTCTCTTCTTATAACTGCCCTGTGATCCCGTCTAACCGAT
TCCCTACCTTCGCTCAGGATCAGGCTCACCACCTGTTGTCAATGAAGATAACGGCTATCGTTATGACCC
TATCGCAGAGATGAATGGTGCAGTTGCTGTTCTGTTCACTTCCGACGCACTGCTGGTGGGTCGTACCATT
GAAGTGACTGGTGACATCTTCTATGAGAAGAAAGAGAAGACTTATTACATTGACACCTTCATGGCTGAGG
GTGCAATCCCTGACCGTTGGGAAGCAGTGTCTGTAGTTACCACTAAACGTGATGCAACTACTGGTGATGC
TGGAGGTCCTGGTGATGATCACGCAACCGTACTGGCTCGTGCACAGCGTAAGGCTGTATATGTCAAAACC
GAAGGTGCTGCGGCTGCATTCTCTGCTGCCCCAGCAGGTATCCAAGCGGAAGACCTTGTAGCGGCGGTAC
GTGCTGTAATGGCAAATGACATTAAGCCGACTGCAATGAAACCTACTGAGTAACACCTATGCCCTATCTA
CCTTGCGTAGGTAGGGTTCTTTTTGTTAGGAGGATTCATGCCTGTAATTAGACAAACCAGTAAATTAGGA
CATATGATGGAAGATGTGGCCTTCCAGATTATTGATAGTAAGCTGGAAGCGGTAAACTTGTGTATGCGAG
CTATTGGTCGTGAGGGTGTGGATTCCCTCGACTCAGGGGACTTGGACGCAGAAGATGCAAGCAAAATGAT
CGACATCGTATCCCAGCGGTTCCAGTACAACAAAGGAGGTGGCTGGTGGTTCAATCGTGAACCAAACTGG
CAACTTGCACCAGACACTAACGGTGAAGTTAATTTACCTAACAACTGCCTAGCAGTATTGCAGTGTTATG
CTTTAGGTGAAAAGAAAGTACCTATGACTATGCGAGCAGGTAAGCTCTACTCTACTTGGAGTCACACCTT
TGATATGCGTAAGCATGTTAATGCTAATGGTATGATTCGTCTTACCTTACTCACCTTACTACCCTACGAG
CATCTACCTACAAGTGTAATGCAGGCTATTGCCTATCAAGCTGCTGTAGAGTTTATTGTGTCTAAGGATG
CAGATCAGACTAAGCTAGCCACTGCGCAGCAGATAGCCACTCAGCTTCTTATGGATGTACAATCTGAGCA
AATGTCACAGAAGCGATTAAACATGCTGGTACATAACCCTACTCAGCGTCAGTTTGGTATCATGGCTGGT
GGCTCTCAGAATGTACCTGCTTACTCTCATTCACCTTATGAGAGTTGGGCGCTCCGTCCGTGGGAGGATC
GTTAATGGAAGTACAAGGTTCATTAGGTAGACAAATCCAAGGGATTAGCCAGCAGCCGCCAGCGGTACGC
TTGGATGGTCAGTGCACAGCTATGGTTAATATGATACCTGATGTAGTGAATGGTACTCAATCACGCATGG
GTACAACTCATATTGCAAAGATACTTGATGCGGGACTGATGACATGGCTACTCATCATTATCGCAGAGG
TGATGGTGATGAAGAGTATTTCTTCACGTTGAAGAAAGGACAAGTTCCTGAGATATTTGATAAGTATGGG
CGCAAATGTAATGTGACTTCACAAGATGCACCTATGACCTACCTCTCTGAGGTTGTTAATCCAAGGGAAG
ATGTGCAATTCATGACGATAGCTGATGTTACTTTCATGCTTAATCGTAGGAAAGTAGTTAAAGCTAGTAG
CAGGAAGTCACCTAAAGTTGGAAACAAAGCCATTGTGTTTTGTGCGTATGGTCAATATGGTACATCTTAT
TCCATTGTAATTAATGGGGCCAACGCTGCTAGTTTTAAAACACCGGATGGTGGAAGTGCAGACCATGTTG
AACAAATTCGAACTGAACGTATCACTTCTGAATTGTACTCTAAGTTGCAGCAATGGAGCGGTGTGAGTGA
CTATGAAATACAAAGAGACGGTACTAGTATATTTATCGAGAGACGGGATGGTGCTAGCTTTACAATAACA
ACCACCGATGGTGCAAAAGGTAAGGACTTAGTGGCTATCAAGAATAAAGTTAGCTCTACTGACCTACTCC
CTTCTCGTGCGCCTGCTGGTTATAAAGTACAAGTGTGGCCTACTGGCAGCAAACCTGAGTCTCGTTACTG
GCTGCAAGCTGAGCCTAAAGAGGGAAACCTTGTGTCTTGGAAAGAAACAATAGCTGCTGATGTATTACTT
GGGTTTGATAAAGGCACAATGCCTTACATTATTGAACGTACAGATATCATCAACGGCATAGCTCAATTCA
AGATAAGACAAGGTGATTGGGAAGATCGTAAAGTAGGGGATGACTTGACTAACCCTATGCCCTCTTTTAT
TGATGAGGAAGTACCCCAGACAATAGGTGGAATGTTCATGGTGCAGAACCGCCTATGCTTTACAGCAGGT
GAAGCGGTTATTGCTTCTCGTACATCATACTTCTTCGATTTCTTTCGTTATACGGTTATCTCTGCATTGG
CAACTGACCCCTTTGATATTTTCTCAGATGCTAGTGAAGTCTACCAGCTAAAACATGCAGTGACCTTAGA
```

Figure 1H

```
TGGCGCTACCGTGTTGTTCTCTGATAAGTCACAATTCATACTGCCAGGCGATAAGCCTTTAGAGAAGTCA
AATGCACTGCTTAAGCCTGTTACAACATTTGAAGTGAACAATAAAGTGAAGCCAGTAGTAACTGGTGAAT
CGGTAATGTTTGCCACTAATGATGGTTCTTACTCTGGTGTACGAGAGTTCTATACAGACTCTTATAGTGA
CACTAAGAAGGCACAAGCAATCACAAGTCATGTGAATAAACTCATCGAAGGTAACATTACCAACATGGCA
GCAAGCACCAATGTCAACAGGTTACTTGTCACTACCGATAAGTATCGTAACATAATCTACTGCTACGATT
GGTTATGGCAAGGAACAGACCGTGTACAATCAGCATGGCATGTATGGAAGTGGCCTATAGGTACAAAGGT
GCGAGGTATGTTTTATTCTGGTGAATTACTTTACCTGCTCCTTGAGCGAGGAGATGGCGTGTATCTGGAG
AAGATGGACATGGGTGATGCACTAACCTACGGTTTGAATGACCGCATCAGAATGGATAGGCAAGCAGAGT
TAGTCTTCAAGCATTTCAAAGCAGAAGATGAATGGGTATCTGAGCCGCTCCCTTGGGTTCCTACTAACCC
AGAACTTTTAGATTGCATCTTAATCGAGGGTTGGGATTCATATATTGGCGGCTCTTTCTTATTCAAGTAC
AACCCTAGTGACAATACTTTGTCTACAACCTTTGATATGTATGATGACAGCCATGTAAAAGCGAAGGTTA
TTGTTGGTCAGATTTACCCTCAAGAGTTTGAACCTACGCCTGTGGTTATCAGAGACAATCAAGACCGTGT
ATCCTACATTGATGTACCAGTTGTAGGATTGGTTCACCTTAATCTTGACATGTACCCCGATTTCTCCGTA
GAAGTTAAGAATGTGAAGAGTGGTAAAGTACGTAGAGTATTAGCGTCAAACCGTATAGGTGGTGCTCTCA
ATAATACAGTAGGCTATGTTGAACCGAGAGAAGGTGTCTTCAGATTTCCACTGAGAGCTAAGAGCACGGA
TGTTGTTTATCGTATTATTGTAGAGTCACCTCACACATTCCAGCTTCGTGATATTGAGTGGGAAGGGAGC
TACAATCCAACCAAAAGGAGGGTCTAATGGCTATAGGTTCAGCCGTTATGGCTGGTATGTCTTCTATTGG
TAGCATGTTTGCAGGCAGTGGTGCAGCAGCCGCTGCTGGAGGTGCTGCCGCAGGTGGCGGAGGTTTGCTA
GGTTCACTAGGTGGATTCCTAAGTGGCTCTACTGCTGGTTTCTCTAATGCTGGCCTTCTTGGTGCTGGCC
TTCAAGGGTTAGGCTTGATTGGTGATCTATTTGGTGGAAGTGATGAAGCCAAGGCGATGAAGAAAGCACA
AGAAGAGCAATGGCGGCAGCAGCTTATTGCTACACAAGAGGCGTACAAGACAGTGGCAGACGCAGAACGT
TCTGCTGCTAAACAATATCATGCAGATGCAATCAGTAATCAGGCTTCACTGCTACAGCAGCGAGCACAGG
TTGCATTACTTGCTGGGGCTACTGGTACTGGTGGTAATTCTGTGTCCTCTATGCTTAATGACTTAGCAGC
AGATGGCGGCAGGAACCAGAGTACTATCATTGATAACTATGAGAATCAGAAGATTAATTTCACCAACCAG
CTTAAGTCTATCCAACGTGGTGGTCAGATGCAGATGCGTGAGTTTAAGAAGCCTTCTGCTATGAATACCT
TGGTTAAAGGTATTCCAAGTCTGGCATCTGCCTATGTAACTGGTAGTAAGTCTGGCAAGGCATTGGGTAA
AGCCTTAACTGATTCTCGCACATATTCATCTGGAACAAGAGGTATTTAATGGCAATTGAGCGACAAGCAG
TACAAGGTCTGCCACAAGTGCAGGCACTTCTCCTAATGTCATGACCTTTGCACCTCAACAAGTGGGAGG
TGTGGAGGCTGGCGTGGCTTCTACCTCCGGTAGTAGGTTTATCGAAGACCTTATTCGTGCAGCAAGCAGC
GTGGCTGATGTTACCACTGGTATCCTTAATCAGAAGATTGAGGAAGATAAGGTTGTTCAAATGGAACGGG
CATATAACGGATTAATGCCTTCTGAGGATGCAACTCGTGGTGGCGCTCGTGCTAACATGCTTGTCAAAGC
TCAACTGCTAGCTAATGATGAAGCAGCACGAATGAAAGACATGGCTACTCGTTTCCAAGGAACGGATGAC
GAATGGACACAACTTATGGTTGACTCTCGTAATGAGATGCAGAATAAGCTGTTCCAGCAATACCCTGAGT
TGCAAGGTGACAAAGATACTATGCGTATGGTCACTAATGTCTTCCAAGAACAGCAGCCTCAGATTTGGGC
TACACGAACCCAGCATAAACTTGACCGTGAACAAGCAGACCGTGAGGATACCTTTGACGGGCGAGTGGCT
TCTACTTGGGATTCTAATATTGACCCTGAAGCCTCTGGCTATGCTTTACAGGAACGAATCCGCGAAGGTC
TTACTCAAGGATTACTACCTGAACAGATGTACAAGAAGTTAGTCCAGCGAGCAATTTCACTTGCACAAGG
CGGTGATGTTAGCATGGCTGAAAGCCCTGAAGTATGTGAAGGACGATAAGGGTGTTTCTGTTTATGCTAAG
AATCCACAGCTTATCACAGCCATCACTAGTGGTAATGCAGTTTGGGCTAGGAATAATGTAGCTGATGTAA
CTCGTATGTCTTTCGAAGTTAAAGAATCCTACCTTGCAGGTGATTTAACTGATGAAGAATTGTTGGAACG
AGCACAGCACATTAATAATCTGACAGGTAACTCTGTCTTCTCTAATCCAGAACTAGAGGCACTGATGCGC
CAACGGGCTAAGCAGAATGCAGAGCTAGGTGCAATGCAGGATATGCGACGTGAGCTTTACTCCGACCGCC
TGACTGGCTTCCAAGGTAAGACTGATAAAGAGAAGAAGGCTTACATTGATGTTATCAAACAGGATAGCCA
ACTTTATGCAGACCAGCAAATCAAACAACGTGGCTTGGACCCTTACAGTCAAGAGGCTGAAGCTATTCGT
GGTGCAGTGGAAGTGCAGCGCCTGCAATTCATGAACTCCAAAGGCTTAGTGGATGATACCTTTGAGTCTC
GTATCAAAGCCATGGAATCTATGCTATCGCCTGAGCACTTTGCCAAGGGCGAACCACAGGAGTTGATGAC
TATTCGCCAGTTGTGGGAACAGTTACCAGAAGAGAGCCGAGGTGTCTTTGGTGACACGGTGAATGGCTAC
ATGGATAACTACAACACTGCACTACAAATGGGAGAGACACCTTTGCAGGCTGCAAGGTTTGCGCGTAAAG
CACAGCAGAAATTCTCTCGTACTGAGAAGGAAACCAAGAAGTTCAACTCAGCTATTGGAGATGCACTGGA
TGAGGTATCTGGTGCTGGCTGGTTTGATGGTAAAACCGAAGTGTCAGACTTAGGTAAAGCTATTGCGGAA
GAAGAGTTACGAGCTAAGGCCAATATGTTGTGGTCTAGTGGTATGCGTAACATGGATTCCATCAAGAAGG
CTTTAATTACTTGGGGCAATAAACGCTACACTCAATCAGAGGATGCAAAGACTTCCGGTGGCTATTTCAT
TAAAGGTGATTACACTTCTGCATCTGATATGCTTATGTCAGTTGGGAAAGGCGTAAACCCTACCGATGTA
CCTCTGGCGCTTGGTAGGTATGTAGAAACACAGATGCCAGAATTGAAGAAGGAGCTTCAAGAGGGGGAAA
```

Figure 1I

```
CTAAAGATGATATATACATTGATTACAATGAACAGAAAGGTACTTTCGTGATTCGTGCTGGTGCAGCAGG
TCGCCCTCTTTCTGGAGTAATCCCTGTAACCTCTTTAGATACCACTTCACTACTAGATTCTGCCTATCAG
AAGAAAGTAGAGGAACGAGATAAAGGCGAGTATGTTCACCCGTATCGTACAGATATTGGTGCACAAGAGC
CTATGCCAGCTAAACCAACTGCCAAAGATATTGGTAAATTTGGACTAGCTAACTTCCTCATGTCTTCTGC
TTTTGCTTCTGGTGAGAATCTGCCTTCTAACTTCGAGATTAACTATCGAGGTAATATGCAACAATTCTAT
GACAAGCTAGCTATGGATGAGAATAAAGATAAAGTTGGCTTTAATAAGGCAACTGGAACCTTTACTCCAT
ATAAAGACGCTCACGGTGAGTCTATCGGTTACGGTCATTTCTTAACGGAAGAAGAGAAGCGAAACGGGTA
TATTAAGATTGGCGATGAACTAGTTCCCTATCGAGGGTCTATGTCTCAGCTTACAGAGAGCAAGGCTCGC
GCTCTTATGGAGCAAGATGCTAAGAAGCATGTGCCTCCTACTCGTGACTGGAAGATTCCGTTTGACCAGA
TGCACCCTGCACAGCAACGTGGCTTGATGGATTTAAGCTACAATTTAGGTAAAGGTGGAATCCAGAACTC
ACCGCGTGCTCTTGCTGCATTCAAAGCTGGTAAGCTTACGGAGGGCTTATCGAAATGCTGGGCACTGCA
TCAAGTGAAGGTAAGCGTATTCCTGGCCTACTGAAGCGACGCGCTGAGGCATACAATATGGCATCTGCTG
GTGGTGTGCCTAAGATTACCGAAGTGGAGACTCGTGAAGATGGCTCCATGTGGGTTAGGTTTGGTGGACC
TATGCCAGCAGGTTCTGTCTCGGCATGGACTCATAAACGTATTGGCGCGGATGGTTGGTATCAGGTTTAT
GAGGCTGCACCTACCAAGTTAGCTAAAGATTCTAAGGTAGGTAAAGTTAAGTTGTAGTACCTAACTCAAG
GCTTGTCTCACATGTGAGACAGGTCTTTATGATAGGCACTATGGAGGAATTATGGAACAAGACATTAAGA
CTAATTGGGCTGGATATGTCCAGTCTACTCCTGAGCCGTTTTCTATTGAGGCGGCTCCGGTATCGGCTCC
TACGATACGCCAGCGTAATGAGTTACAAGAGCAAGTTCTTGAAGCTAAAGCTGACGCTGATATCTTAGGT
GCTGTAGGTGCTGCCTTCCAGAATGAGTGGTTGGCATTCGGAGGCAAGCGGTGGTATGACCGTGCCACTG
CTGATTTCACACCTCAACCAGACTTTGAGATACAACCTGAGCAACGTGAAGCACTACGTTTCAAATATGG
TACGGATATGATGCAGACAATCACTGAGGGTGTTCGTTCTGAGGATGAATTGAACTTCCGTATTCAGAAT
GCGGATGAAGACCTTGAGCGCAATAAGCGCATTGCTCAGGCTGGCTGGGTTGGCTCTGTGGCGACGATTG
GCGCTGCTGTGCTTGACCCTGTGGGATGGGTTGCCTCTATTCCAACCGGTGGTGCCGCTAAAGTTGGACT
CGTAGGCCGTGCTGTGCGTGGCGCTATCGCCGCTGGCGTGAGTAATGCCGCTATTGAATCCGTATTGGTC
CAAGGTGACATGACTCGTGATTTAGATGACATTATGGTAGCACTGGGTTCCGGTATGGCTATGGGTGGCG
TTATTGGCGCTGTAGCGCGTGGTAGGGCCACTAAGCTCAGTGAGCAAGGTGATGACAGGGCTGCTAGCAT
TGTGCGCAGTGCAGACGCAGGGGACCGCTATGTTCGTGCTGTTGCCGATGACAGTATCGGTGCGATGCGT
GTTAAGGGCGCAGAGGTTCTCACTGAGGGTGTATTCGATATCTCCAGTAAGAGTGAAGACCTACTGAAAA
CCTTGCAACGAGAAGGTAATGCGATTGATATGACACCTCGCCGTTGGGCTGGAACTATGTCTGCCCTCGG
TACTGTCGTGCACTCATCTAAAGATGCAAGTATCCGAGGCCTTGGTGCTCGTCTGTTTGAATCCCCACAA
GGTCTAGGTATGCAGAAGGCATCTGCTAGTCTTATGCAGAATACTAACTTAAATCGCCTGAAATCTGCTG
ATATGAACCGCTTCAATGATGGGTTTGATTTGTGGCTTAAAGAGAATAATATCAATCCAGTAGCAGGGCA
TACCAACTCTCATTATGTACAGCAATACAATGAAAAGGTGTGGGAGGCAGTGCGTATTGGCATGGATGAG
TCTACACCTAAATCTATCCGCATGGCTGCTGAGGGACAACAGGCTATGTACAGAGAGGCGCTGGCTTTAC
GTCAACGTTCTGGTGAAGCGGGATTTGAAAAGGTAAAAGCCGACAACAAATATATGCCTGATATCTTTGA
TAGTATGAAAGCCAGACGTCAATTCGATATGCACGATAAAGAAGACATCATCGAACTTTTCTCTCGTGCC
TACCAGAATGGCGCTCGTAAGATTCCAAAGGAAGCAGCAGATGAGATTGCACGAGCACAGGTAAATCGCG
TTGCTGATGCTACCTTAACTGGAAAGCTTAGTTTTGAAAAGGCAATGTCAGGTCAGACTAAGGCAGAGTA
TGAAGCTATCATGCGTAAGGCAGGCTTCAGTGATGAAGAAATTGAAAAGATGATAGAAGCTCTGGATAAC
AAAGAAACCAGAGATAACATCTCTAACCGAGCTAAAATGAGTTTAGGATTAGATGTTACTCAAGAATACA
ATGGCATTCGTATGCGTGACTTCATGAATACCAACGTGGAAGAGCTAACAGATAACTATATGAAGGAAGC
AGCAGGTGGCGCTGCATTGGCTCGCCAAGGCTTCTCTACCTATCAGGCTGCACTTAATGCAATTGACCTT
GTAGAGCGAAATGCACGAAACGCGGCTAAGGATAGCAAGGCTAGTTTGGCATTAGATGAAGAGATTCGTC
AGATGCGAGAAGGTCTTCGCCTGATTATGGGCAAGTCGATTGATGCAGACCCACAGGCTATATCTACTAA
GATGATGCGTCGTGGTCGTGATATCACAGGTGTGCTTCGCTTAGGTCAAATGGGCTTCGCACAGCTAGGT
GAACTTGCCAACTTTATGGGTGAATTTGGTATTGCTGCAACTACTATGGCTTTAGGTAAGCAATTCCGCT
TCACCTCTAAGGCGTTGCGTAATGGCGATGGCTTCTTCCGAGATAAGAACTTAGCTGAGGTTGAGAGAAT
GGTGGGGTACATTGGTGAGGATAACTGGCTAACAACTAAGGGTGCACGTCCTGATGAATTTGGTGATGTA
ACCACAGTAAGAGGGATGATGGCTCACTTTGACCAATCCATGAACTCAATACGTCGTGCTCAAACCAACC
TATCACTCTTCCGCATGGCACAGGGTTCTCTGGAGCGAATGACTAATAGGCAAATAGCTTTGTCTTTCAT
TGACCACCTTGAAGGCAAGAAGATTATTCCTCAGAAGAAACTGGAGGAACTTGGTCTTACTCAGGAGTTC
ATGACTAACCTACAGAAGCACTATGATGCTAACTCTAAAGGTTCTGGCTTGCTTGGCTTTGATACAATGC
CTTATGCCATGGGTGAAACTTTAGCTAATGCTATTCGTCGTAAGTCAGGTCTAATCATCCAACGTAACTT
CATTGGTGATGAAGGTATCTGGATGAACAAAGCACTAGGTAAGACATTTGCACAGCTTAAGTCATTCTCT
```

Figure 1J

```
CTTGTATCTGGTGAGAAGCAATTTGGTCGAGGGATTCGCCACGATAAAATTGGTCTTGCTAAGAAGACAG
CTTACGGGTTTGCTTTGGGTTCAATAGTGTATGCGGCAAAAGCCTATGTGAACTCTATTGGGCGAGAAGA
CCAAGATGAATATTTGGAAGAGAAGTTATCGCCTAAAGGGTTGGCCTTTGGTGCAATGGGTATGATGAGT
ACAACTGCTGTATTTAGTCTAGGTGGAGATTTCTTAGGTGGCCTAGGTGTTCTACCTTCCGAACTCATTC
AATCACGCTATGAAGCAGGTTTCCAAAGTAAGGGTCTGATTGACCAAATACCTCTGGTTGGCGTTGGTGC
AGATGCAGTAAATCTGGCTAACTCAATCAAGAAGTATGCAGAAGGTGACACAGAAGGTGTAGATATCGCT
AAGCGAGCACTCCGTCTTGTGCCACTTACCAATATAATAGGTGTCCAAAACGCATTGCGTTATGGCTTAG
ATGAACTGGAGGATTGATGAGTTATACTTTCACAGAACATACAGCCAATGGTACGCAAGTCACCTATCCT
TTTAGCTTTGCTGGTAGGGATAAAGGTTATCTTCGTGCCTCAGATGTGATAGTGGAGTCTCTTCAAGGTA
ACACTTGGATTGAAGTTACATCTGGCTGGCAACTAACTGGCACGCACCAGATTACTTTTGATGTAGCACC
AGTTGCAGGTTTGAAGTTCCGTATTCGAAGGGAAGTACAAAAAGAATATCCATACGCTGAGTTTGACCGT
GGTGTTACCTTGGATATGAAGTCTTTAAATGGTTCTTTCATTCATATACTGGAGATTACACAGGAGTTAC
TTGACGGGTTTTATCCAGAAGGATACTTCATTAAACAGAATGTAAGCTGGGGCGGCAATAAGATTACTGA
TTTGGCTGATGGCACAAATCCGGGAGATGCAGTAAATAAAGGGCAGCTTGATGCCATCGACAAGAAGCAT
ACAGATTGGAACGCCAAACAGGACATTGAGATTGCTGGCCTTAAGGCTGGTATGACTTCTGGTATTGCGC
ACAGAACTGTTCCTTGGTACACGATAGCCCAAGGTGGTGAGATTTCCGTAAAACCACCTTATGAATTTCA
AGATGCACTAGTTTTCCTTAATGGGGTATTGCAGCACCAAATTGTAGGCGCATACTCTATAAGCAACAAC
ACTATCACTTTCGCAGAGCCGCTTGTGGCTGGTACAGAGGTGTATGTGCTGATTGGTAGTCGTGTGGCTA
CATCTGAACCTAATATTCAGTTGGAGTTGAACTTTGACTTAGTAGAAGGCCAACAAGTAGTACAGATTGG
CTCTGCATTTAAGTACATTGAGGTCTACCTTGATGGATTATTACAACCTAAACTTGCTTATCAGGTAGAC
GGTGACATTGTTACTTTCTCAGAAAGAGTACCAGAATGCCGGATGACTGCTAAGATTATCACAGCATAAG
GAGGTGGGATGATTAACTCCGAACTGGTAGATAGTGGTGTGAAGCTTGCGCCACCTGCACTCATATCAGG
TGGGTACTTCCTCGGTATCAGTTGGGATAATTGGGTGTTAATAGCAACATTCATTTATACCGTGTTGCAA
ATTGGGGACTGGTTTTATAATAAGTTCAAGATTTGGAGGGAGAAGCGTGAGCGTACACAATAAACATGCA
GCTACAGAGGACGAGGTTGGCATTCTGCATGGTGCTATTACCAAAATCTTCAATAAGAAAGCACAGGCAA
TACTGGACACTATAGAAGAAGACCCTGATGCAGCATTACATTTAGTGTCTGGTAAGGATATTGGTGCGAT
GTGTAAGTGGGTTCTTGATAACGGCATTACCGCCACACCTGCTGCACAGCAGGAAGAGTCCAAGTTATCT
AAGCGCCTCAAGGCTATCCGAGAGGCATCCAGTGGTAAGATAATTCAATTCACTAAGGAGGATTGATGGC
TAAGGCAAGAGAATCACAAGCGGAGGCTCTTGCCAGATGGGAGATGCTACAGGAGTTACAGCAGACCTTT
CCTTACACCGCGGAAGGTTTGCTTCTCTTTGCAGATACAGTTATTCATAACTTAATTGCAGGCAACCCTC
ATCTGATTCGTATGCAGGCGGATATCTTGAAGTTCCTATTTTACGGACACAAGTACCGCCTCATCGAAGC
GCCTCGTGGTATCGCTAAGACAACACTATCAGCAATCTATACGGTATTCCGTATTATTCATGAACCGCAT
AAGCGTATCATGGTTGTGTCCCAAAACGCCAAGCGAGCAGAGGAAATCGCAGGTTGGGTAGTTAAAATCT
TCCGTGGCTTAGACTTTCTTGAGTTTATGCTGCCGGATATCTACGCTGGGGACCGTGCATCCGTTAAGGC
GTTTGAGATTCATTACACCCTACGTGGTAGTGATAAGTCTCCTTCTGTATCCTGTTACTCAATCGAAGCA
GGTATGCAGGGTGCTCGTGCTGATATTATTCTAGCGGATGACGTAGAGTCGATGCAGAATGCTCGTACGG
CAGCGGGCCGTGCCTTGCTTGAGGAGCTGACTAAGGAGTTTGAATCTATCAACCAGTTTGGGGATATCAT
TTACCTTGGTACACCTCAGAACGTAAACTCTATCTACAACAACCTACCTGCTCGTGGTTACTCTGTTCGT
ATCTGGACTGCGCGTTACCCTTCAGTAGAGCAAGAGCAATGTTATGGCGACTTCCTTGCACCTATGATTG
TTCAAGATATGAAGGACAACCCAGCACTTCGCTCAGGGTACGGGTTGGATGGTAATAGTGGTGCACCTTG
TGCCCCTGAAATGTATGATGATGAAGTCCTGATTGAGAAGGAAATCTCTCAGGGTGCTGCTAAGTTCCAG
CTTCAGTTCATGCTTAACACTCGCATGATGGATGCTGACAGATACCCATTACGCCTGAACAATCTAATCT
TCACCTCGTTTGGTACAGAGGAAGTCCCTGTGATGCCTACGTGGAGTAATGATTCCATAAACATCATTGG
TGATGCACCTAAGTATGGTAACAAGCCTACGGATTTCATGTACAGACCTGTAGCTCGCCCATATGAATGG
GGTGCTGTCTCCCGCAAGATTATGTATATTGACCCTGCGGGTGGTGGTAAGAACGGAGATGAGACGGGTG
TAGCCATCGTATTCCTGCACGGCACATTCATTTATGTGTATCAGTGCTTTGGTGTACCTGGCGGATACCG
AGAGTCGTCCCTGAATCGCATTGTGCAGGCCGCAAAGCAGGCGGGTGTTAAAGAGGTATTCATTGAGAAG
AACTTTGGTCATGGCGCGTTTGAGGCGGTAATTAAGCCGTACTTTGAACGAGAGTGGCCTGTAACTCTGG
AAGAGGATTACGCCACCGGACAGAAAGAGTTGCGTATCATTGAGACGCTGGAGCCGCTCATGGCAGCCCA
TAGGCTTATCTTCAATGCAGAGATGGTGAAGTCAGACTTTGAGTCGGTACAGCACTATCCGCTTGAACTA
CGCATGTCCTACAGTCTTTTCAATCAAATGTCGAACATAACGATTGAGAAGAACAGCCTCCGGCACGATG
ACCGCCTAGACGCCCTGTATGGCGCTATACGGCAATTAACTTCTCAGATAGACTATGACGAGGTTACACG
GATTAATCGCCTCAGAGCGCAGGAGATGCGCGATTACATCCATGCTATGAACACACCTCATCTACGCAGG
GCAATGCTATATGGAGATTACGGTACTGAGCGAAGAGTGACCAACACTTCCGTAGCGATGCAGCAGCGAG
```

Figure 1K

```
TTTACGGGCAGAACTACCGAAATAAATCGGCAAGCAGAAATACACTTTCTGCAAGGATTTCAAGGACTTA
TTAATTACTGGACACTATAGAAGGAAGGCCCAGATAATAAGAGAAAATAATAGGTAATATATATATAGGT
TAACCTAGGTTATATAGGTATGCCTTAGTATGGGTGTACTCCTGTACACCCTATTCCTTACTACCTTACT
ATATTTACATAATAGGAGAGAGACAATGGCTAATGATTATAGTAGTCAACCATTAACAGGTAAGTCTAAG
AGAAAGCAGGTACAACCTGTAAGTGAAGAACTAATGCTTCCGGTGCTCAAAAAGAGGAAGTTAGTAAGA
AAAGCAATGTTATTAATGATGCCACCAAATCAGGTAAACAGAAAGGGGCCATGGTGTGCCTTGAAGTGAA
AGGTGGTGTATTGAAGATTGCTATCGCGGTTGATGGCAAAGAAGATTCAGAGTGGAAGTTAGTAACAGTG
GAACCAACTGTTAACCCAGTTTAAGATAAGGAGGAAGATTACATGGCTAAATATGGTACTACAGGTTCTG
TTACTGGTCAGGCTTTTCGAGTAAAAGCAGTACAAACTATTGCAACGGCAATCCCGATGCCTGTTGTTAA
AGAAGAAGACCTTAAGAGTAAAGACCACCCTATCAACATCAAACATTTATCAGGTAAACAGAAAGGTGCA
ATGGTTGCTCTTGAGAAAGGTGACACAACCTTACATATTGCTGTTGCACGTGGTAGTGAACCCACAGACC
CTTGGGATGTAACTGGTATGGAAAAGGACGCTGTTACTCCAGCAGGGGTATAATAATGCTTAATAAATAC
TTCAAGCGTAAAGAGTTTGCTTGCCGTTGTGGGTGCGGTACATCCACTGTTGATGCTGAATTACTACAGG
TAGTCACAGATGTGCGTGAGCACTTTGGTTCTCCTGTAGTTATCACTTCGGGTCATCGCTGTGCTAAGCA
CAATGCCAATGTAGGTGGCGCTAAGAACTCCATGCATCTTACTGGTAAGGCTGCTGACATTAAAGTGTCT
GGCATATTACCTTCTGAAGTGCATAAGTATCTTACTAGCAAATACCAAGGCAAGTATGGTATAGGTAAGT
ATAACTCCTTCACTCACATCGATGTACGGGATGGTTGTGCGCGATGGTAAGATGTGTTGAATGGTGTGAG
CGTATGGTTGCCCAAGCTGCCGAGGATGGCAACTATGATGACTGGAAGAACTACTCTGACTTGTTAGCTC
AATGGAAAGGGAGATGCAATGAAAAAGCTGTTTAAGTCTAAGAAGGTTGTAGGTGCACTGGTTGCACTTG
TTATTGCTCTTGTTTCTGTAGGTCTTGGTGTAGACCTTGGCTCTGGCACGGAATCCTCTGTGACAGATGT
GGTCTGCCAAGTGATCACCTGTGAATAAGTTTCTAGAAGTTCTGGCAGGTCTTATTGGCCTGCTTGTCTC
TGCTAAGAAGAAACAAGAAGAGAAGGAGGCACAAAGTGAAGCGAATCATGTTAGTGACAACCCTTCTGAT
TGGTTCGCTGACCACTTCCGGGTGTCAGCAGGCGTTACCAGAGAAAGCAATGGTGAAACCTCTGAGGCCG
ACGCTGACGGCAGTTTACGAGGTAGACGATAAGGTCTGCTTTAGTAAGCCTGACGCTACAAAACTTGGTT
TGTACATTCTCTCGCTAGAACGCGGATACAATTAATACATAGCTTTATGTATCAGTGTCTTACGATTTAC
TGGACACTATAGAAGAGGTAAGATAGCGCCGTTCTTTTGAGCGGCCTATTACTAGCCAATCTTCATAGGG
AGGGTTGGAAAGTAATAGGAGATAGCATGGCTAAATTAACCAAACCTAATACTGAAGGAATCTTGCATAA
AGGACAATCTTTGTATGAGTACCTTGATGCGAGAGTTTTAACATCAAAGCCGTTTGGTGCTGCAGGTGAC
GCCACTACTGATGATACGGAGGTTATAGCTGCTTCATTAAACTCTCAGAAAGCTGTCACAGTCTCAGATG
GTGTATTCTCTAGCTCTGGTATTAACAGTAATTACTGTAACTTAGACGGCAGGGGTAGTGGCGTGCTAAG
TCACCGTTCAAGTACAGGTAACTACTTAGTATTTAACAATCTACGTGCAGGTCGCTTAAGTAATATTACG
GTAGAAAGTAATAAGGCGACTGATACAACTCAGGGACAGCAGGTATCCCTTGCTGGTGGAAGTGATGTTA
CTGTAAGTGACGTTAACTTCTCAAACGTTAAAGGTACTGGTTTCAGTTTAATCGCATACCCTAATGATGC
GCCACCTGATGGACTTATGATTAAAGGCATTCGAGGTAGCTATTCCGGCTATGCTACTAATAAGGCAGCC
GGATGCGTACTTGCTGATTCCTCAGTTAACTCCCTCATAGATAACGTCATTGCTAAGAACTACCCTCAGT
TCGGAGCAGTAGAGTTGAAAGGTACAGCCAGTTACAACATAGTCAGTAATGTTATAGGGACAGATTGCCA
GCATGTAACTTACAACGGCACTGAAGGGCCAATAGCTCCTTCTAATAACCTTATCAAGGGGGTGATGGCT
AATAACCCTAAGTATGCAGCGGTTGTTGCAGGCAAAGGAAGTACGAACTTAATCTCAGACGTGCTCGTAG
ATTACTCAACTTCTGATGCTAGGCAGGCTCATGGTGTTACAGTAGAGGGTTCTGATAACGTCATAAATAA
TGTGCTTATGTCAGGATGTGATGGTACTAACTCTTTAGGACAAGGGCAGACTGCTACAATTGCACGCTTT
ATAGGTACAGCTAATAACAACTATGCGTCTGTATTTCCTAGCTACAGTGCTACAGGTGTTATTACTTTCG
AATCCGGCTCTACCCGTAACTTCGTAGAGGTAAAGCACCCTGGCAGGAGAAACGACCTTCTCAGTTCTGC
TAGTACTATTGACGGTGCAGCTACTATTGACGGCACTAGTAATAGTAACGTAGTGCACGCACCTGCCTTA
GGGCAGTACATAGGTAGTATGTCAGGTAGGTTCGAATGGCGGATTAAGTCCATGTCACTCCCTTCAGGCG
TTCTTACTTCTGCTGATAAGTACAGAATGCTTGGAGATGGTGCTGTGTCATTAGCTGTAGGTGGGGCAC
TTCTTCTCAAGTTCGCCTATTTACTTCTGATGGTACTTCTCGGACAGTGTCCCTCACCAACGGTAACGTG
CGTCTTTCTACCAGTAGCACAGGCTTTTTGCAGTTAGGTGCTGATGCAATGACCCCAGACAGTACTGGTA
CATACGCATTAGGTTCCGCCAGCCGAGCATGGTCTGGCGGTTTTACTCAAGCAGCATTCACTGTTACCTC
AGATGCTCGGTGTAAAACAGAACCTCTTACTATCTCAGATGCCTTACTGGATGCTTGGTCTGAAGTTGAC
TTTGTGCAGTTTCAGTATTTGGATCGTGTTGAGGAGAAGGGTGCAGACTCAGCTAGATGGCACTTCGGTA
TCATCGCTCAGCGAGCTAAGGAGGCTTTCGAACGTCACGGTATAGATGCACATCGCTATGGCTTCTTGTG
CTTCGACAGTTGGGATGATGTATACGAGGAAGATGCCAATGGCTCTCGTAAACTGATTACACCAGCAGGT
TCCCGCTACGGTATTCGTTACGAGGAAGTACTGATATTAGAGGCTGCGTTGATGCGGCGGACTATTAAGC
GTATGCAGGAAGCACTAGCTTCCCTGCCTAAGTAAGCAACAGGCAGTGCGTAAGCACTGCTTTTAGCGCA
```

Figure 1L

```
ACTTTTCTTAAAGGTTATCACGGTGGTAGCCTTTCAGAAAAGGAGGTTACATGATTCAAAGACTAGGTTC
TTCATTAGTTAAATTCAAGAGTAAAATAGCAGGTGCAATCTGGCGTAACTTGGATGACAAGCTCACCGAG
GTTGTATCGCTTAAAGATTTTGGAGCCAAAGGTGATGGTAAGACAAACGACCAAGATGCAGTAAATGCAG
CGATGGCTTCAGGTAAGAGAATTGACGGTGCTGGTGCTACTTACAAAGTATCATCTTTACCTGATATGGA
GCGATTCTATAACACCCGCTTCGTATGGGAACGTTTAGCAGGTCAACCTCTTTACTATGTGAGTAAAGGT
TTTATCAATGGTGAACTATATAAAATCACGGATAACCCTTATTACAATGCTTGGCCTCAAGACAAAGCGT
TTGTATATGAGAACGTGATATATGCACCTTACATGGGTAGTGACCGTCATGGTGTTAGTCGTCTGCATGT
ATCATGGGTTAAGTCTGGTGACGATGGTCAAACATGGTCTACTCCAGAGTGGTTAACTGATCTGCATCCA
GATTACCCTACAGTGAACTATCATTGTATGAGTATGGGTGTATGTCGCAACCGTCTGTTTGCCATGATTG
AAACACGTACTTTAGCCAAGAACAAACTAACCAATTGTGCATTGTGGATCGCCCTATGTCTCGTAGTCT
GCATCTTACTGGTGGTATCACTAAGGCTGCAAATCAGCAATATGCAACAATACATGTACCAGATCACGGA
CTATTCGTGGGCGATTTTGTTAACTTCTCTAATTCTGCGGTAACAGGTGTATCAGGTGATATGACTGTTG
CAACGGTAATAGATAAGGACAACTTCACGGTTCTTACACCTAACCAGCAGACTTCAGATTTGAATAACGC
TGGAAAGAGTTGGCACATGGGTACTTCTTTCCATAAGTCTCCATGGCGTAAGACAGATCTTGGTCTAATC
CCTAGTGTCACAGAGGTGCATAGCTTTGCTACTATTGATAACAATGGCTTTGTTATGGGCTATCATCAAG
GTGATGTAGCTCCACGAGAAGTTGGTCTTTTCTACTTCCCTGATGCTTTCAATAGCCCATCTAATTATGT
TCGTCGTCAGATACCATCTGAGTATGAACCAGATGCGTCAGAGCCATGCATCAAGTACTATGACGGTGTA
TTATACCTTATCACTCGTGGCACTCTTGGTGACAGACTTGGAAGCTCTTTGCATCGTAGTAGAGATATAG
GTCAGACTTGGGAGTCACTGAGATTTCCACATAATGTTCATCATACTACCCTACCTTTTGCTAAAGTAGG
AGATGACCTTATTATGTTTGGTTCAGAACGTGCAGAAAATGAATGGGAAGCAGGTGCACCAGATGATCGT
TACAAGGCATCTTATCCTCGTACCTTCTATGCACGATTGAATGTAAACAATTGGAATGCAGATGATATTG
AATGGGTTAACATCACAGACCAAATCTATCAAGGTGACATTGTGAACTCTAGTGTAGGTGTAGGTTCGGT
AGTAGTTAAAGACAGCTACATTTACTATATCTTTGGTGGCGAAAACCATTTCAACCCAATGACTTATGGT
GACAACAAAGGTAAAGACCCATTTAAAGGTCATGGACACCCTACTGATATATACTGCTATAAGATGCAGA
TTGCAAATGACAATCGTGTATCTCGTAAGTTTACATATGGTGCAACTCCGGGTCAAGCTATACCTACTTT
CATGGGTACTGATGGAATACGAAATATCCCTGCACCTTTGTATTTCTCAGATAACATTGTTACAGAGGAT
ACTAAAGTTGGACACTTAACACTTAAAGCAAGCACAAGTTCCAATATACGATCTGAAGTGCAGATGGAAG
GTGAATATGGCTTTATTGGCAAGTCTGTTCCAAAGGACAACCCAACTGGTCAACGTTTGATTATTTGTGG
TGGAGAAGAGACTTCGTCCTCTTCAGGTGCACAGATAACTTTGCACGGCTCTAATTCAAGTAAGGCTAAT
CGTATCACTTATAACGGAAATGAGCACCTATTCCAAGGTGCACCAATCATGCCTGCTGTAGATAACCAGT
TTGCTGCTGGTGGACCTAGTAACCGATTCACTACCATCTACCTAGGTAGTGACCCTGTTACAACTTCAGA
TGCTGACCACAAGTACAGTATCTCTAGTATTAATACCAAGGTGTTAAAGGCTTGGAGCAGGGTTGGTTTT
AAACAGTATGGTTTGAATAGTGAAGCAGAGAGGGACCTTGATAGCATACACTTCGGTGTCTTGGCTCAGG
ATATTGTAGCTGCTTTTGAAGCTGAAGGGTTGGATGCCATTAAGTATGGAATTGTGTCCTTCGAAGAAGG
TAGGTACGGTGTGAGGTATAGTGAAGTTCTAATACTAGAGGCTGCTTATACTCGTTATCGTTTAGACAAG
TTAGAGGAGATGTATGCCACTAATAAAATCAGTTAAGCAAGCTGCTGTACTCCAGAACACAGAAGAGCTT
ATTCAATCAGGACGTGACCCTAAGCAGGCTTATGCCATTGCCAAGGATGTTCAACGTCGTGCCATGAAGA
AACCTTCTGCATCTTCTGCGTAAGCAGGTTAATATCTTAGTATAAACAAGGGCAGACTTAGGTTTGTCCT
TAGTGTATTCCAAAGGAGGTAACATGCTGAAAGATGGTTGGGTTTCATATGACCCTACAGACCCTAAGAA
TTGGCTACAGGTTATCGCTATAGCTTGTGCAGGTAGCCTATTGGCTGCCCTGATGTATTCATTATGGATG
TACACAAAGTAACCAAAGTCAAAATTTTGATGTAGGCGTGTGTCAGCTCTCTCGCCCTCGCCCTCGCCGG
GTTGTCCCCATAGGGTGGCCTGAGGGAATCCGTCTTCGACGGGCAGGGCTGATGTACTCCTTGTCTAGTA
CAAGGGAGGCGGAGGGAACGCCTAGGGAGGCCTAGGAATGGCTTAGTGGTGGACAAGGTGATTACCTTAG
TGAAGCCTCTTAGTGCATTCCTGAGGCCATTCAGGGCGTTTATGAGGGATTGACAGGGTGTGAGGGCGTG
GGCTA
```

Figure 2

>K1-5 site sgRNAs 86+89 donor template (homologous recombination substrate) (SEQ ID NO:2)
TGACAGCCACGGCATACAAGGTTACATTAAGCATCAAGACGGCGACGTCTTTAAACATCCCGCTCTTTAACAATAC
GGTTTGTGTCTTGATAGGCTAACTAACTAACTAAGGTAATTATCATGAAAGGGTTAATTTGTGTAGAACGTATGGT
CAATGGTAAACTTGAAATATTACCACTGGAAAACCAATCTAGCTTCAAAGAGTGGTATGGCTGTTTCTCACTGATTT
AAGGTAAAGGCTGGCACTAGTCAGCCTATCAAGGCGCAAACCAAGCTCTTTAACAATTTGGATGGTAGCTTCTTAG
TCTGGATAGGTTAAACCTAGGAGATTCTCTTGAGTCTCCTATAATGTAACCTAACTAACTAAATGAGGATTAAAAG
AGGAGATATACAATGGTTTTTACGCTTGAGGACTTCGTTGGTGACTGGCGTCAAACCGCGGGGTATAATCTTGATC
AGGTCCTGGAGCAGGGCGGAGTTTCGTCCTTATTCCAGAACTTAGGGGTAAGTGTTACGCCGATTCAGCGCATCG
TGCTGAGTGGAGAGAATGGATTGAAAATTGACATTCACGTTATCATTCCGTATGAGGGTTTGAGTGGAGACCAGA
TGGGACAGATTGAAAAGATTTTCAAAGTGGTGTATCCCGTCGATGACCATCACTTTAAAGTAATTCTGCACTATGG
GACCCTTGTGATCGACGGTGTAACGCCAAACATGATTGACTATTTCGGTCGCCCTTACGAAGGTATCGCCGTCTTC
GACGGAAAAAAAATCACTGTCACGGGAACATTATGGAACGGAAATAAAATTATCGACGAACGTCTGATCAATCCT
GATGGAAGCCTGTTATTTCGCGTTACGATCAATGGAGTGACCGGATGGCGTTTATGCGAACGTATTTTGGCTTAAA
GAGGAGATATACAATGGAACGCAACGCAAATGCATATTATAATTTATTAGCAGCTACGGTTGAAGCCTTTAATGAA
CGCATCCAATTCGACGAAATCCGTGAGGGCGACGACTATAGCGACGCCCTTCATGAGGTTGTAGACAGCAATGTT
CCAGTTTATTACAGCGAAATCTTTACAGTGATGGCTGCTGATGGTATTGATGTTGATTTTGAGGATGCTGGTTTGAT
TCCTGACACGAAGGATGTAACCAAGATTCTACAAGCTCGCATCTATGAAGCTCTTTATAATGATGTACCAAATGAC
AGCGATGTAGTTTGGTGTGAAGGCGAAGAAGAGGAAGAATAAGGATGGAAAAGCAATATAACTTTATCTTTTCAG
ACGGTGTAACCCTGAAGTGT

Figure 3

K1-5 site sgRNAs 1112+1122 donor template (homologous recombination substrate) (SEQ ID NO: 3)

ACGTCCAGCCTCCTTCCTAGATATTCCTGAGATTATAAACCTTGGGAATAAATATGTGGAAGAGGAAGTCAAGGTT
GTAGCCCACCACTCAGCCTCATGGAATGCAGAACAAAGTGCCATAACCTTTGTGCATCTCTTAATAGAGACCCACC
ACTCAGCCTCATGGAATGCAGAACAAAGTGCACATAACCTTTGTGCATCTCTTAGTAGAGAAGATTTATCCCTATG
GGTTGCTGTAGATGAAGGGCAGATTGTAGGGTTCCTGTGGGCTGGCTATCACGAGTTGGCCCCTTGGACACCTGT
AAGAGTTGCCTCTGACATTCTCTTTTATATTATACCAGAGAGAAGGGGAACACTACTTGGTATGCGCTTAATTAAG
GCATTGAAACAGTGGGCATCAGATAATGAATGCTCTGAAGTGCGTTTAAGTATTGCAAGTGGCATCAACGAGGAG
CGCGTAGGGCGCATGTACAAACGGCTCGGCTTTGAACCGTTTGGCACTGTGTATAACCTGAAGTTCTAAAGAGGA
GATATACAATGGTTTTTACGCTTGAGGACTTCGTTGGTGACTGGCGTCAAACCGCGGGTATAATCTTGATCAGGT
CCTGGAGCAGGGCGGAGTTTCGTCCTTATTCCAGAACTTAGGGGTAAGTGTTACGCCGATTCAGCGCATCGTGCT
GAGTGGAGAGAATGGATTGAAAATTGACATTCACGTTATCATTCCGTATGAGGGTTTGAGTGGAGACCAGATGGG
ACAGATTGAAAAGATTTTCAAAGTGGTGTATCCCGTCGATGACCATCACTTTAAAGTAATTCTGCACTATGGGACC
CTTGTGATCGACGGTGTAACGCCAAACATGATTGACTATTTCGGTCGCCCTTACGAAGGTATCGCCGTCTTCGACG
GAAAAAAAATCACTGTCACGGGAACATTATGGAACGGAAATAAAATTATCGACGAACGTCTGATCAATCCTGATG
GAAGCCTGTTATTTCGCGTTACGATCAATGGAGTGACCGGATGGCGTTTATGCGAACGTATTTTGGCTTAAAGAGG
AGATATACAATGGGTGTTGTAAAGAAAGCATTTAAGGCTATCGGTCTTGCTCAAGATGCACCACGTATTGAAGCCA
AAGTCCCAGCACAGCAGCTTGAGCGTAAGCCTGAGACTGAAGCTGAAGATATTCAAATTGGTGCAGGGGATGAT
GCTACTGCATCTGCAAAAGGTAAGCGTGGCCTTGTCCGTCCGGTAGCTTCTAGCTTGAAGGTGTAATATGAAACAG
AGCATAGATTTGGAGTATGGAGGTAAGCGGTCTAAGATACCTAAGCTATGGGAGAAGTTCTCCAATAAACGTAGC
TCTTTCCTTGATAGGGCGAAGCATTACTCCAAATTAACCTTGCCCTATC

Figure 4A

>K1-5 BAR 2.5 (Site specified by sgRNAs 86+89) (SEQ ID NO: 4)
TCGCCCTCGCCCTCGCCGGGTTGTCCCCATAGGGTGGCCTGAGGGAATCCGTCTTCGACGGGCAGGGCTGATGTACTCCTTGTCTAGTACAA
GGGAGGCGGAGGGAACGCCTAGGGAGGCCTAGGAATGGCTTAGTGGTGGACAAGGTGATTACCTTAGTGAAGCCTCTTAGTGCATTCCTGA
GGCCATTCAGGGCGTTTATGAGGGATTGACAGGGTGTGAGGGCGTGGGCTATCTGTTCCTTTGCTCCTCACTTCGTTCGTCGCTGCGGTAGCC
TGATGTGTACCTTAGGTTATTCCTTGATGGATAGCTTAGGTTAGCCTTAGTGGATTACCTTAGTTAAAGCCTTAGTGCTTCACTTAGTATCAGCT
TAGTAGTGTACCTTAGTAAGTCTTAGTGTCTTCTCTTAGTGATTGCACATGCAAGCATGTAAGATGCTAATAGGTCGCGGTCGGCAGACCGCT
AAAGAAAGAGAATGGTAATAAGATGCAGTAGGAGGAACACCAGAAGCCTAGCCAACCTAAGCTATCCTAGCTCTATATCTATTGCTTTTCCTT
AGTCTAACACGTTAGACAACCTATCTTATTCTTAGTGATGGTAACTTAGTGTTGACAAGATAATCTTAGTGTAATACTATGCATCACGTAGGCG
GTGCTGAGGCACCTAGTAGCCAGCTAGTAAGGCATACGAAGAGACTAGCGCTTACATTGCTCTTTAACAATTTGCTTAGTGTAACCTATGTAT
GCCGTGGTTAACTACTTATTGAATGAGGTATTAACTATGACATTAAATAACCGTGAACTGTCCGTTCTCTTCACTCTGTTGTGCTACATGATTCG
TAACAACGAATTACTTACAGATGATGAGTTAGCCTTGTATCACCGCTTTCTTAACGAAGGTTGGACCGATACAGTTAATCAATACCGTAACATG
ATAGATGAGTTGAGGGAGGGTAAATAATGTATCAACATGAGGTATTCTTTGAATCAGCTAGCGAAGCTATTCGCTTCCGTGATGATATGATG
CAAGCTGGTGTAGGCGTTGATGTGTATCACTATTTGATAGATTACGACACTGAATATCACCGAGTTACCTTAGTATCTGAGTATGACAACCAA
GTCATTACTGAGTATCTAGGCAGTGAAGATTACGATTACGATGAAGTAATCACGACAAATCTCTAAATTAACTGTTGACAGCCACGGCATACA
AGGTTACATTAAGCATCAAGACGGCGACGTCTTTAAACATCCCGCTCTTTAACAATACGGTTTGTGTCTTGATAGGCTAACTAACTAACTAAGG
TAATTATCATGAAAGGGTTAATTTGTGTAGAACGTATGGTCAATGGTAAACTTGAAATATTACCACTGGAAAACCAATCTAGCTTCAAAGAGT
GGTATGGCTGTTTCTCACTGATTTAAGGTAAAGGCTGGCACTAGTCAGCCTATCAAGGCGCAAACCAAGCTCTTTAACAATTTGGATGGTAGC
TTCTTAGTCTGGATAGGTTAAACCTAGGAGATTCTCTTGAGTCTCCTATAATGTAACCTAACTAACTAAATGAGGATTAAAAGAGGAGATATA
CAATGGTTTTTACGCTTGAGGACTTCGTTGGTGACTGGCGTCAAACCGCGGGGTATAATCTTGATCAGGTCCTGGAGCAGGGCGGAGTTTCG
TCCTTATTCCAGAACTTAGGGGTAAGTGTTACGCCGATTCAGCGCATCGTGCTGAGTGGAGAGAATGGATTGAAAATTGACATTCACGTTATC
ATTCCGTATGAGGGTTTGAGTGGAGACCAGATGGGACAGATTGAAAAGATTTTCAAAGTGGTGTATCCCGTCGATGACCATCACTTTAAAGT
AATTCTGCACTATGGGACCCTTGTGATCGACGGTGTAACGCCAAACATGATTGACTATTTCGGTCGCCCTTACGAAGGTATCGCCGTCTTCGA
CGGAAAAAAAATCACTGTCACGGGAACATTATGGAACGGAAATAAAATTATCGACGAACGTCTGATCAATCCTGATGGAAGCCTGTTATTTC
GCGTTACGATCAATGGAGTGACCGGATGGCGTTTATGCGAACGTATTTTGGCTTAAAGAGGAGATATACAATGGAACGCAACGCAAATGCAT
ATTATAATTTATTAGCAGCTACGGTTGAAGCCTTTAATGAACGCATCCAATTCGACGAAATCCGTGAGGGCGACGACTATAGCGACGCCCTTC
ATGAGGTTGTAGACAGCAATGTTCCAGTTTATTACAGCGAAATCTTTACAGTGATGGCTGCTGATGGTATTGATGTTGATTTTGAGGATGCTG
GTTTGATTCCTGACACGAAGGATGTAACCAAGATTCTACAAGCTCGCATCTATGAAGCTCTTTATAATGATGTACCAAATGACAGCGATGTAG
TTTGGTGTGAAGGCGAAGAAGAGGAAGAATAAGGATGGAAAAGCAATATAACTTTATCTTTTCAGACGGTGTAACCCTGAAGTGTTCCCTAC
GATTCGCACAAATTCGTGAGGAAGTACTAGGCACTACATACAAACTATTTAGCTGACACTATAAGAGAAGGCTTAACAAGGCGTTACTAAGG
TAGCGCCTGATTAAACTTTCACTTACTAGGAGTTGAGATTATGAAAACCTTGATTGGATGCTTCTTGTTGGCTTCTCTTGCTCTGGCATTTACCG
CTAAAGCTGGTTATGACGCTTATAAAGTAGAACAAGCCCAGCAAGACTGGGCCAAAAAAAAGTTCAACTTGTGCAGCAAGAGCAACACCTAC
GAGTACTGCAACAAAACACTAAGACACTTATGGAAAGAGTAACTAGCCTATAGCCCACCTGAGTGGGCTATGTGATATTTACTTAACACTATA
TAAGGTGATTACTATGACTACTGAAAACACCCTCGTGTCTGTCCGTGAAGCTGCAACCGCTGAAATCAAGCAACATTTAGACAATATCGGCAC
TTCTTACATCAAAGTAGGGGCTTGTCTGAATGAGTTACGCGGAGACTTTGAAGGTCAAAAAGAGTTTTTAGCCTATGTTGAAGCAGAGTTTGC
CATTAAGAAGGCACAATGTTACAAGCTGATGAGTGTAGCCCGTGTCTTTGAAGGCGATGATCGCTTTAAAGGCGTGGCGATGCGTGTAATGC
TGGCGCTTGTTCCTTTCGCTGATGAAAATATAATCATGGAGAAGGCCGCAGAACTCGCCGCAAATGGCAAGCTGGACACTAATGCCGTAAAC
GCCCTGATTGAACCTAAGAAAGAGTCAAAGGCCGAAACGGTACAATCTAAGGCTGAGACAGTAAAACCGCAGGAGAACGCGACTGAGTCCG
CAGAATCACATGAAATGCAAGCGCCGCAGGTAGTGCCACCCGCGAGCGAGCAGGAGTCCGACGAATCAGCACCTTGGGAAGAGGAAAGCA
AACCGGAAGCGCCAAAGGCAGCTCCGATGGATAACACGGCTAATACTGAGAATGCCGCTATTGCTGGTCTGCTGGCACAAATTAAAGCACTG
ACTGAGCAATTACAGGCAGCCAATGACCGCATCGCCTCCTTAAGTAGCGCACGCGAAAGCAAGAAGGCATCCGCACCTATGCTGCCGCAGTT
CAAATCTTCCTGCTTCTACGCTCGCTTAGGCTTGAGCGCGGAGGAGGCAACGAAGAAAACAGCAGTTAACAAGGCACGCCGCGAACTGGTTA
AGCTGGGATACGGTGAAGGCCATGAGGCATGGCCCTTAATCTCTGAGGCAGTAGAAGAGTTGACTAAGTAACCTTATCGGTGGCATCTTCTT
AGGTGTCACCTATTAAGGTTTCTTTCACTAGGAGTAAACAAGATGCAAGGCCTACACGCTATTCAACTTCAACTTGAAGAAGAAATGTTTAAC
GGCGGTATCCGTCGCTTTGAAGCGGACCAACAACGCCAGATTGCATCCGGTAATGAATCAGACACGGCATGGAATCGCCGCTTATTGTCCGA
GTTAATCGCGCCAATGGCTGAAGGTATTCAGGCATACAAGGAAGAGTATGAAGGTAAAAGAGGCCGTGCACCGCGTGCATTAGCTTTCATTA
ACTGCGTAGAAAACGAAGTGGCAGCATATATCACGATGAAAATCGTTATGGATATGCTGAACACGGATGTAACCTTGCAGGCTATAGCCATG
AATGTAGCTGACCGCATTGAGGACCAAGTACGTTTTAGCAAGCTGGAAGGTCACGCCGCCAAATACTTTGAAAAAGTTAAGAAGTCACTTAA
GGCAAGTAAGACTAAATCATATCGCCATGCGCACAACGTAGCGGTAGTGGCTGAGAAGTCAGTAGCTGACCGTGACGCTGATTTCTCCCGCT

Figure 4B

```
GGGAGGCATGGCCTAAAGACACCTTGCTGCAAATTGGGATGACCTTGCTTGAAATCTTAGAGAATAGCGTATTCTTCAACGGGCAACCTGTCT
TCCTCCGCACCTTGCGCACTAATGGCGGCAAACATGGTGTTTACTACCTACAGACTAGTGAACACGTAGGTGAGTGGATAACTGCATTCAAAG
AGCACGTAGCGCAACTGAGTCCTGCCTATGCTCCTTGCGTCATCCCTCCGCGTCCGTGGGTATCACCTTTTAACGGCGGTTTCCACACTGAGAA
AGTAGCAAGCCGTATTCGTCTGGTAAAAGGAAACCGCGAACACGTCCGCAAGCTGACCAAAAAGCAAATGCCAGAGGTTTACAAGGCTGTT
AACGCGTTGCAGGCGACTAAATGGCAGGTTAACAAGGAAGTTTTACAGGTTGTGGAAGACGTCATCCGTCTAGACCTAGGTTATGGTGTACC
TTCCTTTAAACCACTCATTGACCGCGAGAACAAGCCAGCTAATCCAGTGCCGCTAGAATTTCAGCACCTACGGGGCCGTGAACTGAAAGAAAT
GCTTACGCCGGAACAATGGCAAGCCTTTATCAACTGGAAAGGTGAATGTACTAAGCTGTACACCGCTGAAACTAAGCGCGGAAGCAAATCGG
CGGCAACCGTTCGCATGGTTGGTCAGGCCCGTAAATATAGCCAGTTCGACGCAATCTACTTCGTGTATGCACTGGACAGCCGCAGCCGCGTCT
ACGCGCAATCTAGCACACTCTCACCGCAATCAAATGACTTGGGCAAGGCCTTGCTCCGTTTTACCGAAGGGCAGCGTCTTGATAGCGCTGAG
GCGCTTAAGTGGTTTTTGGTGAACGGGGCTAATAACTGGGGTTGGGATAAGAAAACTTTTGACGTGCGCACCGCTAACGTGCTGGATAGTGA
ATTTCAAGACATGTGCCGCGACATTGCAGCGGATCCGCTGACCTTCACTCAATGGGTAAATGCCGACTCCCCTTACGGCTTCCTTGCATGGTG
CTTTGAATATGCGCGTTATCTGGATGCACTGGATGAAGGCACGCAAGACCAATTCATGACGCACCTCCCAGTCCATCAAGATGGTAGTTGTTC
TGGTATCCAGCACTACAGTGCTATGCTACGCGATGCAGTAGGTGCGAAAGCAGTAAACCTTAAGCCCTCTGACTCTCCTCAAGATATTTATGG
TGCCGTTGCGCAGGTAGTAATTCAGAAGAATTATGCATACATGAATGCAGAGGATGCGGAAACCTTCACTTCTGGCAGCGTGACTTTAACAG
GTGCGGAGCTGCGTAGTATGGCTAGTGCGTGGGATATGATAGGAATCACTCGCGGCCTGACCAAAAAGCCCGTAATGACACTACCTTATGGC
AGCACACGTCTAACCTGCCGTGAGTCAGTGATTGATTATATCGTTGATTTAGAAGAAAAAGAGGCCCAACGGGCTATTGCGGAAGGGCGTAC
CGCCAATCCTGTACACCCTTTTGATAATGACCGTAAAGACAGCCTGACACCTAGCGCAGCTTATAACTATATGACAGCTTTAATCTGGCCTTCT
ATTTCGGAAGTGGTTAAAGCCCCTATAGTGGCAATGAAAATGATTCGTCAGCTTGCCCGTTTCGCAGCTAAAAGGAATGAAGGCTTAGAGTA
TACCCTGCCTACTGGCTTCATCTTGCAACAAAAGATTATGGCTACTGATATGCTCCGCGTATCTACTTGCTTGATGGGAGAAATCAAGATGAGT
CTACAGATTGAAACAGACGTAGTGGATGAAACGGCAATGATGGGCGCTGCTGCTCCTAACTTTGTGCATGGTCATGATGCCAGCCACCTTATC
TTAACAGTCTGCGACCTTGTTGATAAAGGGATTACATCTATCGCAGTTCATGACTCTTTTGGCACTCATGCAGGCCGTACAGCCGACCTTC
GTGATAGCTTAAGGGCAGAAATGGTGAAGATGTATCAAGGCCGTAATGCACTGCAAAGCCTGCTAGATGAGCACGAAGAACGCTGGTTAGT
TGATACCGGAATACAAGTACCAGAGCAAGGGGAGTTTGACCTTAACGAAATCTTAGTTTCAGACTATTGCTTCGCATAATATTAATAGGCCAT
TCCTTCGGGAGTGGCCTTTCTTTTACCTACTACCTGTAACATTTCATTAACATAAAAGTGTCTCACATGTGAGACTTATTTACCGGACACTATAG
GATAGCCGTCGGAGACGGGAAAGAAAGGGAAGATAAAGGATATAAAGGAAGTAATAGGTATTAAAGGTTATATAGGTTATCTAGGAATAC
CTATTACCTTCTTCCTTCCTCTTATTACCACTCAGAGGAAGGGCAGACCTAGGTTGTCTCACATGTGAGACTTCGTATTTACCGGACAGTATAG
ATAAGATTAACTCACTTTGGAGATTTAACCATGCGCAACTTTGAGAAGATGGCCCGTAAAGCTAACCGTTTTGACATGGAAGAGGGGCAGAA
GAAAGGCAAGAAGCTGAATAAGCCTGTCCGTGACCGTGCATCTAAACGCGCTGCGTGGGAGTTCTAAGTTATGGCTATTATTCAGAATGTAC
CGTGTCCTGCCTGTCAAAAGAATGGACATGATATTACTGGCAACCATCTCATGATATTTGATGATGGTGCCGGCTACTGTAATCGTGGACACT
TTCATGATAATGGTAGACCTTACTATCACAAGCCGGAAGGTGGCATCGAGATAACCGAGTTATCTATTACTGGCAATATCAAATATACACCTTC
TCAATTCAAAGAAATGGAGAAGGAAGGGAAGATAAGCGACCCTAAATTACGTGCCATCGCACTTGGTGGTATGCGTATGAAAGACCGTTGG
GAGGTCATGAATGAACAAGAAAGGGCAGAGCAAGAAGCAGAGTGGAAACTTGATGTTGAATGGTTCCTCACGCTTAAGCGTAAGAACCTTG
TTTCCAGGCACATTCGCGGCGACATTTGCGCATTGTATGATGTACGTGTTGGGCACGATGAAGAGGGTAGAGTCTCACGGCATTACTATCCGC
GCTTCGAAAAAGGTGAGCTAGTAGGCGCTAAGTGTCGCACATTACCTAAAGATTTTAAGTTTGGTCATTTAGGTAAACTCTTTGGTATGCAAG
ATCTTTTCGGTATGAATACTTTGTCTCACGTGTTAGACAAGGGAAGACGAAAGGATTGCTTGCTCATTGTCGGCGGCGAACTGGATGCACTAG
CAGCGCAGCAGATGCTCCTTGATTCTGCCAAGGGTACTAAGTGGGAAGGCCAGCCATACCATGTATGGTCTGTCAACAAAGGCGAGTCTTGC
CTTGAAGAGATAGTGCAGAACCGTGAGCATATCGCCCAATTCAAGAAGATTATATGGGGTTTTGATGGAGATGAGGTAGGGCAGAAGCAGA
ATCAGCAAGCGGCTCGCCTGTTTCCTGGTAAATCCTATATCCTTGAATACCCCTCTGGTTGCAAAGATGCTAACAAGGCATTGATGGCTGGCA
AGGCTAAAGAATTTGTAGATGCATGGTTTAATGCCAAGTCATCTGATGAAGTCTTTGGTAGCCAGATTAAATCTATCGCATCTCAAAGGGATA
AGCTCAAGGCTGCACGTCCAGAGCAAGGACTGTCATGGCCTTGGCCTAAGCTGAACAAGGTAACGCTAGGTATTCGTAAGAACCAGCTTATC
ATTGTAGGTGCAGGGTCTGGTGTAGGTAAGACTGAGTTCCTTCGTGAAGTAGTTAAGCACCTCATTGAAGAACACGGTGAATCTGTAGGCAT
CATTTCTACAGAAGACCCGATGGTCAAGGTGTCCCGTGCTTTTATCGGCAAGTGGATTGATAAGCGTATTGAGTTACCTCCAACCAACGACCC
GAAAGAAGACGGATACCGTGAGGTGTTCGACTATACCGAGGAAGAAGCTAACGCCGCCATTGATTATGTAGCTGATACAGGTAAGCTGTTTG
TAGCTGACCGTAGAGGGTGACTATTCGATGGAAAAGGTAGAGCAAACTTGCCTAGAGTTTGAGGCTATGGGTATTTCTAATATCATCATTGATA
ACTTAACGGGGATTAAATTAGATGAGCGTGCTTTTGGTGGGAAGGTTGGTGCACTTGATGAATGCGTCAAGCGGATTGGTACTATCAAAGAC
CGACACCCGGTTACTATATTCCTTGTATCACACCTTACACGTCCTCCGGCAAACCGTACCCAACACGAAGAAGGTGGCGAAGTTATCCTTTCTG
ACTTCCGAGGCTCAGGCGCTATCGGATTCTGGGCATCTTACGCCTTGGGGATTGAGCGTAATACAAGAGCTGAAACGCTTGACGAAAGGACT
ACCACGTACATCTCATGTGTCAAAGACCGCGACCAAGGTATCTACACTGGAACCAAGGTCATGCTTAAGGGTGACATTCAAACCGGACGTTTA
ATGGAACCACAAGCCCGTACTAAGTCATTTGATACAGGTGAAGCAAGGCAACAAGAAGTACCAGATTTACCGGATACTATAGAAGAGACTAC
CTTCGATGAAGAAAGTGAGTTCTGATTAGTGTATTTATCAGGCTTGTCTCACATGTGAGACAGGCTCTTATTAAGTACATTAAATAACTGGAG
ATTGATTATGTATAACTTAGTGTTGAATGTAGGTGACTTTGTACGCAACATCAAGAAAGATTCAAGTCGCTATCTTTGCCGTGGTGTTGTAACC
```

Figure 4C

```
TTTGTAGGTGAGAACCTGTATTATGTAGAATATCGCAGTGGTGTTAAGCAATATTACCACAAGAAGACAGCACATAAATATCTTGAAAAGATT
GTAGAGATAAACAATCAATGTAAGTGCATACATGATGAGGTTTGCGATAAATGTGCTCGCCAGATGCTTAAGAATTTCCTAGCTCCTCTTTATT
ATGGTGCTGGTCCTCAAACACTAGCAGAGTGCATGGCAGAAAAGAAAACCACACTCAAGAAAGAGCGTCGCAATGTAATCACTGGTAAGAC
TCAAAGTGAGATGATTAAGCAATGTGGCACTGCATTAGGTGTTACACAGTTTAATACTCGTGCATTGGGTAAATCCACAGGACAAGCTATGGT
AAAGATTGGAGAAGCCATGATGCATCCAAATGTACCTGTGCGAATCATGGATGTTGACCATGCAATCACAGAACAAGGTACGCAACGACGTG
TAATTAATAAGCATTTTGCCGACACTATAGAAGGCATTATTCGTAAGCAAGGGTTGAAAGGTCTTCACATCTTAAATGGTGAAGAATTACTGT
ACCTACCTATCGTTACTGAAGAAACATACGTGAATATCTAAGGAGTTAATCATGACTAAGGTATTAATTTATATGCGTGGACCTCATAAATGCT
ATGCAGTTGTAGCACCAAATGGTGTTAAGCCTTATCGTACTTCAAAAAGATTGGCATTAATAGGTGCTAGTAGTAGTGCAAGTTCCAAATGG
AACTTTTTGGTCATTGGACTGAAAGGCAATTCCGTGAGGATTTTAAAGTCATTGGCAGCTTCATGGTGAAATATGCAGAATAAACATAGTCTT
AGAATGTTCGATGGTCATGAAAACCTGCAAGCCAAGATTACTAACCAAGCCTTCCTGTTCGCACAGTTAACTATGGCTGAGGCTAAGAAGAAT
AGTCTCACTCGTGAACAGGTTATCAAGGAGGCCACTTGGGAACCACACCAAGGTAAATATATGGGCCACAAATTAACTGTAACACGCAGTCG
ATAAGTCAAGGGTTGTCCAACGTGTTGGACAGCCTTTCATCATATTGATTGGGAGGTATTAAATGACTAAGTTTACTATGCAAGACCTCATTA
AATTACGTGATGAAATAGAATCACCGGAAGTTAATACAGAGTTTCACTACATTGATCCACGAGATAAACGAGAGATTCCTGATTATCAGATTG
AGACGGAGTTAATGTATGAAGATTATTGATTGGAAGAAGGAAGCAGAAGGCCGTATCCTAGTGATGGATGCGGAGGCTAAAGGCCTGCTGG
GTGCTATCCGCTACGGTCATCGTGAAGATGTACACATTATTTGCTGCATGGACTTGCTCACCACTGAGGAGTTCCTCTTCTTCGACCCATATGA
GATGCGTGACCCTGAAGCAAGGGAACACTTGAAAGAGTGGGAAGGCCATCAAGATGGGACCTTGGTTGATGGTGTTAACTTCCTAAAGCAC
TGTGAAGCCATCGTCTCACAGAACTTCCTAGGCTATGACGGGCTTCTCTTTGAGAAAGCCTTCCCTGACATCTGGAAGGGATTTAACTACACC
GAGAGGCGCGGCAAGGGCAGACTACGTGCTGACTTGTGTCCGGTACGCGTCATGGATACGCTGGTCATGAGTCGCCTGTTAAACCCAGATA
GACGCCTTCCTCCGCAAGCATATGCCAAAGGTATGGGTAACGTTGCCCCTCACTCAATTGAGGCGCACGGCATTCGTATAGGCCGTTATAAGC
CGGAGAACGAGGATTGGTCTAAACTAACTGACCACATGGTACATCGTGTACGCGAGGACGTGGCGATAGGCCGTGACCTATTCCTCTGGCTA
TTTAACGGAGAATGGACGGAGCACAAACGCCGTGGCGTGAATAAACGCACTGGCCTAGGTATTGAGACAGCCTTCCACATGGAGTCCATTGT
GACGCTGGAGATGAGCCGTCAGGCCGAGCGTGGATTCCGTCTGGATATAGATAAAGCATTAGCACGATGCGAGGAATTGGACGCTAAGATT
GATGAGACAGTCGCAGCGTTCCGTCCGCACATGCCTATGCGTATCAAGTCTAAACCTTTTAAACCGGAAGAAAAGAATGAAGTATGCCAACG
CGCAAATGAGTATGGAGCTAGCAACAATATACCTACTGTCCTTGACCCCTCTCACTTTCTTCACGCAGAGAGACGAGGAGATCGCAAGACAGT
ATGGAGTGTCACTACTAAGTCTGGTGATTGGTCGGCTAGCGTCAAGAAAGACTTTCCTCACCTTAGAGGAAACCGTAATGACACGCCAAGTG
TCAAGTGGATTGGCGCTTACTCGCCTGTTACTTTCGAAGAGATTCCCTTGGGTAACAGGGATACAGTTAAGCAAGTGCTCTATGATTATGGAT
GGAAAGGTGTTGAATTTAACGATACCGAGCAAGCGCATCTCGATGAGCATGGCGTATTACCCAAGCCTTGGAGTGGGAAGATAAATGAAAA
GTCCCTTACTTTATGGCAAGAGAGAGCCGCACGTGAAGGTAAAACAGTCCCTGATTGGTGCTTGGGTATCGCTGCATGGTACATACTCGTATC
CCGTCGTGGTCAGATCCTCAACCGTGGTGACGTTGAAGCCTTCGACCAGAAGGGGGTGTGGCCTTCGCAAGCTGGTATACGAAAGTGTCGCG
GCCTTGTACCTGTAGCATTTAACAAGGAGTTAGGAATCAATGCGCAGCAATACTACGAAAGGTACGGATGCTGGCCTACGTCAGACAAGGAT
GACGGAGAATGGCGTGTGCCAGCTATTGCTATTAGTATTGGAACTTCTACGTTCCGTATGCGTCATCGTAACGTGGTTAATATTCCTGCCCGT
GGCTTGTATCCTTTACGTGATTTATTCATAGCAGGGAAAGGCAAGCTAATCCTTGGTTGTGACGGTGCAGGTCTTGAACTGCGTGTCCTGTCT
CACTTCATGAATGACCCTGAGTACCAAGAGATTGTACTGCACGGTGATATTCATACGCATAACCAGATGAAGGCTGGTCTTCCTAAGCGTGAT
ATGGCGAAGACATTTATATATGCCTTCCTATATGGGTCTGGTATAGCTAACCTTGCAGCAGTATGTGGTGTTACTGAGGAAGAAATGGAGGA
AGTTGTGGCAAGATTTGAGGTTGAACTACCATCTCTTGCACGTCTTCGTGAGAATGTTATCGCACAAGGTAACAAGTTTGGCTACCTACAAGC
ACCTGATGGTCATTGGGGTCGCATCCGTATGTCTGGTGGTGAACTTAAAGAACACACTATGCTTAACGTACTACTCCAGATGACTGGTTCTCT
GTGTATGAAATACGCATTGGTCAGAGCGTTTGCAGTGATGCGCAAGGAAGGTGTGGCCTTAGATAGCATGGGAAACCCTTGCGGTATAGCT
AACGTGCACGATGAAATCCAGATGGAAGTCCCTGAAGATGAGGTCTTGTATCTCAACTACGACTTGCCTTTCACCTTAGAAGGGTTCGAAACA
GAGAAGGCTGCTGTGAAAGCAGTGTTCGATGCAGAGGAGAAACGTGTTCATGTGGATTCTGAAGGACGTATGTGGTCTGCTGCAAATCTCG
TTAGTGTTGATGCTGGTGTACTTCATTGCCAGCGTCGTTATCACCGTGCAGGGCATATCATTGCCGACGCAATGACCTGGGCGGGTCAGTACC
TGAAGATGCGTTGTCCGATGGCAGGTGAGTATAAGATTGGTGCAAGTTGGAAGGAAACACACTGATGGACAGGTTTGATATTGTTTGCCTAT
TCTCTACCTTCTTTCTTATATTCCTTATGCTTGCTTGCTATGGAAGTATGCGATTAGATATACCTGATGAAGAGGAGGGTTACGATTGATGCAG
GCATCTTTTATTATTCTTGGAGTCATATTATTTATGGTAGTATTCTGGGCTTTCTCTGGCATTGACCCAGATTGTGATGGTAACTACGACTGAGT
TATACTCAAGGTCACTTACGAGTGGCCTTTATGAATAACTTATTCCTACTTATTTTGTCTAACATGATTTACTGGACACTATAGAAGGAAAGCAT
AGGTAATCTAGGTTTATAAGGTAGTATAGGTAATTAAGTAAATATAGGAGATATAAATATGTCTATGGTAACTACTCTGGTATTCGTGGCTCA
ATACTTTCGTGGTCTTGCTAATAAGTTCAAGTCCAAGGCTATCAAAGCTATTGAGGCTCGCATCGAAGCAGTACAGGCAGAGCAAGTTAAAGT
TGAAGAACATCGTAGTTCTCAAATGATTGACTGTCATAACCGCTACTATGCATCTCGTGATGAACTAAATGCACGTCAAGTCAAAGAGGTAGA
AGATATGCTGGCACGTCACCAGCAAGAGCGTGACAGCCTGAAAGCTGAATTTGAAGAGAACAAGGCATCAATTGCTCTTGTACATCAAGCTG
CATCTGACAGTCTGAAGAAAGAGATTGTTATGCTGGAAATCGAACTGGATAACCTGACCAAATAAGGGGGGTTATGATGGAAGAAGTAAT
TCAAGCTAAACATGTAGGTATTATCTTTCGCGATCTAGAGCAGCGTAAAGTTGCAGGTCATACTCGTCTGGCTAAAGAGGAAGACACCGCAAT
CACTACTGTAGAACAAGCAGATGCCTATCGTGGACCAGAGTTCACTCAAGGTGAAACTTGTCACCAATTGAGCCTATCAATTTGTGACACTAT
```

Figure 4D

```
GGCTATTGTAAATGTGCAAGAAGTCGAAGAGGGTGAGTGTGTCAGTTACATCTACCCTTTAGATACTATTGCACGCATTAAGGTAATCCATAA
GTAATTACTAGACACTATAGAACAATAGGTCGGCTTAGTTCGGCCTATGATTGTAAAGTGTTGTTGATGTTGAACCATTGTGCATCTTGCACAA
CCCGATACCGTATAGGGCTTTCTAGTGAGTACATGCTTGTGCTCAGTACAAAGCTAACTGACAATAGGAGACTAAATAAATGGCACGTGGTG
ATTTTGATTTTGGTGCTCAGGTTACTAAATCTGAAGGTAAAGTCTTTAAGAATCCAGAAGTAGGTGATCATGAAGCAGTAATCTCTGGCATCA
TTCATGTTGGTTCCTTCCAAGACATCTTTAAGAAAGGTAATACCACTGAAGTTAAGAAGCCAGCAAACTTTGTTCTGGTTAAGATTGTCCTGAT
GGGTGACGATGACAAGAACGAAGATGGTTCTCGCATGGAACAATGGATGGCTGTGCCTCTGAAGTCTGGTGATAAGGCAACACTGACTAAG
TTCCTGAATGCAGTTGACCCTAAAGAGTTGCTGGGTGGCTTCGATGATTTCATTGGTGAATGCCTGACTGCAACGATGGTCGGTTCTGGTGAT
AAGAATGACGATGGCTCATTCAAGTATGTTAACTGGAAGGGATTTGGTGGTATGCCGGACAAGCTGAAGAAACTGGTCATTGCTCAGGTTGA
AGAGGAAGGTCTGTCTATGACAGGTCACATTACCTTCGACAAGCTGACCAAAGAAATCCTTGATGACATCCCAGCCAACTTGGTGCGTCAATA
CTTCCTGAACGAGACGCCTCGTGGTAAGAACCTGTCTGTTGCTGGTTCTCACGTAGAAGCAATCATTAAAGCTGCTCGTGAAGAAGACCCAGA
ATGGAAGAAGGCTAAGAAGAAAGACGAGGAAGATGCTACCCCAGCTAATCGTAAATCTCTGGATACTGGTGAGTCTGTTCCACAGGAAGTA
CCTGAAGCAGAAGATACTCCTGCACCGGAGATGGATGAGGACGCGGAATATTAAGGAGAAAGGATGAAAGTACAAATCGTAACCCTGCACT
GCAAGAAAGGAATTACAACTCTTGGCGGCAACACTTTTCACTCCTTCTCTGAAGGGGACACATATGCCGACCTGCACTACATCTGGCGCGACG
GACAGCACGTGGTGAACTACAGCGACCCAGCTACGGGGAAACGCCACGGCGTATCGCTTCCGGCGCATGACATTGCTCAGGTGAACACAGT
TTTATAAAGTCTCACGTGTGAGACAAATCGGTGTCCGGTATTTACTGGACACTATAGAAGAGAAGAATTTTAATCGGCGATAATGCCATAACC
AACAAAAGGAGAATTTAATATGTTCAAGATTGAAACTATCGTAAACCGTGTTGTTAAAGGTGCTGCTCTGGTATCCGTTGAGTCTTTCATTATC
GTCGATGAAACTGATCAACTGGTAGCTGGTACTAAGGCTTACGATACCCGTGAAGAAGCTCAGGCTAAGATTGACAGCATGGGTAACTTCGC
TGCTGGTCTGGAGTTCGCTCGTGCTTGCTTCCCTGAGCAGGCTGACAAAGCTCAGATTGGTAAGGCTAATATCGTAGCTGAATATCTGGATTG
GGTTGCTGCTGGTAAACCAGTGAAAGAAGTTAAGGCTGCTGAAGAAGCTGAAGCTCCAGCAGAAGAAGTAGCTGCACCGGAAACTCCGGTA
AGTGAAGAGGAAGAATTTTGATAATAGCAGGTGTTGCCTCTGTTAGTCCTAGCTGACTATCACGCTCACCTCATCTAATGCCCTGTCTGCCTTA
GTGTAGGCAGGGTCTTTTGCGTAATAGTTATTGGAGAATGAATTATGCCGACTATTGAATCTCGAATTGAACTGGACATTAGCTACAATGCAA
TCACCAGACAGTATATTGGGGTTGCCTATGATTACAAAACTGGTGAGAAGCTAGTGGAGGTGAGACAATGGGATGACTATTGGTTAAGACA
GAACCTCCATGATGCGGTGTCCTCCTTCCTGAAGGAGTGGCCTACATGCGACCAAACTTCGACTTCGGAGCTACAGTATCGGAAGACAATAAC
CTGTTGCTGTGGCCAACTGAAGGTAATCGAATCGCTTTAATAGATGCTGATATGTTACCTTACATCATAGGGTATACAATCAGTGATATGACTT
ATGTACGAGCCACAACTCGTGTTAAGTCAGGGCAAGTCCCCTCAATCAAAGATACACCTGAGTGTAAGCAAGCGTGTGACCGTGTGAACTCC
TTGCTTAACTCTTGGGTGTATGCAGCAGAATGTGATGCAGCTAAGTTGTTCATGACGAAATCAGAAGCTAACTTCCGTGTCCGCCTAGCATTC
ACCAAGCCTTATAAAGGTCAACGTAAGACCGAGAAGCCTCCATTCTTCTATGAATTGCGAGAGCATCTCTTAGAGGTTCACGGTGCAATCTTG
GCAGATGGAGAGGAAGCAGATGACCTCATGAGTATCGCACAATGGGACAGCCACCGCCGCTTCCAGCAAGATACAGGTAACGAGTTCCCTA
TCGGTAGTCCAGAGCATAAAGCATTCTCTGATACTTGCATCGTTTCCTTGGATAAGGATTTGATGATTGTTCCCGGTTGGCATCTACAGCCGGG
TCAAGAGAAGAAATGGGTAGAGCCTATGGGTTGGCTTGAGCTACGCCGTAAGGCTAATGGGCAAGTCAAAGATCTAAAAGGTGCTGGCCTC
ATGTTCCACTATGCACAGATGATTATCGGTGATGATATTGATAACTATGCTGGCATACCAGGTCGTGGTGCTAAATATGCCTATGATCTTCTCA
AAGATTGTAAGACAGAGAAAGAGTTGTACATGGCAGTGCTGGGTGCTTACAAGGCTAAGTTCGGGCATGGACAAGTTAAAATTAAGAATTA
CCGAGGTGGTTATCGTATCGGCAAAGCCTTTGACCTAATGCTTGAGTGTGGTCGCTTATCTCACATGGCAAGATTCAAGGGTGATATATGGCG
AGCCGATAAGAACCCAATCTTGTGGGGAGATGATGCGGAATGGTTAGCAAATTAAAATCATCGGAGGTGGCAGCTTATAAGAAGGAATTGC
TAGATAAGCAAGGATGGAAATGCCCTCTGTGTGGCGGCAGTCTCAAAGCTGTCACACCTGTAAACCGTGTACTTGACCATGACCATGAGACA
GGATTCTGCCGCGCTGTTGTATGCCGAGGCTGCAATGGTGCGGAAGGGAAGATTAAGGGTGTTATCTCTGGTTATGGTAAGGCTGGTAACA
ACCGTTACTTCCAGCTTCAATGGTTAGAGCGACTATATGAATACTGGAAGTTACATAGTACGCCTCAGACAGATAAGTTATATCACAAACATC
AAACGGAGGCAGAGAAGCGCGAGGCTAAGAACCGTAAGGCACGCCTTGCTTATGCAAGAAAGAAGGAGGTTAAAGTTGGGTAAGCTGCGC
AGCTTGTACAAAGACTCCGAGGTACTTGATGCAATCGAGCAAGCTACCGACGAGAAAGGTAATGTTAACTACAATGAGATGGCACGTGTATT
ATCGTGTCATACTGTGGGTAAGAAGATTACCCGCCAGTTGGCTCGATACTGGCATGGTCAATTCAAGAAGACCAAGAAGAATGGTGATTACT
ACCAGACCCTTCTGCAAGAAGATAAGCGTATCAAAGAAGAGCGTAAGCTCAGGACTCCTGACCGCTACGAGGATTTGGCTATTGTGCCATTG
CCTGACTCGCCTCATCGAAGTGTACTGGTGATCCCTGATACTCATGCACCTTATGAGCACCCAGATACCCTAGAGTTCCTTGCAGCCGTGGCA
GCACGTTACCGTCCAGACACAGTGGTACACCTAGGAGATGAGGCAGACAAACATGCCCTGTCATTCCACGATTCGGACCCAAATCTGGATAG
TGCTGGCATGGAGTTAGAGAAGGCTCGTATCTTCATGCACAAATTGCACAAGATGTTCCCTGTGATGCGCCTGTGTCACTCTAACCACGGCTC
TATGCACTTCCGTAAGGCAAGCGCCAAAGGCATCCCTGTGCAATACCTGCGCACCTATCGTGAAGTCTTCTTCCCGCAGGGAGGTGGCGACC
AGTGGGATTGGCAACATACGCACGTCCTTGAGTTGCCGAATGGTGAACAAGTGGCATTCAAGCATCAACCTGCTGGCTCTGTCCTAGCAGAT
GCAGCGCATGAGCGTATGAACCTTGTGTGTGGTCACTTGCACGGTAAGATGTCTGTGGAGTACGCACGTAATACACATGAACAGTATTGGGC
TGTGCAAGGTGGCTGCTTAATTGATGAGTCATCCCGTGCATTTGCCTATGGTCGTGAGTCTAAATACAAGCCAGCATTAGGTTGTGTGGTCAT
TCTGGAGGGTGTGCCTCACATTGTCCCGATGCAAACCAATAGCGACAACCGTTGGATTGGCAAGATTTAGTTGACACTATAGAACAAAGGGC
TAGGTAAGACTTTATCGGCTGGCGTATCCAAATGATATTGCACTAGCCCTTGATTGTATAGTGAATGGAGGATTCAATATGTCACACTATGAA
TGTAAGAAGTGTCATAAGCGTTATGATTACTGTACTTGTGGTCAAGAGAAAACATCTTTTAAAGTTGGAGACAAGGTATTTCGTAATGAAAAA
```

Figure 4E

```
GATTCGATTCCTTGGAATCAATACTGCAAAGAAGCTGGTATTGACCCTGATAGCCCTGTAACCATAGATGATATTGATGGCATTAACTTGTGCT
TTCGTGAGGTGAGGGGTACAGGTTGGGATTCCAAAAAATTCAAACTTGCATCTGATAAGTTAGACAACAATATGGTAATTAAGCCTAAGCAC
TACGAGTTCTTTGATGGCGTAGAGGCAATCACTATCATTGCCCGCAGTATGACCGAGAAGCAATTCGCTGGCTATTGCATGGGTAATGCTTTG
AAGTACCGTCTACGTGCAGGTAAGAAGTTCAACACTGAAGAAGACCTGAAGAAAGCAGATTACTACAAAGAGTTATTCCAGAAGCATCGTCA
CGAATGTATTGATGAGGATATTTGATATGAATATCTTTGAGTTCCTAGGTCTTCCAGAAGACCACCGCAATCACCCATTCATGCTGGTGAAGC
ATCGCGGTGAAGTTCCTGAGAAGAAATTAACTTTTCCATGTTATGCACAGGTGAAACGAGATGGTATCTTTTCTGCTGTTGTTGTTCGCACTGA
TGGTGTCGTTGGCATTTTTGGTCGCACTGGTAAGAAATTGGCAAACACTGAAGGACTCGAACAAGCCTTTGCTACCTTTCCGGTTGGCATTTA
TCTTGGTGAGCTTCAGTCTATGGCCATTGATATCTACCTTGAGGCAATCTCTGGGGTTGTGAACCCCAATCGCACTGAGCCACTTGATTTCATA
GGCCAGCAGATTAAAGACAACCTGTATATCGACTTCTTCGATATGTTAACTATTAAGGCATTCCATGATGGATTCACTGATGTTTCTTATCTCA
AACGTTACGATGCTTTACATCGTCGTATCGGCGCTCATCTTAGCGGGTGCAACGCTATCCTTCCTATCACTCCTTGCCATAATGAGCGAGAAGT
TGAAGCGTTTGCGCAAGAGCAAATAGATGCAGGACGTGAGGGTGCTGTATTCAAACTGGACTGCGATTATGAAGCAGGACACAAAGGTTAT
CGTCAGACTAAAGAAGTCCGTAAGGTAACCTATGACCTTACTTGTATTGGCTTTGAAGAAGGTAAAGGCAAATACAAAGGTAAGGTAGCTAA
CCTCATTTTCAAATGGAAAGGAGGCAAGACAATCAAAGCTATGTTAGGTAAGGGGTGGACTCATGCAGATGCAGAGCAGATGTTCCACGAC
ATTAAACATGGTGGACGATTGAATGTCATTGGTAAAATCTTTGAAGTCAAAGGTCTTCAGGATTCAAGCAAGGGCAACATTCGTCTGCCCAAA
GCGGGAGAATTAAGACATGACAAAGATGAACCAGATTTCTTTTGATAGCATGAAGGCAACTCGTGCAGTTGAGGTAGCAGAAGCTATCTTCG
AAACTTTATCCTGTGGCATGGAAGTGCCATATACTTTACTTGCTGATGCAGAAGAACTTGGTCTTTCTGTAGAAGCTATCCAAGAGAAGGTTG
ACGAATTATATGGTACAGACGAAGAAGAAACCGACGATTTCATTTGAAGGAATGGAGATGCTTGAGATGATTCTCAAGCCTTCTTCTCCTAAG
GTGACTAAGACTCATGAAGAGTTAATCGTTGATGAAGTTAAGCGTTACATCATGGATTGTGTCAGAGCACAACTGGTGGTCCAATGATACGT
CCAGCCTCCTTCCTAGATATTCCTGAGATTATAAACCTTGGGAATAAATATGTGGAAGAGGAAGTCAAGGTTGTAGCCCACCACTCAGCCTCA
TGGAATGCAGAACAAAGTGCCATAACCTTTGTGCATCTCTTAATAGAGACCCACCACTCAGCCTCATGGAATGCAGAACAAAGTGCACATAAC
CTTTGTGCATCTCTTAGTAGAGAAGATTTATCCCTATGGGTTGCTGTAGATGAAGGGCAGATTGTAGGGTTCCTGTGGGCTGGCTATCACGAG
TTGGCCCCTTGGACACCTGTAAGAGTTGCCTCTGACATTCTCTTTTATATTATACCAGAGAGGCGAGGAACACTACTTGGTATGCGTCTCATCA
AAGCCCTAAAGCAATGGGCTAGTGATAATGAATGCTCTGAGGTTCGCCTGTCTATCGCCTCTGGTATTAATGAAGAACGTGTCGGACGTATGT
ATAAGCGACTTGGCTTTGAACCGTTTGGCACTGTGTATAACCTGAAGTTCTAAGGAGATAACATGGGTGTTGTAAAGAAAGCATTTAAGGCT
ATCGGTCTTGCTCAAGATGCACCACGTATTGAAGCCAAAGTCCCAGCACAGCAGCTTGAGCGTAAGCCTGAGACTGAAGCTGAAGATATTCA
AATTGGTGCAGGGGATGATGCTACTGCATCTGCAAAAGGTAAGCGTGGCCTTGTCCGTCCGGTAGCTTCTAGCTTGAAGGTGTAATATGAAA
CAGAGCATAGATTTGGAGTATGGAGGTAAGCGGTCTAAGATACCTAAGCTATGGGAGAAGTTCTCCAATAAACGTAGCTCTTTCCTTGATAG
GGCGAAGCATTACTCCAAATTAACCTTGCCCTATCTGATGAATGACAAAGGTGATAACGAGACTTCGCAGAATGGATGGCAAGGTGTAGGTG
CTCAGGCAACCAACCATCTAGCCAACAAGCTAGCGCAAGTACTATTCCCTGCACAGCGTTCCTTCTTCCGTGTAGACTTAACTGCACAAGGTGA
GAAGGTTCTTAATCAGCGTGGCCTGAAGAAGACAGAGCTAGCTACCATCTTCGCTCAAGTGGAAACACGGGCAATGAAAGAGTTAGAGCAA
CGTCAATTCCGGCCTGCTGTAGTAGAAGCATTTAAGCATCTTATTGTTGCTGGCAGCTGTATGCTATACAAGCCGAGCAAAGGTGCAATCAGT
GCTATCCCAATGCATCACTACGTAGTTAACCGTGATACCAATGGCGACCTGTTAGACATTATCTTGCTACAAGAGAAAGCCTTACGTACCTTTG
ACCCAGCTACACGTGCGGTAGTAGAGGTTGGCCTGAAAGGTAAGAAGTGCAAGGAAGATGACAGCGTTAAGCTGTACACACATGCTAAGTA
TCTTGGTGATGGATTTTGGGAACTCAAGCAATCTGCTGATGATATCCCTGTGGGTAAGGTGAGTAAAATCAAATCAGAAAAGCTACCTTTCAT
CCCATTAACTTGGAAGCGAAGCTATGGTGAGGATTGGGGTCGACCTCTTGCAGAGGATTACTCCGGTGATTTATTCGTTATCCAATTCTTATCT
GAAGCGGTTGCCCGTGGTGCTGCGCTGATGGCAGATATCAAGTACCTGATTCGTCCTGGTGCTCAAACTGATGTTGACCACTTTGTTAACTCT
GGCACTGGTGAGGTTGTCACTGGTGTAGAAGAAGACATCCATATTGTACAGTTAGGTAAGTACGCAGACCTCACACCTATTAGCGCGGTTCT
AGAGGTATACACTCGCCGTATCGGTGTTGTCTTCATGATGGAGACAATGACACGCCGTGACGCCGAACGTGTTACTGCTGTAGAAATCCAGC
GAGATGCGTTAGAGATTGAGCAGAACATGGGTGGTGTATACTCCCTCTTTGCTACTACTATGCAATCGCCAGTAGCGATGTGGGGTCTGCTG
GAGGCAGGGGAGTCCTTCACTAGTGACTTAGTGGACCCTGTGATTATCACAGGTATTGAAGCTTTAGGACGCATGGCTGAGTTGGATAAACT
GGCTAACTTTGCTCAGTATATGTCACTGCCATTACAATGGCCTGAGCCTGTCCTAGCTGCTGTGAAATGGCCTGACTATATGGATTGGGTGCG
TGGTCAAATCTCTGCTGAACTGCCGTTCCTTAAATCGGCTGAAGAGATGGCACAAGAACAGGAAGCACAGATGCAAGCACAGCAAGCACAG
ATGCTTGAAGAAGGTGTGGCTAAGGCCGTGCCGGGTGTAATTCAACAAGAACTTAAGGAGGCGTAATGTCTTTCTCATTTACTGAACCGTCA
ACCACTCACCCTACTGCTGAAGAGGGTCCGGTAGAAACCAAGGAGGTAACAACTGATGCTGCTACTACTGATGCTCCTGCTGACGCTGGCAC
TTCTGTACAAGATGACAATGCTGGTCACAACCTACTGAAGACACCGGAGGAGAAGCTTCTGGACAGCCTTCAGAAAAAGGAGACAATGGC
GGAGAGAATGGTGAACCTAAGCCAGATGATACCGCGACCGACACTGAGGAAGTGCAATACTTCTTCGGAGAACATGAAGTAACAGTAGACA
TCCCACAGGATGTAACTGACAGCCTTAAAGAGAAAGGCATTGATGCCAAGCAGGTTGCCAAGGAACTCTATTCCAAAGGTGGCAAGTTTGAA
CTGTCAGATGCAACCAAGCAGAAATTGTATGATGCTTTGGCAAGTTTGCGGTAGATGCTTACCTATCAGGTCTAAAGGCTCAAAATGAAGCC
TTCTTCCTGAAAGAAGCCAACGCAGCTAAAGAGTTGGAAGCAGCTAACACCCAACGCTTCTCTGATGTTTCTAAGGAAATTGGTGGCGAAGA
AGGTTGGTCCCGTCTTGAGGAGTGGGCACTTGAAGCGCTGTCTGATGACGAACTAATGGCATTCAATGCGGTGATGGAATCTGGCAACCAGT
ACCTGCAACAATATGCTGTTCGTGAACTGGAGGGTCGTCGTAAGCAGGCACAGGGGGATGATAAGCCATCCCTGATTGAGCCATCAGCACCT
```

Figure 4F

```
GCTAAGGCTAATGAAGAGAATGGCCCACTGACGCGAGATCAGTACGTTCAAGCAATCGCAACTCTTAGCCAGAAGTACGGCAATGACCGTAA
AGCTATGGCAGAAGCTCAGGCTAAACTGGACGCCCGTCGCCGTGCTGGCATGGCTCGCGGTATCTAATTCAGTATTTACTGGACACTATAGA
AGGGAGAAAAGTTCTCCCTAGTTATCAATTTGATTTATAAGGAGATTATAATACATGTCTACACCGAATACTCTGACTAACGTTGCTGTATCTG
CGTCCGGTGAGGTTGACAGCCTTCTCATTGAGAAGTTTAATGGTAAGGTCAATGAGCAGTACCTGAAAGGTGAGAACATTCTGTCCTACTTTG
ATGTACAAACTGTTACTGGCACTAACACAGTGAGCAACAAATATTTGGGCGAAACTGAGTTGCAGGTGCTAGCACCGGGTCAGTCCCCTAAT
GCCACCCCTACTCAGGCGGATAAAAACCAGTTGGTAATTGATACCACTGTCATTGCTCGTAACACTGTGGCTCACATCCACGATGTACAAGGT
GACATCGATAGCCTGAAACCAAAACTGGCTATGAACCAAGCCAAGCAACTGAAACGTCTGGAAGACCAGATGGCAATTCAGCAGATGCTGTT
AGGCGGTATTGCTAACACCAAGGCCGAACGTAACAAGCCGCGTGTTAAAGGGCATGGCTTCTCTATCAACGTTAACGTAACTGAGAGTGAAG
CACTGGCTAACCCTCAGTATGTTATGGCTGCGGTAGAGTATGCTCTGGAGCAACAGCTTGAGCAGGAAGTGGACATCTCTGATGTAGCTATC
ATGATGCCGTGGAAGTTCTTCAATGCTTTGCGTGATGCAGACCGAATTGTAGATAAGACTTACACTATCAGCCAGTCTGGTGCAACCATTAAT
GGCTTCGTTCTCTCTTCTTATAACTGCCCTGTGATCCCGTCTAACCGATTCCCTACCTTCGCTCAGGATCAGGCTCACCACCTGTTGTCTAATGA
AGATAACGGCTATCGTTATGACCCTATCGCAGAGATGAATGGTGCAGTTGCTGTTCTGTTCACTTCCGACGCACTGCTGGTGGGTCGTACCAT
TGAAGTGACTGGTGACATCTTCTATGAGAAGAAAGAGAAGACTTATTACATTGACACCTTCATGGCTGAGGGTGCAATCCCTGACCGTTGGG
AAGCAGTGTCTGTAGTTACCACTAAACGTGATGCAACTACTGGTGATGCTGGAGGTCCTGGTGATGATCACGCAACCGTACTGGCTCGTGCA
CAGCGTAAGGCTGTATATGTCAAAACCGAAGGTGCTGCGGCTGCATTCTCTGCTGCCCCAGCAGGTATCCAAGCGGAAGACCTTGTAGCGGC
GGTACGTGCTGTAATGGCAAATGACATTAAGCCGACTGCAATGAAACCTACTGAGTAACACCTATGCCCTATCTACCTTGCGTAGGTAGGGTT
CTTTTTGTTAGGAGGATTCATGCCTGTAATTAGACAAACCAGTAAATTAGGACATATGATGGAAGATGTGGCCTTCCAGATTATTGATAGTAA
GCTGGAAGCGGTAAACTTGTGTATGCGAGCTATTGGTCGTGAGGGTGTGGATTCCCTGACTCAGGGGACTTGGACGCAGAAGATGCAAGC
AAAATGATCGACATCGTATCCCAGCGGTTCCAGTACAACAAAGGAGGTGGCTGGTGGTTCAATCGTGAACCAAACTGGCAACTTGCACCAGA
CACTAACGGTGAAGTTAATTTACCTAACAACTGCCTAGCAGTATTGCAGTGTTATGCTTTAGGTGAAAAGAAAGTACCTATGACTATGCGAGC
AGGTAAGCTCTACTCTACTTGGAGTCACACCTTTGATATGCGTAAGCATGTTAATGCTAATGGTATGATTCGTCTTACCTTACTCACCTTACTAC
CCTACGAGCATCTACCTACAAGTGTAATGCAGGCTATTGCCTATCAAGCTGCTGTAGAGTTTATTGTGTCTAAGGATGCAGATCAGACTAAGC
TAGCCACTGCGCAGCAGATAGCCACTCAGCTTCTTATGGATGTACAATCTGAGCAAATGTCACAGAAGCGATTAAACATGCTGGTACATAACC
CTACTCAGCGTCAGTTTGGTATCATGGCTGGTGGCTCTCAGAATGTACCTGCTTACTCTCATTCACCTTATGAGAGTTGGGCGCTCCGTCCGTG
GGAGGATCGTTAATGGAAGTACAAGGTTCATTAGGTAGACAAATCCAAGGGATTAGCCAGCAGCCGCCAGCGGTACGCTTGGATGGTCAGT
GCACAGCTATGGTTAATATGATACCTGATGTAGTGAATGGTACTCAATCACGCATGGGTACAACTCATATTGCAAAGATACTTGATGCGGGG
ACTGATGACATGGCTACTCATCATTATCGCAGAGGTGATGGTGATGAAGAGTATTTCTTCACGTTGAAGAAAGGACAAGTTCCTGAGATATTT
GATAAGTATGGGCGCAAATGTAATGTGACTTCACAAGATGCACCTATGACCTACCTCTCTGAGGTTGTTAATCCAAGGGAAGATGTGCAATTC
ATGACGATAGCTGATGTTACTTTCATGCTTAATCGTAGGAAAGTAGTTAAAGCTAGTAGCAGGAAGTCACCTAAAGTTGGAAACAAAGCCATT
GTGTTTTGTGCGTATGGTCAATATGGTACATCTTATTCCATTGTAATTAATGGGGCCAACGCTGCTAGTTTTAAAACACCGGATGGTGGAAGT
GCAGACCATGTTGAACAAATTCGAACTGAACGTATCACTTCTGAATTGTACTCTAAGTTGCAGCAATGGAGCGGTGTGAGTGACTATGAAATA
CAAAGAGACGGTACTAGTATATTTATCGAGAGACGGGATGGTGCTAGCTTTACAATAACAACCACCGATGGTGCAAAAGGTAAGGACTTAGT
GGCTATCAAGAATAAAGTTAGCTCTACTGACCTACTCCCTTCTCGTGCGCCTGCTGGTTATAAAGTACAAGTGTGGCCTACTGGCAGCAAACC
TGAGTCTCGTTACTGGCTGCAAGCTGAGCCTAAAGAGGGAAACCTTGTGTCTTGGAAAGAAACAATAGCTGCTGATGTATTACTTGGGTTTG
ATAAAGGCACAATGCCTTACATTATTGAACGTACAGATATCATCAACGGCATAGCTCAATTCAAGATAAGACAAGGTGATTGGGAAGATCGT
AAAGTAGGGGATGACTTGACTAACCCTATGCCCTCTTTTATTGATGAGGAAGTACCCCAGACAATAGGTGGAATGTTCATGGTGCAGAACCG
CCTATGCTTTACAGCAGGTGAAGCGGTTATTGCTTCTCGTACATCATACTTCTTCGATTTCTTTCGTTATACGGTTATCTCTGCATTGGCAACTG
ACCCCTTTGATATTTCTCAGATGCTAGTGAAGTCTACCAGCTAAAACATGCAGTGACCTTAGATGGCGCTACCGTGTTGTTCTCTGATAAGTC
ACAATTCATACTGCCAGGCGATAAGCCTTTAGAGAAGTCAAATGCACTGCTTAAGCCTGTTACAACATTTGAAGTGAACAATAAAGTGAAGCC
AGTAGTAACTGGTGAATCGGTAATGTTTGCCACTAATGATGGTTCTTACTCTGGTGTACGAGAGTTCTATACAGACTCTTATAGTGACACTAA
GAAGGCACAAGCAATCACAAGTCATGTGAATAAACTCATCGAAGGTAACATTACCAACATGGCAGCAAGCACCAATGTCAACAGGTTACTTG
TCACTACCGATAAGTATCGTAACATAATCTACTGCTACGATTGGTTATGGCAAGGAACAGACCGTGTACAATCAGCATGGCATGTATGGAAGT
GGCCTATAGGTACAAAGGTGCGAGGTATGTTTTATTCTGGTGAATTACTTTACCTGCTCCTTGAGCGAGGAGATGGCGTGTATCTGGAGAAG
ATGGACATGGGTGATGCACTAACCTACGGTTTGAATGACCGCATCAGAATGGATAGGCAAGCAGAGTTAGTCTTCAAGCATTTCAAAGCAGA
AGATGAATGGGTATCTGAGCCGCTCCCTTGGGTTCCTACTAACCCAGAACTTTTAGATTGCATCTTAATCGAGGGTTGGGATTCATATATTGGC
GGCTCTTTCTTATTCAAGTACAACCCTAGTGACAATACTTTGTCTACAACCTTTGATATGTATGATGACAGCCATGTAAAAGCGAAGGTTATTG
TTGGTCAGATTTACCCTCAAGAGTTTGAACCTACGCCTGTGGTTATCAGAGACAATCAAGACCGTGTATCCTACATTGATGTACCAGTTGTAG
GATTGGTTCACCTTAATCTTGACATGTACCCCGATTTCTCCGTAGAAGTTAAGAATGTGAAGAGTGGTAAAGTACGTAGAGTATTAGCGTCAA
ACCGTATAGGTGGTGCTCTCAATAATACAGTAGGCTATGTTGAACCGAGAGAAGGTGTCTTCAGATTTCCACTGAGAGCTAAGAGCACGGAT
GTTGTTTATCGTATTATTGTAGAGTCACCTCACACATTCCAGCTTCGTGATATTGAGTGGGAAGGGAGCTACAATCCAACCAAAAGGAGGGTC
TAATGGCTATAGGTTCAGCCGTTATGGCTGGTATGTCTTCTATTGGTAGCATGTTTGCAGGCAGTGGTGCAGCAGCCGCTGCTGGAGGTGCT
```

Figure 4G

```
GCCGCAGGTGGCGGAGGTTTGCTAGGTTCACTAGGTGGATTCCTAAGTGGCTCTACTGCTGGTTTCTCTAATGCTGGCCTTCTTGGTGCTGGC
CTTCAAGGGTTAGGCTTGATTGGTGATCTATTTGGTGGAAGTGATGAAGCCAAGGCGATGAAGAAAGCACAAGAAGAGCAATGGCGGCAGC
AGCTTATTGCTACACAAGAGGCGTACAAGACAGTGGCAGACGCAGAACGTTCTGCTGCTAAACAATATCATGCAGATGCAATCAGTAATCAG
GCTTCACTGCTACAGCAGCGAGCACAGGTTGCATTACTTGCTGGGGCTACTGGTACTGGTGGTAATTCTGTGTCCTCTATGCTTAATGACTTA
GCAGCAGATGGCGGCAGGAACCAGAGTACTATCATTGATAACTATGAGAATCAGAAGATTAATTTCACCAACCAGCTTAAGTCTATCCAACGT
GGTGGTCAGATGCAGATGCGTGAGTTTAAGAAGCCTTCTGCTATGAATACCTTGGTTAAAGGTATTCCAAGTCTGGCATCTGCCTATGTAACT
GGTAGTAAGTCTGGCAAGGCATTGGGTAAAGCCTTAACTGATTCTCGCACATATTCATCTGGAACAAGAGGTATTTAATGGCAATTGAGCGA
CAAGCAGTACAAGGTCTGCCACAAGTGCAGGCCACTTCTCCTAATGTCATGACCTTTGCACCTCAACAAGTGGGAGGTGTGGAGGCTGGCGT
GGCTTCTACCTCCGGTAGTAGGTTTATCGAAGACCTTATTCGTGCAGCAAGCAGCGTGGCTGATGTTACCACTGGTATCCTTAATCAGAAGAT
TGAGGAAGATAAGGTTGTTCAAATGGAACGGGCATATAACGGATTAATGCCTTCTGAGGATGCAACTCGTGGTGGCGCTCGTGCTAACATGC
TTGTCAAAGCTCAACTGCTAGCTAATGATGAAGCAGCACGAATGAAAGACATGGCTACTCGTTTCCAAGGAACGGATGACGAATGGACACAA
CTTATGGTTGACTCTCGTAATGAGATGCAGAATAAGCTGTTCCAGCAATACCCTGAGTTGCAAGGTGACAAAGATACTATGCGTATGGTCACT
AATGTCTTCCAAGAACAGCAGCCTCAGATTTGGGCTACACGAACCCAGCATAAACTTGACCGTGAACAAGCAGACCGTGAGGATACCTTTGA
CGGGCGAGTGGCTTCTACTTGGGATTCTAATATTGACCCTGAAGCCTCTGGCTATGCTTTACAGGAACGAATCCGCGAAGGTCTTACTCAAGG
ATTACTACCTGAACAGATGTACAAGAAGTTAGTCCAGCGAGCAATTTCACTTGCACAAGGCGGTGATGTTAGCATGGCTGAAGCCCTGAAGT
ATGTGAAGGACGATAAGGGTGTTTCTGTTTATGCTAAGAATCCACAGCTTATCACAGCCATCACTAGTGGTAATGCAGTTTGGGCTAGGAATA
ATGTAGCTGATGTAACTCGTATGTCTTTCGAAGTTAAAGAATCCTACCTTGCAGGTGATTTAACTGATGAAGAATTGTTGGAACGAGCACAGC
ACATTAATAATCTGACAGGTAACTCTGTCTTCTCTAATCCAGAACTAGAGGCACTGATGCGCCAACGGGCTAAGCAGAATGCAGAGCTAGGT
GCAATGCAGGATATGCGACGTGAGCTTTACTCCGACCGCCTGACTGGCTTCCAAGGTAAGACTGATAAAGAGAAGAAGGCTTACATTGATGT
TATCAAACAGGATAGCCAACTTTATGCAGACCAGCAAATCAAACAACGTGGCTTGGACCCTTACAGTCAAGAGGCTGAAGCTATTCGTGGTG
CAGTGGAAGTGCAGCGCCTGCAATTCATGAACTCCAAAGGCTTAGTGGATGATACCTTTGAGTCTCGTATCAAAGCCATGGAATCTATGCTAT
CGCCTGAGCACTTTGCCAAGGGCGAACCACAGGAGTTGATGACTATTCGCCAGTTGTGGGAACAGTTACCAGAAGAGAGCCGAGGTGTCTTT
GGTGACACGGTGAATGGCTACATGGATAACTACAACACTGCACTACAAATGGGAGAGACACCTTTGCAGGCTGCAAGGTTTGCGCGTAAAG
CACAGCAGAAAATTCTCTCGTACTGAGAAGGAAACCAAGAAGTTCAACTCAGCTATTGGAGATGCACTGGATGAGGTATCTGGTGCTGGCTGG
TTTGATGGTAAAACCGAAGTGTCAGACTTAGGTAAAGCTATTGCGGAAGAAGAGTTACGAGCTAAGGCCAATATGTTGTGGTCTAGTGGTAT
GCGTAACATGGATTCCATCAAGAAGGCTTTAATTACTTGGGGCAATAAACGCTACACTCAATCAGAGGATGCAAAGACTTCCGGTGGCTATTT
CATTAAAGGTGATTACACTTCTGCATCTGATATGCTTATGTCAGTTGGGAAAGGCGTAAACCCTACCGATGTACCTCTGGCGCTTGGTAGGTA
TGTAGAAACACAGATGCCAGAATTGAAGAAGGAGCTTCAAGAGGGGGAAACTAAAGATGATATATACATTGATTACAATGAACAGAAAGGT
ACTTTCGTGATTCGTGCTGGTGCAGCAGGTCGCCCTCTTTCTGGAGTAATCCCTGTAACCTCTTTAGATACCACTTCACTACTAGATTCTGCCTA
TCAGAAGAAAGTAGAGGAACGAGATAAAGGCGAGTATGTTCACCCGTATCGTACAGATATTGGTGCACAAGAGCCTATGCCAGCTAAACCA
ACTGCCAAAGATATTGGTAAATTTGGACTAGCTAACTTCCTCATGTCTTCTGCTTTTGCTTCTGGTGAGAATCTGCCTTCTAACTTCGAGATTAA
CTATCGAGGTAATATGCAACAATTCTATGACAAGCTAGCTATGGATGAGAATAAAGATAAAGTTGGCTTTAATAAGGCAACTGGAACCTTTAC
TCCATATAAAGACGCTCACGGTGAGTCTATCGGTTACGGTCATTTCTTAACGGAAGAAGAGAAGCGAAACGGGTATATTAAGATTGGCGATG
AACTAGTTCCCTATCGAGGGTCTATGTCTCAGCTTACAGAGAGCAAGGCTCGCGCTCTTATGGAGCAAGATGCTAAGAAGCATGTGCCTCCTA
CTCGTGACTGGAAGATTCCGTTTGACCAGATGCACCCTGCACAGCAACGTGGCTTGATGGATTTAAGCTACAATTTAGGTAAAGGTGGAATCC
AGAACTCACCGCGTGCTCTTGCTGCATTCAAAGCTGGTAAGCTTACGGAGGGCTTTATCGAAATGCTGGGCACTGCATCAAGTGAAGGTAAG
CGTATTCCTGGCCTACTGAAGCGACGCGCTGAGGCATACAATATGGCATCTGCTGGTGGTGTGCCTAAGATTACCGAAGTGGAGACTCGTGA
AGATGGCTCCATGTGGGTTAGGTTTGGTGGACCTATGCCAGCAGGTTCTGTCTCGGCATGGACTCATAAACGTATTGGCGCGGATGGTTGGT
ATCAGGTTTATGAGGCTGCACCTACCAAGTTAGCTAAAGATTCTAAGGTAGGTAAAGTTAAGTTGTAGTACCTAACTCAAGGCTTGTCTCACA
TGTGAGACAGGTCTTTATGATAGGCACTATGGAGGAATTATGGAACAAGACATTAAGACTAATTGGGCTGGATATGTCCAGTCTACTCCTGA
GCCGTTTTCTATTGAGGCGGCTCCGGTATCGGCTCCTACGATACGCCAGCGTAATGAGTTACAAGAGCAAGTTCTTGAAGCTAAAGCTGACGC
TGATATCTTAGGTGCTGTAGGTGCTGCCTTCCAGAATGAGTGGTTGGCATTCGGAGGCAAGCGGTGGTATGACCGTGCCACTGCTGATTTCA
CACCTCAACCAGACTTTGAGATACAACCTGAGCAACGTGAAGCACTACGTTTCAAATATGGTACGGATATGATGCAGACAATCACTGAGGGT
GTTCGTTCTGAGGATGAATTGAACTTCCGTATTCAGAATGCGGATGAAGACCTTGAGCGCAATAAGCGCATTGCTCAGGCTGGCTGGGTTGG
CTCTGTGGCGACGATTGGCGCTGCTGTGCTTGACCCTGTGGGATGGGTTGCCTCTATTCCAACCGGTGGTGCCGCTAAAGTTGGACTCGTAG
GCCGTGCTGTGCGTGGCGCTATCGCCGCTGGCGTGAGTAATGCCGCTATTGAATCCGTATTGGTCCAAGGTGACATGACTCGTGATTTAGAT
GACATTATGGTAGCACTGGGTTCCGGTATGGCTATGGGTGGCGTTATTGGCGCTGTAGCGCGTGGTAGGGCCACTAAGCTCAGTGAGCAAG
GTGATGACAGGGCTGCTAGCATTGTGCGCAGTGCAGACGCAGGGGACCGCTATGTTCGTCGTGTTGCCGATGACAGTATCGGTGCGATGCG
TGTTAAGGGCGCAGAGGTTCTCACTGAGGGTGTATTCGATATCTCCAGTAAGAGTGAAGACCTACTGAAAACCTTGCAACGAGAAGGTAATG
CGATTGATATGACACCTCGCCGTTGGGCTGGAACTATGTCTGCCCTCGGTACTGTCGTGCACTCATCAAAGATGCAAGTATCCGAGGCCTTG
GTGCTCGTCTGTTTGAATCCCCACAAGGTCTAGGTATGCAGAAGGCATCTGCTAGTCTTATGCAGAATACTAACTTAAATCGCCTGAAATCTGC
```

Figure 4H

```
TGATATGAACCGCTTCAATGATGGGTTTGATTTGTGGCTTAAAGAGAATAATATCAATCCAGTAGCAGGGCATACCAACTCTCATTATGTACA
GCAATACAATGAAAAGGTGTGGGAGGCAGTGCGTATTGGCATGGATGAGTCTACACCTAAATCTATCCGCATGGCTGCTGAGGGACAACAG
GCTATGTACAGAGAGGCGCTGGCTTTACGTCAACGTTCTGGTGAAGCGGGATTTGAAAAGGTAAAAGCCGACAACAAATATATGCCTGATAT
CTTTGATAGTATGAAAGCCAGACGTCAATTCGATATGCACGATAAAGAAGACATCATCGAACTTTTCTCTCGTGCCTACCAGAATGGCGCTCG
TAAGATTCCAAAGGAAGCAGCAGATGAGATTGCACGAGCACAGGTAAATCGCGTTGCTGATGCTACCTTAACTGGAAAGCTTAGTTTTGAAA
AGGCAATGTCAGGTCAGACTAAGGCAGAGTATGAAGCTATCATGCGTAAGGCAGGCTTCAGTGATGAAGAAATTGAAAAGATGATAGAAGC
TCTGGATAACAAAGAAACCAGAGATAACATCTCTAACCGAGCTAAAATGAGTTTAGGATTAGATGTTACTCAAGAATACAATGGCATTCGTAT
GCGTGACTTCATGAATACCAACGTGGAAGAGCTAACAGATAACTATATGAAGGAAGCAGCAGGTGGCGCTGCATTGGCTCGCCAAGGCTTCT
CTACCTATCAGGCTGCACTTAATGCAATTGACCTTGTAGAGCGAAATGCACGAAACGCGGCTAAGGATAGCAAGGCTAGTTTGGCATTAGAT
GAAGAGATTCGTCAGATGCGAGAAGGTCTTCGCCTGATTATGGGCAAGTCGATTGATGCAGACCCACAGGCTATATCTACTAAGATGATGCG
TCGTGGTCGTGATATCACAGGTGTGCTTCGCTTAGGTCAAATGGGCTTCGCACAGCTAGGTGAACTTGCCAACTTTATGGGTGAATTTGGTAT
TGCTGCAACTACTATGGCTTTAGGTAAGCAATTCCGCTTCACCTCTAAGGCGTTGCGTAATGGCGATGGCTTCTTCCGAGATAAGAACTTAGCT
GAGGTTGAGAGAATGGTGGGGTACATTGGTGAGGATAACTGGCTAACAACTAAGGGTGCACGTCCTGATGAATTTGGTGATGTAACCACAG
TAAGAGGGATGATGGCTCACTTTGACCAATCCATGAACTCAATACGTCGTGCTCAAACCAACCTATCACTCTTCCGCATGGCACAGGGTTCTCT
GGAGCGAATGACTAATAGGCAAATAGCTTTGTCTTTCATTGACCACCTTGAAGGCAAGAAGATTATTCCTCAGAAGAAACTGGAGGAACTTG
GTCTTACTCAGGAGTTCATGACTAACCTACAGAAGCACTATGATGCTAACTCTAAAGGTTCTGGCTTGCTTGGCTTTGATACAATGCCTTATGC
CATGGGTGAAACTTTAGCTAATGCTATTCGTCGTAAGTCAGGTCTAATCATCCAACGTAACTTCATTGGTGATGAAGGTATCTGGATGAACAA
AGCACTAGGTAAGACATTTGCACAGCTTAAGTCATTCTCTCTTGTATCTGGTGAGAAGCAATTTGGTCGAGGGATTCGCCACGATAAAATTGG
TCTTGCTAAGAAGACAGCTTACGGGTTTGCTTTGGGTTCAATAGTGTATGCGGCAAAAGCCTATGTGAACTCTATTGGGCGAGAAGACCAAG
ATGAATATTTGGAAGAGAAGTTATCGCCTAAAGGGTTGGCCTTTGGTGCAATGGGTATGATGAGTACAACTGCTGTATTTAGTCTAGGTGGA
GATTTCTTAGGTGGCCTAGGTGTTCTACCTTCCGAACTCATTCAATCACGCTATGAAGCAGGTTTCCAAAGTAAGGGTCTGATTGACCAAATAC
CTCTGGTTGGCGTTGGTGCAGATGCAGTAAATCTGGCTAACTCAATCAAGAAGTATGCAGAAGGTGACACAGAAGGTGTAGATATCGCTAAG
CGAGCACTCCGTCTTGTGCCACTTACCAATATAATAGGTGTCCAAAACGCATTGCGTTATGGCTTAGATGAACTGGAGGATTGATGAGTTATA
CTTTCACAGAACATACAGCCAATGGTACGCAAGTCACCTATCCTTTTAGCTTTGCTGGTAGGGATAAAGGTTATCTTCGTGCCTCAGATGTGAT
AGTGGAGTCTCTTCAAGGTAACACTTGGATTGAAGTTACATCTGGCTGGCAACTAACTGGCACGCACCAGATTACTTTTGATGTAGCACCAGT
TGCAGGTTTGAAGTTCCGTATTCGAAGGGAAGTACAAAAAGAATATCCATACGCTGAGTTTGACCGTGGTGTTACCTTGGATATGAAGTCTTT
AAATGGTTCTTTCATTCATATACTGGAGATTACACAGGAGTTACTTGACGGGTTTTATCCAGAAGGATACTTCATTAAACAGAATGTAAGCTG
GGGCGGCAATAAGATTACTGATTTGGCTGATGGCACAAATCCGGGAGATGCAGTAAATAAAGGGCAGCTTGATGCCATCGACAAGAAGCAT
ACAGATTGGAACGCCAAACAGGACATTGAGATTGCTGGCCTTAAGGCTGGTATGACTTCTGGTATTGCGCACAGAACTGTTCCTTGGTACAC
GATAGCCCAAGGTGGTGAGATTTCCGTAAAACCACCTTATGAATTTCAAGATGCACTAGTTTTCCTTAATGGGGTATTGCAGCACCAAATTGT
AGGCGCATACTCTATAAGCAACAACACTATCACTTTCGCAGAGCCGCTTGTGGCTGGTACAGAGGTGTATGTGCTGATTGGTAGTCGTGTGG
CTACATCTGAACCTAATATTCAGTTGGAGTTGAACTTTGACTTAGTAGAAGGCCAACAAGTAGTACAGATTGGCTCTGCATTTAAGTACATTG
AGGTCTACCTTGATGGATTATTACAACCTAAACTTGCTTATCAGGTAGACGGTGACATTGTTACTTTCTCAGAAAGAGTACCAGAATGCCGGA
TGACTGCTAAGATTATCACAGCATAAGGAGGTGGGATGATTAACTCCGAACTGGTAGATAGTGGTGTGAAGCTTGCGCCACCTGCACTCATA
TCAGGTGGGTACTTCCTCGGTATCAGTTGGGATAATTGGGTGTTAATAGCAACATTCATTTATACCGTGTTGCAAATTGGGGACTGGTTTTAT
AATAAGTTCAAGATTTGGAGGGAGAAGCGTGAGCGTACACAATAAACATGCAGCTACAGAGGACGAGGTTGGCATTCTGCATGGTGCTATT
ACCAAAATCTTCAATAAGAAAGCACAGGCAATACTGGACACTATAGAAGAAGACCCTGATGCAGCATTACATTTAGTGTCTGGTAAGGATATT
GGTGCGATGTGTAAGTGGGTTCTTGATAACGGCATTACCGCCACACCTGCTGCACAGCAGGAAGAGTCCAAGTTATCTAAGCGCCTCAAGGC
TATCCGAGAGGCATCCAGTGGTAAGATAATTCAATTCACTAAGGAGGATTGATGGCTAAGGCAAGAGAATCACAAGCGGAGGCTCTTGCCA
GATGGGAGATGCTACAGGAGTTACAGCAGACCTTTCCTTACACCGCGGAAGGTTTGCTTCTCTTTGCAGATACAGTTATTCATAACTTAATTGC
AGGCAACCCTCATCTGATTCGTATGCAGGCGGATATCTTGAAGTTCCTATTTTACGGACACAAGTACCGCCTCATCGAAGCGCCTCGTGGTAT
CGCTAAGACAACACTATCAGCAATCTATACGGTATTCCGTATTATTCATGAACCGCATAAGCGTATCATGGTTGTGTCCCAAAACGCCAAGCG
AGCAGAGGAAATCGCAGGTTGGGTAGTTAAAATCTTCCGTGGCTTAGACTTTCTTGAGTTTATGCTGCCGGATATCTACGCTGGGGACCGTGC
ATCCGTTAAGGCGTTTGAGATTCATTACACCCTACGTGGTAGTGATAAGTCTCCTTCTGTATCCTGTTACTCAATCGAAGCAGGTATGCAGGGT
GCTCGTGCTGATATTATTCTAGCGGATGACGTAGAGTCGATCAGAATGCTCGTACGGCAGCGGGCCGTGCCTTGCTTGAGGAGCTGACTAA
GGAGTTTGAATCTATCAACCAGTTTGGGGATATCATTTACCTTGGTACACCTCAGAACGTAAACTCTATCTACAACAACCTACCTGCTCGTGGT
TACTCTGTTCGTATCTGGACTGCGCGTTACCCTTCAGTAGAGCAAGAGCAATGTTATGGCGACTTCCTTGCACCTATGATTGTTCAAGATATGA
AGGACAACCCAGCACTTCGCTCAGGGTACGGGTTGGATGGTAATAGTGGTGCACCTTGTGCCCCTGAAATGTATGATGATGAAGTCCTGATT
GAGAAGGAAATCTCTCAGGGTGCTGCTAAGTTCCAGCTTCAGTTCATGCTTAACACTCGCATGATGGATGCTGACAGATACCCATTACGCCTG
AACAATCTAATCTTCACCTCGTTTGGTACAGAGGAAGTCCCTGTGATGCCTACGTGGAGTAATGATTCCATAAACATCATTGGTGATGCACCTA
AGTATGGTAACAAGCCTACGGATTTCATGTACAGACCTGTAGCTCGCCCATATGAATGGGGTGCTGTCTCCCGCAAGATTATGTATATTGACC
```

Figure 4I

```
CTGCGGGTGGTGGTAAGAACGGAGATGAGACGGGTGTAGCCATCGTATTCCTGCACGGCACATTCATTTATGTGTATCAGTGCTTTGGTGTA
CCTGGCGGATACCGAGAGTCGTCCCTGAATCGCATTGTGCAGGCCGCAAAGCAGGCGGGTGTTAAAGAGGTATTCATTGAGAAGAACTTTG
GTCATGGCGCGTTTGAGGCGGTAATTAAGCCGTACTTTGAACGAGAGTGGCCTGTAACTCTGGAAGAGGATTACGCCACCGGACAGAAAGA
GTTGCGTATCATTGAGACGCTGGAGCCGCTCATGGCAGCCCATAGGCTTATCTTCAATGCAGAGATGGTGAAGTCAGACTTTGAGTCGGTAC
AGCACTATCCGCTTGAACTACGCATGTCCTACAGTCTTTTCAATCAAATGTCGAACATAACGATTGAGAAGAACAGCCTCCGGCACGATGACC
GCCTAGACGCCCTGTATGGCGCTATACGGCAATTAACTTCTCAGATAGACTATGACGAGGTTACACGGATTAATCGCCTCAGAGCGCAGGAG
ATGCGCGATTACATCCATGCTATGAACACACCTCATCTACGCAGGGCAATGCTATATGGAGATTACGGTACTGAGCGAAGAGTGACCAACAC
TTCCGTAGCGATGCAGCAGCGAGTTTACGGGCAGAACTACCGAAATAAATCGGCAAGCAGAAATACACTTTCTGCAAGGATTTCAAGGACTT
ATTAATTACTGGACACTATAGAAGGAAGGCCCAGATAATAAGAGAAAATAATAGGTAATATATATATAGGTTAACCTAGGTTATATAGGTAT
GCCTTAGTATGGGTGTACTCCTGTACACCCTATTCCTTACTACCTTACTATATTTACATAATAGGAGAGAGACAATGGCTAATGATTATAGTAG
TCAACCATTAACAGGTAAGTCTAAGAGAAAGCAGGTACAACCTGTAAGTGAAGAACTAATGCTTCCGGTGCTCAAAAAAGAGGAAGTTAGTA
AGAAAAGCAATGTTATTAATGATGCCACCAAATCAGGTAAACAGAAAGGGGCCATGGTGTGCCTTGAAGTGAAAGGTGGTGTATTGAAGAT
TGCTATCGCGGTTGATGGCAAAGAAGATTCAGAGTGGAAGTTAGTAACAGTGGAACCAACTGTTAACCCAGTTTAAGATAAGGAGGAAGAT
TACATGGCTAAATATGGTACTACAGGTTCTGTTACTGGTCAGGCTTTTCGAGTAAAAGCAGTACAAACTATTGCAACGGCAATCCCGATGCCT
GTTGTTAAAGAAGAAGACCTTAAGAGTAAAGACCACCCTATCAACATCAAACATTTATCAGGTAAACAGAAAGGTGCAATGGTTGCTCTTGA
GAAAGGTGACACAACCTTACATATTGCTGTTGCACGTGGTAGTGAACCCACAGACCCTTGGGATGTAACTGGTATGGAAAAGGACGCTGTTA
CTCCAGCAGGGGTATAATAATGCTTAATAAATACTTCAAGCGTAAAGAGTTTGCTTGCCGTTGTGGGTGCGGTACATCCACTGTTGATGCTGA
ATTACTACAGGTAGTCACAGATGTGCGTGAGCACTTTGGTTCTCCTGTAGTTATCACTTCGGGTCATCGCTGTGCTAAGCACAATGCCAATGTA
GGTGGCGCTAAGAACTCCATGCATCTTACTGGTAAGGCTGCTGACATTAAAGTGTCTGGCATATTACCTTCTGAAGTGCATAAGTATCTTACTA
GCAAATACCAAGGCAAGTATGGTATAGGTAAGTATAACTCCTTCACTCACATCGATGTACGGGATGGTTGTGCGCGATGGTAAGATGTGTTG
AATGGTGTGAGCGTATGGTTGCCCAAGCTGCCGAGGATGGCAACTATGATGACTGGAAGAACTACTCTGACTTGTTAGCTCAATGGAAAGG
GAGATGCAATGAAAAGCTGTTTAAGTCTAAGAAGGTTGTAGGTGCACTGGTTGCACTTGTTATTGCTCTTGTTTCTGTAGGTCTTGGTGTAG
ACCTTGGCTCTGGCACGGAATCCTCTGTGACAGATGTGGTCTGCCAAGTGATCACCTGTGAATAAGTTTCTAGAAGTTCTGGCAGGTCTTATT
GGCCTGCTTGTCTCTGCTAAGAAGAAACAAGAAGAGAAGGAGGCACAAAGTGAAGCGAATCATGTTAGTGACAACCCTTCTGATTGGTTCGC
TGACCACTTCCGGGTGTCAGCAGGCGTTACCAGAGAAAGCAATGGTGAAACCTCTGAGGCCGACGCTGACGGCAGTTTACGAGGTAGACGA
TAAGGTCTGCTTTAGTAAGCCTGACGCTACAAAACTTGGTTTGTACATTCTCTCGCTAGAACGCGGATACAATTAATACATAGCTTTATGTATC
AGTGTCTTACGATTTACTGGACACTATAGAAGAGGTAAGATAGCGCCGTTCTTTTGAGCGGCCTATTACTAGCCAATCTTCATAGGGAGGGTT
GGAAAGTAATAGGAGATAGCATGGCTAAATTAACCAAACCTAATACTGAAGGAATCTTGCATAAAGGACAATCTTTGTATGAGTACCTTGAT
GCGAGAGTTTAACATCAAAGCCGTTTGGTGCTGCAGGTGACGCCACTACTGATGATACGGAGGTTATAGCTGCTTCATTAAACTCTCAGAAA
GCTGTCACAGTCTCAGATGGTGTATTCTCTAGCTCTGGTATTAACAGTAATTACTGTAACTTAGACGGCAGGGGTAGTGGCGTGCTAAGTCAC
CGTTCAAGTACAGGTAACTACTTAGTATTTAACAATCTACGTGCAGGTCGCTTAAGTAATATTACGGTAGAAAGTAATAAGGCGACTGATACA
ACTCAGGGACAGCAGGTATCCCTTGCTGGTGGAAGTGATGTTACTGTAAGTGACGTTAACTTCTCAAACGTTAAAGGTACTGGTTTCAGTTTA
ATCGCATACCCTAATGATGCGCCACCTGATGGACTTATGATTAAAGGCATTCGAGGTAGCTATTCCGGCTATGCTACTAATAAGGCAGCCGGA
TGCGTACTTGCTGATTCCTCAGTTAACTCCCTCATAGATAACGTCATTGCTAAGAACTACCCTCAGTTCGGAGCAGTAGAGTTGAAAGGTACA
GCCAGTTACAACATAGTCAGTAATGTTATAGGGACAGATTGCCAGCATGTAACTTACAACGGCACTGAAGGGCCAATAGCTCCTTCTAATAAC
CTTATCAAGGGGGTGATGGCTAATAACCCTAAGTATGCAGCGGTTGTTGCAGGCAAAGGAAGTACGAACTTAATCTCAGACGTGCTCGTAGA
TTACTCAACTTCTGATGCTAGGCAGGCTCATGGTGTTACAGTAGAGGGTTCTGATAACGTCATAAATAATGTGCTTATGTCAGGATGTGATGG
TACTAACTCTTTAGGACAAGGGCAGACTGCTACAATTGCACGCTTTATAGGTACAGCTAATAACAACTATGCGTCTGTATTTCCTAGCTACAGT
GCTACAGGTGTTATTACTTTCGAATCCGGCTCTACCCGTAACTTCGTAGAGGTAAAGCACCCTGGCAGGAGAAACGACCTTCTCAGTTCTGCT
AGTACTATTGACGGTGCAGCTACTATTGACGGCACTAGTAATAGTAACGTAGTGCACGCACCTGCCTTAGGGCAGTACATAGGTAGTATGTC
AGGTAGGTTCGAATGGCGGATTAAGTCCATGTCACTCCCTTCAGGCGTTCTTACTTCTGCTGATAAGTACAGAATGCTTGGAGATGGTGCTGT
GTCATTAGCTGTAGGTGGGGGCACTTCTTCTCAAGTTCGCCTATTTACTTCTGATGGTACTTCTCGGACAGTGTCCCTCACCAACGGTAACGTG
CGTCTTTCTACCAGTAGCACAGGCTTTTTGCAGTTAGGTGCTGATGCAATGACCCCAGACAGTACTGGTACATACGCATTAGGTTCCGCCAGC
CGAGCATGGTCTGGCGGTTTTACTCAAGCAGCATTCACTGTTACCTCAGATGCTCGGTGTAAAACAGAACCTCTTACTATCTCAGATGCCTTAC
TGGATGCTTGGTCTGAAGTTGACTTTGTGCAGTTTCAGTATTTGGATCGTGTTGAGGAGAAGGGTGCAGACTCAGCTAGATGGCACTTCGGT
ATCATCGCTCAGCGAGCTAAGGAGGCTTTCGAACGTCACGGTATAGATGCACATCGCTATGGCTTCTTGTGCTTCGACAGTTGGGATGATGTA
TACGAGGAAGATGCCAATGGCTCTCGTAAACTGATTACACCAGCAGGTTCCCGCTACGGTATTCGTTACGAGGAAGTACTGATATTAGAGGC
TGCGTTGATGCGGCGGACTATTAAGCGTATGCAGGAAGCACTAGCTTCCCTGCCTAAGTAAGCAACAGGCAGTGCGTAAGCACTGCTTTTAG
CGCAACTTTTCTTAAAGGTTATCACGGTGGTAGCCTTTCAGAAAAGGAGGTTACATGATTCAAAGACTAGGTTCTTCATTAGTTAAATTCAAGA
GTAAAATAGCAGGTGCAATCTGGCGTAACTTGGATGACAAGCTCACCGAGGTTGTATCGCTTAAAGATTTTGGAGCCAAAGGTGATGGTAAG
ACAAACGACCAAGATGCAGTAAATGCAGCGATGGCTTCAGGTAAGAGAATTGACGGTGCTGGTGCTACTTACAAAGTATCATCTTTACCTGA
```

Figure 4J

```
TATGGAGCGATTCTATAACACCCGCTTCGTATGGGAACGTTTAGCAGGTCAACCTCTTTACTATGTGAGTAAAGGTTTTATCAATGGTGAACTA
TATAAAATCACGGATAACCCTTATTACAATGCTTGGCCTCAAGACAAAGCGTTTGTATATGAGAACGTGATATATGCACCTTACATGGGTAGT
GACCGTCATGGTGTTAGTCGTCTGCATGTATCATGGGTTAAGTCTGGTGACGATGGTCAAACATGGTCTACTCCAGAGTGGTTAACTGATCTG
CATCCAGATTACCCTACAGTGAACTATCATTGTATGAGTATGGGTGTATGTCGCAACCGTCTGTTTGCCATGATTGAAACACGTACTTTAGCCA
AGAACAAACTAACCAATTGTGCATTGTGGGATCGCCCTATGTCTCGTAGTCTGCATCTTACTGGTGGTATCACTAAGGCTGCAAATCAGCAAT
ATGCAACAATACATGTACCAGATCACGGACTATTCGTGGGCGATTTTGTTAACTTCTCTAATTCTGCGGTAACAGGTGTATCAGGTGATATGA
CTGTTGCAACGGTAATAGATAAGGACAACTTCACGGTTCTTACACCTAACCAGCAGACTTCAGATTTGAATAACGCTGGAAAGAGTTGGCACA
TGGGTACTTCTTTCCATAAGTCTCCATGGCGTAAGACAGATCTTGGTCTAATCCCTAGTGTCACAGAGGTGCATAGCTTTGCTACTATTGATAA
CAATGGCTTTGTTATGGGCTATCATCAAGGTGATGTAGCTCCACGAGAAGTTGGTCTTTTCTACTTCCCTGATGCTTTCAATAGCCCATCTAATT
ATGTTCGTCGTCAGATACCATCTGAGTATGAACCAGATGCGTCAGAGCCATGCATCAAGTACTATGACGGTGTATTATACCTTATCACTCGTG
GCACTCTTGGTGACAGACTTGGAAGCTCTTTGCATCGTAGTAGAGATATAGGTCAGACTTGGGAGTCACTGAGATTTCCACATAATGTTCATC
ATACTACCCTACCTTTTGCTAAAGTAGGAGATGACCTTATTATGTTTGGTTCAGAACGTGCAGAAAATGAATGGGAAGCAGGTGCACCAGAT
GATCGTTACAAGGCATCTTATCCTCGTACCTTCTATGCACGATTGAATGTAAACAATTGGAATGCAGATGATATTGAATGGGTTAACATCACA
GACCAAATCTATCAAGGTGACATTGTGAACTCTAGTGTAGGTGTAGGTTCGGTAGTAGTTAAAGACAGCTACATTTACTATATCTTTGGTGGC
GAAAACCATTTCAACCCAATGACTTATGGTGACAACAAAGGTAAAGACCCATTTAAAGGTCATGGACACCCTACTGATATATACTGCTATAAG
ATGCAGATTGCAAATGACAATCGTGTATCTCGTAAGTTTACATATGGTGCAACTCCGGGTCAAGCTATACCTACTTTCATGGGTACTGATGGA
ATACGAAATATCCCTGCACCTTTGTATTTCTCAGATAACATTGTTACAGAGGATACTAAAGTTGGACACTTAACACTTAAAGCAAGCACAAGTT
CCAATATACGATCTGAAGTGCAGATGGAAGGTGAATATGGCTTTATTGGCAAGTCTGTTCCAAAGGACAACCCAACTGGTCAACGTTTGATTA
TTTGTGGTGGAGAAGAGACTTCGTCCTCTTCAGGTGCACAGATAACTTTGCACGGCTCTAATTCAAGTAAGGCTAATCGTATCACTTATAACG
GAAATGAGCACCTATTCCAAGGTGCACCAATCATGCCTGCTGTAGATAACCAGTTTGCTGCTGGTGGACCTAGTAACCGATTCACTACCATCT
ACCTAGGTAGTGACCCTGTTACAACTTCAGATGCTGACCACAAGTACAGTATCTCTAGTATTAATACCAAGGTGTTAAAGGCTTGGAGCAGGG
TTGGTTTTAAACAGTATGGTTTGAATAGTGAAGCAGAGAGGGACCTTGATAGCATACACTTCGGTGTCTTGGCTCAGGATATTGTAGCTGCTT
TTGAAGCTGAAGGGTTGGATGCCATTAAGTATGGAATTGTGTCCTTCGAAGAAGGTAGGTACGGTGTGAGGTATAGTGAAGTTCTAATACTA
GAGGCTGCTTATACTCGTTATCGTTTAGACAAGTTAGAGGAGATGTATGCCACTAATAAAATCAGTTAAGCAAGCTGCTGTACTCCAGAACAC
AGAAGAGCTTATTCAATCAGGACGTGACCCTAAGCAGGCTTATGCCATTGCCAAGGATGTTCAACGTCGTGCCATGAAGAAACCTTCTGCATC
TTCTGCGTAAGCAGGTTAATATCTTAGTATAAACAAGGGCAGACTTAGGTTTGTCCTTAGTGTATTCCAAAGGAGGTAACATGCTGAAAGATG
GTTGGGTTTCATATGACCCTACAGACCCTAAGAATTGGCTACAGGTTATCGCTATAGCTTGTGCAGGTAGCCTATTGGCTGCCCTGATGTATTC
ATTATGGATGTACACAAAGTAACCAAAGTCAAAATTTTGATGTAGGCGTGTGTCAGCTCTCTCGCCCTCGCCCTCGCCGGGTTGTCCCCATAG
GGTGGCCTGAGGGAATCCGTCTTCGACGGGCAGGGCTGATGTACTCCTTGTCTAGTACAAGGGAGGCGGAGGGAACGCCTAGGGAGGCCT
AGGAATGGCTTAGTGGTGGACAAGGTGATTACCTTAGTGAAGCCTCTTAGTGCATTCCTGAGGCCATTCAGGGCGTTTATGAGGGATTGACA
GGGTGTGAGGGCGTGGGCTA
```

Figure 5A

>K1-5 BAR 2.5 (Site specified by sgRNAs 1112+1122) (SEQ ID NO: 5)
TCGCCCTCGCCCTCGCCGGGTTGTCCCCATAGGGTGGCCTGAGGGAATCCGTCTTCGACGGGCAGGGCTGATGTACTCCTTGTCTAGTACAA
GGGAGGCGGAGGGAACGCCTAGGGAGGCCTAGGAATGGCTTAGTGGTGGACAAGGTGATTACCTTAGTGAAGCCTCTTAGTGCATTCCTGA
GGCCATTCAGGGCGTTTATGAGGGATTGACAGGGTGTGAGGGCGTGGGCTATCTGTTCCTTTGCTCCTCACTTCGTTCGTCGCTGCGGTAGCC
TGATGTGTACCTTAGGTTATTCCTTGATGGATAGCTTAGGTTAGCCTTAGTGGATTACCTTAGTTAAAGCCTTAGTGCTTCACTTAGTATCAGCT
TAGTAGTGTACCTTAGTAAGTCTTAGTGTCTTCTCTTAGTGATTGCACATGCAAGCATGTAAGATGCTAATAGGTCGCGGTCGGCAGACCGCT
AAAGAAAGAGAATGGTAATAAGATGCAGTAGGAGGAACACCAGAAGCCTAGCCAACCTAAGCTATCCTAGCTCTATATCTATTGCTTTTCCTT
AGTCTAACACGTTAGACAACCTATCTTATTCTTAGTGATGGTAACTTAGTGTTGACAAGATAATCTTAGTGTAATACTATGCATCACGTAGGCG
GTGCTGAGGCACCTAGTAGCCAGCTAGTAAGGCATACGAAGAGACTAGCGCTTACATTGCTCTTTAACAATTTGCTTAGTGTAACCTATGTAT
GCCGTGGTTAACTACTTATTGAATGAGGTATTAACTATGACATTAAATAACCGTGAACTGTCCGTTCTCTTCACTCTGTTGTGCTACATGATTCG
TAACAACGAATTACTTACAGATGATGAGTTAGCCTTGTATCACCGCTTTCTTAACGAAGGTTGGACCGATACAGTTAATCAATACCGTAACATG
ATAGATGAGTTGAGGGAGGGTAAATAATGTATCAACATGAGGTATTCTTTGAATCAGCTAGCGAAGCTATTCGCTTCCGTGATGATATGATG
CAAGCTGGTGTAGGCGTTGATGTGTATCACTATTTGATAGATTACGACACTGAATATCACCGAGTTACCTTAGTATCTGAGTATGACAACCAA
GTCATTACTGAGTATCTAGGCAGTGAAGATTACGATTACGATGAAGTAATCACGACAAATCTCTAAATTAACTGTTGACAGCCACGGCATACA
AGGTTACATTAAGCATCAAGACGGCGACGTCTTTAAACATCCCGCTCTTTAACAATACGGTTTGTGTCTTGATAGGCTAACTAACTAACTAAGG
TAATTATCATGAAAGGGTTAATTTGTGTAGAACGTATGGTCAATGGTAAACTTGAAATATTACCACTGGAAAACCAATCTAGCTTCAAAGAGT
GGTATGGCTGTTTCTCACTGATTTAAGGTAAAGGCTGGCACTAGTCAGCCTATCAAGGCGCAAACCAAGCTCTTTAACAATTTGGATGGTAGC
TTCTTAGTCTGGATAGGTTAAACCTAGGAGATTCTCTTGAGTCTCCTATAATGTAACCTAACTAACTAAATGAGGATTAAATCATGGAACGCAA
TGCTAACGCTTACTACAACCTTCTGGCTGCAACTGTTGAAGCATTCAACGAGCGTATTCAGTTTGATGAGATTCGCGAAGGTGATGATTACTCT
GATGCACTACATGAGGTTGTAGACAGCAATGTTCCAGTTTATTACAGCGAAATCTTTACAGTGATGGCTGCTGATGGTATTGATGTTGATTTT
GAGGATGCTGGTTTGATTCCTGACACGAAGGATGTAACCAAGATTCTACAAGCTCGCATCTATGAAGCTCTTTATAATGATGTACCAAATGAC
AGCGATGTAGTTTGGTGTGAAGGCGAAGAAGAGGAAGAATAAGGATGGAAAAGCAATATAACTTTATCTTTTCAGACGGTGTAACCCTGAA
GTGTTCCCTACGATTCGCACAAATTCGTGAGGAAGTACTAGGCACTACATACAAACTATTTAGCTGACACTATAAGAGAAGGCTTAACAAGGC
GTTACTAAGGTAGCGCCTGATTAAACTTTCACTTACTAGGAGTTGAGATTATGAAAACCTTGATTGGATGCTTCTTGTTGGCTTCTCTTGCTCT
GGCATTTACCGCTAAAGCTGGTTATGACGCTTATAAAGTAGAACAAGCCCAGCAAGACTGGGCCAAAAAAAAGTTCAACTTGTGCAGCAAGA
GCAACACCTACGAGTACTGCAACAAAACACTAAGCACTTATGGAAAGAGTAACTAGCCTATAGCCCACCTGAGTGGGCTATGTGATATTTAC
TTAACACTATATAAGGTGATTACTATGACTACTGAAAACACCCTCGTGTCTGTCCGTGAAGCTGCAACCGCTGAAATCAAGCAACATTTAGAC
AATATCGGCACTTCTTACATCAAAGTAGGGGCTTGTCTGAATGAGTTACGCGGAGACTTTGAAGGTCAAAAAGAGTTTTTAGCCTATGTTGAA
GCAGAGTTTGCCATTAAGAAGGCACAATGTTACAAGCTGATGAGTGTAGCCCGTGTCTTTGAAGGCGATGATCGCTTTAAAGGCGTGGCGAT
GCGTGTAATGCTGGCGCTTGTTCCTTTCGCTGATGAAAATATAATCATGGAGAAGGCCGCAGAACTCGCCGCAAATGGCAAGCTGGACACTA
ATGCCGTAAACGCCCTGATTGAACCTAAGAAAGAGTCAAAGGCCGAAACGGTACAATCTAAGGCTGAGACAGTAAAACCGCAGGAGAACGC
GACTGAGTCCGCAGAATCACATGAAATGCAAGCGCCGCAGGTAGTGCCACCCGCGAGCGAGCAGGAGTCCGACGAATCAGCACCTTGGGAA
GAGGAAAGCAAACCGGAAGCGCCAAAGGCAGCTCCGATGGATAACACGGCTAATACTGAGAATGCCGCTATTGCTGGTCTGCTGGCACAAA
TTAAAGCACTGACTGAGCAATTACAGGCAGCCAATGACCGCATCGCCTCCTTAAGTAGCGCACGCGAAAGCAAGAAGGCATCCGCACCTATG
CTGCCGCAGTTCAAATCTTCCTGCTTCTACGCTCGCTTAGGCTTGAGCGCGGAGGAGGCAACGAAGAAAACAGCAGTTAACAAGGCACGCCG
CGAACTGGTTAAGCTGGGATACGGTGAAGGCCATGAGGCATGGCCCTTAATCTCTGAGGCAGTAGAAGAGTTGACTAAGTAACCTTATCGGT
GGCATCTTCTTAGGTGTCACCTATTAAGGTTTCTTTCACTAGGAGTAAACAAGATGCAAGGCCTACACGCTATTCAACTTCAACTTGAAGAAGA
AATGTTTAACGGCGGTATCCGTCGCTTTGAAGCGGACCAACAACGCCAGATTGCATCCGGTAATGAATCAGACACGGCATGGAATCGCCGCT
TATTGTCCGAGTTAATCGCGCCAATGGCTGAAGGTATTCAGGCATACAAGGAAGAGTATGAAGGTAAAAGAGGCCGTGCACCGCGTGCATT
AGCTTTCATTAACTGCGTAGAAAACGAAGTGGCAGCATATATCACGATGAAATCGTTATGGATATGCTGAACACGGATGTAACCTTGCAGG
CTATAGCCATGAATGTAGCTGACCGGCATTGAGGACCAAGTACGTTTTAGCAAGCTGGAAGGTCACGCCGCCAAATACTTTGAAAAAGTTAAG
AAGTCACTTAAGGCAAGTAAGACTAAATCATATCGCCATGCGCACAACGTAGCGGTAGTGGCTGAGAAGTCAGTAGCTGACCGTGACGCTGA
TTTCTCCCGCTGGGAGGCATGGCCTAAAGACACCTTGCTGCAAATTGGGATGACCTTGCTTGAAATCTTAGAGAATAGCGTATTCTTCAACGG
GCAACCTGTCTTCCTCCGCACCTTGCGCACTAATGGCGGCAAACATGGTGTTTACTACCTACAGACTAGTGAACACGTAGGTGAGTGGATAAC
TGCATTCAAAGAGCACGTAGCGCAACTGAGTCCTGCCTATGCTCCTTGCGTCATCCCTCCGCGTCCGTGGGTATCACCTTTTAACGGCGGTTTC
CACACTGAGAAAGTAGCAAGCCGTATTCGTCTGGTAAAAGGAAACCGCGAACACGTCCGCAAGCTGACCAAAAAGCAAATGCCAGAGGTTT
ACAAGGCTGTTAACGCGTTGCAGGCGACTAAATGGCAGGTTAACAAGGAAGTTTTACAGGTTGTGGAAGACGTCATCCGTCTAGACCTAGGT
TATGGTGTACCTTCCTTTAAACCACTCATTGACCGCGAGAACAAGCCAGCTAATCCAGTGCCGCTAGAATTTCAGCACCTACGGGCCGTGAA
CTGAAAGAAATGCTTACGCCGGAACAATGGCAAGCCTTTATCAACTGGAAAGGTGAATGTACTAAGCTGTACACCGCTGAAACTAAGCGCGG

Figure 5B

```
AAGCAAATCGGCGGCAACCGTTCGCATGGTTGGTCAGGCCCGTAAATATAGCCAGTTCGACGCAATCTACTTCGTGTATGCACTGGACAGCC
GCAGCCGCGTCTACGCGCAATCTAGCACACTCTCACCGCAATCAAATGACTTGGGCAAGGCCTTGCTCCGTTTTACCGAAGGGCAGCGTCTTG
ATAGCGCTGAGGCGCTTAAGTGGTTTTTGGTGAACGGGGCTAATAACTGGGGTTGGGATAAGAAAACTTTTGACGTGCGCACCGCTAACGTG
CTGGATAGTGAATTTCAAGACATGTGCCGCGACATTGCAGCGGATCCGCTGACCTTCACTCAATGGGTAAATGCCGACTCCCCTTACGGCTTC
CTTGCATGGTGCTTTGAATATGCGCGTTATCTGGATGCACTGGATGAAGGCACGCAAGACCAATTCATGACGCACCTCCCAGTCCATCAAGAT
GGTAGTTGTTCTGGTATCCAGCACTACAGTGCTATGCTACGCGATGCAGTAGGTGCGAAAGCAGTAAACCTTAAGCCCTCTGACTCTCCTCAA
GATATTTATGGTGCCGTTGCGCAGGTAGTAATTCAGAAGAATTATGCATACATGAATGCAGAGGATGCGGAAACCTTCACTTCTGGCAGCGT
GACTTTAACAGGTGCGGAGCTGCGTAGTATGGCTAGTGCGTGGGATATGATAGGAATCACTCGCGGCCTGACCAAAAAGCCCGTAATGACA
CTACCTTATGGCAGCACACGTCTAACCTGCCGTGAGTCAGTGATTGATTATATCGTTGATTTAGAAGAAAAAGAGGCCCAACGGGCTATTGCG
GAAGGGCGTACCGCCAATCCTGTACACCCTTTTGATAATGACCGTAAAGACAGCCTGACACCTAGCGCAGCTTATAACTATATGACAGCTTTA
ATCTGGCCTTCTATTTCGGAAGTGGTTAAAGCCCCTATAGTGGCAATGAAAATGATTCGTCAGCTTGCCCGTTTCGCAGCTAAAAGGAATGAA
GGCTTAGAGTATACCCTGCCTACTGGCTTCATCTTGCAACAAAAGATTATGGCTACTGATATGCTCCGCGTATCTACTTGCTTGATGGGAGAAA
TCAAGATGAGTCTACAGATTGAAACAGACGTAGTGGATGAAACGGCAATGATGGGCGCTGCTGCTCCTAACTTTGTGCATGGTCATGATGCC
AGCCACCTTATCTTAACAGTCTGCGACCTTGTTGATAAAGGGATTACATCTATCGCAGTTATTCATGACTCTTTTGGCACTCATGCAGGCCGTA
CAGCCGACCTTCGTGATAGCTTAAGGGCAGAAATGGTGAAGATGTATCAAGGCCGTAATGCACTGCAAAGCCTGCTAGATGAGCACGAAGA
ACGCTGGTTAGTTGATACCGGAATACAAGTACCAGAGCAAGGGGAGTTTGACCTTAACGAAATCTTAGTTTCAGACTATTGCTTCGCATAATA
TTAATAGGCCATTCCTTCGGGAGTGGCCTTTCTTTTACCTACTACCTGTAACATTTCATTAACATAAAAGTGTCTCACATGTGAGACTTATTTAC
CGGACACTATAGGATAGCCGTCGGAGACGGGAAAGAAAGGGAAGATAAAGGATATAAAGGAAGTAATAGGTATTAAAGGTTATATAGGTT
ATCTAGGAATACCTATTACCTTCTTCCTTCCTCTTATTACCACTCAGAGGAAGGGCAGACCTAGGTTGTCTCACATGTGAGACTTCGTATTTACC
GGACAGTATAGATAAGATTAACTCACTTTGGAGATTTAACCATGCGCAACTTTGAGAAGATGGCCCGTAAAGCTAACCGTTTTGACATGGAA
GAGGGGCAGAAGAAAGGCAAGAAGCTGAATAAGCCTGTCCGTGACCGTGCATCTAAACGCGCTGCGTGGGAGTTCTAAGTTATGGCTATTA
TTCAGAATGTACCGTGTCCTGCCTGTCAAAAGAATGGACATGATATTACTGGCAACCATCTCATGATATTTGATGATGGTGCCGGCTACTGTA
ATCGTGGACACTTTCATGATAATGGTAGACCTTACTATCACAAGCCGGAAGGTGGCATCGAGATAACCGAGTTATCTATTACTGGCAATATCA
AATATACACCTTCTCAATTCAAAGAAATGGAGAAGGAAGGGAAGATAAGCGACCCTAAATTACGTGCCATCGCACTTGGTGGTATGCGTATG
AAAGACCGTTGGGAGGTCATGAATGAACAAGAAAGGGCAGAGCAAGAAGCAGAGTGGAAACTTGATGTTGAATGGTTCCTCACGCTTAAGC
GTAAGAACCTTGTTTCCAGGCACATTCGCGGCGACATTTGCGCATTGTATGATGTACGTGTTGGGCACGATGAAGAGGGTAGAGTCTCACGG
CATTACTATCCGCGCTTCGAAAAAGGTGAGCTAGTAGGCGCTAAGTGTCGCACATTACCTAAAGATTTTAAGTTTGGTCATTTAGGTAAACTCT
TTGGTATGCAAGATCTTTTCGGTATGAATACTTTGTCTCACGTGTTAGACAAGGGAAGACGAAAGGATTGCTTGCTCATTGTCGGCGGCGAAC
TGGATGCACTAGCAGCGCAGCAGATGCTCCTTGATTCTGCCAAGGGTACTAAGTGGGAAGGCCAGCCATACCATGTATGGTCTGTCAACAAA
GGCGAGTCTTGCCTTGAAGAGATAGTGCAGAACCGTGAGCATATCGCCCAATTCAAGAAGATTATATGGGGTTTTGATGGAGATGAGGTAG
GGCAGAAGCAGAATCAGCAAGCGGCTCGCCTGTTTCCTGGTAAATCCTATATCCTTGAATACCCCTCTGGTTGCAAAGATGCTAACAAGGCAT
TGATGGCTGGCAAGGCTAAAGAATTTGTAGATGCATGGTTTAATGCCAAGTCATCTGATGAAGTCTTTGGTAGCCAGATTAAATCTATCGCAT
CTCAAAGGGATAAGCTCAAGGCTGCACGTCCAGAGCAAGGACTGTCATGGCCTTGGCCTAAGCTGAACAAGGTAACGCTAGGTATTCGTAAG
AACCAGCTTATCATTGTAGGTGCAGGGTCTGGTGTAGGTAAGACTGAGTTCCTTCGTGAAGTAGTTAAGCACCTCATTGAAGAACACGGTGA
ATCTGTAGGCATCATTTCTACAGAAGACCCGATGGTCAAGGTGTCCCGTGCTTTTATCGGCAAGTGGATTGATAAGCGTATTGAGTTACCTCC
AACCAACGACCCGAAAGAAGACGGATACCGTGAGGTGTTCGACTATACCGAGGAAGAAGCTAACGCCGCCATTGATTATGTAGCTGATACA
GGTAAGCTGTTTGTAGCTGACCTAGAGGGTGACTATTCGATGGAAAAGGTAGAGCAAACTTGCCTAGAGTTTGAGGCTATGGGTATTTCTAA
TATCATCATTGATAACTTAACGGGGATTAAATTAGATGAGCGTGCTTTTGGTGGGAAGGTTGGTGCACTTGATGAATGCGTCAAGCGGATTG
GTACTATCAAAGACCGACACCCGGTTACTATATTCCTTGTATCACACCTTACACGTCCTCCGGCAAACCGTACCCAACACGAAGAAGGTGGCG
AAGTTATCCTTTCTGACTTCCGAGGCTCAGGCGCTATCGGATTCTGGGCATCTTACGCCTTGGGGATTGAGCGTAATACAAGAGCTGAAACGC
TTGACGAAAGGACTACCACGTACATCTCATGTGTCAAAGACCGCGACCAAGGTATCTACACTGGAACCAAGGTCATGCTTAAGGGTGACATT
CAAACCGGACGTTTAATGGAACCACAAGCCCGTACTAAGTCATTTGATACAGGTGAAGCAAGGCAACAAGAAGTACCAGATTTACCGGATAC
TATAGAAGAGACTACCTTCGATGAAGAAAGTGAGTTCTGATTAGTGTATTTATCAGGCTTGTCTCACATGTGAGACAGGTCTTATTAAGTAC
ATTAAATAACTGGAGATTGATTATGTATAACTTAGTGTTGAATGTAGGTGACTTTGTACGCAACATCAAGAAAGATTCAAGTCGCTATCTTTGC
CGTGGTGTTGTAACCTTTGTAGGTGAGAACCTGTATTATGTAGAATATCGCAGTGGTGTTAAGCAATATTACCACAAGAAGACAGCACATAAA
TATCTTGAAAAGATTGTAGAGATAAACAATCAATGTAAGTGCATACATGATGAGGTTTGCGATAAATGTGCTCGCCAGATGCTTAAGAATTTC
CTAGCTCCTCTTTATTATGGTGCTGGTCCTCAAACACTAGCAGAGTGCATGGCAGAAAAGAAAACCACACTCAAGAAAGAGCGTCGCAATGT
AATCACTGGTAAGACTCAAAGTGAGATGATTAAGCAATGTGGCACTGCATTAGGTGTTACACAGTTTAATACTCGTGCATTGGGTAAATCCAC
AGGACAAGCTATGGTAAAGATTGGAGAAGCCATGATGCATCCAAATGTACCTGTGCGAATCATGGATGTTGACCATGCAATCACAGAACAAG
GTACGCAACGACGTGTAATTAATAAGCATTTTGCCGACACTATAGAAGGCATTATTCGTAAGCAAGGGTTGAAAGGTCTTCACATCTTAAATG
GTGAAGAATTACTGTACCTACCTATCGTTACTGAAGAAACATACGTGAATATCTAAGGAGTTAATCATGACTAAGGTATTAATTTATATGCGT
```

Figure 5C

GGACCTCATAAATGCTATGCAGTTGTAGCACCAAATGGTGTTAAGCCTTATCGTACTTCAAAAAGATTGGCATTAATAGGTGCTAGTAGTAGT
GCAAGTTTCCAAATGGAACTTTTTGGTCATTGGACTGAAAGGCAATTCCGTGAGGATTTTAAAGTCATTGGCAGCTTCATGGTGAAATATGCA
GAATAAACATAGTCTTAGAATGTTCGATGGTCATGAAAACCTGCAAGCCAAGATTACTAACCAAGCCTTCCTGTTCGCACAGTTAACTATGGC
TGAGGCTAAGAAGAATAGTCTCACTCGTGAACAGGTTATCAAGGAGGCCACTTGGGAACCACACCAAGGTAAATATATGGGCCACAAATTAA
CTGTAACACGCAGTCGATAAGTCAAGGGTTGTCCAACGTGTTGGACAGCCTTTCATCATATTGATTGGGAGGTATTAAATGACTAAGTTTACT
ATGCAAGACCTCATTAAATTACGTGATGAAATAGAATCACCGGAAGTTAATACAGAGTTTCACTACATTGATCCACGAGATAAACGAGAGATT
CCTGATTATCAGATTGAGACGGAGTTAATGTATGAAGATTATTGATTGGAAGAAGGAAGCAGAAGGCCGTATCCTAGTGATGGATGCGGAG
GCTAAAGGCCTGCTGGGTGCTATCCGCTACGGTCATCGTGAAGATGTACACATTATTTGCTGCATGGACTTGCTCACCACTGAGGAGTTCCTC
TTCTTCGACCCATATGAGATGCGTGACCCTGAAGCAAGGGAACACTTGAAAGAGTGGGAAGGCCATCAAGATGGGACCTTGGTTGATGGTG
TTAACTTCCTAAAGCACTGTGAAGCCATCGTCTCACAGAACTTCCTAGGCTATGACGGGCTTCTCTTTGAGAAAGCCTTCCCTGACATCTGGAA
GGGATTTAACTACACCGAGAGGCGCGGCAAGGGCAGACTACGTGCTGACTTGTGTCCGGTACGCGTCATGGATACGCTGGTCATGAGTCGC
CTGTTAAACCCAGATAGACGCCTTCCTCCGCAAGCATATGCCAAAGGTATGGGTAACGTTGCCCCTCACTCAATTGAGGCGCACGGCATTCGT
ATAGGCCGTTATAAGCCGGAGAACGAGGATTGGTCTAAACTAACTGACCACATGGTACATCGTGTACGCGAGGACGTGGCGATAGGCCGTG
ACCTATTCCTCTGGCTATTTAACGGAGAATGGACGGAGCACAAACGCCGTGGCGTGAATAAACGCACTGGCCTAGGTATTGAGACAGCCTTC
CACATGGAGTCCATTGTGACGCTGGAGATGAGCCGTCAGGCCGAGCGTGGATTCCGTCTGGATATAGATAAAGCATTAGCACGATGCGAGG
AATTGGACGCTAAGATTGATGAGACAGTCGCAGCGTTCCGTCCGCACATGCCTATGCGTATCAAGTCTAAACCTTTTAAACCGGAAGAAAAG
AATGAAGTATGCCAACGCGCAAATGAGTATGGAGCTAGCAACAATATACCTACTGTCCTTGACCCCTCTCACTTTCTTCACGCAGAGAGACGA
GGGAGATCGCAAGACAGTATGGAGTGTCACTACTAAGTCTGGTGATTGGTCGGCTAGCGTCAAGAAAGACTTTCCTCACCTTAGAGGAAACCG
TAATGACACGCCAAGTGTCAAGTGGATTGGCGCTTACTCGCCTGTTACTTTCGAAGAGATTCCCTTGGGTAACAGGGATACAGTTAAGCAAGT
GCTCTATGATTATGGATGGAAAGGTGTTGAATTTAACGATACCGAGCAAGCGCATCTCGATGAGCATGGCGTATTACCCAAGCCTTGGAGTG
GGAAGATAAATGAAAAGTCCCTTACTTTATGGCAAGAGAGAGCCGCACGTGAAGGTAAAACAGTCCCTGATTGGTGCTTGGGTATCGCTGCA
TGGTACATACTCGTATCCCGTCGTGGTCAGATCCTCAACCGTGGTGACGTTGAAGCCTTCGACCAGAAGGGGGTGTGGCCTTCGCAAGCTGG
TATACGAAAGTGTCGCGGCCTTGTACCTGTAGCATTTAACAAGGAGTTAGGAATCAATGCGCAGCAATACTACGAAAGGTACGGATGCTGGC
CTACGTCAGACAAGGATGACGGAGAATGGCGTGTGCCAGCTATTGCTATTAGTATTGGAACTTCTACGTTCCGTATGCGTCATCGTAACGTGG
TTAATATTCCTGCCCGTGGCTTGTATCCTTTACGTGATTTATTCATAGCAGGGAAAGGCAAGCTAATCCTTGGTTGTGACGGTGCAGGTCTTGA
ACTGCGTGTCCTGTCTCACTTCATGAATGACCCTGAGTACCAAGAGATTGTACTGCACGGTGATATTCATACGCATAACCAGATGAAGGCTGG
TCTTCCTAAGCGTGATATGGCGAAGACATTTATATATGCCTTCCTATATGGGTCTGGTATAGCTAACCTTGCAGCAGTATGTGGTGTTACTGAG
GAAGAAATGGAGGAAGTTGTGGCAAGATTTGAGGTTGAACTACCATCTCTTGCACGTCTTCGTGAGAATGTTATCGCACAAGGTAACAAGTT
TGGCTACCTACAAGCACCTGATGGTCATTGGGGTCGCATCCGTATGTCTGGTGGTGAACTTAAAGAACACACTATGCTTAACGTACTACTCCA
GATGACTGGTTCTCTGTGTATGAAATACGCATTGGTCAGAGCGTTTGCAGGTGATGCGCAAGGAAGGTGTGGCCTTAGATAGCATGGGAAACC
CTTGCGGTATAGCTAACGTGCACGATGAAATCCAGATGGAAGTCCCTGAAGATGAGGTCTTGTATCTCAACTACGACTTGCCTTTCACCTTAG
AAGGGTTCGAAACAGAGAAGGCTGCTGTGAAAGCAGTGTTCGATGCAGAGGAGAAACGTGTTCATGTGGATTCTGAAGGACGTATGTGGTC
TGCTGCAAATCTCGTTAGTGTTGATGCTGGTGTACTTCATTGCCAGCGTCGTTATCACCGTGCAGGGCATATCATTGCCGACGCAATGACCTG
GGCGGGTCAGTACCTGAAGATGCGTTGTCCGATGGCAGGTGAGTATAAGATTGGTGCAAGTTGGAAGGAAACACACTGATGGACAGGTTTG
ATATTGTTTGCCTATTCTCTACCTTCTTTCTTATATTCCTTATGCTTGCTTGCTATGGAAGTATGCGATTAGATATACCTGATGAAGAGGAGGGT
TACGATTGATGCAGGCATCTTTTATTATTCTTGGAGTCATATTATTTATGGTAGTATTCTGGGCTTTCTCTGGCATTGACCCAGATTGTGATGGT
AACTACGACTGAGTTATACTCAAGGTCACTTACGAGTGGCCTTTATGAATAACTTATTCCTACTTATTTTGTCTAACATGATTTACTGGACACTA
TAGAAGGAAAGCATAGGTAATCTAGGTTTATAAGGTAGTATAGGTAATTAAGTAAATATAGGAGATATAAATATGTCTATGGTAACTACTCTG
GTATTCGTGGCTCAATACTTTCGTGGTCTTGCTAATAAGTTCAAGTCCAAGGCTATCAAAGCTATTGAGGCTCGCATCGAAGCAGTACAGGCA
GAGCAAGTTAAAGTTGAAGAACATCGTAGTTCTCAAATGATTGACTGTCATAACCGCTACTATGCATCTCGTGATGAACTAAATGCACGTCAA
GTCAAAGAGGTAGAAGATATGCTGGCACGTCACCAGCAAGAGCGTGACAGCCTGAAAGCTGAATTTGAAGAGAACAAGGCATCAATTGCTC
TTGTACATCAAGCTGCATCTGACAGTCTGAAGAAAGAGATTGTTATGCTGGAAATCGAACTGGATAACCTGACCAAATAAGGGGGGGTTATG
ATGGAAGAAGTAATTCAAGCTAAACATGTAGGTATTATCTTTCGCGATCTAGAGCAGCGTAAAGTTGCAGGTCATACTCGTCTGGCTAAAGA
GGAAGACACCGCAATCACTACTGTAGAACAAGCAGATGCCTATCGTGGACCAGAGTTCACTCAAGGTGAAACTTGTCACCAATTGAGCCTAT
CAATTTGTGACACTATGGCTATTGTAAATGTGCAAGAAGTCGAAGAGGGTGAGTGTGTCAGTTACATCTACCCTTTAGATACTATTGCACGCA
TTAAGGTAATCCATAAGTAATTACTAGACACTATAGAACAATAGGTCGGCTTAGTTCGGCCTATGATTGTAAAGTGTTGTTGATGTTAACCA
TTGTGCATCTTGCACAACCCGATACCGTATAGGGCTTTCTAGTGAGTACATGCTTGTGCTCAGTACAAAGCTAACTGACAATAGGAGACTAAA
TAAATGGCACGTGGTGATTTTGATTTTGGTGCTCAGGTTACTAAATCTGAAGGTAAAGTCTTTAAGAATCCAGAAGTAGGTGATCATGAAGCA
GTAATCTCTGGCATCATTCATGTTGGTTCCTTCCAAGACATCTTTAAGAAAGGTAATACCACTGAAGTTAAGAAGCCAGCAAACTTTGTTCTGG
TTAAGATTGTCCTGATGGGTGACGATGACAAGAACGAAGATGGTTCTCGCATGGAACAATGGATGGCTGTGCCTCTGAAGTCTGGTGATAAG
GCAACACTGACTAAGTTCCTGAATGCAGTTGACCCTAAAGAGTTGCTGGGTGGCTTCGATGATTTCATTGGTGAATGCCTGACTGCAACGATG

Figure 5D

```
GTCGGTTCTGGTGATAAGAATGACGATGGCTCATTCAAGTATGTTAACTGGAAGGGATTTGGTGGTATGCCGGACAAGCTGAAGAAACTGGT
CATTGCTCAGGTTGAAGAGGAAGGTCTGTCTATGACAGGTCACATTACCTTCGACAAGCTGACCAAAGAAATCCTTGATGACATCCCAGCCAA
CTTGGTGCGTCAATACTTCCTGAACGAGACGCCTCGTGGTAAGAACCTGTCTGTTGCTGGTTCTCACGTAGAAGCAATCATTAAAGCTGCTCG
TGAAGAAGACCCAGAATGGAAGAAGGCTAAGAAGAAAGACGAGGAAGATGCTACCCCAGCTAATCGTAAATCTCTGGATACTGGTGAGTCT
GTTCCACAGGAAGTACCTGAAGCAGAAGATACTCCTGCACCGGAGATGGATGAGGACGCGGAATATTAAGGAGAAAGGATGAAAGTACAA
ATCGTAACCCTGCACTGCAAGAAAGGAATTACAACTCTTGGCGGCAACACTTTTCACTCCTTCTCTGAAGGGGACACATATGCCGACCTGCAC
TACATCTGGCGCGACGGACAGCACGTGGTGAACTACAGCGACCCAGCTACGGGGAAACGCCACGGCGTATCGCTTCCGGCGCATGACATTG
CTCAGGTGAACACAGTTTTATAAAGTCTCACGTGTGAGACAAATCGGTGTCCGGTATTTACTGGACACTATAGAAGAGAAGAATTTTAATCGG
CGATAATGCCATAACCAACAAAAGGAGAATTTAATATGTTCAAGATTGAAACTATCGTAAACCGTGTTGTTAAAGGTGCTGCTCTGGTATCCG
TTGAGTCTTTCATTATCGTCGATGAAACTGATCAACTGGTAGCTGGTACTAAGGCTTACGATACCCGTGAAGAAGCTCAGGCTAAGATTGACA
GCATGGGTAACTTCGCTGCTGGTCTGGAGTTCGCTCGTGCTTGCTTCCCTGAGCAGGCTGACAAAGCTCAGATTGGTAAGGCTAATATCGTAG
CTGAATATCTGGATTGGGTTGCTGCTGGTAAACCAGTGAAAGAAGTTAAGGCTGCTGAAGAAGCTGAAGCTCCAGCAGAAGAAGTAGCTGC
ACCGGAAACTCCGGTAAGTGAAGAGGAAGAATTTTGATAATAGCAGGTGTTGCCTCTGTTAGTCCTAGCTGACTATCACGCTCACCTCATCTA
ATGCCCTGTCTGCCTTAGTGTAGGCAGGGTCTTTTGCGTAATAGTTATTGGAGAATGAATTATGCCGACTATTGAATCTCGAATTGAACTGGA
CATTAGCTACAATGCAATCACCAGACAGTATATTGGGGTTGCCTATGATTACAAAACTGGTGAGAAGCTAGTGGAGGTGAGACAATGGGATG
ACTATTGGTTAAGACAGAACCTCCATGATGCGGTGTCCTCCTTCCTGAAGGAGTGGCCTACATGCGACCAAACTTCGACTTCGGAGCTACAGT
ATCGGAAGACAATAACCTGTTGCTGTGGCCAACTGAAGGTAATCGAATCGCTTTAATAGATGCTGATATGTTACCTTACATCATAGGGTATAC
AATCAGTGATATGACTTATGTACGAGCCACAACTCGTGTTAAGTCAGGGCAAGTCCCCTCAATCAAAGATACACCTGAGTGTAAGCAAGCGT
GTGTCCGCCTAGCATTCACCAAGCCTTATAAAGGTCAACGTAAGACCGAGAAGCCTCCATTCTTCTATGAATTGCGAGAGCATCTCTTAGAGG
TTCACGGTGCAATCTTGGCAGATGGAGAGGAAGCAGATGACCTCATGAGTATCGCACAATGGGACAGCCACCGCCGCTTCCAGCAAGATACA
GGTAACGAGTTCCCTATCGGTAGTCCAGAGCATAAAGCATTCTCTGATACTTGCATCGTTTCCTTGGATAAGGATTTGATGATTGTTCCCGGTT
GGCATCTACAGCCGGGTCAAGAGAAGAAATGGGTAGAGCCTATGGGTTGGCTTGAGCTACGCCGTAAGGCTAATGGGCAAGTCAAAGATCT
AAAAGGTGCTGGCCTCATGTTCCACTATGCACAGATGATTATCGGTGATGATATTGATAACTATGCTGGCATACCAGGTCGTGGTGCTAAATA
TGCCTATGATCTTCTCAAAGATTGTAAGACAGAGAAAGAGTTGTACATGGCAGTGCTGGGTGCTTACAAGGCTAAGTTCGGGCATGGACAAG
TTAAAATTAAGAATTACCGAGGTGGTTATCGTATCGGCAAAGCCTTTGACCTAATGCTTGAGTGTGGTCGCTTATCTCACATGGCAAGATTCA
AGGGTGATATATGGCGAGCCGATAAGAACCCAATCTTGTGGGGAGATGATGCGGAATGGTTAGCAAATTAAAATCATCGGAGGTGGCAGCT
TATAAGAAGGAATTGCTAGATAAGCAAGGATGGAAATGCCCTCTGTGTGGCGGCAGTCTCAAAGCTGTCACACCTGTAAACCGTGTACTTGA
CCATGACCATGAGACAGGATTCTGCCGCGCTGTTGTATGCCGAGGCTGCAATGGTGCGGAAGGGAAGATTAAGGGTGTTATCTCTGGTTATG
GTAAGGCTGGTAACAACCGTTACTTCCAGCTTCAATGGTTAGAGCGACTATATGAATACTGGAAGTTACATAGTACGCCTCAGACAGATAAGT
TATATCACAAACATCAAACGGAGGCAGAGAAGCGCGAGGCTAAGAACCGTAAGGCACGCCTTGCTTATGCAAGAAAGAAGGAGGTTAAAGT
TGGGTAAGCTGCGCAGCTTGTACAAAGACTCCGAGGTACTTGATGCAATCGAGCAAGCTACCGACGAGAAAGGTAATGTTAACTACAATGAG
ATGGCACGTGTATTATCGTGTCATACTGTGGGTAAGAAGATTACCCGCCAGTTGGCTCGATACTGGCATGGTCAATTCAAGAAGACCAAGAA
GAATGGTGATTACTACCAGACCCTTCTGCAAGAAGATAAGCGTATCAAAGAAGAGCGTAAGCTCAGGACTCCTGACCGCTACGAGGATTTGG
CTATTGTGCCATTGCCTGACTCGCCTCATCGAAGTGTACTGGTGATCCCTGATACTCATGCACCTTATGAGCACCCAGATACCCTAGAGTTCCT
TGCAGCCGTGGCAGCACGTTACCGTCCAGACACAGTGGTACACCTAGGAGATGAGGCAGACAAACATGCCCTGTCATTCCACGATTCGGACC
CAAATCTGGATAGTGCTGGCATGGAGTTAGAGAAGGCTCGTATCTTCATGCACAAATTGCACAAGATGTTCCCTGTGATGCGCCTGTGTCACT
CTAACCACGGCTCTATGCACTTCCGTAAGGCAAGCGCCAAAGGCATCCCTGTGCAATACCTGCGCACCTATCGTGAAGTCTTCTTCCCGCAGG
GAGGTGGCGACCAGTGGGATTGGCAACATACGCACGTCCTTGAGTTGCCGAATGGTGAACAAGTGGCATTCAAGCATCAACCTGCTGGCTCT
GTCCTAGCAGATGCAGCGCATGAGCGTATGAACCTTGTGTGTGGTCACTTGCACGGTAAGATGTCTGTGGAGTACGCACGTAATACACATGA
ACAGTATTGGGCTGTGCAAGGTGGCTGCTTAATTGATGAGTCATCCCGTGCATTTGCCTATGGTCGTGAGTCTAAATACAAGCCAGCATTAGG
TTGTGTGGTCATTCTGGAGGGTGTGCCCTCACATTGTCCCGATGCAAACCAATAGCGACAACCGTTGGATTGGCAAGATTTAGTTGACACTATA
GAACAAAGGGCTAGGTAAGACTTTATCGGCTGGCGTATCCAAATGATATTGCACTAGCCCTTGATTGTATAGTGAATGGAGGATTCAATATGT
CACACTATGAATGTAAGAAGTGTCATAAGCGTTATGATTACTGTACTTGTGGTCAAGAGAAAACATCTTTTAAAGTTGGAGACAAGGTATTTC
GTAATGAAAAAGATTCGATTCCTTGGAATCAATACTGCAAAGAAGCTGGTATTGACCCTGATAGCCCTGTAACCATAGATGATATTGATGGCA
TTAACTTGTGCTTTCGTGAGGTGAGGGGTACAGGTTGGGATTCCAAAAAATTCAAACTTGCATCTGATAAGTTAGACAACAATATGGTAATTA
AGCCTAAGCACTACGAGTTCTTTGATGGCTAGAGGCAATCACTATCATTGCCCGCAGTATGACCGAGAAGCAATTCGCTGGCTATTGCATGG
GTAATGCTTTGAAGTACCGTCTACGTGCAGGTAAGAAGTTCAACACTGAAGAAGACCTGAAGAAAGCAGATTACTACAAAGAGTTATTCCAG
AAGCATCGTCACGAATGTATTGATGAGGATATTTGATATGAATATCTTTGAGTTCCTAGGTCTTCCAGAAGACCACCGCAATCACCCATTCATG
CTGGTGAAGCATCGCGGTGAAGTTCCTGAGAAGAAATTAACTTTTCCATGTTATGCACAGGTGAAACGAGATGGTATCTTTTCTGCTGTTGTT
GTTCGCACTGATGGTGTCGTTGGCATTTTTGGTCGCACTGGTAAGAAATTGGCAAACACTGAAGGACTCGAACAAGCCTTTGCTACCTTTCCG
```

Figure 5E

GTTGGCATTTATCTTGGTGAGCTTCAGTCTATGGCCATTGATATCTACCTTGAGGCAATCTCTGGGGTTGTGAACCCCAATCGCACTGAGCCAC
TTGATTTCATAGGCCAGCAGATTAAAGACAACCTGTATATCGACTTCTTCGATATGTTAACTATTAAGGCATTCCATGATGGATTCACTGATGT
TTCTTATCTCAAACGTTACGATGCTTTACATCGTCGTATCGGCGCTCATCTTAGCGGGTGCAACGCTATCCTTCCTATCACTCCTTGCCATAATG
AGCGAGAAGTTGAAGCGTTTGCGCAAGAGCAAATAGATGCAGGACGTGAGGGTGCTGTATTCAAACTGGACTGCGATTATGAAGCAGGACA
CAAAGGTTATCGTCAGACTAAAGAAGTCCGTAAGGTAACCTATGACCTTACTTGTATTGGCTTTGAAGAAGGTAAAGGCAAATACAAAGGTA
AGGTAGCTAACCTCATTTTCAAATGGAAAGGAGGCAAGACAATCAAAGCTATGTTAGGTAAGGGGTGGACTCATGCAGATGCAGAGCAGAT
GTTCCACGACATTAAACATGGTGGACGATTGAATGTCATTGGTAAAATCTTTGAAGTCAAAGGTCTTCAGGATTCAAGCAAGGGCAACATTCG
TCTGCCCAAAGCGGGAGAATTAAGACATGACAAAGATGAACCAGATTTCTTTTGATAGCATGAAGGCAACTCGTGCAGTTGAGGTAGCAGAA
GCTATCTTCGAAACTTTATCCTGTGGCATGGAAGTGCCATATACTTTACTTGCTGATGCAGAAGAACTTGGTCTTTCTGTAGAAGCTATCCAAG
AGAAGGTTGACGAATTATATGGTACAGACGAAGAAGAAACCGACGATTTCATTTGAAGGAATGGAGATGCTTGAGATGATTCTCAAGCCTTC
TTCTCCTAAGGTGACTAAGACTCATGAAGAGTTAATCGTTGATGAAGTTAAGCGTTACATCATGGATTGTGTCAGAGCACAACTGGTGGTCCA
ATGATACGTCCAGCCTCCTTCCTAGATATTCCTGAGATTATAAACCTTGGGAATAAATATGTGGAAGAGGAAGTCAAGGTTGTAGCCCACCAC
TCAGCCTCATGGAATGCAGAACAAAGTGCCATAACCTTTGTGCATCTCTTAATAGAGACCCACCACTCAGCCTCATGGAATGCAGAACAAAGT
GCACATAACCTTTGTGCATCTCTTAGTAGAGAAGATTTATCCCTATGGGTTGCTGTAGATGAAGGGCAGATTGTAGGGTTCCTGTGGGCTGGC
TATCACGAGTTGGCCCCTTGGACACCTGTAAGAGTTGCCTCTGACATTCTCTTTTATATTATACCAGAGAGAAGGGGAACACTACTTGGTATGC
GCTTAATTAAGGCATTGAAACAGTGGGCATCAGATAATGAATGCTCTGAAGTGCGTTTAAGTATTGCAAGTGGCATCAACGAGGAGCGCGTA
GGGCGCATGTACAAACGGCTCGGCTTTGAACCGTTTGGCACTGTGTATAACCTGAAGTTCTAAAGAGGAGATATACAATGGTTTTTACGCTTG
AGGACTTCGTTGGTGACTGGCGTCAAACCGCGGGGTATAATCTTGATCAGGTCCTGGAGCAGGGCGGAGTTTCGTCCTTATTCCAGAACTTA
GGGGTAAGTGTTACGCCGATTCAGCGCATCGTGCTGAGTGGAGAGAATGGATTGAAAATTGACATTCACGTTATCATTCCGTATGAGGGTTT
GAGTGGAGACCAGATGGGACAGATTGAAAAGATTTTCAAAGTGGTGTATCCCGTCGATGACCATCACTTTAAAGTAATTCTGCACTATGGGA
CCCTTGTGATCGACGGTGTAACGCCAAACATGATTGACTATTTCGGTCGCCCTTACGAAGGTATCGCCGTCTTCGACGGAAAAAAAAATCACTG
TCACGGGAACATTATGGAACGGAAATAAAATTATCGACGAACGTCTGATCAATCCTGATGGAAGCCTGTTATTTCGCGTTACGATCAATGGAG
TGACCGGATGGCGTTTATGCGAACGTATTTTGGCTTAAAGAGGAGATATACAATGGGTGTTGTAAAGAAAGCATTTAAGGCTATCGGTCTTG
CTCAAGATGCACCACGTATTGAAGCCAAAGTCCCAGCACAGCAGCTTGAGCGTAAGCCTGAGACTGAAGCTGAAGATATTCAAATTGGTGCA
GGGGATGATGCTACTGCATCTGCAAAAGGTAAGCGTGGCCTTGTCCGTCCGGTAGCTTCTAGCTTGAAGGTGTAATATGAAACAGAGCATAG
ATTTGGAGTATGGAGGTAAGCGGTCTAAGATACCTAAGCTATGGGAGAAGTTCTCCAATAAACGTAGCTCTTTCCTTGATAGGGCGAAGCAT
TACTCCAAATTAACCTTGCCCTATCTGATGAATGACAAAGGTGATAACGAGACTTCGCAGAATGGATGGCAAGGTGTAGGTGCTCAGGCAAC
CAACCATCTAGCCAACAAGCTAGCGCAAGTACTATTCCCTGCACAGCGTTCCTTCTTCCGTGTAGACTTAACTGCACAAGGTGAGAAGGTTCTT
AATCAGCGTGGCCTGAAGAAGACAGAGCTAGCTACCATCTTCGCTCAAGTGGAAACACGGGCAATGAAAGAGTTAGAGCAACGTCAATTCC
GGCCTGCTGTAGTAGAAGCATTTAAGCATCTTATTGTTGCTGGCAGCTGTATGCTATACAAGCCGAGCAAAGGTGCAATCAGTGCTATCCCAA
TGCATCACTACGTAGTTAACCGTGATACCAATGGCGACCTGTTAGACATTATCTTGCTACAAGAGAAAGCCTTACGTACCTTTGACCCAGCTAC
ACGTGCGGTAGTAGAGGTTGGCCTGAAAGGTAAGAAGTGCAAGGAAGATGACAGCGTTAAGCTGTACACACATGCTAAGTATCTTGGTGAT
GGATTTTGGGAACTCAAGCAATCTGCTGATGATATCCCTGTGGGTAAGGTGAGTAAAATCAAATCAGAAAAGCTACCTTTCATCCCATTAACT
TGGAAGCGAAGCTATGGTGAGGATTGGGGTCGACCTCTTCAGAGGATTACTCCGGTGATTTATTCGTTATCCAATTCTTATCTGAAGCGGTT
GCCCGTGGTGCTGCGCTGATGGCAGATATCAAGTACCTGATTCGTCCTGGTGCTCAAACTGATGTTGACCACTTTGTTAACTCTGGCACTGGT
GAGGTTGTCACTGGTGTAGAAGAAGACATCCATATTGTACAGTTAGGTAAGTACGCAGACCTCACACCTATTAGCGCGGTTCTAGAGGTATA
CACTCGCCGTATCGGTGTTGTCTTCATGATGGAGACAATGACACGCCGTGACGCCGAACGTGTTACTGCTGTAGAAATCCAGCGAGATGCGT
TAGAGATTGAGCAGAACATGGGTGGTGTATACTCCCTCTTTGCTACTACTATGCAATCGCCAGTAGCGATGTGGGGTCTGCTGGAGGCAGGG
GAGTCCTTCACTAGTGACTTAGTGGACCCTGTGATTATCACAGGTATTGAAGCTTTAGGACGCATGGCTGAGTTGGATAAACTGGCTAACTTT
GCTCAGTATATGTCACTGCCATTACAATGGCCTGAGCCTGTCCTAGCTGCTGTGAAATGGCCTGACTATATGGATTGGGTGCGTGGTCAAATC
TCTGCTGAACTGCCGTTCCTTAAATCGGCTGAAGAGATGGCACAAGAACAGGAAGCACAGATGCAAGCACAGCAAGCACAGATGCTTGAAG
AAGGTGTGGCTAAGGCCGTGCCGGGTGTAATTCAACAAGAACTTAAGGAGGCGTAATGTCTTTCTCATTTACTGAACCGTCAACCACTCACCC
TACTGCTGAAGAGGGTCCGGTAGAAACCAAGGAGGTAACAACTGATGCTGCTACTACTGATGCTCCTGCTGACGCTGGCACTTCTGTACAAG
ATGACAATGCTGGTGCACAACCTACTGAAGACACCGGAGGAGAAGCTTCTGGACAGCCTTCAGAAAAAGGAGACAATGGCGGAGAGAATG
GTGAACCTAAGCCAGATGATACCGCGACCGACACTGAGGAAGTGCAATACTTCTTCGGAGAACATGAAGTAACAGTAGACATCCCACAGGAT
GTAACTGACAGCCTTAAAGAGAAAGGCATTGATGCCAAGCAGGTTGCCAAGGAACTCTATTCCAAAGGTGGCAAGTTTGAACTGTCAGATGC
AACCAAGCAGAAATTGTATGATGCTTTTGGCAAGTTTGCGGTAGATGCTTACCTATCAGGTCTAAAGGCTCAAAATGAAGCCTTCTTCCTGAA
AGAAGCCAACGCAGCTAAAGAGTTGGAAGCAGCTAACACCCAACGCTTCTCTGATGTTTCTAAGGAAATTGGTGGCAAGAAGGTTGGTCCC
GTCTTGAGGAGTGGGCACTTGAAGCGCTGTCTGATGACGAACTAATGGCATTCAATGCGGTGATGGAATCTGGCAACCAGTACCTGCAACAA
TATGCTGTTCGTGAACTGGAGGGTCGTCGTAAGCAGGCACAGGGGGATGATAAGCCATCCCTGATTGAGCCATCAGCACCTGCTAAGGCTAA
TGAAGAGAATGGCCCCACTGACGCGAGATCAGTACGTTCAAGCAATCGCAACTCTTAGCCAGAAGTACGGCAATGACCGTAAAGCTATGGCA

Figure 5F

```
GAAGCTCAGGCTAAACTGGACGCCCGTCGCCGTGCTGGCATGGCTCGCGGTATCTAATTCAGTATTTACTGGACACTATAGAAGGGAGAAAA
GTTCTCCCTAGTTATCAATTTGATTTATAAGGAGATTATAATACATGTCTACACCGAATACTCTGACTAACGTTGCTGTATCTGCGTCCGGTGA
GGTTGACAGCCTTCTCATTGAGAAGTTTAATGGTAAGGTCAATGAGCAGTACCTGAAAGGTGAGAACATTCTGTCCTACTTTGATGTACAAAC
TGTTACTGGCACTAACACAGTGAGCAACAAATATTTGGGCGAAACTGAGTTGCAGGTGCTAGCACCGGGTCAGTCCCCTAATGCCACCCCTAC
TCAGGCGGATAAAAACCAGTTGGTAATTGATACCACTGTCATTGCTCGTAACACTGTGGCTCACATCCACGATGTACAAGGTGACATCGATAG
CCTGAAACCAAAACTGGCTATGAACCAAGCCAAGCAACTGAAACGTCTGGAAGACCAGATGGCAATTCAGCAGATGCTGTTAGGCGGTATTG
CTAACACCAAGGCCGAACGTAACAAGCCGCGTGTTAAAGGGCATGGCTTCTCTATCAACGTTAACGTAACTGAGAGTGAAGCACTGGCTAAC
CCTCAGTATGTTATGGCTGCGGTAGAGTATGCTCTGGAGCAACAGCTTGAGCAGGAAGTGGACATCTCTGATGTAGCTATCATGATGCCGTG
GAAGTTCTTCAATGCTTTGCGTGATGCAGACCGAATTGTAGATAAGACTTACACTATCAGCCAGTCTGGTGCAACCATTAATGGCTTCGTTCTC
TCTTCTTATAACTGCCCTGTGATCCCGTCTAACCGATTCCCTACCTTCGCTCAGGATCAGGCTCACCACCTGTTGTCTAATGAAGATAACGGCTA
TCGTTATGACCCTATCGCAGAGATGAATGGTGCAGTTGCTGTTCTGTTCACTTCCGACGCACTGCTGGTGGGTCGTACCATTGAAGTGACTGG
TGACATCTTCTATGAGAAGAAAGAGAAGACTTATTACATTGACACCTTCATGGCTGAGGGTGCAATCCCTGACCGTTGGGAAGCAGTGTCTGT
AGTTACCACTAAACGTGATGCAACTACTGGTGATGCTGGAGGTCCTGGTGATGATCACGCAACCGTACTGGCTCGTGCACAGCGTAAGGCTG
TATATGTCAAAACCGAAGGTGCTGCGGCTGCATTCTCTGCTGCCCCAGCAGGTATCCAAGCGGAAGACCTTGTAGCGGCGGTACGTGCTGTA
ATGGCAAATGACATTAAGCCGACTGCAATGAAACCTACTGAGTAACACCTATGCCCTATCTACCTTGCGTAGGTAGGGTTCTTTTTGTTAGGA
GGATTCATGCCTGTAATTAGACAAACCAGTAAATTAGGACATATGATGGAAGATGTGGCCTTCCAGATTATTGATAGTAAGCTGGAAGCGGT
AAACTTGTGTATGCGAGCTATTGGTCGTGAGGGTGTGGATTCCCTCGACTCAGGGGACTTGGACGCAGAAGATGCAAGCAAAATGATCGAC
ATCGTATCCCAGCGGTTCCAGTACAACAAAGGAGGTGGCTGGTGGTTCAATCGTGAACCAAACTGGCAACTTGCACCAGACACTAACGGTGA
AGTTAATTTACCTAACAACTGCCTAGCAGTATTGCAGTGTTATGCTTTAGGTGAAAAGAAAGTACCTATGACTATGCGAGCAGGTAAGCTCTA
CTCTACTTGGAGTCACACCTTTGATATGCGTAAGCATGTTAATGCTAATGGTATGATTCGTCTTACCTTACTCACCTTACTACCCTACGAGCATC
TACCTACAAGTGTAATGCAGGCTATTGCCTATCAAGCTGCTGTAGAGTTTATTGTGTCTAAGGATGCAGATCAGACTAAGCTAGCCACTGCGC
AGCAGATAGCCACTCAGCTTCTTATGGATGTACAATCTGAGCAAATGTCACAGAAGCGATTAAACATGCTGGTACATAACCCTACTCAGCGTC
AGTTTGGTATCATGGCTGGTGGCTCTCAGAATGTACCTGCTTACTCTCATTCACCTTATGAGAGTTGGGCGCTCCGTCCGTGGGAGGATCGTT
AATGGAAGTACAAGGTTCATTAGGTAGACAAATCCAAGGGATTAGCCAGCAGCCGCCAGCGGTACGCTTGGATGGTCAGTGCACAGCTATG
GTTAATATGATACCTGATGTAGTGAATGGTACTCAATCACGCATGGGTACAACTCATATTGCAAAGATACTTGATGCGGGGACTGATGACATG
GCTACTCATCATTATCGCAGAGGTGATGGTGATGAAGAGTATTTCTTCACGTTGAAGAAAGGACAAGTTCCTGAGATATTTGATAAGTATGG
GCGCAAATGTAATGTGACTTCACAAGATGCACCTATGACCTACCTCTCTGAGGTTGTTAATCCAAGGGAAGATGTGCAATTCATGACGATAGC
TGATGTTACTTTCATGCTTAATCGTAGGAAAGTAGTTAAAGCTAGTAGCAGGAAGTCACCTAAAGTTGGAAACAAAGCCATTGTGTTTTGTGC
GTATGGTCAATATGGTACATCTTATTCCATTGTAATTAATGGGGCCAACGCTGCTAGTTTTAAAACACCGGATGGTGGAAGTGCAGACCATGT
TGAACAAATTCGAACTGAACGTATCACTTCTGAATTGTACTCTAAGTTGCAGCAATGGAGCGGTGTGAGTGACTATGAAATACAAAGAGACG
GTACTAGTATATTTATCGAGAGACGGGATGGTGCTAGCTTTACAATAACAACCACCGATGGTGCAAAAGGTAAGGACTTAGTGGCTATCAAG
AATAAAGTTAGCTCTACTGACCTACTCCCTTCTCGTGCGCCTGCTGGTTATAAAGTACAAGTGTGGCCTACTGGCAGCAAACCTGAGTCTCGTT
ACTGGCTGCAAGCTGAGCCTAAAGAGGGAAACCTTGTGTCTTGGAAAGAAACAATAGCTGCTGATGTATTACTTGGGTTTGATAAAGGCACA
ATGCCTTACATTATTGAACGTACAGATATCATCAACGGCATAGCTCAATTCAAGATAAGACAAGGTGATTGGGAAGATCGTAAAGTAGGGGA
TGACTTGACTAACCCTATGCCCTCTTTTATTGATGAGGAAGTACCCCAGACAATAGGTGGAATGTTCATGGTGCAGAACCGCCTATGCTTTACA
GCAGGTGAAGCGGTTATTGCTTCTCGTACATCATACTTCTTCGATTTCTTTCGTTATACGGTTATCTCTGCATTGGCAACTGACCCCTTTGATAT
TTTCTCAGATGCTAGTGAAGTCTACCAGCTAAAACATGCAGTGACCTTAGATGGCGCTACCGTGTTGTTCTCTGATAAGTCACAATTCATACTG
CCAGGCGATAAGCCTTTAGAGAAGTCAAATGCACTGCTTAAGCCTGTTACAACATTTGAAGTGAACAATAAAGTGAAGCCAGTAGTAACTGG
TGAATCGGTAATGTTTGCCACTAATGATGGTTCTTACTCTGGTGTACAGAGGTTCTATACAGACTCTTATAGTGACACTAAGAAGGCACAAGC
AATCACAAGTCATGTGAATAAACTCATCGAAGGTAACATTACCAACATGGCAGCAAGCACCAATGTCAACAGGTTACTTGTCACTACCGATAA
GTATCGTAACATAATCTACTGCTACGATTGGTTATGGCAAGGAACAGACCGTGTACAATCAGCATGGCATGTATGGAAGTGGCCTATAGGTA
CAAAGGTGCGAGGTATGTTTATTCTGGTGAATTACTTTACCTGCTCCTTGAGCGAGGAGATGGCGTGTATCTGGAGAAGATGGACATGGGT
GATGCACTAACCTACGGTTTGAATGACCGCATCAGAATGGATAGGCAAGCAGAGTTAGTCTTCAAGCATTTCAAAGCAGAAGATGAATGGGT
ATCTGAGCCGCTCCCTTGGGTTCCTACTAACCCAGAACTTTTAGATTGCATCTTAATCGAGGGTTGGGATTCATATATTGGCGGCTCTTTCTTAT
TCAAGTACAACCCTAGTGACAATACTTTGTCTACAACCTTTGATATGTATGATGACAGCCATGAAAAGCGAAGGTTATTGTTGGTCAGATTTA
CCCTCAAGAGTTTGAACCTACGCCTGTGGTTATCAGAGACAATCAAGACCGTGTATCCTACATTGATGTACCAGTTGTAGGATTGGTTCACCTT
AATCTTGACATGTACCCCGATTTCTCCGTAGAAGTTAAGAATGTGAAGAGTGGTAAAGTACGTAGAGTATTAGCGTCAAACCGTATAGGTGG
TGCTCTCAATAATACAGTAGGCTATGTTGAACCGAGAGAAGGTGTCTTCAGATTTCCACTGAGAGCTAAGAGCACGGATGTTGTTTATCGTAT
TATTGTAGAGTCACCTCACACATTCCAGCTTCGTGATATTGAGTGGGAAGGGAGCTACAATCCAACCAAAAGGAGGGTCTAATGGCTATAGG
TTCAGCCGTTATGGCTGGTATGTCTTCTATTGGTAGCATGTTTGCAGGCAGTGGTGCAGCAGCCGCTGCTGGAGGTGCTGCCGCAGGTGGCG
GAGGTTTGCTAGGTTCACTAGGTGGATTCCTAAGTGGCTCTACTGCTGGTTTCTCTAATGCTGGCCTTCTTGGTGCTGGCCTTCAAGGGTTAG
```

Figure 5G

```
GCTTGATTGGTGATCTATTTGGTGGAAGTGATGAAGCCAAGGCGATGAAGAAAGCACAAGAAGAGCAATGGCGGCAGCAGCTTATTGCTAC
ACAAGAGGCGTACAAGACAGTGGCAGACGCAGAACGTTCTGCTGCTAAACAATATCATGCAGATGCAATCAGTAATCAGGCTTCACTGCTAC
AGCAGCGAGCACAGGTTGCATTACTTGCTGGGGCTACTGGTACTGGTGGTAATTCTGTGTCCTCTATGCTTAATGACTTAGCAGCAGATGGCG
GCAGGAACCAGAGTACTATCATTGATAACTATGAGAATCAGAAGATTAATTTCACCAACCAGCTTAAGTCTATCCAACGTGGTGGTCAGATGC
AGATGCGTGAGTTTAAGAAGCCTTCTGCTATGAATACCTTGGTTAAAGGTATTCCAAGTCTGGCATCTGCCTATGTAACTGGTAGTAAGTCTG
GCAAGGCATTGGGTAAAGCCTTAACTGATTCTCGCACATATTCATCTGGAACAAGAGGTATTTAATGGCAATTGAGCGACAAGCAGTACAAG
GTCTGCCACAAGTGCAGGCCACTTCTCCTAATGTCATGACCTTTGCACCTCAACAAGTGGGAGGTGTGGAGGCTGGCGTGGCTTCTACCTCCG
GTAGTAGGTTTATCGAAGACCTTATTCGTGCAGCAAGCAGCGTGGCTGATGTTACCACTGGTATCCTTAATCAGAAGATTGAGGAAGATAAG
GTTGTTCAAATGGAACGGGCATATAACGGATTAATGCCTTCTGAGGATGCAACTCGTGGTGGCGCTCGTGCTAACATGCTTGTCAAAGCTCAA
CTGCTAGCTAATGATGAAGCAGCACGAATGAAAGACATGGCTACTCGTTTCCAAGGAACGGATGACGAATGGACACAACTTATGGTTGACTC
TCGTAATGAGATGCAGAATAAGCTGTTCCAGCAATACCCTGAGTTGCAAGGTGACAAAGATACTATGCGTATGGTCACTAATGTCTTCCAAGA
ACAGCAGCCTCAGATTTGGGCTACACGAACCCAGCATAAACTTGACCGTGAACAAGCAGACCGTGAGGATACCTTTGACGGGCGAGTGGCTT
CTACTTGGGATTCTAATATTGACCCTGAAGCCTCTGGCTATGCTTTACAGGAACGAATCCGCGAAGGTCTTACTCAAGGATTACTACCTGAACA
GATGTACAAGAAGTTAGTCCAGCGAGCAATTTCACTTGCACAAGGCGGTGATGTTAGCATGGCTGAAGCCCTGAAGTATGTGAAGGACGATA
AGGGTGTTTCTGTTTATGCTAAGAATCCACAGCTTATCACAGCCATCACTAGTGGTAATGCAGTTTGGGCTAGGAATAATGTAGCTGATGTAA
CTCGTATGTCTTTCGAAGTTAAAGAATCCTACCTTGCAGGTGATTTAACTGATGAAGAATTGTTGGAACGAGCACAGCACATTAATAATCTGA
CAGGTAACTCTGTCTTCTCTAATCCAGAACTAGAGGCACTGATGCGCCAACGGGCTAAGCAGAATGCAGAGCTAGGTGCAATGCAGGATATG
CGACGTGAGCTTTACTCCGACCGCCTGACTGGCTTCCAAGGTAAGACTGATAAAGAGAAGAAGGCTTACATTGATGTTATCAAACAGGATAG
CCAACTTTATGCAGACCAGCAAATCAAACAACGTGGCTTGGACCCTTACAGTCAAGAGGCTGAAGCTATTCGTGGTGCAGTGGAAGTGCAGC
GCCTGCAATTCATGAACTCCAAAGGCTTAGTGGATGATACCTTTGAGTCTCGTATCAAAGCCATGGAATCTATGCTATCGCCTGAGCACTTTGC
CAAGGGCGAACCACAGGAGTTGATGACTATTCGCCAGTTGTGGGAACAGTTACCAGAAGAGAGCCGAGGTGTCTTTGGTGACACGGTGAAT
GGCTACATGGATAACTACAACACTGCACTACAAATGGGAGAGACACCTTTGCAGGCTGCAAGGTTTGCGCGTAAAGCACAGCAGAAATTCTC
TCGTACTGAGAAGGAAACCAAGAAGTTCAACTCAGCTATTGGAGATGCACTGGATGAGGTATCTGGTGCTGGCTGGTTTGATGGTAAAACCG
AAGTGTCAGACTTAGGTAAAGCTATTGCGGAAGAAGAGTTACGAGCTAAGGCCAATATGTTGTGGTCTAGTGGTATGCGTAACATGGATTCC
ATCAAGAAGGCTTTAATTACTTGGGGCAATAAACGCTACACTCAATCAGAGGATGCAAAGACTTCCGGTGGCTATTTCATTAAAGGTGATTAC
ACTTCTGCATCTGATATGCTTATGTCAGTTGGGAAAGGCGTAAACCCTACCGATGTACCTCTGGCGCTTGGTAGGTATGTAGAAACACAGATG
CCAGAATTGAAGAAGGAGCTTCAAGAGGGGGAAACTAAAGATGATATATACATTGATTACAATGAACAGAAAGGTACTTTCGTGATTCGTGC
TGGTGCAGCAGGTCGCCCTCTTTCTGGAGTAATCCCTGTAACCTCTTAGATACCACTTCACTACTAGATTCTGCCTATCAGAAGAAAGTAGAG
GAACGAGATAAAGGCGAGTATGTTCACCCGTATCGTACAGATATTGGTGCACAAGAGCCTATGCCAGCTAAACCAACTGCCAAAGATATTGG
TAAATTTGGACTAGCTAACTTCCTCATGTCTTCTGCTTTTGCTTCTGGTGAGAATCTGCCTTCTAACTTCGAGATTAACTATCGAGGTAATATGC
AACAATTCTATGACAAGCTAGCTATGGATGAGAATAAAGATAAAGTTGGCTTTAATAAGGCAACTGGAACCTTTACTCCATATAAAGACGCTC
ACGGTGAGTCTATCGGTTACGGTCATTTCTTAACGGAAGAAGAGAAGCGAAACGGGTATATTAAGATTGGCGATGAACTAGTTCCCTATCGA
GGGTCTATGTCTCAGCTTACAGAGAGCAAGGCTCGCGCTCTTATGGAGCAAGATGCTAAGAAGCATGTGCCTCCTACTCGTGACTGGAAGAT
TCCGTTTGACCAGATGCACCCTGCACAGCAACGTGGCTTGATGGATTTAAGCTACAATTTAGGTAAAGGTGGAATCCAGAACTCACCGCGTGC
TCTTGCTGCATTCAAAGCTGGTAAGCTTACGGAGGGCTTTATCGAAATGCTGGGCACTGCATCAAGTGAAGGTAAGCGTATTCCTGGCCTACT
GAAGCGACGCGCTGAGGCATACAATATGGCATCTGCTGGTGGTGTGCCTAAGATTACCGAAGTGGAGACTCGTGAAGATGGCTCCATGTGG
GTTAGGTTTGGTGGACCTATGCCAGCAGGTTCTGTCTCGGCATGGACTCATAAACGTATTGGCGCGGATGGTTGGTATCAGGTTTATGAGGC
TGCACCTACCAAGTTAGCTAAAGATTCTAAGGTAGGTAAAGTTAAGTTGTAGTACCTAACTCAAGGCTTGTCTCACATGTGAGACAGGTCTTT
ATGATAGGCACTATGGAGGAATTATGGAACAAGACATTAAGACTAATTGGGCTGGATATGTCCAGTCTACTCCTGAGCCGTTTTCTATTGAGG
CGGCTCCGGTATCGGCTCCTACGATACGCCAGCGTAATGAGTTACAAGAGCAAGTTCTTGAAGCTAAAGCTGACGCTGATATCTTAGGTGCT
GTAGGTGCTGCCTTCAGAATGAGTGGTTGGCATTCGGAGGCAAGCGGTGGTATGACCGTGCCACTGCTGATTTCACACCTCAACCAGACTTT
GAGATACAACCTGAGCAACGTGAAGCACTACGTTTCAAATATGGTACGGATATGATGCAGACAATCACTGAGGGTGTTCGTTCTGAGGATGA
ATTGAACTTCCGTATTCAGAATGCGGATGAAGACCTTGAGCGCAATAAGCGCATTGCTCAGGCTGGCTGGGTTGGCTCTGTGGGCGACGATTG
GCGCTGCTGTGCTTGACCCTGTGGGATGGGTTGCCTCTATTCCAACCGGTGGTGCCGCTAAAGTTGGACTCGTAGGCCGTGCTGTGCGTGGC
GCTATCGCCGCTGGCGTGAGTAATGCCGCTATTGAATCCGTATTGGTCCAAGGTGACATGACTCGTGATTTAGATGACATTATGGTAGCACTG
GGTTCCGGTATGGCTATGGGTGGCGTTATTGGCGCTGTAGCGCGTGGTAGGGCCACTAAGCTCAGTGAGCAAGGTGATGACAGGGCTGCTA
GCATTGTGCGCAGTGCAGACGCAGGGGACCGCTATGTTCGTGCTGTTGCCGATGACAGTATCGGTGCGATGCGTGTTAAGGGCGCAGAGGT
TCTCACTGAGGGTGTATTCGATATCTCCAGTAAGAGTGAAGACCTACTGAAAACCTTGCAACGAGAAGGTAATGCGATTGATATGACACCTCG
CCGTTGGGCTGGAACTATGTCTGCCCTCGGTACTGTCGTGCACTCATCTAAAGATGCAAGTATCCGAGGCCTTGGTGCTCGTCTGTTTGAATC
CCCACAAGGTCTAGGTATGCAGAAGGCATCTGCTAGTCTTATGCAGAATACTAACTTAAATCGCCTGAAATCTGCTGATATGAACCGCTTCAA
TGATGGGTTTGATTTGTGGCTTAAAGAGAATAATATCAATCCAGTAGCAGGGCATACCAACTCTCATTATGTACAGCAATACAATGAAAAGGT
```

Figure 5H

```
GTGGGAGGCAGTGCGTATTGGCATGGATGAGTCTACACCTAAATCTATCCGCATGGCTGCTGAGGGACAACAGGCTATGTACAGAGAGGCG
CTGGCTTTACGTCAACGTTCTGGTGAAGCGGGATTTGAAAAGGTAAAAGCCGACAACAAATATATGCCTGATATCTTTGATAGTATGAAAGCC
AGACGTCAATTCGATATGCACGATAAAGAAGACATCATCGAACTTTTCTCTCGTGCCTACCAGAATGGCGCTCGTAAGATTCCAAAGGAAGCA
GCAGATGAGATTGCACGAGCACAGGTAAATCGCGTTGCTGATGCTACCTTAACTGGAAAGCTTAGTTTTGAAAAGGCAATGTCAGGTCAGAC
TAAGGCAGAGTATGAAGCTATCATGCGTAAGGCAGGCTTCAGTGATGAAGAAATTGAAAAGATGATAGAAGCTCTGGATAACAAAGAAACC
AGAGATAACATCTCTAACCGAGCTAAAATGAGTTTAGGATTAGATGTTACTCAAGAATACAATGGCATTCGTATGCGTGACTTCATGAATACC
AACGTGGAAGAGCTAACAGATAACTATATGAAGGAAGCAGCAGGTGGCGCTGCATTGGCTCGCCAAGGCTTCTCTACCTATCAGGCTGCACT
TAATGCAATTGACCTTGTAGAGCGAAATGCACGAAACGCGGCTAAGGATAGCAAGGCTAGTTTGGCATTAGATGAAGAGATTCGTCAGATGC
GAGAAGGTCTTCGCCTGATTATGGGCAAGTCGATTGATGCAGACCCACAGGCTATATCTACTAAGATGATGCGTCGTGGTCGTGATATCACA
GGTGTGCTTCGCTTAGGTCAAATGGGCTTCGCACAGCTAGGTGAACTTGCCAACTTTATGGGTGAATTTGGTATTGCTGCAACTACTATGGCT
TTAGGTAAGCAATTCCGCTTCACCTCTAAGGCGTTGCGTAATGGCGATGGCTTCTTCCGAGATAAGAACTTAGCTGAGGTTGAGAGAATGGT
GGGGTACATTGGTGAGGATAACTGGCTAACAACTAAGGGTGCACGTCCTGATGAATTTGGTGATGTAACCACAGTAAGAGGGATGATGGCT
CACTTTGACCAATCCATGAACTCAATACGTCGTGCTCAAACCAACCTATCACTCTTCCGCATGGCACAGGGTTCTCTGGAGCGAATGACTAATA
GGCAAATAGCTTTGTCTTTCATTGACCACCTTGAAGGCAAGAAGATTATTCCTCAGAAGAAACTGGAGGAACTTGGTCTTACTCAGGAGTTCA
TGACTAACCTACAGAAGCACTATGATGCTAACTCTAAAGGTTCTGGCTTGCTTGGCTTTGATACAATGCCTTATGCCATGGGTGAAACTTTAGC
TAATGCTATTCGTCGTAAGTCAGGTCTAATCATCCAACGTAACTTCATTGGTGATGAAGGTATCTGGATGAACAAAGCACTAGGTAAGACATT
TGCACAGCTTAAGTCATTCTCTCTTGTATCTGGTGAGAAGCAATTTGGTCGAGGGATTCGCCACGATAAAATTGGTCTTGCTAAGAAGACAGC
TTACGGGTTTGCTTTGGGTTCAATAGTGTATGCGGCAAAAGCCTATGTGAACTCTATTGGGCGAGAAGACCAAGATGAATATTTGGAAGAGA
AGTTATCGCCTAAAGGGTTGGCCTTTGGTGCAATGGGTATGATGAGTACAACTGCTGTATTTAGTCTAGGTGGAGATTTCTTAGGTGGCCTAG
GTGTTCTACCTTCCGAACTCATTCAATCACGCTATGAAGCAGGTTTCCAAAGTAAGGGTCTGATTGACCAAATACCTCTGGTTGGCGTTGGTGC
AGATGCAGTAAATCTGGCTAACTCAATCAAGAAGTATGCAGAAGGTGACACAGAAGGTGTAGATATCGCTAAGCGAGCACTCCGTCTTGTGC
CACTTACCAATATAATAGGTGTCCAAAACGCATTGCGTTATGGCTTAGATGAACTGGAGGATTGATGAGTTATACTTTCACAGAACATACAGC
CAATGGTACGCAAGTCACCTATCCTTTTAGCTTTGCTGGTAGGGATAAAGGTTATCTTCGTGCCTCAGATGTGATAGTGGAGTCTCTTCAAGGT
AACACTTGGATTGAAGTTACATCTGGCTGGCAACTAACTGGCACGCACCAGATTACTTTTGATGTAGCACCAGTTGCAGGTTTGAAGTTCCGT
ATTCGAAGGGAAGTACAAAAAGAATATCCATACGCTGAGTTTGACCGTGGTGTTACCTTGGATATGAAGTCTTTAAATGGTTCTTTCATTCATA
TACTGGAGATTACACAGGAGTTACTTGACGGGTTTTATCCAGAAGGATACTTCATTAAACAGAATGTAAGCTGGGCGGCAATAAGATTACT
GATTTGGCTGATGGCACAAATCCGGGAGATGCAGTAAATAAAGGGCAGCTTGATGCCATCGACAAGAAGCATACAGATTGGAACGCCAAAC
AGGACATTGAGATTGCTGGCCTTAAGGCTGGTATGACTTCTGGTATTGCGCACAGAACTGTTCCTTGGTACACGATAGCCCAAGGTGGTGAG
ATTTCCGTAAAACCACCTTATGAATTTCAAGATGCACTAGTTTCTCTTAATGGGGTATTGCAGCACCAAATTGTAGGCGCATACTCTATAAGCA
ACAACACTATCACTTTCGCAGAGCCGCTTGTGGCTGGTACAGAGGTGTATGTGCTGATTGGTAGTCGTGTGGCTACATCTGAACCTAATATTC
AGTTGGAGTTGAACTTTGACTTAGTAGAAGGCCAACAAGTAGTACAGATTGGCTCTGCATTTAAGTACATTGAGGTCTACCTTGATGGATTAT
TACAACCTAAACTTGCTTATCAGGTAGACGGTGACATTGTTACTTTCTCAGAAAGAGTACCAGAATGCCGGATGACTGCTAAGATTATCACAG
CATAAGGAGGTGGGATGATTAACTCCGAACTGGTAGATAGTGGTGTGAAGCTTGCGCCACCTGCACTCATATCAGGTGGGTACTTCCTCGGT
ATCAGTTGGGATAATTGGGTGTTAATAGCAACATTCATTTATACCGTGTTGCAAATTGGGGACTGGTTTTATAATAAGTTCAAGATTTGGAGG
GAGAAGCGTGAGCGTACACAATAAACATGCAGCTACAGAGGACGAGGTTGGCATTCTGCATGGTGCTATTACCAAAATCTTCAATAAGAAAG
CACAGGCAATACTGGACACTATAGAAGAAGACCCTGATGCAGCATTACATTTAGTGTCTGGTAAGGATATTGGTGCGATGTGTAAGTGGGTT
CTTGATAACGGCATTACCGCCACACCTGCTGCACAGCAGGAAGAGTCCAAGTTATCTAAGCGCCTCAAGGCTATCCGAGAGGCATCCAGTGG
TAAGATAATTCAATTCACTAAGGAGGATTGATGGCTAAGGCAAGAGAATCACAAGCGGAGGCTCTTGCCAGATGGGAGATGCTACAGGAGT
TACAGCAGACCTTTCCTTACACCGCGGAAGGTTTGCTTCTCTTTGCAGATACAGTTATTCATAACTTAATTGCAGGCAACCCTCATCTGATTCGT
ATGCAGGCGGATATCTTGAAGTTCCTATTTTACGGACACAAGTACCGCCTCATCGAAGCGCCTCGTGGTATCGCTAAGACAACACTATCAGCA
ATCTATACGGTATTCCGTATTATTCATGAACCGCATAAGCGTATCATGGTTGTGTCCAAAACGCCAAGCGAGCAGAGGAAATCGCAGGTTG
GGTAGTTAAAATCTTCCGTGGCTTAGACTTTCTTGAGTTTATGCTGCCGGATATCTACGCTGGGGACCGTGCATCCGTTAAGGCGTTTGAGAT
TCATTACACCCTACGTGGTAGTGATAAGTCTCCTTCTGTATCCTGTTACTCAATCGAAGCAGGTATGCAGGGTGCTCGTGCTGATATTATTCTA
GCGGATGACGTAGAGTCGATCAGAATGCTCGTACGGCAGCGGGCCGTGCCTTGCTTGAGGAGCTGACTAAGGAGTTTGAATCTATCAACC
AGTTTGGGGATATCATTTACCTTGGTACACCTCAGAACGTAAACTCTATCTACAACAACCTACCTGCTCGTGGTTACTCTGTTCGTATCTGGACT
GCGCGTTACCCTTCAGTAGAGCAAGAGCAATGTTATGGCGACTTCCTTGCACCTATGATTGTTCAAGATATGAAGGACAACCCAGCACTTCGC
TCAGGGTACGGGTTGGATGGTAATAGTGGTGCACCTTGTGCCCCTGAAATGTATGATGATGAAGTCCTGATTGAGAAGGAAATCTCTCAGGG
TGCTGCTAAGTTCCAGCTTCAGTTCATGCTTAACACTCGCATGATGGATGCTGACAGATACCCATTACGCCTGAACAATCTAATCTTCACCTCG
TTTGGTACAGAGGAAGTCCCTGTGATGCCTACGTGGAGTAATGATTCCATAAACATCATTGGTGATGCACCTAAGTATGGTAACAAGCCTACG
GATTTCATGTACAGACCTGTAGCTCGCCCATATGAATGGGGTGCTGTCTCCCGCAAGATTATGTATATTGACCCTGCGGGTGGTGGTAAGAAC
GGAGATGAGACGGGTGTAGCCATCGTATTCCTGCACGGCACATTCATTTATGTGTATCAGTGCTTTGGTGTACCTGGCGGATACCGAGAGTC
```

Figure 5I

GTCCCTGAATCGCATTGTGCAGGCCGCAAAGCAGGCGGGTGTTAAAGAGGTATTCATTGAGAAGAACTTTGGTCATGGCGCGTTTGAGGCG
GTAATTAAGCCGTACTTTGAACGAGAGTGGCCTGTAACTCTGGAAGAGGATTACGCCACCGGACAGAAAGAGTTGCGTATCATTGAGACGCT
GGAGCCGCTCATGGCAGCCCATAGGCTTATCTTCAATGCAGAGATGGTGAAGTCAGACTTTGAGTCGGTACAGCACTATCCGCTTGAACTAC
GCATGTCCTACAGTCTTTTCAATCAAATGTCGAACATAACGATTGAGAAGAACAGCCTCCGGCACGATGACCGCCTAGACGCCCTGTATGGCG
CTATACGGCAATTAACTTCTCAGATAGACTATGACGAGGTTACACGGATTAATCGCCTCAGAGCGCAGGAGATGCGCGATTACATCCATGCTA
TGAACACACCTCATCTACGCAGGGCAATGCTATATGGAGATTACGGTACTGAGCGAAGAGTGACCAACACTTCCGTAGCGATGCAGCAGCGA
GTTTACGGGCAGAACTACCGAAATAAATCGGCAAGCAGAAATACACTTTCTGCAAGGATTTCAAGGACTTATTAATTACTGGACACTATAGAA
GGAAGGCCCAGATAATAAGAGAAAATAATAGGTAATATATATATAGGTTAACCTAGGTTATATAGGTATGCCTTAGTATGGGTGTACTCCTGT
ACACCCTATTCCTTACTACCTTACTATATTTACATAATAGGAGAGAGACAATGGCTAATGATTATAGTAGTCAACCATTAACAGGTAAGTCTAA
GAGAAAGCAGGTACAACCTGTAAGTGAAGAACTAATGCTTCCGGTGCTCAAAAAAGAGGAAGTTAGTAAGAAAAGCAATGTTATTAATGAT
GCCACCAAATCAGGTAAACAGAAAGGGGCCATGGTGTGCCTTGAAGTGAAAGGTGGTGTATTGAAGATTGCTATCGCGGTTGATGGCAAAG
AAGATTCAGAGTGGAAGTTAGTAACAGTGGAACCAACTGTTAACCCAGTTTAAGATAAGGAGGAAGATTACATGGCTAAATATGGTACTACA
GGTTCTGTTACTGGTCAGGCTTTTCGAGTAAAAGCAGTACAAACTATTGCAACGGCAATCCCGATGCCTGTTGTTAAAGAAGAAGACCTTAAG
AGTAAAGACCACCCTATCAACATCAAACATTTATCAGGTAAACAGAAAGGTGCAATGGTTGCTCTTGAGAAAGGTGACACAACCTTACATATT
GCTGTTGCACGTGGTAGTGAACCCACAGACCCTTGGGATGTAACTGGTATGGAAAAGGACGCTGTTACTCCAGCAGGGGTATAATAATGCTT
AATAAATACTTCAAGCGTAAAGAGTTTGCTTGCCGTTGTGGGTGCGGTACATCCACTGTTGATGCTGAATTACTACAGGTAGTCACAGATGTG
CGTGAGCACTTTGGTTCTCCTGTAGTTATCACTTCGGGTCATCGCTGTGCTAAGCACAATGCCAATGTAGGTGGCGCTAAGAACTCCATGCAT
CTTACTGGTAAGGCTGCTGACATTAAAGTGTCTGGCATATTACCTTCTGAAGTGCATAAGTATCTTACTAGCAAATACCAAGGCAAGTATGGT
ATAGGTAAGTATAACTCCTTCACTCACATCGATGTACGGGATGGTTGTGCGCGATGGTAAGATGTGTTGAATGGTGTGAGCGTATGGTTGCC
CAAGCTGCCGAGGATGGCAACTATGATGACTGGAAGAACTACTCTGACTTGTTAGCTCAATGGAAAGGGAGATGCAATGAAAAAGCTGTTTA
AGTCTAAGAAGGTTGTAGGTGCACTGGTTGCACTTGTTATTGCTCTTGTTTCTGTAGGTCTTGGTGTAGACCTTGGCTCTGGCACGGAATCCTC
TGTGACAGATGTGGTCTGCCAAGTGATCACCTGTGAATAAGTTTCTAGAAGTTCTGGCAGGTCTTATTGGCCTGCTTGTCTCTGCTAAGAAGA
AACAAGAAGAGAAGGAGGCACAAAGTGAAGCGAATCATGTTAGTGACAACCCTTCTGATTGGTTCGCTGACCACTTCCGGGTGTCAGCAGG
CGTTACCAGAGAAAGCAATGGTGAAACCTCTGAGGCCGACGCTGACGGCAGTTTACGAGGTAGACGATAAGGTCTGCTTTAGTAAGCCTGAC
GCTACAAAACTTGGTTTGTACATTCTCTCGCTAGAACGCGGATACAATTAATACATAGCTTTATGTATCAGTGTCTTACGATTTACTGGACACT
ATAGAAGAGGTAAGATAGCGCCGTTCTTTTGAGCGGCCTATTACTAGCCAATCTTCATAGGGAGGGTTGGAAAGTAATAGGAGATAGCATG
GCTAAATTAACCAAACCTAATACTGAAGGAATCTTGCATAAAGGACAATCTTTGTATGAGTACCTTGATGCGAGAGTTTTAACATCAAAGCCG
TTTGGTGCTGCAGGTGACGCCACTACTGATGATACGGAGGTTATAGCTGCTTCATTAAACTCTCAGAAAGCTGTCACAGTCTCAGATGGTGTA
TTCTCTAGCTCTGGTATTAACAGTAATTACTGTAACTTAGACGGCAGGGGTAGTGGCGTGCTAAGTCACCGTTCAAGTACAGGTAACTACTTA
GTATTTAACAATCTACGTGCAGGTCGCTTAAGTAATATTACGGTAGAAAGTAATAAGGCGACTGATACAACTCAGGGACAGCAGGTATCCCTT
GCTGGTGGAAGTGATGTTACTGTAAGTGACGTTAACTTCTCAAACGTTAAAGGTACTGGTTTCAGTTTAATCGCATACCCTAATGATGCGCCA
CCTGATGGACTTATGATTAAAGGCATTCGAGGTAGCTATTCCGGCTATGCTACTAATAAGGCAGCCGGATGCGTACTTGCTGATTCCTCAGTT
AACTCCCTCATAGATAACGTCATTGCTAAGAACTACCCTCAGTTCGGAGCAGTAGAGTTGAAAGGTACAGCCAGTTACAACATAGTCAGTAAT
GTTATAGGGACAGATTGCCAGCATGTAACTTACAACGGCACTGAAGGGCCAATAGCTCCTTCTAATAACCTTATCAAGGGGGTGATGGCTAA
TAACCCTAAGTATGCAGCGGTTGTTGCAGGCAAAGGAAGTACGAACTTAATCTCAGACGTGCTCGTAGATTACTCAACTTCTGATGCTAGGCA
GGCTCATGGTGTTACAGTAGAGGGTTCTGATAACGTCATAAATAATGTGCTTATGTCAGGATGTGATGGTACTAACTCTTTAGGACAAGGGC
AGACTGCTACAATTGCACGCTTTATAGGTACAGCTAATAACAACTATGCGTCTGTATTTCCTAGCTACAGTGCTACAGGTGTTATTACTTTCGA
ATCCGGCTCTACCCGTAACTTCGTAGAGGTAAAGCACCCTGGCAGGAGAAACGACCTTCTCAGTTCTGCTAGTACTATTGACGGTGCAGCTAC
TATTGACGGCACTAGTAATAGTAACGTAGTGCACGCACCTGCCTTAGGGCAGTACATAGGTAGTATGTCAGGTAGGTTCGAATGGCGGATTA
AGTCCATGTCACTCCCTTCAGGCGTTCTTACTTCTGCTGATAAGTACAGAATGCTTGGAGATGGTGCTGTGTCATTAGCTGTAGGTGGGGCA
CTTCTTCTCAAGTTCGCCTATTTACTTCTGATGGTACTTCTCGGACAGTGTCCCTCACCAACGGTAACGTGCGTCTTTCTACCAGTAGCACAGGC
TTTTTGCAGTTAGGTGCTGATGCAATGACCCCAGACAGTACTGGTACATACGCATTAGGTTCCGCCAGCCGAGCATGGTCTGGCGGTTTTACT
CAAGCAGCATTCACTGTTACCTCAGATGCTCGGTGTAAAACAGAACCTCTTACTATCTCAGATGCCTTACTGGATGCTTGGTCTGAAGTTGACT
TTGTGCAGTTTCAGTATTTGGATCGTGTTGAGGAGAAGGGTGCAGACTCAGCTAGATGGCACTTCGGTATCATCGCTCAGCGAGCTAAGGAG
GCTTTCGAACGTCACGGTATAGATGCACATCGCTATGGCTTCTTGTGCTTCGACAGTTGGGATGATGTATACGAGGAAGATGCCAATGGCTCT
CGTAAACTGATTACACCAGCAGGTTCCCGCTACGGTATTCGTTACGAGGAAGTACTGATATTAGAGGCTGCGTTGATGCGGCGGACTATTAA
GCGTATGCAGGAAGCACTAGCTTCCCTGCCTAAGTAAGCAACAGGCAGTGCGTAAGCACTGCTTTTAGCGCAACTTTTCTTAAAGGTTATCAC
GGTGGTAGCCTTTCAGAAAAGGAGGTTACATGATTCAAAGACTAGGTTCTTCATTAGTTAAATTCAAGAGTAAAATAGCAGGTGCAATCTGG
CGTAACTTGGATGACAAGCTCACCGAGGTTGTATCGCTTAAAGATTTTGGAGCCAAAGGTGATGGTAAGACAAACGACCAAGATGCAGTAAA
TGCAGCGATGGCTTCAGGTAAGAGAATTGACGGTGCTGGTGCTACTTACAAAGTATCATCTTTACCTGATATGGAGCGATTCTATAACACCCG
CTTCGTATGGGAACGTTTAGCAGGTCAACCTCTTTACTATGTGAGTAAAGGTTTTATCAATGGTGAACTATATAAAATCACGGATAACCCTTAT

Figure 5J

```
TACAATGCTTGGCCTCAAGACAAAGCGTTTGTATATGAGAACGTGATATATGCACCTTACATGGGTAGTGACCGTCATGGTGTTAGTCGTCTG
CATGTATCATGGGTTAAGTCTGGTGACGATGGTCAAACATGGTCTACTCCAGAGTGGTTAACTGATCTGCATCCAGATTACCCTACAGTGAAC
TATCATTGTATGAGTATGGGTGTATGTCGCAACCGTCTGTTTGCCATGATTGAAACACGTACTTTAGCCAAGAACAAACTAACCAATTGTGCAT
TGTGGGATCGCCCTATGTCTCGTAGTCTGCATCTTACTGGTGGTATCACTAAGGCTGCAAATCAGCAATATGCAACAATACATGTACCAGATC
ACGGACTATTCGTGGGCGATTTTGTTAACTTCTCTAATTCTGCGGTAACAGGTGTATCAGGTGATATGACTGTTGCAACGGTAATAGATAAGG
ACAACTTCACGGTTCTTACACCTAACCAGCAGACTTCAGATTTGAATAACGCTGGAAAGAGTTGGCACATGGGTACTTCTTTCCATAAGTCTCC
ATGGCGTAAGACAGATCTTGGTCTAATCCCTAGTGTCACAGAGGTGCATAGCTTTGCTACTATTGATAACAATGGCTTTGTTATGGGCTATCAT
CAAGGTGATGTAGCTCCACGAGAAGTTGGTCTTTTCTACTTCCCTGATGCTTTCAATAGCCCATCTAATTATGTTCGTCGTCAGATACCATCTGA
GTATGAACCAGATGCGTCAGAGCCATGCATCAAGTACTATGACGGTGTATTATACCTTATCACTCGTGGCACTCTTGGTGACAGACTTGGAAG
CTCTTTGCATCGTAGTAGAGATATAGGTCAGACTTGGGAGTCACTGAGATTTCCACATAATGTTCATCATACTACCCTACCTTTTGCTAAAGTA
GGAGATGACCTTATTATGTTTGGTTCAGAACGTGCAGAAAATGAATGGGAAGCAGGTGCACCAGATGATCGTTACAAGGCATCTTATCCTCG
TACCTTCTATGCACGATTGAATGTAAACAATTGGAATGCAGATGATATTGAATGGGTTAACATCACAGACCAAATCTATCAAGGTGACATTGT
GAACTCTAGTGTAGGTGTAGGTTCGGTAGTAGTTAAAGACAGCTACATTTACTATATCTTTGGTGGCGAAAACCATTTCAACCCAATGACTTAT
GGTGACAACAAAGGTAAAGACCCATTTAAAGGTCATGGACACCCTACTGATATATACTGCTATAAGATGCAGATTGCAAATGACAATCGTGT
ATCTCGTAAGTTTACATATGGTGCAACTCCGGGTCAAGCTATACCTACTTTCATGGGTACTGATGGAATACGAAATATCCCTGCACCTTTGTAT
TTCTCAGATAACATTGTTACAGAGGATACTAAAGTTGGACACTTAACACTTAAAGCAAGCACAAGTTCCAATATACGATCTGAAGTGCAGATG
GAAGGTGAATATGGCTTTATTGGCAAGTCTGTTCCAAAGGACAACCCAACTGGTCAACGTTTGATTATTTGTGGTGGAGAAGAGACTTCGTCC
TCTTCAGGTGCACAGATAACTTTGCACGGCTCTAATTCAAGTAAGGCTAATCGTATCACTTATAACGGAAATGAGCACCTATTCCAAGGTGCA
CCAATCATGCCTGCTGTAGATAACCAGTTTGCTGCTGGTGGACCTAGTAACCGATTCACTACCATCTACCTAGGTAGTGACCCTGTTACAACTT
CAGATGCTGACCACAAGTACAGTATCTCTAGTATTAATACCAAGGTGTTAAAGGCTTGGAGCAGGGTTGGTTTTAAACAGTATGGTTTGAATA
GTGAAGCAGAGAGGGACCTTGATAGCATACACTTCGGTGTCTTGGCTCAGGATATTGTAGCTGCTTTTGAAGCTGAAGGGTTGGATGCCATT
AAGTATGGAATTGTGTCCTTCGAAGAAGGTAGGTACGGTGTGAGGTATAGTGAAGTTCTAATACTAGAGGCTGCTTATACTCGTTATCGTTTA
GACAAGTTAGAGGAGATGTATGCCACTAATAAAATCAGTTAAGCAAGCTGCTGTACTCCAGAACACAGAAGAGCTTATTCAATCAGGACGTG
ACCCTAAGCAGGCTTATGCCATTGCCAAGGATGTTCAACGTCGTGCCATGAAGAAACCTTCTGCATCTTCTGCGTAAGCAGGTTAATATCTTA
GTATAAACAAGGGCAGACTTAGGTTTGTCCTTAGTGTATTCCAAAGGAGGTAACATGCTGAAAGATGGTTGGGTTTCATATGACCCTACAGA
CCCTAAGAATTGGCTACAGGTTATCGCTATAGCTTGTGCAGGTAGCCTATTGGCTGCCCTGATGTATTCATTATGGATGTACACAAAGTAACC
AAAGTCAAAATTTTGATGTAGGCGTGTGTCAGCTCTCTCGCCCTCGCCCTCGCCGGGTTGTCCCCATAGGGTGGCCTGAGGGAATCCGTCTTC
GACGGGCAGGGCTGATGTACTCCTTGTCTAGTACAAGGGAGGCGGAGGGAACGCCTAGGGAGGCCTAGGAATGGCTTAGTGGTGGACAAG
GTGATTACCTTAGTGAAGCCTCTTAGTGCATTCCTGAGGCCATTCAGGGCGTTTATGAGGGATTGACAGGGTGTGAGGGCGTGGGCTA
```

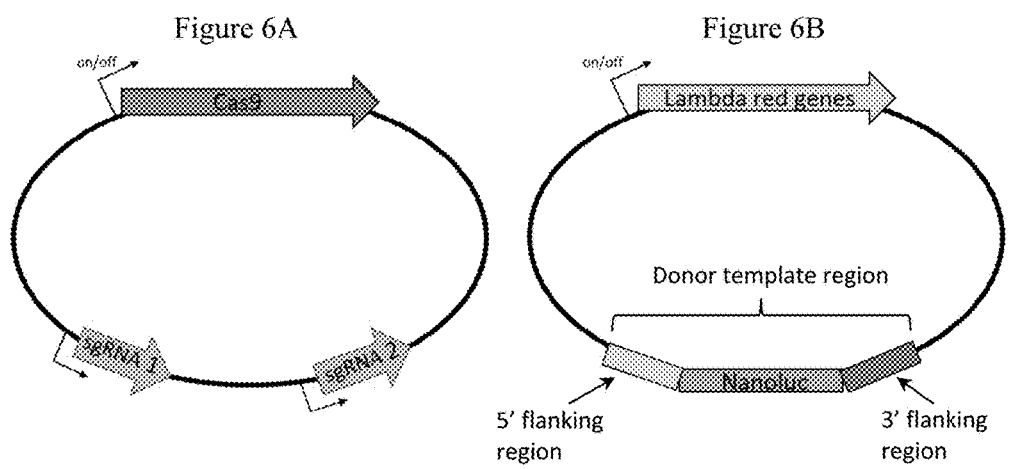

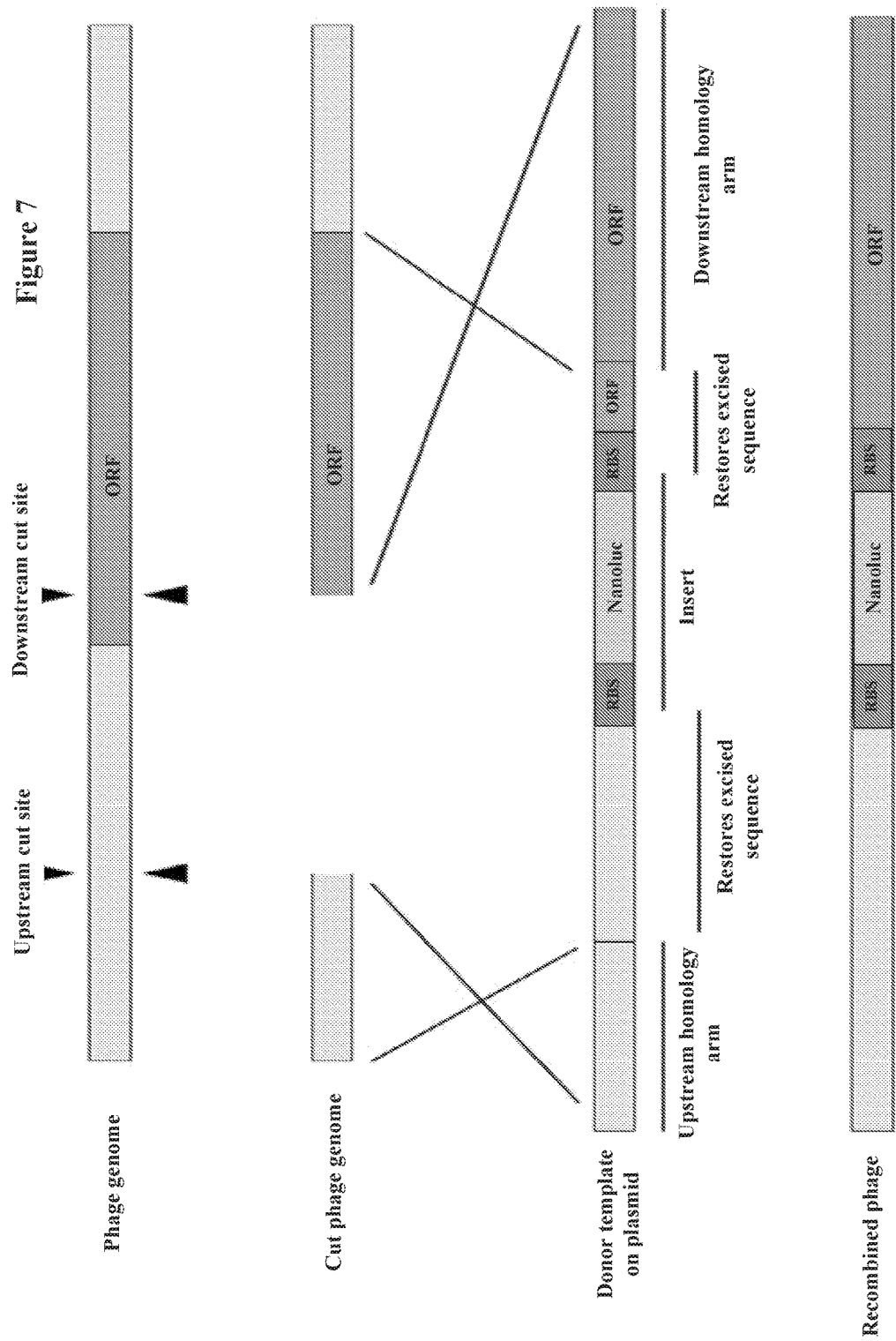

Figure 8

```
Downstream cut site (sgRNA 89)
    D   D   Y   S   D   A   L   H   E   V   V
                                ▼
GATGATTACTCTGATGCACTACATGAGTTGTA  Sequence in K1-5 genome
|| || ||    || || ||  |||||||||||
GACGACTATAGCGACGCCCTTCATGAGGTTGTA Sequence in donor template
                                ▲
    D   D   Y   S   D   A   L   H   E   V   V Protospacer sequence
PAM sequence
▼ = Cas9 cut site
```

Figure 13

One hour infection of K1 *E. coli* maintained under ampicillin selection to prevent carryover of cells used for recombination (which express Nanoluc)

Used to re-infect for round 2

Individual plaques were obtained from these diluted lysates
- sgRNAs 86+89: 24/24 recombinant (100%)
- sgRNAs 1112+1122: 11/24 recombinant (45.8%)

Figure 14
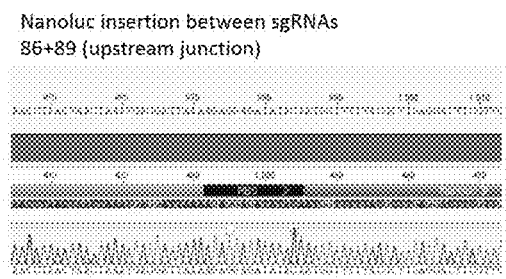
Nanoluc insertion between sgRNAs
86+89 (upstream junction)
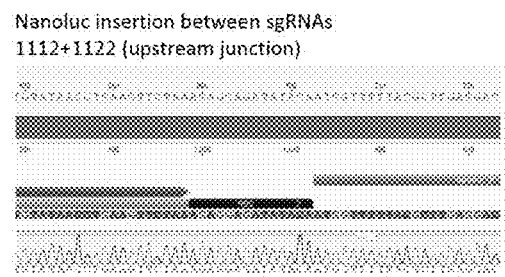
Nanoluc insertion between sgRNAs
1112+1122 (upstream junction)

Figure 15

5' AACCTAACTAACTAAATGAGGATTAAAAGAGGAGATATACAATGGTTTTTACGCTTGAGGACTTCGTT 3' (SEQ ID NO: 10)

5' TGTATAACCTGAAGTTCTAAAGAGGAGATATACAATGGTTTTTACGCTTGAGGAC 3' (SEQ ID NO: 11)

Figure 17
sgRNA 86+89
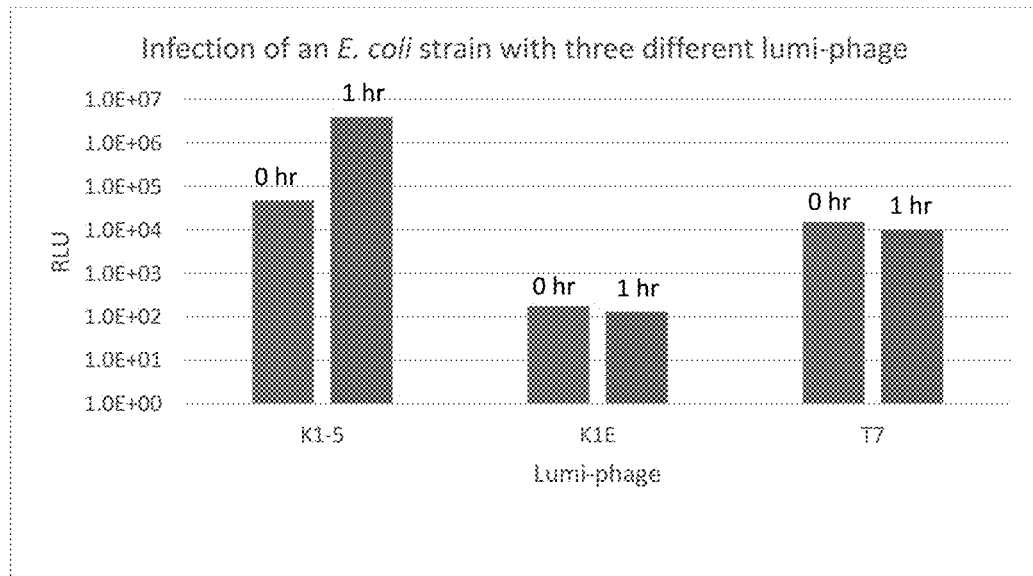
sgRNA 1112+1122
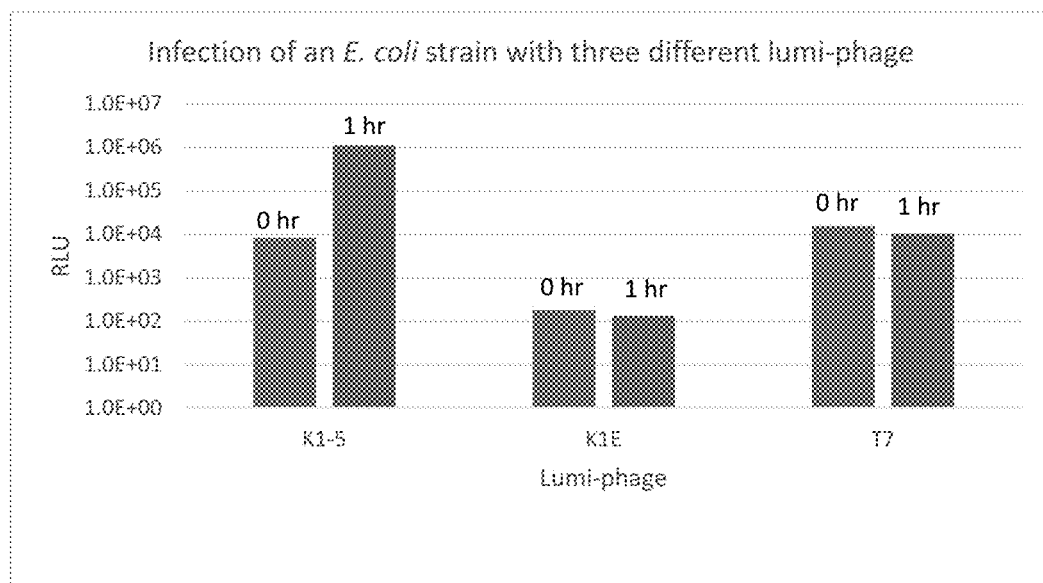

RECOMBINANT K1-5 BACTERIOPHAGES AND USES THEREOF

CROSS-REFERENCE TO RELATED APPLICATIONS

This application claims the benefit of and priority to U.S. Provisional Appl. No. 62/456,783, filed Feb. 9, 2017, and U.S. Provisional Appl. No. 62/515,223, filed Jun. 5, 2017, the disclosures of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Feb. 22, 2018, is named 102590-0617_SL.txt and is 183,395 bytes in size.

TECHNICAL FIELD

The present technology relates generally to compositions including recombinant K1-5 bacteriophages, methods for making the same, and uses thereof. The recombinant K1-5 bacteriophages disclosed herein are useful for the identification and/or antibiotic susceptibility profiling of specific bacterial strains/species present in a sample.

BACKGROUND

The following description of the background of the present technology is provided simply as an aid in understanding the present technology and is not admitted to describe or constitute prior art to the present technology.

Bacterial infections may complicate a patient's existing medical condition, and in some cases, may lead to death. Patients suffering from various bacterial infections often present with similar symptoms, thus making it difficult to accurately identify and characterize the bacterial species or strain responsible for the infection. Accurate identification of the bacteria through conventional lab tests can be challenging and may require incubation periods of up to several days. Additionally, some bacterial strains are not amenable to culturing and in vitro analysis in light of their fastidious nature. In other situations, the observable behavior of some bacterial strains is not readily distinguishable from others. Moreover, individual strains of a particular bacterial species may exhibit resistance to otherwise effective antibiotics.

Early and accurate identification of the bacterial strain(s) responsible for a patient's illness and determining its susceptibility to various antibiotics is an important aspect of the treatment selection decision process.

SUMMARY OF THE PRESENT TECHNOLOGY

In one aspect, the present disclosure provides a recombinant K1-5 bacteriophage nucleic acid sequence, wherein the nucleic acid sequence between (a) position 1,571 and 1,690 of SEQ ID NO: 1 or (b) position 19,979 and 20,165 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof. In certain embodiments, the open reading frame of the heterologous nucleic acid sequence is operably linked to an expression control sequence that is capable of directing expression of the reporter protein. The expression control sequence may be an inducible promoter or a constitutive promoter. Additionally or alternatively, in some embodiments, the recombinant K1-5 bacteriophage nucleic acid sequence comprises a sequence selected from the group consisting of SEQ ID NO: 2, SEQ ID NO: 3, SEQ ID NO: 4, SEQ ID NO: 5, SEQ ID NO: 10 and SEQ ID NO: 11.

Examples of fluorescent protein include, but are not limited to, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOκ, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa. Examples of chemiluminescent protein include, but are not limited to, β-galactosidase, horseradish peroxidase (HRP), or alkaline phosphatase. Examples of bioluminescent protein include, but are not limited to, Aequorin, firefly luciferase, *Renilla* luciferase, red luciferase, luxAB, or nanoluciferase. In some embodiments, the bioluminescent protein is nanoluciferase.

In one aspect, the present disclosure provides a vector comprising any of the recombinant K1-5 bacteriophage nucleic acid sequences disclosed herein, as well as bacterial host cells comprising the vectors of the present technology. In some embodiments, the bacterial host cell expresses K1 and/or K5 capsule genes. The bacterial host cell may be a natural or non-natural host for K1-5 bacteriophage.

In another aspect, the present disclosure provides a recombinant K1-5 bacteriophage comprising any of the recombinant K1-5 bacteriophage nucleic acid sequences of the present technology. Also provided herein are recombinant K1-5 bacteriophages comprising a nucleic acid sequence selected from the group consisting of SEQ ID NO: 2, SEQ ID NO: 3, SEQ ID NO: 4, SEQ ID NO: 5, SEQ ID NO: 10 and SEQ ID NO: 11. The recombinant K1-5 bacteriophage of the present technology specifically infects *E. coli* strains that express either K1 or K5 capsule genes. In some embodiments, the *E. coli* strains that express either K1 or K5 capsule genes are selected from the group consisting of ATCC #11775, ATCC #700973, ATCC #23506, ATCC #23508, and MS101.

In one aspect, the present disclosure provides a bacterial host cell comprising a recombinant K1-5 bacteriophage disclosed herein. In some embodiments, the bacterial host cell expresses K1 and/or K5 capsule genes. The bacterial host cell may be a natural or non-natural host for K1-5 bacteriophage.

In one aspect, the present disclosure provides a method for identifying at least one bacterial strain or species that expresses K1 and/or K5 capsule genes in a test sample obtained from a subject comprising (a) contacting the test sample comprising bacterial cells with a recombinant K1-5 bacteriophage of the present technology; and (b) detecting the expression of the reporter protein of the recombinant K1-5 bacteriophage, wherein detection of the reporter protein indicates the presence of at least one bacterial strain or species that expresses K1 and/or K5 capsule genes in the test sample. In some embodiments of the method, the expression of the reporter protein is measured in about 5, 10, 15, 20, 25, 30, 35, 40, 45, 50, 55, 60, 65, 70, 75, 80, 85, or 90 minutes after contacting the test sample comprising bacterial cells with the recombinant K1-5 bacteriophage.

In another aspect, the present disclosure provides a method for determining the antibiotic susceptibility of a bacterial strain or species in a test sample obtained from a subject comprising (a) infecting a plurality of test samples comprising bacterial cells with a recombinant K1-5 bacteriophage of the present technology and an antibiotic, wherein the plurality of test samples is derived from the subject; (b) detecting the expression of the reporter protein of the recombinant K1-5 bacteriophage in the plurality of test samples; and (c) determining that the antibiotic is effective in inhibiting the bacterial strain or species in a test sample when the reporter protein expression levels of the recombinant K1-5 phage infected bacterial cells in the test sample are reduced relative to that observed in an untreated control sample comprising bacterial cells, wherein the untreated control sample is derived from the subject. In some embodiments, the bacterial strain or species in the test sample expresses K1 and/or K5 capsule genes. The expression of the reporter protein may be measured in about 5, 10, 15, 20, 25, 30, 35, 40, 45, 50, 55, 60, 65, 70, 75, 80, 85, or 90 minutes after infecting the plurality of test samples comprising bacterial cells with the recombinant K1-5 bacteriophage.

Additionally or alternatively, in some embodiments of the methods disclosed herein, the test sample is blood, sputum, mucus, lavage, saliva, or a swab obtained from the subject. In some embodiments, the subject is human.

In certain embodiments of the method, the antibiotic is selected from the group consisting of rifampicin, tetracycline, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim (Bs) and vancomycin.

In one aspect, the present disclosure provides methods for making a recombinant K1-5 bacteriophage of the present technology in a bacterial host cell. In some embodiments, the method comprises (a) contacting a non-recombinant K1-5 bacteriophage genome with a first sgRNA-CRISPR enzyme complex and a second sgRNA-CRISPR enzyme complex in vivo under conditions where (i) the first sgRNA-CRISPR enzyme complex cleaves a first protospacer sequence 5' ACTAAATGAGGATTAAATCA 3' (SEQ ID NO: 6) within the non-recombinant K1-5 bacteriophage genome; and (ii) the second sgRNA-CRISPR enzyme complex cleaves a second protospacer sequence 5' TTACTCTGATGCACTACATG 3' (SEQ ID NO: 7) within the non-recombinant K1-5 bacteriophage genome to produce a cleaved non-recombinant K1-5 bacteriophage genome; and (b) recombining in vivo the cleaved non-recombinant K1-5 bacteriophage genome with a heterologous nucleic acid sequence in the presence of a recombination system under conditions to produce the recombinant K1-5 bacteriophage genome, wherein the bacterial host cell is infected with the non-recombinant K1-5 bacteriophage genome, and wherein the heterologous nucleic acid sequence comprises an open reading frame that encodes a bioluminescent protein, a fluorescent protein, a chemiluminescent protein, or any combination thereof. In some embodiments, the first sgRNA-CRISPR enzyme complex comprises Cas9 and a first sgRNA having the sequence of SEQ ID NO: 16. Additionally or alternatively, in certain embodiments, the second sgRNA-CRISPR enzyme complex comprises Cas9 and a second sgRNA having the sequence of SEQ ID NO: 17. The recombination system may be endogenous or non-endogenous to the bacterial host cell.

In other embodiments, the method comprises (a) contacting a non-recombinant K1-5 bacteriophage genome with a first sgRNA-CRISPR enzyme complex and a second sgRNA-CRISPR enzyme complex in vivo under conditions where (i) the first sgRNA-CRISPR enzyme complex cleaves a first protospacer sequence 5' TATATTATACCAGAGAGGCG 3' (SEQ ID NO: 8) within the non-recombinant K1-5 bacteriophage genome; and (ii) the second sgRNA-CRISPR enzyme complex cleaves a second protospacer sequence 5' GAAGTTCTAAGGAGATAACA 3' (SEQ ID NO: 9) within the non-recombinant K1-5 bacteriophage genome to produce a cleaved non-recombinant K1-5 bacteriophage genome; and (b) recombining in vivo the cleaved non-recombinant K1-5 bacteriophage genome with a heterologous nucleic acid sequence in the presence of a recombination system under conditions to produce the recombinant K1-5 bacteriophage genome, wherein the bacterial host cell is infected with the non-recombinant K1-5 bacteriophage genome, and wherein the heterologous nucleic acid sequence comprises an open reading frame that encodes a bioluminescent protein, a fluorescent protein, a chemiluminescent protein, or any combination thereof. In some embodiments, the first sgRNA-CRISPR enzyme complex comprises Cas9 and a first sgRNA having the sequence of SEQ ID NO: 18. Additionally or alternatively, in certain embodiments, the second sgRNA-CRISPR enzyme complex comprises Cas9 and a second sgRNA having the sequence of SEQ ID NO: 19. The recombination system may be endogenous or non-endogenous to the bacterial host cell.

Additionally or alternatively, in some embodiments of the methods disclosed herein, the cleaved non-recombinant K1-5 bacteriophage genome comprises a first cleaved bacteriophage genomic fragment and a second cleaved bacteriophage genomic fragment. In certain embodiments of the methods disclosed herein, the heterologous nucleic acid sequence comprises a 5' flanking region that is homologous to the 3' end of the first cleaved bacteriophage genomic fragment, and a 3' flanking region that is homologous to the 5' end of the second cleaved bacteriophage genomic fragment.

Additionally or alternatively, in some embodiments of the methods disclosed herein, the recombination system is a non-endogenous recombination system that is induced in the bacterial host cell. The non-endogenous recombination system may comprise lambda Red proteins Gam, Exo, and Beta operably linked to an inducible promoter. In some embodiments of the methods disclosed herein, the inducible promoter is araB and the non-endogenous recombination system is induced by the addition of arabinose.

Additionally or alternatively, in some embodiments of the methods disclosed herein, the bacterial host cell comprises a non-endogenous CRISPR expression vector comprising a nucleic acid sequence that encodes a first sgRNA, a second sgRNA, and a CRISPR enzyme. In some embodiments, the first sgRNA and the second sgRNA are operably linked to a constitutive promoter. In certain embodiments, the CRISPR enzyme is a Cas protein selected from the group consisting of Cas1, Cas1B, Cas2, Cas3, Cas4, Cas5, Cash, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. The CRISPR enzyme may be operably linked to an inducible promoter, such as a tetracycline-inducible promoter.

In another aspect, the present disclosure provides sgRNAs that are useful for making the recombinant K1-5 bacteriophages disclosed herein. In some embodiments, the sgRNA sequence is selected from the group consisting of SEQ ID NO: 16, SEQ ID NO: 17, SEQ ID NO: 18 and SEQ ID NO: 19.

Also disclosed herein are kits comprising one or more coded/labeled vials that contain the recombinant K1-5 bacteriophage of the present technology, instructions for use, and optionally at least one antibiotic.

BRIEF DESCRIPTION OF THE DRAWINGS

FIGS. 1A-1L show the complete genome sequence of non-recombinant K1-5 phage (GenBank Accession No.: AY370674.1; SEQ ID NO: 1).

FIG. 2 shows the heterologous nucleic acid sequence that was inserted into K1-5 phage genomic DNA that was cleaved after position 1,571 and after position 1,689 of SEQ ID NO: 1 using single guide RNAs (sgRNAs) sgRNA 86 and sgRNA 89 (SEQ ID NO: 2). The underlined sequences represent the homologous 5' and 3' flanking regions of the heterologous nucleic acid sequence.

FIG. 3 shows the heterologous nucleic acid sequence that was inserted into K1-5 phage genomic DNA that was cleaved after position 19,979 and after position 20,164 of SEQ ID NO: 1 using sgRNA 1112 and sgRNA 1122 (SEQ ID NO: 3).

FIGS. 4A-4J show the complete genome sequence of the recombinant NanoLuc® K1-5 phage that was cleaved with sgRNA 86 and sgRNA 89 (SEQ ID NO: 4).

FIG. 5A-5J show the complete genome sequence of the recombinant NanoLuc® K1-5 phage that was cleaved with sgRNA 1112 and sgRNA 1122 (SEQ ID NO: 5).

FIG. 6A shows a kanamycin-resistant CRISPR expression vector comprising the Cas9 gene operably linked to a tetracycline inducible promoter and two sgRNAs that are constitutively transcribed. FIG. 6B shows a gentamicin-resistant recombination expression vector comprising the lambda red operon (Exo, Beta, Gam) operably linked to an arabinose-inducible promoter and a heterologous nucleic acid sequence comprising the nanoluciferase gene as well as 5' and 3' flanking regions that are homologous to a portion of the non-recombinant K1-5 phage genome.

FIG. 7 shows a general schematic of the donor template design and recombination between a cleaved phage genome and the donor template. Two double-stranded breaks are generated by Cas9 at sites specified by the two sgRNAs. In some instances, Cas9 cleavage excises a phage DNA sequence that is important for phage viability. The donor template contains any exogenous reporter gene inserts like nanoluciferase, but must also restore the function of excised phage sequences. The 5' and 3' flanking regions of the donor template are homologous to the DNA sequences immediately adjacent to the two cleavage sites in the phage genome, and are necessary for repairing double-stranded breaks via homologous recombination.

FIG. 8 shows an example of codon reassignment to prevent Cas9 cleavage of the recombinant K1-5 phage. Alternate codons were used to encode the same amino acids where ever possible along the 20 bp protospacer sequence and NGG PAM sequence of a target site so as to create gaps in the alignment that would prevent sgRNA recognition in recombinant K1-5 phage sequences. There were amino acids to the right of the precise cleavage site that were deliberately not modified because it would have created an imperfect homology and potentially interfered with strand invasion during DNA repair. FIG. 8 discloses SEQ ID NOS 21, 20, 22 and 23, respectively, in order of appearance.

FIG. 13 shows the luminescence activity profile of the recombinant K1-5 phages of the present technology.

FIG. 14 shows the verification of the upstream junction between nanoluciferase and the intended insertion site of the phage genome via Sanger sequencing. FIG. 14 discloses the three sequences in the left-hand image as SEQ ID NO: 10 and the three sequences in the right-hand image as SEQ ID NO: 11.

FIG. 15 shows the upstream junction sequences of the nanoluciferase insertion in the recombinant K1-5 phage genome cleaved by sgRNAs 86 and 89 (SEQ ID NO: 10) and sgRNAs 1112 and 1122 (SEQ ID NO: 11).

FIG. 17 shows that the recombinant NanoLuc® K1-5 phages of the present technology successfully infected an E. coli clinical isolate that was incapable of being infected with a recombinant nanoluciferase expressing K1E phage or a recombinant nanoluciferase expressing T7 phage. An E. coli clinical isolate (designated as B3) was infected with the recombinant NanoLuc® K1-5 phages disclosed herein, a recombinant NanoLuc® K1E phage, and a recombinant NanoLuc® T7 phage for 1 hour.

DETAILED DESCRIPTION

Figure 9:
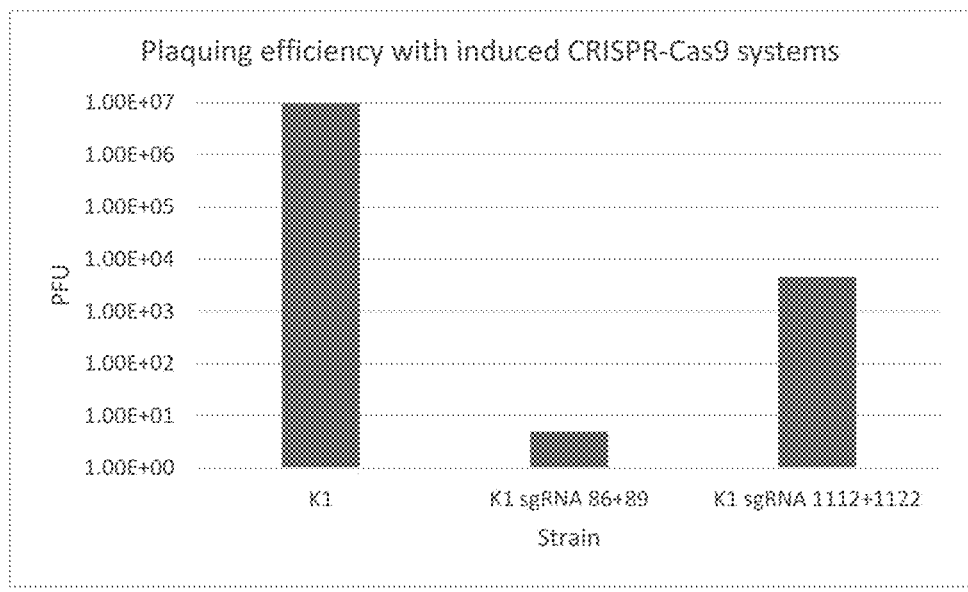
FIG. 9 shows that the plaquing efficiency was reduced when K1-5 phage was plated on a bacterial strain comprising an inducible CRISPR-Cas9 system that targeted the K1-5 phage genome.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like.

Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, "bacteriophage" or "phage" refers to a virus that infects bacteria. Bacteriophages are obligate intracellular parasites that multiply inside bacteria by co-opting some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid can be either DNA or RNA (but not both).

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, an "expression control sequence" refers to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences.

As used herein, a "heterologous nucleic acid sequence" is any sequence placed at a location in the genome where it does not normally occur. A heterologous nucleic acid sequence may comprise a sequence that does not naturally occur in a bacteriophage, or it may comprise only sequences naturally found in the bacteriophage, but placed at a non-normally occurring location in the genome. In some embodiments, the heterologous nucleic acid sequence is not a natural phage sequence. In certain embodiments, the heterologous nucleic acid sequence is a natural phage sequence that is derived from a different phage. In other embodiments, the heterologous nucleic acid sequence is a sequence that occurs naturally in the genome of a wild-type phage but is then relocated to another site where it does not naturally occur, rendering it a heterologous sequence at that new site.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+ PDB+GenBank CDS translations+SwissProtein+SPupdate+ PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, a "host cell" is a bacterial cell that can be infected by a phage to yield progeny phage particles. A host cell can form phage particles from a particular type of phage genomic DNA. In some embodiments, the phage genomic DNA is introduced into the host cell by infecting the host cell with a phage. In some embodiments, the phage genomic DNA is introduced into the host cell using transformation, electroporation, or any other suitable technique. In some embodiments, the phage genomic DNA is substantially pure when introduced into the host cell. In some embodiments, the phage genomic DNA is present in a vector when introduced into the host cell. The definition of host cell can vary from one phage to another. For example, E. coli may be the natural host cell for a particular type of phage, but Klebsiella pneumoniae is not.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/ or entities are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, "operably linked" means that expression control sequences are positioned relative to a nucleic acid of interest to initiate, regulate or otherwise control transcription of the nucleic acid of interest.

As used herein, a "phage genome" or "bacteriophage genome" includes naturally occurring phage genomes and derivatives thereof. Generally, the derivatives possess the ability to propagate in the same hosts as the naturally occurring phage. In some embodiments, the only difference between a naturally occurring phage genome and a derivative phage genome is at least one of a deletion or an addition of nucleotides from at least one end of the phage genome (if the genome is linear) or at least one point in the genome (if the genome is circular).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous to the organism (originating from the same organism or progeny thereof) or exogenous (originating from a different organism or progeny thereof). By way of example, a promoter sequence can be substituted (e.g., by homologous recombination) for the native promoter of a gene in the genome of an organism, such that this gene has an altered expression pattern. This gene would be "recombinant" because it is separated from at least some of the sequences that naturally flank it. A nucleic acid is also considered "recombinant" if it contains any modifications that do not naturally occur in the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, a "recombinant bacteriophage genome" is a bacteriophage genome that has been genetically modified by the insertion of a heterologous nucleic acid sequence into the bacteriophage genome. A "recombinant bacteriophage" means a bacteriophage that comprises a recombinant bacteriophage genome. In some embodiments, the bacteriophage genome is modified by recombinant DNA technology to introduce a heterologous nucleic acid sequence into the genome at a defined site. In some embodiments, the heterologous nucleic acid sequence is introduced with no corresponding loss of endogenous phage genomic nucleotides. In other words, if bases N1 and N2 are adjacent in the wild-type bacteriophage genome, the heterologous nucleic acid sequence is inserted between N1 and N2. Thus, in the resulting recombinant bacteriophage genome, the heterologous nucleic acid sequence is flanked by nucleotides N1 and N2. In some embodiments, endogenous phage nucleotides are removed or replaced during the insertion of the heterologous nucleic acid sequence. For example, in some embodiments, the heterologous nucleic acid sequence is inserted in place of some or all of the endogenous phage sequence which is removed. In some embodiments, endogenous phage sequences are removed from a position in the phage genome distant from the site(s) of insertion of the heterologous nucleic acid sequences.

As used herein, a "recombinant K1-5 bacteriophage" or "recombinant K1-5 phage" means a K1-5 bacteriophage whose genomic DNA comprises a heterologous nucleic acid sequence that encodes a bioluminescent protein, a fluorescent protein, a chromogenic protein, or any combination thereof.

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

As used herein, "a sub-sample" refers to one or more samples containing bacterial cells that are derived from a test sample obtained from a subject. In some embodiments, the sub-sample is void of non-bacterial cells (e.g., human cells). In some embodiments, the sub-sample contains lysed human cells.

As used herein, "test sample" refers to a sample taken from a subject that is to be assayed for the presence of bacteria and/or for the antibiotic susceptibility of bacteria present in the sample. In some embodiments, the test sample is blood, sputum, mucus, lavage, or saliva. In certain embodiments, the test sample is a swab from a subject.

As used herein, the terms "subject," "individual," or "patient" are used interchangeably and refer to an individual organism, a vertebrate, a mammal, or a human. In certain embodiments, the individual, patient or subject is a human.

As used herein, a "vector" refers to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

Bacteriophage

Bacteriophage are obligate intracellular parasites that multiply inside bacteria by co-opting some or all of the host biosynthetic machinery. Phages contain nucleic acid and protein, and may be enveloped by a lipid membrane. Depending upon the phage, the nucleic acid genome can be either DNA or RNA but not both, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances no more than 500,000 bp. The number and amount of individual types of protein in phage particles will vary depending upon the phage. The proteins function in infection and to protect the nucleic acid genome from environmental nucleases.

Phage genomes come in a variety of sizes and shapes (e.g., linear or circular). Most phages range in size from 24-200 nm in diameter. The capsid is composed of many copies of one or more phage proteins, and acts as a protective envelope around the phage genome. Many phages have tails attached to the phage capsid. The tail is a hollow tube through which the phage nucleic acid passes during infection. The size of the tail can vary and some phages do not even have a tail structure. In the more complex phages, the tail is surrounded by a contractile sheath which contracts during infection of the bacterial host cell. At the end of the tail, phages have a base plate and one or more tail fibers attached to it. The base plate and tail fibers are involved in the binding of the phage to the host cell.

Lytic or virulent phages are phages which can only multiply in bacteria and lyse the bacterial host cell at the end of the life cycle of the phage. The lifecycle of a lytic phage begins with an eclipse period. During the eclipse phase, no infectious phage particles can be found either inside or outside the host cell. The phage nucleic acid takes over the host biosynthetic machinery and phage specific mRNAs and proteins are produced. Early phage mRNAs code for early proteins that are needed for phage DNA synthesis and for shutting off host DNA, RNA and protein biosynthesis. In some cases, the early proteins actually degrade the host chromosome. After phage DNA is made late mRNAs and late proteins are made. The late proteins are the structural proteins that comprise the phage as well as the proteins needed for lysis of the bacterial cell. In the next phase, the phage nucleic acid and structural proteins are assembled and infectious phage particles accumulate within the cell. The bacteria begin to lyse due to the accumulation of the phage lysis protein, leading to the release of intracellular phage particles. The number of particles released per infected cell can be as high as 1000 or more. Lytic phage may be enumerated by a plaque assay. The assay is performed at a low enough concentration of phage such that each plaque arises from a single infectious phage. The infectious particle that gives rise to a plaque is called a PFU (plaque forming unit).

Lysogenic phages are those that can either multiply via the lytic cycle or enter a quiescent state in the host cell. In the quiescent state, the phage genome exists as a prophage (i.e., it has the potential to produce phage). In most cases, the phage DNA actually integrates into the host chromosome and is replicated along with the host chromosome and passed on to the daughter cells. The host cell harboring a prophage is not adversely affected by the presence of the prophage and the lysogenic state may persist indefinitely. The lysogenic state can be terminated upon exposure to adverse conditions. Conditions which favor the termination of the lysogenic state include: desiccation, exposure to UV or ionizing radiation, exposure to mutagenic chemicals, etc. Adverse conditions lead to the production of proteases (rec A protein), the expression of the phage genes, reversal of the integration process, and lytic multiplication.

Recombinant K1-5 Phage Compositions of the Present Technology

K1-5 is a 44,385 bp, terminally redundant, lytic bacteriophage (GenBank Accession No.: AY370674.1; see FIGS. 1A-1L) that infects numerous E. coli strains that express either K1 or K5 capsule genes. The recombinant K1-5 bacteriophage of the present technology specifically infects E. coli strains that express either K1 or K5 capsule genes. In some embodiments, the E. coli strains that express either K1 or K5 capsule genes are selected from the group consisting of ATCC #11775, ATCC #700973, ATCC #23506, ATCC #23508, and MS101.

In one aspect, the present disclosure provides a recombinant K1-5 bacteriophage nucleic acid sequence, wherein the nucleic acid sequence between (a) position 1,571 and 1,690 of SEQ ID NO: 1 or (b) position 19,979 and 20,165 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof. In some embodiments, the heterologous nucleic acid sequence further comprises at least one segment that corresponds to at least part of the excised endogenous phage genome sequence between position 1,571 and 1,690 of SEQ ID NO: 1 or (b) position 19,979 and 20,165 of SEQ ID NO: 1.

The present disclosure also provides a recombinant K1-5 bacteriophage nucleic acid sequence, wherein the nucleic acid sequence between (a) position 1090 and 1751 of SEQ ID NO: 1, (b) position 1098 and 1798 of SEQ ID NO: 1, (c) position 1120 and 1810 of SEQ ID NO: 1, (d) position 1200 and 1857 of SEQ ID NO: 1, (e) position 1205 and 1883 of SEQ ID NO: 1, (f) position 1209 and 1904 of SEQ ID NO: 1, (g) position 1230 and 1939 of SEQ ID NO: 1, (h) position 1253 and 1950 of SEQ ID NO: 1, (i) position 1266 and 1967 of SEQ ID NO: 1, (j) position 1300 and 1983 of SEQ ID NO: 1, (k) position 1317 and 2033 of SEQ ID NO: 1, (1) position 1373 and 2054 of SEQ ID NO: 1, (m) position 1519 and 2158 of SEQ ID NO: 1, (n) position 19484 and 20224 of SEQ ID NO: 1, (o) position 19532 and 20288 of SEQ ID NO: 1, (p) position 19541 and 20322 of SEQ ID NO: 1, (q) position 19619 and 20330 of SEQ ID NO: 1, (r) position 19639 and 20348 of SEQ ID NO: 1, (s) position 19732 and 20407 of SEQ ID NO: 1, (t) position 19757 and 20428 of SEQ ID NO: 1, (u) position 19793 and 20502 of SEQ ID NO: 1, (v) position 19824 and 20542 of SEQ ID NO: 1, (w) position 19857 and 20557 of SEQ ID NO: 1, (y) position 19897 and 20580 of SEQ ID NO: 1, or (z) position 19923 and 20638 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof.

Also disclosed herein are recombinant K1-5 bacteriophages that comprise any recombinant K1-5 bacteriophage nucleic acid sequence disclosed herein. In some embodiments, the reporter protein(s) encoded by the heterologous nucleic acid sequence produces a detectable signal upon exposure to the appropriate stimuli, and the resulting signal permits detection of bacterial host cells infected by a recombinant K1-5 phage of the present technology.

In certain embodiments, the open reading frame encodes a reporter protein that serves as a marker that can be identified by screening bacterial host cells infected by a recombinant K1-5 phage of the present technology. Examples of such markers include by way of example and without limitation: a fluorescent label, a luminescent label, a chemiluminescence label, or an enzymatic label. In some embodiments, the heterologous nucleic acid sequence further comprises sequences naturally found in the bacteriophage, but placed at a non-normally occurring location in the genome.

In some embodiments, the length of the heterologous nucleic acid sequence is at least 100 bases, at least 200 bases, at least 300 bases, at least 400 bases, at least 500 bases, at least 600 bases, at least 700 bases, at least 800 bases, at least 900 bases, at least 1 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In certain embodiments, the heterologous nucleic acid sequence comprises a length that is less than or equal to a length selected from the group consisting of 1 kb, 2 kb, 3 kb, 4 kb, 5 kb, 6 kb, 7 kb, 8 kb, 9 kb, and 10 kb. In some embodiments, the heterologous nucleic acid sequence comprises a length that is less than or equal to the maximum length of heterologous nucleic acid sequence that can be packaged into a phage particle comprising the phage genome.

In some embodiments, the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments, the heterologous nucleic acid sequence is inserted into the K1-5 phage genome with no loss of endogenous K1-5 phage genomic sequence. In some embodiments, the heterologous nucleic acid sequence replaces an endogenous K1-5 phage genomic sequence. In some embodiments, the heterologous nucleic acid sequence includes an endogenous K1-5 phage genomic sequence that was previously excised from the phage genome.

In certain embodiments, the heterologous nucleic acid sequence replaces an endogenous K1-5 phage genomic sequence that is less than the length of the heterologous nucleic acid sequence. Accordingly, in some embodiments, the length of the recombinant K1-5 phage genome is longer than the length of the wild-type K1-5 phage genome. In some embodiments, the heterologous nucleic acid sequence replaces an endogenous K1-5 phage genomic sequence that is greater than the length of the heterologous nucleic acid sequence. Thus, in some embodiments, the length of the recombinant K1-5 phage genome is shorter than the length of the wild-type K1-5 phage genome. In certain embodiments, the heterologous nucleic acid sequence replaces an endogenous K1-5 phage genomic sequence that is equal to the length of the heterologous nucleic acid sequence.

In certain embodiments, the open reading frame of the heterologous nucleic acid sequence encodes a reporter protein that confers a phenotype of interest on a host cell infected by a recombinant K1-5 phage of the present technology. In some embodiments, the phenotype of interest is the expression of the gene product encoded by the open reading frame of the heterologous nucleic acid sequence.

In certain embodiments, the open reading frame of the heterologous nucleic acid sequence is operably linked to an expression control sequence that is capable of directing expression of the open reading frame, wherein the open reading frame encodes a reporter protein (e.g., a bioluminescent protein, a fluorescent protein, a chemiluminescent protein, or any combination thereof). In some embodiments, the expression control sequence is located within the heterologous nucleic acid sequence. In other embodiments, the expression control sequence is located in the endogenous K1-5 phage genome sequence. For example, the open reading frame may be inserted into the K1-5 phage genome downstream of or in the place of an endogenous K1-5 phage open reading frame sequence. In some embodiments, the expression control sequence is an inducible promoter or a constitutive promoter (e.g., sarA promoter or lpp promoter). See e.g., Djordjevic & Klaenhammer, *Methods in Cell Science* 20(1):119-126 (1998). The inducible promoter or constitutive promoter may be an endogenous K1-5 phage promoter sequence, a phage promoter sequence that is non-endogenous to K1-5 phage, or a bacterial host promoter sequence. Additionally or alternatively, in some embodiments, the inducible promoter is a pH-sensitive promoter, or a temperature sensitive promoter.

In some embodiments, the heterologous nucleic acid sequence comprises a first open reading frame and at least one supplemental open reading frame. In certain embodiments, the first and the at least one supplemental open reading frames are operably linked to the same expression control sequences. In some embodiments, the first and the at least one supplemental open reading frames are operably linked to different expression control sequences.

Fluorescent proteins include, but are not limited to, blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOκ, mKO2, mOrange, and mOrange2), red fluorescent proteins (for example, mRaspberry, mCherry, dsRed, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatable fluorescent proteins (for example, PA-GFP, PAmCherry1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), fluorescein, rhodamine, and photoswitchable fluorescent proteins (for example, Dronpa).

Examples of bioluminescent proteins are aequorin (derived from the jellyfish *Aequorea victoria*) and luciferases (including luciferases derived from firefly and *Renilla*, nanoluciferase, red luciferase, luxAB, and the like). These proteins have also been genetically separated into two distinct functional domains that will generate light only when the protein domains are closely co-localized. A variety of emission spectrum-shifted mutant derivatives of both of these proteins have been generated over the past decade and have been used for multi-color imaging and co-localization within a living cell.

Examples of chemiluminescent protein include β-galactosidase, horseradish peroxidase (HRP), and alkaline phosphatase. Peroxidases generate peroxide that oxidizes luminol in a reaction that generates light, whereas alkaline phosphatases remove a phosphate from a substrate molecule, destabilizing it and initiating a cascade that results in the emission of light.

In some embodiments, the open reading frame of the heterologous nucleic acid sequence comprises an epitope that can be detected with an antibody or other binding molecule. For example, an antibody that recognizes the epitope may be directly linked to a signal generating moiety (such as by covalent attachment of a chemiluminescent or fluorescent protein), or can be detected using at least one additional binding reagent such as a secondary antibody, directly linked to a signal generating moiety. In some embodiments, the epitope is absent in wild-type K1-5 bacteriophage and the bacterial host cell. Accordingly, detection of the epitope in a sample demonstrates the presence of a bacterial host cell infected by a recombinant K1-5 phage comprising a heterologous nucleic acid sequence, wherein the open reading frame of the heterologous nucleic acid sequence comprises the epitope. In other embodiments, the open reading frame of the heterologous nucleic acid sequence comprises a polypeptide tag sequence, such that the expression product of the open reading frame comprises the tag fused to a polypeptide or protein encoded by the open reading frame (e.g., poly-histidine, FLAG, Glutathione S-transferase (GST) etc.).

In some embodiments, the open reading frame of the heterologous nucleic acid sequence comprises a biotin binding protein such as avidin, streptavidin, or neutrAvidin that can be detected with a biotin molecule conjugated to an enzyme (e.g., β-galactosidase, horseradish peroxidase (HRP), and alkaline phosphatase) or an antibody. In some embodiments, the antibody conjugated to a biotin molecule may be directly linked to a signal generating moiety (such as by covalent attachment of a chemiluminescent or fluorescent protein), or can be detected using at least one additional binding reagent such as a secondary antibody, directly linked to a signal generating moiety.

Also disclosed herein are recombinant K1-5 bacteriophages comprising any of the recombinant K1-5 bacteriophage nucleic acid sequences disclosed herein. In some embodiments, the recombinant K1-5 bacteriophages comprise a nucleic acid sequence selected from the group consisting of SEQ ID NO: 2, SEQ ID NO: 3, SEQ ID NO: 4, SEQ ID NO: 5, SEQ ID NO: 10 and SEQ ID NO: 11.

In another aspect, the present disclosure provides a vector comprising any of the recombinant K1-5 bacteriophage nucleic acid sequences disclosed herein, as well as bacterial host cells comprising the vectors of the present technology. In some embodiments, the bacterial host cell expresses K1 and/or K5 capsule genes. The bacterial host cell may be a natural or non-natural host for K1-5 bacteriophage.

The present disclosure also provides a bacterial host cell comprising a recombinant K1-5 bacteriophage disclosed herein. In some embodiments, the bacterial host cell expresses K1 and/or K5 capsule genes. The bacterial host cell may be a natural or non-natural host for K1-5 bacteriophage.

Methods of Making Recombinant K1-5 Bacteriophage of the Present Technology

In one aspect, the present disclosure provides methods for making a recombinant K1-5 bacteriophage of the present technology in a bacterial host cell. The bacterial host cell may be a non-natural bacterial host cell or a natural bacterial host cell for K1-5 bacteriophage.

In some embodiments, the method comprises (a) contacting a non-recombinant K1-5 bacteriophage genome with a first sgRNA-CRISPR enzyme complex and a second sgRNA-CRISPR enzyme complex in vivo under conditions where (i) the first sgRNA-CRISPR enzyme complex cleaves a first protospacer sequence 5' ACTAAATGAGGAT-TAAATCA 3' (SEQ ID NO: 6) within the non-recombinant K1-5 bacteriophage genome; and (ii) the second sgRNA-CRISPR enzyme complex cleaves a second protospacer sequence 5' TTACTCTGATGCACTACATG 3' (SEQ ID NO: 7) within the non-recombinant K1-5 bacteriophage genome to produce a cleaved non-recombinant K1-bacteriophage genome; and (b) recombining in vivo the cleaved non-recombinant K1-5 bacteriophage genome with a heterologous nucleic acid sequence in the presence of a recombination system under conditions to produce the recombinant K1-5 bacteriophage genome, wherein the bacterial host cell is infected with the non-recombinant K1-5 bacteriophage genome, and wherein the heterologous nucleic acid sequence comprises an open reading frame that encodes a bioluminescent protein, a fluorescent protein, a chemiluminescent protein, or any combination thereof. In some embodiments, the first sgRNA-CRISPR enzyme complex comprises Cas9 and a first sgRNA having the sequence of SEQ ID NO: 16. Additionally or alternatively, in certain embodiments, the second sgRNA-CRISPR enzyme complex comprises Cas9 and a second sgRNA having the sequence of SEQ ID NO: 17. The recombination system may be endogenous or non-endogenous to the bacterial host cell.

In other embodiments, the method comprises (a) contacting a non-recombinant K1-5 bacteriophage genome with a first sgRNA-CRISPR enzyme complex and a second sgRNA-CRISPR enzyme complex in vivo under conditions where (i) the first sgRNA-CRISPR enzyme complex cleaves a first protospacer sequence 5' TATATTATACCAGAGAG-GCG 3' (SEQ ID NO: 8) within the non-recombinant K1-5 bacteriophage genome; and (ii) the second sgRNA-CRISPR enzyme complex cleaves a second protospacer sequence 5' GAAGTTCTAAGGAGATAACA 3' (SEQ ID NO: 9) within the non-recombinant K1-5 bacteriophage genome to produce a cleaved non-recombinant K1-5 bacteriophage genome; and (b) recombining in vivo the cleaved non-recombinant K1-5 bacteriophage genome with a heterologous nucleic acid sequence in the presence of a recombination system under conditions to produce the recombinant K1-5 bacteriophage genome, wherein the bacterial host cell is infected with the non-recombinant K1-5 bacteriophage genome, and wherein the heterologous nucleic acid sequence comprises an open reading frame that encodes a bioluminescent protein, a fluorescent protein, a chemiluminescent protein, or any combination thereof. In some embodiments, the first sgRNA-CRISPR enzyme complex comprises Cas9 and a first sgRNA having the sequence of SEQ ID NO: 18. Additionally or alternatively, in certain embodiments, the second sgRNA-CRISPR enzyme complex comprises Cas9 and a second sgRNA having the sequence of SEQ ID NO: 19. The recombination system may be endogenous or non-endogenous to the bacterial host cell.

The cleaved non-recombinant K1-5 bacteriophage genome comprises a first cleaved bacteriophage genomic fragment and a second cleaved bacteriophage genomic fragment. In certain embodiments of the methods disclosed herein, the heterologous nucleic acid sequence comprises a 5' flanking region that is homologous to the 3' end of the first cleaved bacteriophage genomic fragment, and a 3' flanking region that is homologous to the 5' end of the second cleaved bacteriophage genomic fragment.

In some embodiments of the methods disclosed herein, the homologous 5' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the homologous 3' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the recombination system is a non-endogenous recombination system that is induced in the bacterial host cell. The non-endogenous recombination system may include a recombination expression vector that comprises lambda Red proteins Gam, Exo, and Beta operably linked to an inducible promoter. In some embodiments of the methods disclosed herein, the inducible promoter is araB and the non-endogenous recombination system is induced by the addition of arabinose. In some embodiments, the recombination expression vector further comprises the heterologous nucleic acid sequence. In other embodiments, the expression vector comprising the heterologous nucleic acid sequence is separate and distinct from the recombination expression vector comprising lambda Red proteins.

In other embodiments of the methods disclosed herein, the recombination system is a non-endogenous recombination system that includes a recombination expression vector comprising RecET (RecE, RecT) operons operably linked to an inducible promoter, and optionally the heterologous nucleic acid sequence. In some embodiments, the inducible promoter is araB and the non-endogenous recombination system is induced by the addition of arabinose. In other embodiments, the expression vector comprising the heterologous nucleic acid sequence is separate and distinct from the recombination expression vector comprising RecET.

In another embodiment of the methods disclosed herein, the recombination system is a non-endogenous recombination system that includes a recombination expression vector comprising RecA recombinase or a RecA gain-of-function variant operably linked to an inducible promoter and optionally the heterologous nucleic acid sequence. In some embodiments, the inducible promoter is araB and the non-endogenous recombination system is induced by the addition of arabinose. In other embodiments, the expression vector comprising the heterologous nucleic acid sequence is separate and distinct from the recombination expression vector comprising RecA recombinase or the RecA gain-of-function variant.

Additionally or alternatively, in some embodiments of the methods disclosed herein, the bacterial host cell comprises a non-endogenous CRISPR expression vector comprising a nucleic acid sequence that encodes a first sgRNA, a second sgRNA, and a CRISPR enzyme. In some embodiments, the first sgRNA and the second sgRNA are operably linked to a constitutive promoter. In some embodiments, the sequence of the first sgRNA and the second sgRNA is SEQ ID NO: 16 and SEQ ID NO: 17. In other embodiments, the sequence of the first sgRNA and the second sgRNA is SEQ ID NO: 18 and SEQ ID NO: 19.

A variety of CRISPR enzymes are available for use in conjunction with the disclosed methods of the present disclosure. In some embodiments, the CRISPR enzyme is a Type II CRISPR enzyme. In some embodiments, the CRISPR enzyme catalyzes DNA cleavage. In some embodiments, the CRISPR enzyme catalyzes RNA cleavage. In some embodiments, the CRISPR enzyme is any Cas9 protein, for instance any naturally-occurring bacterial Cas9 as well as any variants, homologs or orthologs thereof. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or variants thereof. The CRISPR enzyme may be operably linked to an inducible promoter, such as a tetracycline-inducible promoter. In some embodiments, the CRISPR enzyme cleaves both strands of the target nucleic acid at the Protospacer Adjacent Motif (PAM) site.

In another aspect, the present disclosure provides sgRNAs that are useful for making the recombinant K1-5 bacteriophages disclosed herein. In some embodiments, the sgRNA sequence is selected from the group consisting of SEQ ID NO: 16, SEQ ID NO: 17, SEQ ID NO: 18 and SEQ ID NO: 19. The design of sgRNAs that are capable of cleaving at the other K1-5 genomic positions described herein, is within the scope of one of ordinary skill in the art.

Bacterial Identification and Antibiotic Susceptibility Profiling Methods of the Present Technology Accurate identification of bacterial species within a biological sample informs the selection of suitable therapies for treating bacterial infections. The recombinant K1-5 bacteriophages disclosed herein may be used to identify bacteria present within a biological sample (e.g., whole blood, plasma, serum). Such methods entail contacting the biological sample with a recombinant K1-5 bacteriophage disclosed herein, and detecting the presence of bacterial host cells infected by the recombinant K1-5 phage, wherein the recombinant K1-5 phage comprises a heterologous nucleic acid sequence that encodes a detectable gene product, thereby leading to the identification of bacteria present within the biological sample.

Additionally or alternatively, the recombinant K1-5 bacteriophages disclosed herein, may be used in methods for profiling antibiotic susceptibility of bacteria present within a biological sample (e.g., whole blood, plasma, serum). These methods include (a) contacting the biological sample with an antibiotic and a recombinant K1-5 bacteriophage disclosed herein, (b) detecting the presence of bacterial host cells infected by the recombinant K1-5 phage, wherein the recombinant K1-5 phage comprises a heterologous nucleic acid sequence that encodes a detectable gene product, and (c) determining that the antibiotic is effective in inhibiting the bacteria present in the biological sample when the levels of recombinant K1-5 phage infected bacterial host cells is reduced relative to that observed in an untreated control sample.

In one aspect, the present disclosure provides a method for identifying at least one bacterial strain or species in a test sample obtained from a subject comprising (a) separating bacterial cells isolated from the test sample into one or more sub-samples, (b) contacting each sub-sample with at least one recombinant K1-5 bacteriophage disclosed herein, wherein each recombinant K1-5 bacteriophage comprises a heterologous nucleic acid sequence encoding one or more reporter genes, and (c) identifying at least one bacterial strain or species in the test sample by detecting the expression of the one or more reporter genes of the at least one recombinant K1-5 bacteriophage. In certain embodiments, the at least one K1-5 bacteriophage comprises a nucleic acid sequence selected from the group consisting of SEQ ID NO: 2, SEQ ID NO: 3, SEQ ID NO: 4, SEQ ID NO: 5, SEQ ID NO: 10 and SEQ ID NO: 11. In certain embodiments, the method for identifying at least one bacterial strain or species in a test sample does not require the culturing of bacterial cells from the test sample or a sub-sample.

In some embodiments, identification of at least one bacterial strain or species includes detecting the expression of the one or more reporter genes of the at least one recombinant K1-5 bacteriophage, e.g., detectable expression of green fluorescence indicates the presence of bacterial species A in a test sample or sub-sample. In some embodiments, the absence of at least one bacterial strain or species is identified by the lack of detectable expression of the one or more reporter genes of the at least one recombinant K1-5 bacteriophage, e.g., undetectable expression of green fluorescence indicates the lack of bacterial species A in a test sample or sub-sample.

In some embodiments, the at least one recombinant K1-5 bacteriophage infects a single species of bacteria. In certain embodiments, the at least one recombinant K1-5 bacteriophage infects two or more species of bacteria. By way of example, but not by way of limitation, in some embodiments, the species of bacteria that are infected include K1 *E. coli* strains and K5 *E. coli* strains, such as ATCC #11775, ATCC #700973, ATCC #23506, ATCC #23508, and MS101.

In some embodiments, detection of the expression of the reporter gene is detection of the gene product itself, e.g., a fluorescent protein. In some embodiments, detection of the expression of the reporter gene is detection of an enzymatic reaction requiring the expression of the reporter gene, e.g., expression of luciferase to catalyze luciferin to produce light.

In some embodiments, the expression of the one or more reporter genes is detected in about 5, 10, 15, 20, 25, 30, 35, 40, 45, 50, 55, 60, 65, 70, 75, 80, 85, 90 minutes or any time between any two of the preceding values after contacting a sub-sample with the at least one recombinant K1-5 bacteriophage disclosed herein.

The present disclosure also provides a method for identifying at least one bacterial strain or species that expresses K1 and/or K5 capsule genes in a test sample obtained from a subject comprising (a) contacting the test sample comprising bacterial cells with a recombinant K1-5 bacteriophage of the present technology; and (b) detecting the expression of the reporter protein of the recombinant K1-5 bacteriophage, wherein detection of the reporter protein indicates the presence of at least one bacterial strain or species that expresses K1 and/or K5 capsule genes in the test sample. In some embodiments of the method, the expression of the reporter protein is measured in about 5, 10, 15, 20, 25, 30, 35, 40, 45, 50, 55, 60, 65, 70, 75, 80, 85, or 90 minutes after contacting the test sample comprising bacterial cells with the recombinant K1-5 bacteriophage.

Additionally or alternatively, in some embodiments of the methods disclosed herein, the test sample is blood, sputum, mucus, lavage, saliva, or a swab obtained from the subject. In some embodiments, the subject is human.

In another aspect, the present disclosure provides a method for determining the antibiotic susceptibility of a bacterial strain or species in a test sample obtained from a subject comprising (a) separating bacterial cells isolated from the test sample into a plurality of sub-samples, (b) contacting the plurality of sub-samples with a recombinant K1-5 bacteriophage disclosed herein and at least one antibiotic, wherein the recombinant K1-5 bacteriophage comprises a heterologous nucleic acid sequence encoding a reporter gene, and (c) detecting the expression of the reporter gene of the recombinant K1-5 bacteriophage in the presence of each antibiotic. In some embodiments, the method further comprises determining that the bacterial strain or species in the test sample is susceptible to an antibiotic if the reporter gene expression of the recombinant K1-5 bacteriophage in the antibiotic treated sub-sample is decreased relative to that observed in a control sub-sample that is not treated with the antibiotic. In other embodiments, the method further comprises determining that the bacterial strain or species in the test sample is resistant to an antibiotic if the reporter gene expression of the recombinant K1-5 bacteriophage in the antibiotic treated sub-sample is comparable to that observed in a control sub-sample that is not treated with the antibiotic. In certain embodiments, the method for determining the antibiotic susceptibility of a bacterial strain or species in a test sample does not require the culturing of bacterial cells from a test sample or a sub-sample.

Additionally or alternatively, in some embodiments of the recombinant K1-5 bacteriophages of the present technology, the reporter gene is nanoluciferase. In certain embodiments, recombinant K1-5 bacteriophage comprises a nucleic acid sequence selected from the group consisting of SEQ ID NO: 2, SEQ ID NO: 3, SEQ ID NO: 4, SEQ ID NO: 5, SEQ ID NO: 10 and SEQ ID NO: 11.

Examples of antibiotics include one or more of rifampicin, tetracycline, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim (Bs) and vancomycin.

In some embodiments of the method, the differences in the reporter gene expression of the recombinant K1-5 bacteriophage observed in the antibiotic treated sub-sample and the untreated control sub-sample is defined as $\mu$.

Additionally or alternatively, in some embodiments of the method, the expression of the reporter gene is detected in about 5, 10, 15, 20, 25, 30, 35, 40, 45, 50, 55, 60, 65, 70, 75, 80, 85, 90 minutes or any time between any two of the preceding values after contacting a sub-sample with a recombinant K1-5 bacteriophage disclosed herein.

In some embodiments, two or more sub-samples are tested for antibiotic susceptibility in series. In some embodiments, two or more sub-samples are tested for antibiotic susceptibility in parallel. In some embodiments, one or more sub-samples are tested for antibiotic susceptibility in a running assay (where resistance or sensitivity to one antibiotic is determined and the resistance or sensitivity to a second, third, fourth, fifth, etc., antibiotic is being assayed).

In some embodiments of the methods disclosed herein, isolating bacterial cells from a test sample includes incubating the test sample with distilled water to form a mixture, centrifuging the mixture to form a pellet that includes bacterial cells, and re-suspending the pellet to form a bacterial suspension comprising isolated bacterial cells after discarding the supernatant. The pellet may be re-suspended in a phosphate buffer. In some embodiments, the bacterial suspension is divided into one or more sub-samples.

In certain embodiments of the methods disclosed herein, mixing the test sample with distilled water will lead to the lysis of cells that lack cell walls (e.g., mammalian cells and red blood cells) while leaving cells with cell walls (e.g., bacteria) intact. Without wishing to be bound by theory, in some embodiments, the removal of cells that lack cell walls enhances the detection of reporter gene expression in bacterial cells infected with a recombinant K1-5 bacteriophage, as intact non-bacterial cells (e.g., red blood cells) may quench reporter gene expression. In some embodiments of the methods of the present technology, the mixture is about 90% distilled water and 10% test sample, about 80% distilled water and 20% test sample, about 70% distilled water and 30% test sample, about 60% distilled water and 40% test sample, about 50% distilled water and 50% test sample, about 40% distilled water and 60% test sample, about 30% distilled water and 70% test sample, about 20% distilled water and 80% sample, or about 10% distilled water and 90% test sample. In some embodiments of the methods disclosed herein, the mixture is incubated for 1, 2, 3, 4, 5, 6, 7, 8, 9, 10, 11, 12, 13, 14, or 15 minutes, or any time between two of the previously listed time points. Additionally or alternatively, in certain embodiments of the methods disclosed herein, the mixture is centrifuged for 1, 2, 3, 4, 5, 6, 7, 8, 9, 10, 11, 12, 13, 14, or 15 minutes, or any time between two of the previously listed time points.

Additionally or alternatively, in certain embodiments of the methods disclosed herein, each of the one or more sub-samples comprise between about 5 to 500, about 10 to 400, about 20 to 300, about 30 to 300, about 40 to 200 or about 50 to 100 bacterial cells. In some embodiments of the methods disclosed herein, each of the one or more sub-samples comprises between about 100 to 10,000, about 200 to 9,000, about 300 to 8,000, about 400 to 7,000, about 500 to 6,000, about 600 to 5,000, about 700 to 4,000, about 800 to 3,000, about 900 to 2,000, or about 1,000 to 1,500 bacterial cells.

In another aspect, the present disclosure provides a method for determining the antibiotic susceptibility of a bacterial strain or species in a test sample obtained from a subject comprising (a) infecting a plurality of test samples comprising bacterial cells with a recombinant K1-5 bacteriophage of the present technology and an antibiotic, wherein the plurality of test samples is derived from the subject; (b) detecting the expression of the reporter protein of the recombinant K1-5 bacteriophage in the plurality of test samples; and (c) determining that the antibiotic is effective in inhibiting the bacterial strain or species in a test sample when the reporter protein expression levels of the recombinant K1-5 phage infected bacterial cells in the test sample are reduced relative to that observed in an untreated control sample comprising bacterial cells, wherein the untreated control sample is derived from the subject. In some embodiments, the bacterial strain or species in the test sample expresses K1 and/or K5 capsule genes. The expression of the reporter protein may be measured in about 5, 10, 15, 20, 25, 30, 35, 40, 45, 50, 55, 60, 65, 70, 75, 80, 85, or 90 minutes after infecting the plurality of test samples comprising bacterial cells with the recombinant K1-5 bacteriophage. In other embodiments, the method further comprises determining that the bacterial strain or species in the test sample is resistant to the antibiotic when the reporter protein expression levels of the recombinant K1-5 bacteriophage infected bacterial cells in the test sample are comparable to that observed in an untreated control sample comprising bacterial cells, wherein the untreated control sample is derived from the subject.

In any of the above embodiments of the methods of the present technology, the test sample is blood, sputum, mucus, lavage, saliva, or a swab obtained from the subject. In some embodiments of the methods disclosed herein, the test sample is obtained from a mammalian subject, including, for example, farm animals, such as sheep, pigs, cows, and horses; pet animals, such as dogs and cats; and laboratory animals, such as rats, mice and rabbits. In one embodiment, the mammal subject is a human.

Kits

The present technology provides kits including the recombinant K1-5 bacteriophages disclosed herein for bacteria identification and antibiotic susceptibility profiling.

In one aspect, the kits of the present technology comprise one or more coded/labeled vials that contain a plurality of the recombinant K1-5 bacteriophages disclosed herein, and instructions for use. In some embodiments, each coded/labeled vial corresponds to a different recombinant K1-5 bacteriophage. In other embodiments, each coded/labeled vial corresponds to the same recombinant K1-5 bacteriophage. In some embodiments, the kits of the present technology comprise one or more coded/labeled vials that contain at least one recombinant K1-5 bacteriophage comprising a nucleic acid sequence selected from the group consisting of SEQ ID NO: 2, SEQ ID NO: 3, SEQ ID NO: 4, SEQ ID NO: 5, SEQ ID NO: 10 and SEQ ID NO: 11.

In some embodiments, each phage vial is assigned a unique code that identifies the bacteriophage in the phage vial, or the types of bacteria that the bacteriophage strain infects. The unique code can be encoded by a machine discernible pattern, such as a bar code, a QR code, an alphanumeric string, or any other pattern that can be discerned by a reader. Each unique code may be shown as, for example, a bar code sticker on a vial or container storing a corresponding phage sample. In some embodiments, the kit is stored under conditions that permit the preservation of the bacteriophage genomes for extended periods, such as under bacteriophage-specific, controlled temperature, moisture, and pH conditions.

Additionally or alternatively, in some embodiments, the kits further comprise vials containing natural or non-natural bacterial host cells for K1-5 bacteriophage. In some embodiments, the bacterial host cells are *E. coli*. In certain embodiments, the bacterial host cells are *E. coli* strain DH10B.

The kits may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular detection technique for which the kit is intended. Protocols for using these buffers and reagents for performing different steps of the procedure may also be included in the kit. Further optional components of the kits may include expression media for gene products encoded by the heterologous nucleic acids of the recombinant K1-5 bacteriophages disclosed herein, such as a medium containing nutrients and cofactors for bioluminescence, devices such as a lamp configured to illuminate at specific wavelengths of light to detect biofluorescence, and devices for measuring the extent of heterologous nucleic acid expression, such as a photometer or photodetector.

Additionally or alternatively, the kits disclosed herein may also include coded and labeled vials that contain a plurality of antibiotics. In some embodiments, the plurality of antibiotics comprises one or more of rifampicin, tetracycline, levofloxacin, and ampicillin. Other examples of antibiotics include penicillin G, methicillin, oxacillin, amoxicillin, cefadroxil, ceforanid, cefotaxime, ceftriaxone, doxycycline, minocycline, amikacin, gentamicin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim (Bs) and vancomycin.

Additionally or alternatively, in some embodiments, the kits comprise one or more sgRNA sequences selected from the group consisting of SEQ ID NO: 16, SEQ ID NO: 17, SEQ ID NO: 18 and SEQ ID NO: 19.

EXAMPLES

Example 1: Design and Methods for Generating the Recombinant K1-5 Bacteriophages of the Present Technology This Example demonstrates that the methods of the present technology are useful for making the recombinant K1-5 bacteriophages disclosed herein in a bacterial host cell.

Experimental Design.

FIG. 6A shows a kanamycin-resistant CRISPR expression vector comprising the Cas9 gene operably linked to a tetracycline inducible promoter and two sgRNAs that are constitutively transcribed. FIG. 6B shows a gentamicin-resistant recombination expression vector comprising the lambda red operon (Exo, Beta, Gam) operably linked to an arabinose-inducible promoter and a heterologous nucleic acid sequence. Exo is a 5' DNA exonuclease, Beta is a single-stranded binding protein and recombinase, and Gam inhibits the activity of host cell RecBCD. The heterologous nucleic acid sequence comprises the nanoluciferase gene with an upstream ribosome binding site as well as 5' and 3' flanking regions that are homologous to a portion of the non-recombinant K1-5 phage genome (collectively, referred to as the donor template region). The donor template region also contains sequences that restore the function of any K1-5 phage DNA that was excised by the sgRNA-CRISPR enzyme complexes. The 5' and 3' flanking regions (about several hundred base pairs in length) are homologous to the DNA sequences immediately adjacent to the two cleavage sites in the phage genome (FIG. 7), and are necessary for repairing double-stranded breaks via homologous recombination.

When designing the donor template, it was necessary to eliminate the protospacer sites via codon reassignment to prevent Cas9 cleavage of recombinant K1-5 phage. Codon reassignment was used in the donor template to obviate sgRNA recognition, but still encode the same protein (FIG. 8). The K1-5 protospacer sequences along with their adjacent PAM sites (PAM site underlined) are provided below:

```
sgRNA 86
                                        (SEQ ID NO: 12)
   ACTAAATGAGGATTAAATCATGG sgRNA 89
                                        (SEQ ID NO: 13)
   TTACTCTGATGCACTACATGAGG sgRNA 1112
                                        (SEQ ID NO: 14)
   TATATTATACCAGAGAGGCGAGG sgRNA 1122
                                        (SEQ ID NO: 15)
   GAAGTTCTAAGGAGATAACATGG
```

The complete sequences of sgRNA 86, sgRNA 89, sgRNA 1112 and sgRNA 1122 are provided below:

```
sgRNA 86 sequence:
                                        (SEQ ID NO: 16)
ACUAAAUGAGGAUUAAAUCAGUUUUAGAGCUAGAAAUAGCAAGUUAA
AAUAAGGCUAGUCCGUUAUCAACUUGAAAAAGUGGCACCGAGUCGGU
GCUUUUUUU sgRNA 89 sequence:
                                        (SEQ ID NO: 17)
UUACUCUGAUGCACUACAUGGUUUUAGAGCUAGAAAUAGCAAGUUAA
AAUAAGGCUAGUCCGUUAUCAACUUGAAAAAGUGGCACCGAGUCGGU
GCUUUUUUU sgRNA 1112 sequence:
                                        (SEQ ID NO: 18)
UAUAUUAUACCAGAGAGGCGGUUUUAGAGCUAGAAAUAGCAAGUUAA
AAUAAGGCUAGUCCGUUAUCAACUUGAAAAAGUGGCACCGAGUCGGU
GCUUUUUUU sgRNA 1122 sequence:
                                        (SEQ ID NO: 19)
GAAGUUCUAAGGAGAUAACAGUUUUAGAGCUAGAAAUAGCAAGUUAA
AAUAAGGCUAGUCCGUUAUCAACUUGAAAAAGUGGCACCGAGUCGGU
GCUUUUUUU
```

To ensure that the 5' and 3' flanking regions of the donor template were in fact perfectly homologous to the regions adjacent to the cleavage sites, codon reassignment was only done on sequences located to the right of the upstream cut site or to the left of the downstream cut site.

FIG. 2 shows the donor template sequence for K1-5 phage genomic DNA that was cleaved with sgRNA 86 and sgRNA 89 (SEQ ID NO: 2). FIG. 3 shows the donor template sequence for K1-5 phage genomic DNA that was cleaved with sgRNA 1112 and sgRNA 1122 (SEQ ID NO: 3).

The CRISPR expression vector and recombination expression vector were designed to cleave a non-recombinant phage genome at two locations after the bacterial host cell containing both these expression vectors had been infected with a non-recombinant K1-5 bacteriophage. Once cleaved, the ends were acted upon by recombination proteins that facilitated recombination between the phage genome and the donor template region present on the recombination plasmid. This process repaired the double strand breaks, while simultaneously inserting the nanoluciferase gene into the K1-5 phage genome. The recombinant K1-5 phage was not susceptible to Cas9 cleavage. FIGS. 4A-4J show the complete genome sequence of the recombinant NanoLuc® K1-5 phage that was cleaved with sgRNA 86 and sgRNA 89 (SEQ ID NO: 4). FIGS. 5A-5J show the complete genome sequence of the recombinant NanoLuc® K1-5 phage that was cleaved with sgRNA 1112 and sgRNA 1122 (SEQ ID NO: 5).

Experimental Conditions.

K1 *E. coli* strains were generated for cleaving and recombining at locations specified by either sgRNAs 86+89 or sgRNAs 1112+1122. Cells were maintained with 50 µg/mL kanamycin (for the CRISPR expression vector) and 10 µg/mL gentamicin (for the recombination expression vector). Cells were grown while shaking at 37° C. to $OD_{600}$~0.6 and were then subjected to various induction treatments. Cultures were either (1) not induced, (2) induced with 100 ng/mL anhydrotetracycline (aTc) to activate Cas9 expression, (3) induced with 0.2% arabinose to activate lambda red operon expression, or (4) induced with both 100 ng/mL anhydrotetracycline and 0.2% arabinose to activate expression of Cas9 and lambda red genes. Induction was carried out for 2 hours while shaking at 37° C.

K1-5 lysate was then used to infect 200 µL cultures of each bacterial strain/induction condition at $10^6$, $10^4$, and $10^2$ PFU. This infection was given 10 minutes for the phage to adsorb before being added to 3 mL of 0.65% LB top agar. The appropriate inducer was spiked into each top agar tube to maintain induction. The top agar was then spread over an LB agar plate containing the appropriate antibiotics to maintain the CRISPR and recombination expression vectors. The agar plates were incubated in an airtight container for approximately 16 hours at 37° C. Plates with top agar containing phage were washed in LB broth to collect the phage. These plate lysates were used as templates for PCR reactions that assayed for a recombinant junction (spanning from an internal site within the nanoluciferase insertion to a site in the phage genome) and a flanking product (primed from 2 sites flanking the insertion site).

Genotypic Analysis.

Without wishing to be bound by theory, it is believed that continual replication of recombinant K1-5 phage through a bacterial strain that only contained an inducible CRISPR expression vector (but no recombination expression vector) would enrich for the recombinant K1-5 phage because recombinant K1-5 phage would have used the donor template for repairing double-stranded breaks (the donor template utilized altered protospacers that do not exactly match the sgRNAs used for cleaving non-recombinant K1-5 phage genomic DNA) and is thus not susceptible to Cas9 cleavage, whereas wild-type phage would be targeted by the sgRNAs without a means to repair the double-stranded breaks.

A 5 mL culture of strain of K1 *E. coli* containing the inducible Cas9 endonuclease and constitutively expressed sgRNAs (86+89) or sgRNAs (1112+1122) were grown under kanamycin selection (50 µg/mL) to $OD_{600}$~0.6. The culture was then induced with 100 ng/mL anhydrotetracycline for 1 hour at 37° C. while shaking to induce Cas9 expression. Next, 50 µL of the previously collected mixed-population lysates (i.e., Cas9 induced, lambda red induced, or Cas9+lambda red induced plate lysates) were used to infect the pre-induced cutting strain for three hours. During the infection step, the Cas9-sgRNA complexes were expected to cleave the locations specified by sgRNAs 86+89 or sgRNAs 1112+1122 that are present in wild-type phage, but are not present in recombinants. A lysate from this culture was then clarified and used as a template for junctional and flanking PCR. The phage population after this enrichment step was assessed by PCR. The relative abundance of recombinant phage increased after this treatment.

Results.

FIG. 9 shows that the bacterial strains expressing sgRNAs 86+89 and sgRNAs 1112+1122 exhibited a high reduction in plaquing efficiency (~$1.9 \times 10^6$-fold and 2105-fold reduction, respectively) in the absence of homology for repair.

Figure 11:
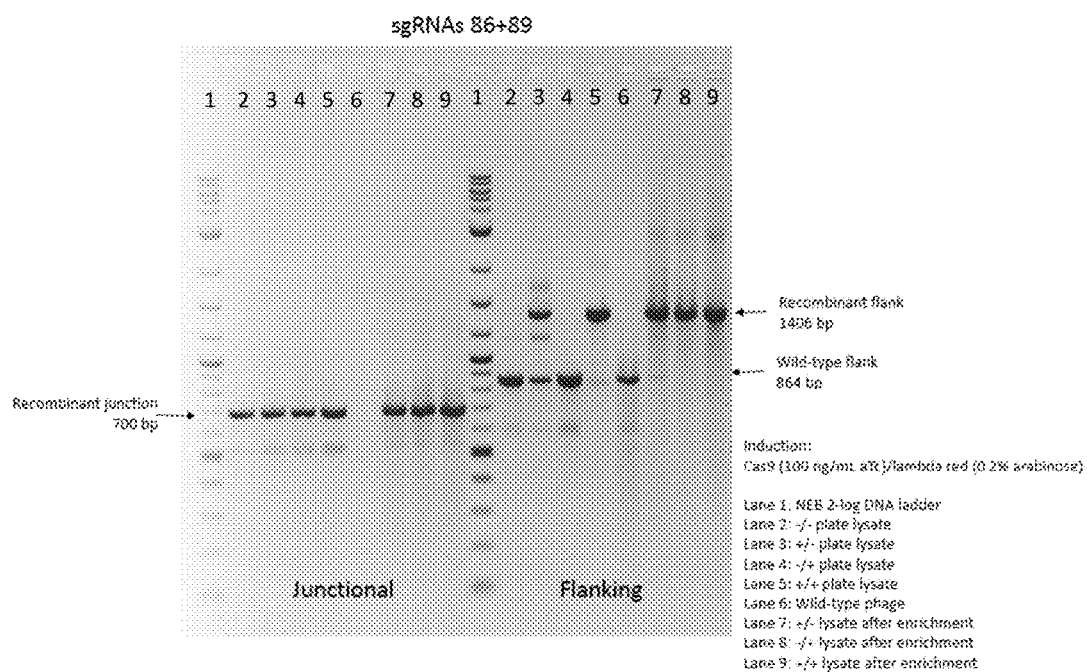
FIG. 11 shows the junctional and flanking PCR assays that tested for the presence of recombinant K1-5 bacteriophage in sgRNAs 86+89 bacterial strain under different induction conditions.

As shown in FIG. 11, all induction conditions within the sgRNAs 86+89 strain produced a detectable quantity of recombinant junctions (700 bp amplicon) that were absent in wild-type K1-5 phage. See junctional PCR lanes 3-5 and 7-9 vs. lane 6 of FIG. 11. The flanking PCR assay provided an estimate of the relative abundance of wild-type and recombinant K1-5 phage. As shown in FIG. 11, induction of lambda red expression alone in the sgRNAs 86+89 strain did not produce a substantial quantity of recombinant flank amplicons, but yielded 864 bp wild-type flank amplicons comparable to that observed in the non-induced sgRNAs 86+89 strain. See flanking PCR lanes 2 and 4 of FIG. 11. In contrast, induction of Cas9 alone in the sgRNAs 86+89 strain produced an approximately equal mixture of 1406 bp recombinant flank amplicons and 864 bp wild-type flank amplicons. See flanking PCR lane 3 of FIG. 11. Induction of both Cas9 and lambda red expression in the sgRNAs 86+89 strain yielded mostly recombinant flank amplicons. See flanking PCR lane 5 of FIG. 11. Enrichment for three hours drastically increased the relative abundance of recombinant K1-5 phage from each starting lysate, particularly in the plate lysate from the strain that was induced for lambda red expression only. Initially, the recombinant K1-5 phage was undetectable by flanking PCR, but after the three hour enrichment step, the recombinant K1-5 phage vastly outnumbered the wild-type non-recombinant phage. See flanking PCR lanes 7-9 of FIG. 11.

Figure 12:
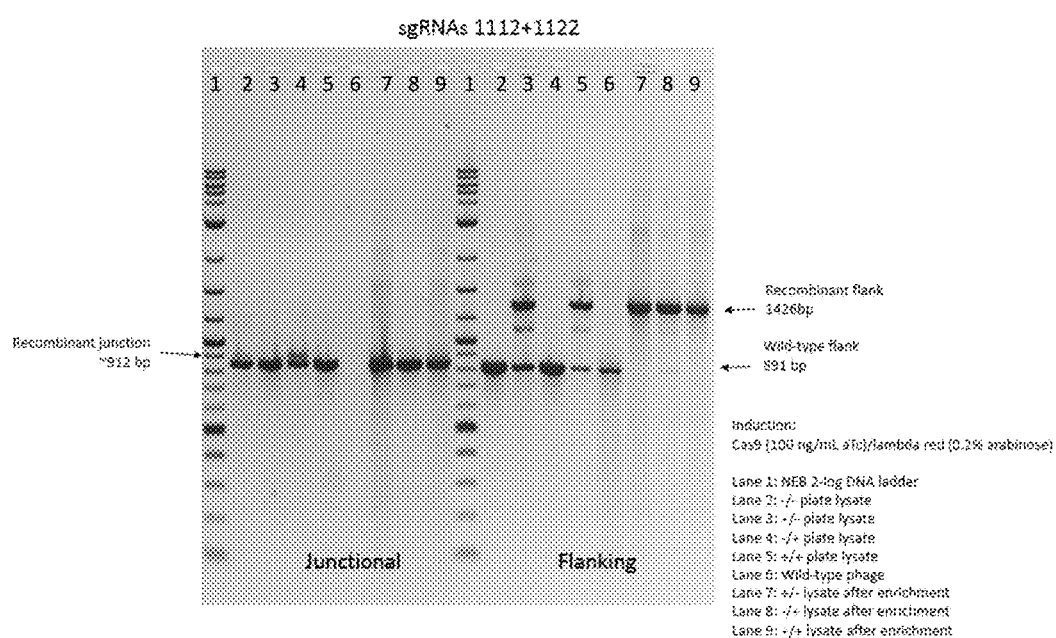
FIG. 12 shows the junctional and flanking PCR assays that tested for the presence of recombinant K1-5 bacteriophage in sgRNAs 1112+1122 bacterial strain under different induction conditions.

As shown in FIG. 12, all induction conditions within the sgRNAs 1112+1122 strain produced a detectable quantity of recombinant junctions (912 bp amplicon) that were absent in wild-type K1-5 phage. See junctional PCR lanes 3-5 and 7-9 vs. lane 6 of FIG. 12. The flanking PCR assay provided an estimate of the relative abundance of wild-type and recombinant K1-5 phage. As shown in FIG. 12, induction of lambda red expression alone in the sgRNAs 1112+1122 strain did not produce a substantial quantity of recombinant flank amplicons, but yielded 891 bp wild-type flank amplicons comparable to that observed in the non-induced sgRNAs 1112+1122 strain. See flanking PCR lanes 2 and 4 of FIG. 12. In contrast, induction of Cas9 alone in the sgRNAs 1112+1122 strain produced a mixture of 1426 bp recombinant flank amplicons and 891 bp wild-type flank amplicons. See flanking PCR lane 3 of FIG. 12. Induction of both Cas9 and lambda red expression in the sgRNAs 1112+1122 strain yielded mostly recombinant flank amplicons. See flanking PCR lane 5 of FIG. 12. However, even a low abundance of recombinant K1-phages could be enriched with a three hour infection in the Cas9 strain that selected against wild-type phage. See flanking PCR lanes 7-9 of FIG. 12.

After passage through an ampicillin-resistant K1 E. coli culture, a lysate for both the recombinant NanoLuc® K1-5 phage modified at sgRNA sites 86+89 and recombinant NanoLuc® K1-5 phage modified at sgRNA sites 1112+1122 was used to infect wild-type K1 E. coli which was plated in a bacterial overlay on LB. Single plaques were isolated and a region spanning the recombination site was amplified via PCR and submitted for Sanger sequencing. FIG. 14 and FIG. 15 show the upstream junction sequences of the nanoluciferase insertion in the recombinant K1-5 phage modified at sgRNA sites 86+89 (SEQ ID NO: 10) and sgRNA sites 1112+1122 (SEQ ID NO: 11).

These results demonstrate that the methods of the present technology are useful for making the recombinant K1-5 bacteriophages disclosed herein in a bacterial host cell. Accordingly, the methods disclosed herein are useful for generating recombinant K1-5 bacteriophages that can be used in the identification and/or antibiotic susceptibility profiling of specific bacterial strains/species (e.g., bacterial strains/species that express K1 and/or K5 capsule genes) present in a sample.

Example 2: Methods for Generating the Recombinant K1-5 Bacteriophages of the Present Technology This Example demonstrates that the methods of the present technology are useful for making the recombinant K1-5 bacteriophages disclosed herein in a bacterial host cell.

Variants of the in vivo phage engineering methodology described in Example 1 was evaluated by attempting to insert the NanoLuc® luciferase gene into a non-recombinant K1-5 phage genome at the insertion sites specified by sgRNAs 86 and 89 using different recombination proteins. The exact same CRISPR expression vector and donor template region described in Example 1 were used in this variant systems.

The CRISPR expression vector comprised a S. pyogenes Cas9 endonuclease operably linked to an anhydrotetracycline-inducible promoter, and two sgRNAs (sgRNA86 and sgRNA 89) operably linked to the constitutive J23119 promoter. The recombination expression vectors included a donor template region comprising the NanoLuc® luciferase gene along with 5' and 3' homologous flanking regions of approximately 300 bp.

The recombination expression vectors contained (1) an arabinose-inducible lambda red operon (Exo, Beta, Gam), (2) an arabinose-inducible Exo, RecA, Gam operon, or (3) no exogenous recombination protein sequences. Bacterial strains containing both the CRISPR expression vector and one of the three recombination expression vectors were grown in 5 mL cultures with 10 mM $MgSO_4$ under antibiotic selection to $OD_{600}$ of ~0.4. These cultures were then split into 1 mL cultures which were induced with 100 ng/mL anhydrotetracycline (aTc), 0.2% arabinose, both, or neither. All cultures were then infected with ~$10^5$ PFU of non-recombinant K1-5 phage overnight at 37° C. while shaking. The following day, cells and debris were removed by centrifugation to obtain 1 μL of phage lysate that could be assayed via flanking PCR. The relative abundance of wild-type and recombinant K1-5 phage could be determined by assessing the differences in the amplicon size: 864 bp for wild-type K1-5 phage and 1406 bp for recombinant K1-5 phage.

Figure 10:
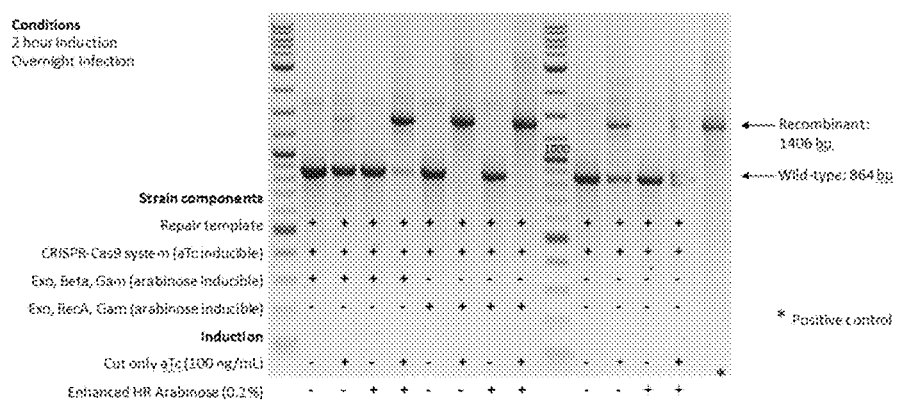
FIG. 10 shows that induction of Cas9 expression in sgRNAs 86+89 bacterial strains was sufficient to produce detectable levels of recombinant NanoLuc® K1-5 phage.

FIG. 10 shows that induction of Cas9 expression alone in all sgRNAs 86+89 bacterial strains was sufficient to produce detectable levels of recombinant NanoLuc® K1-5 phage. Moreover, FIG. 10 also demonstrates that induction of both Cas9 and the recombination protein operons (Exo, Beta, Gam; or Exo, RecA, Gam) in the sgRNAs 86+89 bacterial strains yielded higher levels of NanoLuc® K1-5 phage.

These results demonstrate that the methods of the present technology are useful for making the recombinant K1-5 bacteriophages disclosed herein in a bacterial host cell. Accordingly, the methods disclosed herein are useful for generating recombinant K1-5 bacteriophages that can be used in the identification and/or antibiotic susceptibility profiling of specific bacterial strains/species (e.g., bacterial strains/species that express K1 and/or K5 capsule genes) present in a sample.

Example 3: Functional Activity of the Recombinant K1-5 Bacteriophages of the Present Technology This Example demonstrates that the recombinant K1-5 bacteriophages of the present technology are useful for the identification and/or antibiotic susceptibility profiling of specific bacterial strains/species (e.g., bacterial strains/species that express K1 and/or K5 capsule genes) present in a sample.

To ensure that the genotypically recombinant K1-5 phage described herein are capable of expressing nanoluciferase during active infection, plate lysates were used infect 5 mL cultures of K1 E. coli housing the ampicillin-resistant pUC19 plasmid. The kanamycin and gentamicin resistant strains harboring the CRISPR expression vector and recombination expression vectors would therefore be killed off, or at least strongly selected against, such that any background nanoluciferase expression attributable to the donor template would be minimized. After three hours of infection under ampicillin selection, the lysate was subjected to limiting dilutions to ensure that any residual NanoLuc® protein or NanoLuc®-expressing cells were diluted out, and that any luminescence detected during a subsequent infection was due to active infection by the recombinant K1-5 phages of the present technology.

Briefly, a tenfold dilution series of lysates were used to infect K1 E. coli maintained under ampicillin selection for one hour. In round one, the cutoff for recombinant K1-5 phage being present was observed at 1.0 E-8. See FIG. 13. At dilutions ranging from 1.0 E-3 through 1.0 E-8, a large increase in luminescence was observed in phage infected E. coli samples compared to phage samples containing LB medium only (background NanoLuc® protein or NanoLuc®-expressing cells). The increased luminescence was therefore attributable to active phage infection. The infection from the lowest phage containing dilution (1.0 E-8) was subjected to a second round of limiting dilutions. As shown in FIG. 13, the luminescence activity increased in a cell-dependent manner.

Figure 16:
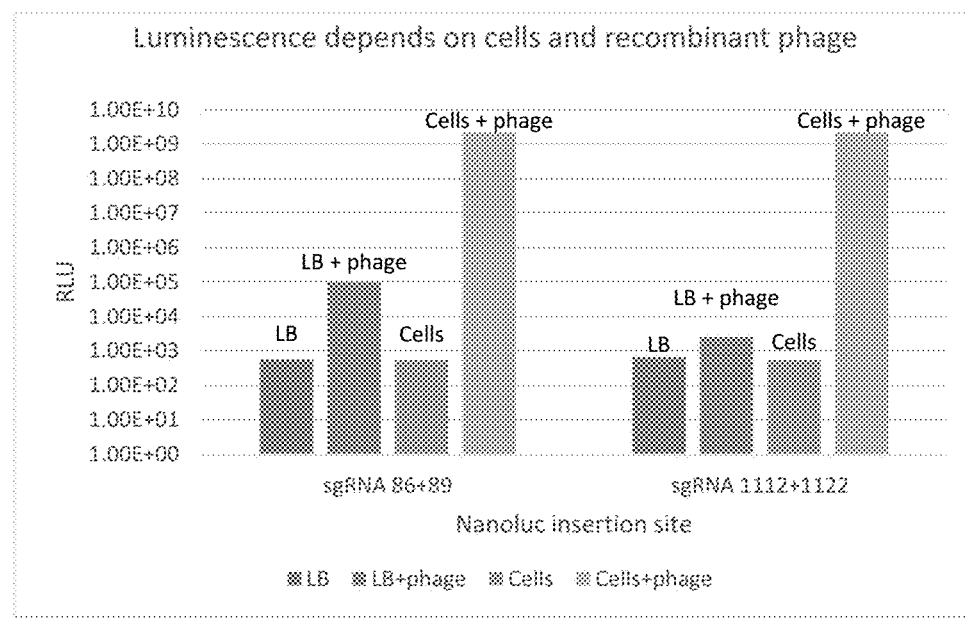
FIG. 16 shows the luminescence activity profile of a recombinant K1-5 phage of the present technology. 100 μL samples of either LB alone, LB+1 μL phage, K1 E. coli cells, or K1 E. coli cells+1 μL phage were incubated for one hour. The high background luminescence of the LB+phage sample can be attributed to the residual nanoluciferase in the unpurified phage lysate. However, active infection of K1 E. coli cells with the recombinant K1-5 phage greatly increased the luminescent signal.
Figure 18A:
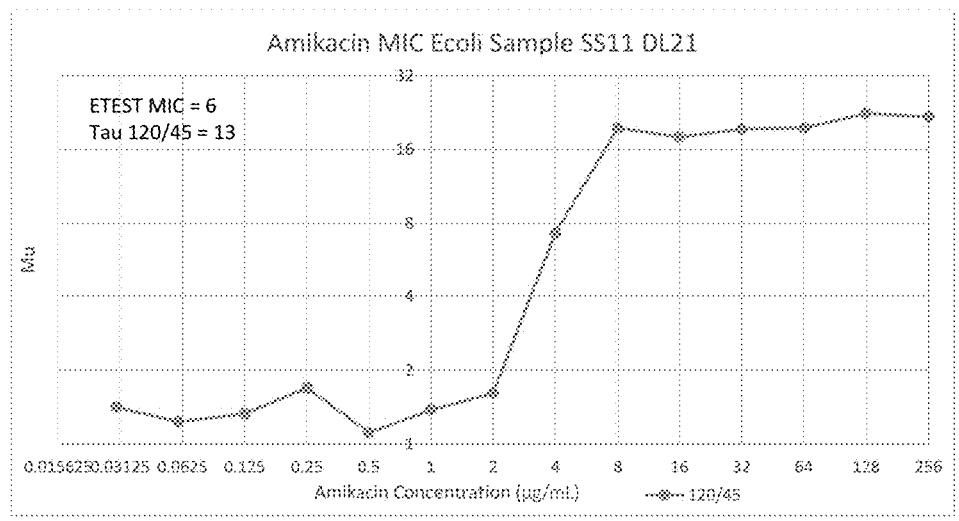
FIG. 18A shows the antibiotic susceptibility profile of an E. coli strain to amikacin using the recombinant K1-5 phages of the present technology.
Figure 18B:
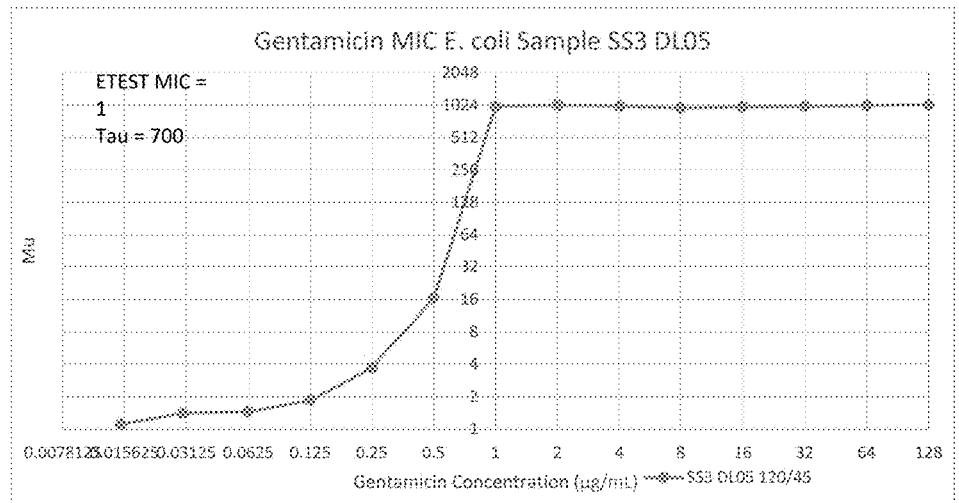
FIG. 18B shows the antibiotic susceptibility profile of an E. coli strain to gentamicin using the recombinant K1-5 phages of the present technology.
Figure 18C:
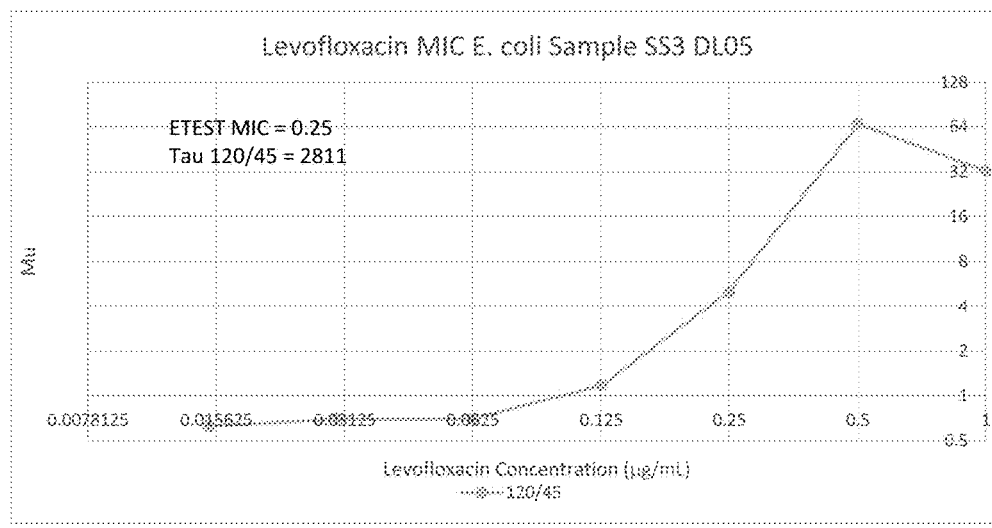
FIG. 18C shows the antibiotic susceptibility profile of an E. coli strain to levofloxacin using the recombinant K1-5 phages of the present technology.
Figure 18D:
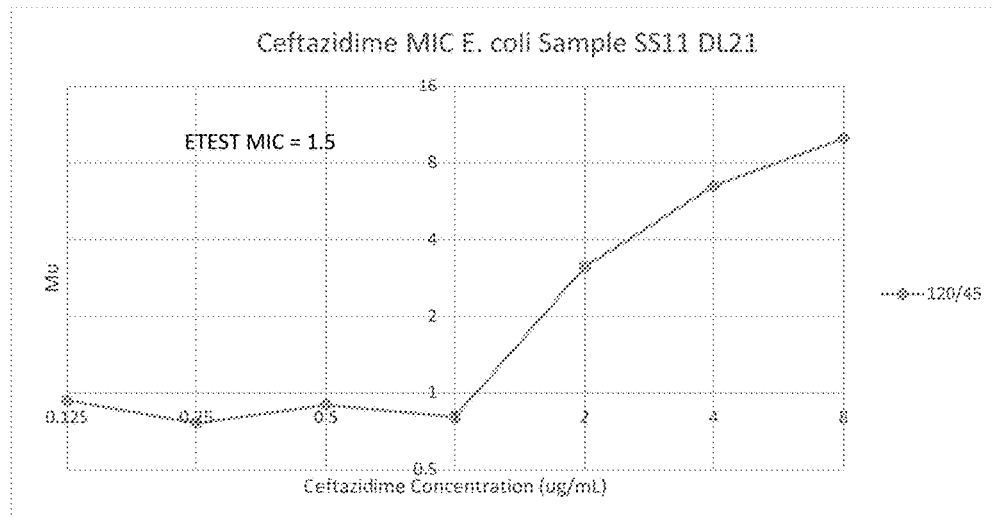
FIG. 18D shows the antibiotic susceptibility profile of an E. coli strain to ceftazidime using the recombinant K1-5 phages of the present technology.

Plaques containing the recombinant K1-5 bacteriophages disclosed herein were used to infect a host population of K1 E. coli for one-hour. The infected bacterial host cells exhibited luminescence that was at least four-five orders of magnitude above the background level. See FIG. 16.

As shown in FIG. 17, the recombinant NanoLuc® K1-5 phages of the present technology successfully infected an E. coli clinical isolate that was incapable of being infected with a recombinant nanoluciferase expressing K1E phage or a recombinant nanoluciferase expressing T7 phage. Only E. coli cells infected with the recombinant NanoLuc® K1-5 phages of the present technology exhibited an increase in relative luminescence units (RLU) during active infection. The high luminescent signal observed in the *E. coli* cells contacted with the recombinant nanoluciferase expressing T7 phage represents background NanoLuc® that was already present in the unpurified lysate. No increase in RLU was observed during active infection (compare T7 infection at 0 hr vs. 1 hr; FIG. 17).

These results demonstrate that the recombinant K1-5 bacteriophages of the present technology are useful for detecting target bacterial strains/species present in a sample. Accordingly, the recombinant K1-5 bacteriophages disclosed herein are useful for the identification and/or antibiotic susceptibility profiling of specific bacterial strains/species (e.g., bacterial strains/species that express K1 and/or K5 capsule genes) present in a sample.

Example 4: Antibiotic Susceptibility Profiling Using the Recombinant K1-5 Bacteriophages of the Present Technology Antibiotics were prepared by performing eleven 2-fold serial dilutions in Mueller Hinton Broth (Sigma, St. Louis, Mo.) in 96 well microtiter plates at a final volume of 100 µl. One column contained broth only and served as a no drug control.

Cells from an overnight growth blood culture in 25% human blood and 75% Tryptic Soy Broth TSB were diluted 1:10 in Mueller Hinton Broth. From this dilution, 5 µl of cells was added to each well of the antibiotic plate. Cells were pretreated with antibiotics (Ceftazidime, Gentamicin, Amikacin, and Levofloxacin) for 120 minutes at 37° C. After the 120 minute pretreatment, 10 µl of phage suspension comprising the recombinant K1-5 phage of the present technology (1E6 pfu/reaction well) was added to each well and incubated at 37° C. for 45 minutes. After infection with the phage, 50 µl of the reaction was added to 50 µl Nano Glo Luciferase Substrate (Promega, Madison, Wis.) in a luminescent plate and read in a luminometer. The minimal inhibitory concentration (MIC) of each sample was determined using the ETEST® method (Biomerieux, St. Louis, Mo.) according to the manufacturer's instructions. The differences in the reporter gene expression of the recombinant K1-5 bacteriophage observed in the antibiotic treated samples and the untreated control samples is defined as µ.

FIGS. 18A-18D demonstrate that the recombinant K1-5 bacteriophages of the present technology were effective in determining the antibiotic susceptibility profile of two different *E. coli* strains SS11 DL21 and SS3 DL05.

These results demonstrate that the recombinant K1-5 bacteriophages of the present technology are useful for determining the antibiotic susceptibility of a bacterial strain or species in a test sample. Accordingly, the recombinant K1-5 bacteriophages disclosed herein are useful for the identification and/or antibiotic susceptibility profiling of specific bacterial strains/species (e.g., bacterial strains/species that express K1 and/or K5 capsule genes) present in a sample.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A recombinant K1-5 bacteriophage nucleic acid sequence, wherein the nucleic acid sequence between (a) position 1,571 and 1,690 of SEQ ID NO: 1 or (b) position 19,979 and 20,165 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof.

2. The recombinant K1-5 bacteriophage nucleic acid sequence of claim 1, wherein the open reading frame of the heterologous nucleic acid sequence is operably linked to an expression control sequence that is capable of directing expression of the reporter protein.

3. The recombinant K1-5 bacteriophage nucleic acid sequence of claim 2, wherein the expression control sequence is an inducible promoter or a constitutive promoter.

4. The recombinant K1-5 bacteriophage nucleic acid sequence of claim 1, wherein the fluorescent protein is selected from the group consisting of TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOκ, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LS S-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa.

5. The recombinant K1-5 bacteriophage nucleic acid sequence of claim 1, wherein the chemiluminescent protein is β-galactosidase, horseradish peroxidase (HRP), or alkaline phosphatase.

6. The recombinant K1-5 bacteriophage nucleic acid sequence of claim 1, wherein the bioluminescent protein is Aequorin, firefly luciferase, Renilla luciferase, red luciferase, luxAB, or nanoluciferase.

7. The recombinant K1-5 bacteriophage nucleic acid sequence of claim 6, wherein the bioluminescent protein is nanoluciferase.

8. A recombinant K1-5 bacteriophage comprising the recombinant K1-5 bacteriophage nucleic acid sequence of claim 1.

9. A recombinant K1-5 bacteriophage comprising a nucleic acid sequence selected from the group consisting of SEQ ID NO: 2, SEQ ID NO: 3, SEQ ID NO: 4, SEQ ID NO: 5, SEQ ID NO: 10 and SEQ ID NO: 11.

10. The recombinant K1-5 bacteriophage of claim 8, wherein the bacteriophage specifically infects E. coli strains that express either K1 or K5 capsule genes.

11. The recombinant K1-5 bacteriophage of claim 10, wherein the E. coli strains that express either K1 or K5 capsule genes are selected from the group consisting of ATCC #11775, ATCC #700973, ATCC #23506, ATCC #23508, and MS101.

12. A bacterial host cell comprising the recombinant K1-5 bacteriophage of claim 8.

13. A vector comprising the recombinant K1-5 bacteriophage nucleic acid sequence of claim 1.

14. A bacterial host cell comprising the vector of claim 13.

15. The bacterial host cell of claim 12, wherein the host cell expresses either K1 or K5 capsule genes, and optionally wherein the host cell is a natural or non-natural host for K1-5 bacteriophage.

16. The bacterial host cell of claim 14, wherein the host cell expresses either K1 or K5 capsule genes, and optionally wherein the host cell is a natural or non-natural host for K1-5 bacteriophage.

17. A kit comprising one or more coded/labeled vials that contain the recombinant K1-5 bacteriophage of claim 8, instructions for use, and optionally at least one antibiotic.

18. A method for identifying at least one bacterial strain or species that expresses K1 and/or K5 capsule genes in a test sample obtained from a subject comprising
(a) contacting the test sample comprising bacterial cells with the recombinant K1-5 bacteriophage of claim 8; and
(b) detecting the expression of the reporter protein of the recombinant K1-5 bacteriophage, wherein detection of the reporter protein indicates the presence of at least one bacterial strain or species that expresses K1 and/or K5 capsule genes in the test sample.

19. The method of claim 18, wherein the expression of the reporter protein is measured in about 5, 10, 15, 20, 25, 30, 35, 40, 45, 50, 55, 60, 65, 70, 75, 80, 85, or 90 minutes after contacting the test sample comprising bacterial cells with the recombinant K1-5 bacteriophage.

20. A method for determining the antibiotic susceptibility of a bacterial strain or species in a test sample obtained from a subject comprising
(a) infecting a plurality of test samples comprising bacterial cells with the recombinant K1-5 bacteriophage of claim 8 and an antibiotic, wherein the plurality of test samples is derived from the subject;
(b) detecting the expression of the reporter protein of the recombinant K1-5 bacteriophage in the plurality of test samples; and
(c) determining that the antibiotic is effective in inhibiting the bacterial strain or species in a test sample when the reporter protein expression levels of the recombinant K1-5 phage infected bacterial cells in the test sample are reduced relative to that observed in an untreated control sample comprising bacterial cells, wherein the untreated control sample is derived from the subject.

21. The method of claim 20, wherein the antibiotic is selected from the group consisting of rifampicin, tetracycline, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim (Bs) and vancomycin.

22. The method of claim 20, wherein the bacterial strain or species in the test sample expresses K1 and/or K5 capsule genes.

23. The method of claim 20, wherein the expression of the reporter protein is measured in about 5, 10, 15, 20, 25, 30, 35, 40, 45, 50, 55, 60, 65, 70, 75, 80, 85, or 90 minutes after infecting the plurality of test samples comprising bacterial cells with the recombinant K1-5 bacteriophage.

24. The method of claim 18, wherein the test sample is blood, sputum, mucus, lavage, saliva, or a swab obtained from the subject.

25. The method of claim 24, wherein the subject is human.

\* \* \* \* \*

SEQUENCE LISTING

<160> NUMBER OF SEQ ID NOS: 23

<210> SEQ ID NO 1
<211> LENGTH: 44385
<212> TYPE: DNA
<213> ORGANISM: Escherichia virus K1-5

<400> SEQUENCE: 1
tcgccctcgc cctcgccggg ttgtccccat agggtggcct gagggaatcc gtcttcgacg    60

```
ggcagggctg atgtactcct tgtctagtac aagggaggcg gagggaacgc ctagggaggc    120
ctaggaatgg cttagtggtg gacaaggtga ttaccttagt gaagcctctt agtgcattcc    180
tgaggccatt cagggcgttt atgagggatt gacagggtgt gagggcgtgg gctatctgtt    240
cctttgctcc tcacttcgtt cgtcgctgcg gtagcctgat gtgtacctta ggttattcct    300
tgatggatag cttaggttag ccttagtgga ttaccttagt taaagcctta gtgcttcact    360
tagtatcagc ttagtagtgt accttagtaa gtcttagtgt cttctcttag tgattgcaca    420
tgcaagcatg taagatgcta ataggtcgcg gtcggcagac cgctaaagaa agagaatggt    480
aataagatgc agtaggagga acaccagaag cctagccaac ctaagctatc ctagctctat    540
atctattgct tttccttagt ctaacacgtt agacaaccta tcttattctt agtgatggta    600
acttagtgtt gacaagataa tcttagtgta atactatgca tcacgtaggc ggtgctgagg    660
cacctagtag ccagctagta aggcatacga agagactagc gcttacattg ctctttaaca    720
atttgcttag tgtaacctat gtatgccgtg gttaactact tattgaatga ggtattaact    780
atgacattaa ataaccgtga actgtccgtt ctcttcactc tgttgtgcta catgattcgt    840
aacaacgaat tacttacaga tgatgagtta gccttgtatc accgctttct taacgaaggt    900
tggaccgata cagttaatca ataccgtaac atgatagatg agttgaggga gggtaaataa    960
tgtatcaaca tgaggtattc tttgaatcag ctagcgaagc tattcgcttc cgtgatgata   1020
tgatgcaagc tggtgtaggc gttgatgtgt atcactattt gatagattac gacactgaat   1080
atcaccgagt taccttagta tctgagtatg acaaccaagt cattactgag tatctaggca   1140
gtgaagatta cgattacgat gaagtaatca cgacaaatct ctaaattaac tgttgacagc   1200
cacggcatac aaggttacat taagcatcaa gacggcgacg tctttaaaca tcccgctctt   1260
taacaatacg gtttgtgtct tgataggcta actaactaac taaggtaatt atcatgaaag   1320
ggttaatttg tgtagaacgt atggtcaatg gtaaacttga atattacca ctggaaaacc   1380 aatctagctt caaagagtgg tatggctgtt tctcactgat ttaaggtaaa ggctggcact   1440
agtcagccta tcaaggcgca aaccaagctc tttaacaatt tggatggtag cttcttagtc   1500
tggataggtt aaacctagga gattctcttg agtctcctat aatgtaacct aactaactaa   1560
atgaggatta aatcatggaa cgcaatgcta acgcttacta caaccttctg gctgcaactg   1620
ttgaagcatt caacgagcgt attcagtttg atgagattcg cgaaggtgat gattactctg   1680
atgcactaca tgaggttgta gacagcaatg ttccagttta ttacagcgaa atctttacag   1740
tgatggctgc tgatggtatt gatgttgatt ttgaggatgc tggtttgatt cctgacacga   1800
aggatgtaac caagattcta caagctcgca tctatgaagc tctttataat gatgtaccaa   1860
atgacagcga tgtagtttgg tgtgaaggcg aagaagagga agaataagga tggaaaagca   1920
atataacttt atctttttcag acggtgtaac cctgaagtgt tccctacgat tcgcacaaat   1980
tcgtgaggaa gtactaggca ctacatacaa actatttagc tgcactatata agagaaggct   2040 taacaaggcg ttactaaggt agcgcctgat taaactttca cttactagga gttgagatta   2100
tgaaaacctt gattggatgc ttcttgttgg cttctcttgc tctggcattt accgctaaag   2160
ctggttatga cgcttataaa gtagaacaag cccagcaaga ctgggccaaa aaaagttca    2220 acttgtgcag caagagcaac acctacgagt actgcaacaa aacactaaga cacttatgga   2280
aagagtaact agcctatagc ccacctgagt gggctatgtg atatttactt aacactatat   2340
aaggtgatta ctatgactac tgaaaacacc ctcgtgtctg tccgtgaagc tgcaaccgct   2400
```

-continued

```
gaaatcaagc aacatttaga caatatcggc acttcttaca tcaaagtagg ggcttgtctg    2460
aatgagttac gcggagactt tgaaggtcaa aaagagtttt tagcctatgt tgaagcagag    2520
tttgccatta agaaggcaca atgttacaag ctgatgagtg tagcccgtgt ctttgaaggc    2580
gatgatcgct ttaaaggcgt ggcgatgcgt gtaatgctgg cgcttgttcc tttcgctgat    2640
gaaaatataa tcatggagaa ggccgcagaa ctcgccgcaa atggcaagct ggacactaat    2700
gccgtaaacg ccctgattga acctaagaaa gagtcaaagg ccgaaacggt acaatctaag    2760
gctgagacag taaaaccgca ggagaacgcg actgagtccg cagaatcaca tgaaatgcaa    2820
gcgccgcagg tagtgccacc cgcgagcgag caggagtccg acgaatcagc accttgggaa    2880
gaggaaagca aaccggaagc gccaaaggca gctccgatgg ataacacggc taatactgag    2940
aatgccgcta ttgctggtct gctggcacaa attaaagcac tgactgagca attacaggca    3000
gccaatgacc gcatcgcctc cttaagtagc gcacgcgaaa gcaagaaggc atccgcacct    3060
atgctgccgc agttcaaatc ttcctgcttc tacgctcgct taggcttgag cgcggaggag    3120
gcaacgaaga aaacagcagt taacaaggca cgccgcgaac tggttaagct gggatacggt    3180
gaaggccatg aggcatggcc cttaatctct gaggcagtag aagagttgac taagtaacct    3240
tatcggtggc atcttcttag gtgtcaccta ttaaggtttc tttcactagg agtaaacaag    3300
atgcaaggcc tacacgctat tcaacttcaa cttgaagaag aaatgtttaa cggcggtatc    3360
cgtcgctttg aagcggacca acaacgccag attgcatccg gtaatgaatc agacacggca    3420
tggaatcgcc gcttattgtc cgagttaatc gcgccaatgg ctgaaggtat tcaggcatac    3480
aaggaagagt atgaaggtaa aagaggccgt gcaccgcgtg cattagcttt cattaactgc    3540
gtagaaaacg aagtggcagc atatatcacg atgaaaatcg ttatggatat gctgaacacg    3600
gatgtaacct tgcaggctat agccatgaat gtagctgacc gcattgagga ccaagtacgt    3660
tttagcaagc tggaaggtca cgccgccaaa tactttgaaa aagttaagaa gtcacttaag    3720
gcaagtaaga ctaaatcata tcgccatgcg cacaacgtag cggtagtggc tgagaagtca    3780
gtagctgacc gtgacgctga tttctcccgc tgggaggcat ggcctaaaga caccttgctg    3840
caaatttggga tgaccttgct tgaaatctta gagaatagcg tattcttcaa cgggcaacct    3900
gtcttcctcc gcaccttgcg cactaatggc ggcaaacatg gtgtttacta cctacagact    3960
agtgaacacg taggtgagtg gataactgca ttcaaagagc acgtagcgca actgagtcct    4020
gcctatgctc cttgcgtcat ccctccgcgt ccgtgggtat cacctttttaa cggcggtttc    4080
cacactgaga aagtagcaag ccgtattcgt ctggtaaaag gaaccgcgca acacgtccgc    4140
aagctgacca aaaagcaaat gccagaggtt tacaaggctg ttaacgcgtt gcaggcgact    4200
aaatggcagg ttaacaagga agttttacag gttgtggaag acgtcatccg tctagaccta    4260
ggttatggtg taccttcctt taaaccactc attgaccgcg agaacaagcc agctaatcca    4320
gtgccgctag aatttcagca cctacggggc cgtgaactga agaaatgct tacgccggaa    4380
caatggcaag cctttatcaa ctggaaaggt gaatgtacta agctgtacac cgctgaaact    4440
aagcgcggaa gcaaatcggc ggcaaccgtt cgcatggttg gtcaggcccg taaatatagc    4500
cagttcgacg caatctactt cgtgtatgca ctggacagcc gcagccgcgt ctacgcgcaa    4560
tctagcacac tctcaccgca atcaaatgac ttgggcaagg ccttgctccg ttttaccgaa    4620
gggcagcgtc ttgatagcgc tgaggcgctt aagtggtttt tggtgaacgg ggctaataac    4680
tgggggttggg ataagaaaac ttttgacgtg cgcaccgcta acgtgctgga tagtgaattt    4740
caagacatgt gccgcgacat tgcagcggat ccgctgacct tcactcaatg ggtaaatgcc    4800
```

```
gactcccctt acggcttcct tgcatggtgc tttgaatatg cgcgttatct ggatgcactg    4860
gatgaaggca cgcaagacca attcatgacg cacctcccag tccatcaaga tggtagttgt    4920
tctggtatcc agcactacag tgctatgcta cgcgatgcag taggtgcgaa agcagtaaac    4980 cttaagcccct ctgactctcc tcaagatatt tatggtgccg ttgcgcaggt agtaattcag   5040
aagaattatg catacatgaa tgcagaggat gcggaaacct tcacttctgg cagcgtgact    5100
ttaacaggtg cggagctgcg tagtatggct agtgcgtggg atatgatagg aatcactcgc    5160
ggcctgacca aaaagcccgt aatgacacta ccttatggca gcacacgtct aacctgccgt    5220
gagtcagtga ttgattatat cgttgattta gaagaaaaag aggcccaacg ggctattgcg    5280
gaagggcgta ccgccaatcc tgtacaccct tttgataatg accgtaaaga cagcctgaca    5340
cctagcgcag cttataacta tatgacagct ttaatctggc cttctatttc ggaagtggtt    5400
aaagccccta tagtggcaat gaaaatgatt cgtcagcttg cccgtttcgc agctaaaagg    5460
aatgaaggct tagagtatac cctgcctact ggcttcatct tgcaacaaaa gattatggct    5520
actgatatgc tccgcgtatc tacttgcttg atgggagaaa tcaagatgag tctacagatt    5580
gaaacagacg tagtggatga acggcaatg atgggcgctg ctgctcctaa ctttgtgcat    5640
ggtcatgatg ccagccacct tatcttaaca gtctgcgacc ttgttgataa agggattaca    5700
tctatcgcag ttattcatga ctcttttggc actcatgcag gccgtacagc cgaccttcgt    5760
gatagcttaa gggcagaaat ggtgaagatg tatcaaggcc gtaatgcact gcaaagcctg    5820
ctagatgagc acgaagaacg ctggttagtt gataccggaa tacaagtacc agagcaaggg    5880
gagtttgacc ttaacgaaat cttagtttca gactattgct tcgcataata ttaataggcc    5940
attccttcgg gagtggcctt tcttttacct actacctgta acatttcatt aacataaaag    6000
tgtctcacat gtgagactta tttaccggac actataggat agccgtcgga gacgggaaag    6060
aaagggaaga taaggatat aaaggaagta ataggtatta aaggttatat aggttatcta    6120
ggaataccta ttaccttctt ccttcctctt attaccactc agaggaaggg cagacctagg    6180
ttgtctcaca tgtgagactt cgtatttacc ggacagtata gataagatta actcactttg    6240
gagatttaac catgcgcaac tttgagaaga tggcccgtaa agctaaccgt tttgacatgg    6300
aagaggggca gaagaaaggc aagaagctga taagcctgt ccgtgaccgt gcatctaaac    6360
gcgctgcgtg ggagttctaa gttatggcta ttattcagaa tgtaccgtgt cctgcctgtc    6420
aaaagaatgg acatgatatt actggcaacc atctcatgat atttgatgat ggtgccggct    6480
actgtaatcg tggacacttt catgataatg gtagaccttat ctatcacaag ccggaaggtg   6540
gcatcgagat aaccgagtta tctattactg gcaatatcaa atatacacct tctcaattca    6600
aagaaatgga gaaggaaggg aagataagcg acctaaatt acgtgccatc gcacttggtg     6660
gtatgcgtat gaaagaccgt tgggaggtca tgaatgaaca agaaagggca gagcaagaag    6720
cagagtggaa acttgatgtt gaatggttcc tcacgcttaa gcgtaagaac cttgtttcca    6780
ggcacattcg cggcgacatt tgcgcattgt atgatgtacg tgttgggcac gatgaagagg    6840
gtagagtctc acggcattac tatccgcgct tcgaaaaagg tgagctagta ggcgctaagt    6900
gtcgcacatt acctaaagat tttaagtttg gtcatttagg taaactcttt ggtatgcaag    6960
atcttttcgg tatgaatact ttgtctcacg tgttagacaa gggaagacga aaggattgct    7020
tgctcattgt cggcggcgaa ctggatgcac tagcagcgca gcagatgctc cttgattctg    7080
ccaagggtac taagtgggaa ggccagccat accatgtatg gtctgtcaac aaaggcgagt    7140
```

```
cttgccttga agagatagtg cagaaccgtg agcatatcgc ccaattcaag aagattatat   7200 gggttttga tggagatgag gtagggcaga agcagaatca gcaagcggct cgcctgtttc    7260
ctggtaaatc ctatatcctt gaataccct ctggttgcaa agatgctaac aaggcattga    7320
tggctggcaa ggctaaagaa tttgtagatg catggtttaa tgccaagtca tctgatgaag   7380
tctttggtag ccagattaaa tctatcgcat ctcaaaggga taagctcaag gctgcacgtc   7440
cagagcaagg actgtcatgg ccttggccta agctgaacaa ggtaacgcta ggtattcgta   7500
agaaccagct tatcattgta ggtgcagggt ctggtgtagg taagactgag ttccttcgtg   7560
aagtagttaa gcacctcatt gaagaacacg gtgaatctgt aggcatcatt tctacagaag   7620
acccgatggt caaggtgtcc cgtgctttta tcggcaagtg gattgataag cgtattgagt   7680
tacctccaac caacgacccg aaagaagacg ataccgtga ggtgttcgac tataccgagg     7740
aagaagctaa cgccgccatt gattatgtag ctgatacagg taagctgttt gtagctgacc   7800
tagagggtga ctattcgatg gaaaggtag agcaaacttg cctagagttt gaggctatgg    7860
gtatttctaa tatcatcatt gataacttaa cggggattaa attagatgag cgtgcttttg   7920
gtgggaaggt tggtgcactt gatgaatgcg tcaagcggat tggtactatc aaagaccgac   7980 accggttac tatattcctt gtatcacacc ttacacgtcc tccggcaaac cgtacccaac    8040
acgaagaagg tggcgaagtt atcctttctg acttccgagg ctcaggcgct atcggattct   8100
gggcatctta cgccttgggg attgagcgta atacaagagc tgaaacgctt gacgaaagga   8160
ctaccacgta catctcatgt gtcaaagacc gcgaccaagg tatctacact ggaaccaagg   8220
tcatgcttaa gggtgacatt caaaccggac gtttaatgga accacaagcc cgtactaagt   8280
catttgatac aggtgaagca aggcaacaag aagtaccaga tttaccggat actatagaag   8340
agactacctt cgatgaagaa agtgagttct gattagtgta tttatcaggc ttgtctcaca   8400
tgtgagacag gctcttatta agtacattaa ataactggag attgattatg tataacttag   8460
tgttgaatgt aggtgacttt gtacgcaaca tcaagaaaga ttcaagtcgc tatctttgcc   8520
gtggtgttgt aacctttgta ggtgagaacc tgtattatgt agaatatcgc agtggtgtta   8580
agcaatatta ccacaagaag acagcacata aatatcttga aaagattgta gagataaaca   8640
atcaatgtaa gtgcatacat gatgaggttt gcgataaatg tgctcgccag atgcttaaga   8700
atttcctagc tcctctttat tatggtgctg gtcctcaaac actagcagag tgcatggcag   8760
aaaagaaaac cacactcaag aaagagcgtc gcaatgtaat cactggtaag actcaaagtg   8820
agatgattaa gcaatgtggc actgcattag gtgttacaca gtttaatact cgtgcattgg   8880
gtaaatccac aggacaagct atggtaaaga ttggagaagc catgatgcat ccaaatgtac   8940
ctgtgcgaat catggatgtt gaccatgcaa tcacagaaca aggtacgcaa cgacgtgtaa   9000
ttaataagca ttttgccgac actatagaag gcattattcg taagcaaggg ttgaaaggtc   9060
ttcacatctt aaatggtgaa gaattactgt acctacctat cgttactgaa gaaacatacg   9120
tgaatatcta aggagttaat catgactaag gtattaatt atatgcgtgg acctcataaa    9180
tgctatgcag ttgtagcacc aaatggtgtt aagccttatc gtacttcaaa aagattggca   9240
ttaataggtg ctagtagtag tgcaagtttc caaatggaac ttttggtca ttggactgaa     9300 aggcaattcc gtgaggattt taaagtcatt ggcagcttca tggtgaaata tgcagaataa    9360
acatagtctt agaatgttcg atggtcatga aaacctgcaa gccaagatta ctaaccaagc   9420
cttcctgttc gcacagttaa ctatggctga ggctaagaag aatagtctca ctcgtgaaca   9480
ggttatcaag gaggccactt gggaaccaca ccaaggtaaa tatatgggcc acaaattaac   9540
```

```
tgtaacacgc agtcgataag tcaagggttg tccaacgtgt tggacagcct ttcatcatat   9600
tgattgggag gtattaaatg actaagttta ctatgcaaga cctcattaaa ttacgtgatg   9660
aaatagaatc accggaagtt aatacagagt ttcactacat tgatccacga gataaacgag   9720
agattcctga ttatcagatt gagacggagt taatgtatga agattattga ttggaagaag   9780
gaagcagaag gccgtatcct agtgatggat gcggaggcta aaggcctgct gggtgctatc   9840
cgctacggtc atcgtgaaga tgtacacatt atttgctgca tggacttgct caccactgag   9900
gagttcctct tcttcgaccc atatgagatg cgtgaccctg aagcaaggga cacttgaaa    9960
gagtgggaag gccatcaaga tgggaccttg gttgatggtg ttaacttcct aaagcactgt  10020
gaagccatcg tctcacagaa cttcctaggc tatgacgggc ttctctttga gaaagccttc  10080
cctgacatct ggaagggatt taactacacc gagaggcgcg gcaagggcag actacgtgct  10140
gacttgtgtc cggtacgcgt catggatacg ctggtcatga gtcgcctgtt aaacccagat  10200
agacgccttc ctccgcaagc atatgccaaa ggtatgggta acgttgcccc tcactcaatt  10260
gaggcgcacg gcattcgtat aggccgttat aagccggaga cgaggattg gtctaaacta   10320
actgaccaca tggtacatcg tgtacgcgag gacgtggcga taggccgtga cctattcctc  10380
tggctattta acggagaatg gacggagcac aaacgccgtg gcgtgaataa acgcactggc  10440
ctaggtattg agacagcctt ccacatggag tccattgtga cgctggagat gagccgtcag  10500
gccgagcgtg gattccgtct ggatatagat aaagcattag cacgatgcga ggaattggac  10560
gctaagattg atgagacagt cgcagcgttc cgtccgcaca tgcctatgcg tatcaagtct  10620
aaaccttttta aaccggaaga aaagaatgaa gtatgccaac gcgcaaatga gtatggagct  10680
agcaacaata tacctactgt ccttgacccc tctcactttc ttcacgcaga gacgcagga   10740
gatcgcaaga cagtatggag tgtcactact aagtctggtg attggtcggc tagcgtcaag  10800
aaagactttc ctcaccttag aggaaaccgt aatgacacgc caagtgtcaa gtggattggc  10860
gcttactcgc ctgttacttt cgaagagatt cccttgggta acagggatac agttaagcaa  10920
gtgctctatg attatggatg gaaaggtgtt gaatttaacg ataccgagca agcgcatctc  10980
gatgagcatg gcgtattacc caagccttgg agtgggaaga taaatgaaaa gtcccttact  11040
ttatggcaag agagagccgc acgtgaaggt aaaacagtcc ctgattggtg cttgggtatc  11100
gctgcatggt acatactcgt atcccgtcgt ggtcagatcc tcaaccgtgg tgacgttgaa  11160
gccttcgacc agaaggggt gtggccttcg caagctggta tacgaaagtg tcgcggcctt  11220
gtacctgtag catttaacaa ggagttagga atcaatgcgc agcaatacta cgaaaggtac  11280
ggatgctggc ctacgtcaga caaggatgac ggagaatggc gtgtgccagc tattgctatt  11340
agtattggaa cttctacgtt ccgtatgcgt catcgtaacg tggttaatat tcctgcccgt  11400
ggcttgtatc ctttacgtga tttattcata gcagggaaag gcaagctaat ccttggttgt  11460
gacggtgcag gtcttgaact gcgtgtcctg tctcacttca tgaatgaccc tgagtaccaa  11520
gagattgtac tgcacggtga tattcatacg cataaccaga tgaaggctgg tcttcctaag  11580
cgtgatatgg cgaagacatt tatatatgcc ttcctatatg ggtctggtat agctaacctt  11640
gcagcagtat gtggtgttac tgaggaagaa atggaggaag ttgtggcaag atttgaggtt  11700
gaactaccat ctcttgcacg tcttcgtgag aatgttatcg cacaaggtaa caagtttggc  11760
tacctacaag cacctgatgg tcattggggt cgcatccgta tgtctggtgg tgaacttaaa  11820
gaacacacta tgcttaacgt actactccag atgactggtt ctctgtgtat gaaatacgca  11880
```

-continued

```
ttggtcagag cgtttgcagt gatgcgcaag gaaggtgtgg ccttagatag catgggaaac   11940
ccttgcggta tagctaacgt gcacgatgaa atccagatgg aagtccctga agatgaggtc   12000
ttgtatctca actacgactt gccttcacc ttagaagggt tcgaaacaga aaggctgct    12060 gtgaaagcag tgttcgatgc agaggagaaa cgtgttcatg tggattctga aggacgtatg   12120
tggtctgctg caaatctcgt tagtgttgat gctggtgtac ttcattgcca gcgtcgttat   12180
caccgtgcag ggcatatcat tgccgacgca atgacctggg cgggtcagta cctgaagatg   12240
cgttgtccga tggcaggtga gtataagatt ggtgcaagtt ggaaggaaac acactgatgg   12300
acaggtttga tattgtttgc ctattctcta ccttctttct tatattcctt atgcttgctt   12360
gctatggaag tatgcgatta gatataccctg atgaagagga gggttacgat tgatgcaggc   12420
atctttattt attcttggag tcatattatt tatggtagta ttctgggctt tctctggcat   12480
tgacccagat tgtgatggta actacgactg agttatactc aaggtcactt acgagtggcc   12540
tttatgaata acttattcct acttattttg tctaacatga tttactggac actatagaag   12600
gaaagcatag gtaatctagg tttataaggt agtataggta attaagtaaa tataggagat   12660
ataaatatgt ctatggtaac tactctggta ttcgtggctc aatactttcg tggtcttgct   12720
aataagttca agtccaaggc tatcaaagct attgaggctc gcatcgaagc agtacaggca   12780
gagcaagtta aagttgaaga acatcgtagt tctcaaatga ttgactgtca taaccgctac   12840
tatgcatctc gtgatgaact aaatgcacgt caagtcaaag aggtagaaga tatgctggca   12900
cgtcaccagc aagagcgtga cagcctgaaa gctgaatttg aagagaacaa ggcatcaatt   12960
gctcttgtac atcaagctgc atctgacagt ctgaagaaag agattgttat gctggaaatc   13020
gaactggata acctgaccaa ataagggggg gttatgatgg aagaagtaat tcaagctaaa   13080
catgtaggta ttatctttcg cgatctgagc cagcgtaaag ttgcaggtca tactcgtctg   13140
gctaaagagg aagacaccgc aatcactact gtagaacaag cagatgccta tcgtggacca   13200
gagttcactc aaggtgaaac ttgtcaccaa ttgagcctat caatttgtga cactatggct   13260
attgtaaatg tgcaagaagt cgaagagggt gagtgtgtca gttacatcta cccctttagat  13320 actattgcac gcattaaggt aatccataag taattactag acactataga acaataggtc   13380
ggcttagttc ggcctatgat tgtaaagtgt tgttgatgtt gaaccattgt gcatcttgca   13440
caacccgata ccgtataggg cttttctagtg agtacatgct tgtgctcagt acaaagctaa   13500
ctgacaatag gagactaaat aaatggcacg tggtgatttt gattttggtg ctcaggttac   13560
taaatctgaa ggtaaagtct ttaagaatcc agaagtaggt gatcatgaag cagtaatctc   13620
tggcatcatt catgttggtt ccttccaaga catctttaag aaaggtaata ccactgaagt   13680
taagaagcca gcaaactttg ttctggttaa gattgtcctg atgggtgacg atgcaagaa    13740 cgaagatggt tctcgcatgg aacaatggat ggctgtgcct ctgaagtctg gtgataaggc   13800
aacactgact aagttcctga atgcagttga ccctaaagag ttgctgggtg gcttcgatga   13860
tttcattggt gaatgcctga ctgcaacgat ggtcggttct ggtgataaga atgacgatgg   13920
ctcattcaag tatgttaact ggaagggatt tggtggtatg ccggacaagc tgaagaaact   13980
ggtcattgct caggttgaag aggaaggtct gtctatgaca ggtcacatta ccttcgacaa   14040
gctgaccaaa gaaatccttg atgacatccc agccaacttg gtgcgtcaat acttcctgaa   14100
cgagacgcct cgtggtaaga acctgtctgt tgctggttct cacgtagaag caatcattaa   14160
agctgctcgt gaagaagacc cagaatggaa gaaggctaag aagaaagacg aggaagatgc   14220
taccccagct aatcgtaaat ctctggatac tggtgagtct gttccacagg aagtacctga   14280
```

```
agcagaagat actcctgcac cggagatgga tgaggacgcg gaatattaag gagaaaggat   14340
gaaagtacaa atcgtaaccc tgcactgcaa gaaaggaatt acaactcttg gcggcaacac   14400
ttttcactcc ttctctgaag gggacacata tgccgacctg cactacatct ggcgcgacgg   14460
acagcacgtg gtgaactaca gcgacccagc tacggggaaa cgccacggcg tatcgcttcc   14520
ggcgcatgac attgctcagg tgaacacagt tttataaagt ctcacgtgtg agacaaatcg   14580
gtgtccggta tttactggac actatagaag agaagaattt taatcggcga taatgccata   14640
accaacaaaa ggagaattta atatgttcaa gattgaaact atcgtaaacc gtgttgttaa   14700
aggtgctgct ctggtatccg ttgagtcttt cattatcgtc gatgaaactg atcaactggt   14760
agctggtact aaggcttacg atacccgtga agaagctcag gctaagattg acagcatggg   14820
taacttcgct gctggtctgg agttcgctcg tgcttgcttc cctgagcagg ctgacaaagc   14880
tcagattggt aaggctaata tcgtagctga atatctggat tgggttgctg ctggtaaacc   14940
agtgaaagaa gttaaggctg ctgaagaagc tgaagctcca gcagaagaag tagctgcacc   15000
ggaaactccg gtaagtgaag aggaagaatt ttgataatag caggtgttgc ctctgttagt   15060
cctagctgac tatcacgctc acctcatcta atgccctgtc tgccttagtg taggcaggat   15120
cttttgcgta atagttattg gagaatgaat tatgccgact attgaatctc gaattgaact   15180
ggacattagc tacaatgcaa tcaccagaca gtatattggg gttgcctatg attacaaaac   15240
tggtgagaag ctagtggagg tgagacaatg ggatgactat tggttaagac agaacctcca   15300
tgatgcggtg tcctccttcc tgaaggagtg gcctacatgc gaccaaactt cgacttcgga   15360
gctacagtat cggaagacaa taacctgttg ctgtggccaa ctgaaggtaa tcgaatcgct   15420
ttaatagatg ctgatatgtt accttacatc atagggtata caatcagtga tatgacttat   15480
gtacgagcca caactcgtgt taagtcaggg caagtcccct caatcaaaga tacacctgag   15540
tgtaagcaag cgtgtgaccg tgtgaactcc ttgcttaact cttgggtgta tgcagcagaa   15600
tgtgatgcag ctaagttgtt catgacgaaa tcagaagcta acttccgtgt ccgcctagca   15660
ttcaccaagc cttataaagg tcaacgtaag accgagaagc ctccattctt ctatgaattg   15720
cgagagcatc tcttagaggt tcacggtgca atcttggcag atggagagga agcagatgac   15780
ctcatgagta tcgcacaatg ggacagccac cgccgcttcc agcaagatac aggtaacgag   15840
ttccctatcg gtagtccaga gcataaagca ttctctgata cttgcatcgt ttccttggat   15900
aaggatttga tgattgttcc cggttggcat ctacagccgg tcaagagaa gaaatgggta   15960 gagcctatgg gttggcttga gctacgccgt aaggctaatg gcaagtcaa agatctaaaa   16020 ggtgctggcc tcatgttcca ctatgcacag atgattatcg gtgatgatat tgataactat   16080
gctggcatac caggtcgtgg tgctaaatat gcctatgatc ttctcaaaga ttgtaagaca   16140
gagaaagagt tgtacatggc agtgctgggt gcttacaagg ctaagttcgg gcatggacaa   16200
gttaaaatta agaattaccg aggtggttat cgtatcggca aagcctttga cctaatgctt   16260
gagtgtggtc gcttatctca catggcaaga ttcaagggtg atatatggcg agccgataag   16320
aacccaatct tgtggggaga tgatgcgaa tggttagcaa attaaaatca tcggaggtgg   16380
cagcttataa gaaggaattg ctagataagc aaggatggaa atgccctctg tgtggcggca   16440
gtctcaaagc tgtcacacct gtaaaccgtg tacttgacca tgaccatgag acaggattct   16500
gccgcgctgt tgtatgccga ggctgcaatg gtgcggaagg gaagattaag ggtgttatct   16560
ctggttatgg taaggctggt aacaaccgtt acttccagct tcaatggtta gagcgactat   16620
```

-continued

```
atgaatactg gaagttacat agtacgcctc agacagataa gttatatcac aaacatcaaa    16680
cggaggcaga gaagcgcgag gctaagaacc gtaaggcacg ccttgcttat gcaagaaaga    16740
aggaggttaa agttgggtaa gctgcgcagc ttgtacaaag actccgaggt acttgatgca    16800
atcgagcaag ctaccgacga gaaaggtaat gttaactaca atgagatggc acgtgtatta    16860
tcgtgtcata ctgtgggtaa aagattacc cgccagttgg ctcgatactg gcatggtcaa     16920
ttcaagaaga ccaagaagaa tggtgattac taccagaccc ttctgcaaga agataagcgt    16980
atcaaagaag agcgtaagct caggactcct gaccgctacg aggatttggc tattgtgcca    17040
ttgcctgact cgcctcatcg aagtgtactg gtgatccctg atactcatgc accttatgag    17100
cacccagata ccctagagtt ccttgcagcc gtggcagcac gttaccgtcc agacacagtg    17160
gtacacctag gagatgaggc agacaaacat gccctgtcat ccacgattc ggacccaaat     17220 ctggatagtg ctggcatgga gttagagaag gctcgtatct tcatgcacaa attgcacaag    17280
atgttccctg tgatgcgcct gtgtcactct aaccacggct ctatgcactt ccgtaaggca    17340
agcgccaaag gcatccctgt gcaatacctg cgcacctatc gtgaagtctt cttcccgcag    17400
ggaggtggcg accagtggga ttggcaacat acgcacgtcc ttgagttgcc gaatggtgaa    17460
caagtggcat tcaagcatca acctgctggc tctgtcctag cagatgcagc gcatgagcgt    17520
atgaaccttg tgtgtggtca cttgcacggt aagatgtctg tggagtacgc acgtaataca    17580
catgaacagt attgggctgt gcaaggtggc tgcttaattg atgagtcatc ccgtgcattt    17640
gcctatggtc gtgagtctaa atacaagcca gcattaggtt gtgtggtcat tctggagggt    17700
gtgcctcaca ttgtcccgat gcaaaccaat agcgacaacc gttggattgg caagatttag    17760
ttgacactat agaacaaagg gctaggtaag actttatcgg ctggcgtatc caatgatat     17820 tgcactagcc cttgattgta tagtgaatgg aggattcaat atgtcacact atgaatgaa     17880 gaagtgtcat aagcgttatg attactgtac ttgtggtcaa gagaaaacat cttttaaagt    17940
tggagacaag gtatttcgta atgaaaaaga ttcgattcct tggaatcaat actgcaaaga    18000
agctggtatt gaccctgata gccctgtaac catagatgat attgatggca ttaacttgtg    18060 cttcgtgag gtgaggggta caggttggga ttccaaaaaa ttcaaacttg catctgataa     18120
gttagacaac aatatggtaa ttaagcctaa gcactacgag ttctttgatg gcgtagaggc    18180
aatcactatc attgcccgca gtatgaccga gaagcaattc gctggctatt gcatgggtaa    18240
tgctttgaag taccgtctac gtgcaggtaa gaagttcaac actgaagaag acctgaagaa    18300
agcagattac tacaaagagt tattccagaa gcatcgtcac gaatgtattg atgaggatat    18360
ttgatatgaa tatctttgag ttcctaggtc ttccagaaga ccaccgcaat cacccattca    18420
tgctggtgaa gcatcgcggt gaagttcctg agaagaaatt aacttttcca tgttatgcac    18480
aggtgaaacg agatggtatc ttttctgctg ttgttgttcg cactgatggt gtcgttggca    18540
tttttggtcg cactggtaag aaattggcaa acactgaagg actcgaacaa gcctttgcta    18600
cctttccggt tggcatttat cttggtgagc ttcagtctat ggccattgat atctaccttg    18660
aggcaatctc tggggttgtg aaccccaatc gcactgagcc acttgatttc ataggccagc    18720
agattaaaga caacctgtat atcgacttct tcgatatgtt aactattaag gcattccatg    18780
atggattcac tgatgtttct tatctcaaac gttacgatgc tttacatcgt cgtatcggcg    18840
ctcatcttag cgggtgcaac gctatccttc ctatcactcc ttgccataat gagcgagaag    18900
ttgaagcgtt tgcgcaagag caaatagatg caggacgtga gggtgctgta ttcaaactgg    18960
actgcgatta tgaagcagga cacaaaggtt atcgtcagac taaagaagtc cgtaaggtaa    19020
```

```
cctatgacct tacttgtatt ggctttgaag aaggtaaagg caaatacaaa ggtaaggtag   19080
ctaacctcat tttcaaatgg aaaggaggca agacaatcaa agctatgtta ggtaagggt   19140 ggactcatgc agatgcagag cagatgttcc acgacattaa acatggtgga cgattgaatg   19200
tcattggtaa aatctttgaa gtcaaaggtc ttcaggattc aagcaagggc aacattcgtc   19260
tgcccaaagc gggagaatta agacatgaca aagatgaacc agatttcttt tgatagcatg   19320
aaggcaactc gtgcagttga ggtagcagaa gctatcttcg aaactttatc ctgtggcatg   19380
gaagtgccat atactttact tgctgatgca gaagaacttg gtctttctgt agaagctatc   19440
caagagaagg ttgacgaatt atatggtaca gacgaagaag aaaccgacga tttcatttga   19500
aggaatggag atgcttgaga tgattctcaa gccttcttct cctaaggtga ctaagactca   19560
tgaagagtta atcgttgatg aagttaagcg ttacatcatg gattgtgtca gagcacaact   19620
ggtggtccaa tgatacgtcc agcctccttc ctagatattc ctgagattat aaaccttggg   19680
aataaatatg tggaagagga agtcaaggtt gtagcccacc actcagcctc atggaatgca   19740
gaacaaagtg ccataacctt tgtgcatctc ttaatagaga cccaccactc agcctcatgg   19800
aatgcagaac aaagtgcaca taacctttgt gcatctctta gtagagaaga tttatcccta   19860
tgggttgctg tagatgaagg gcagattgta gggttcctgt gggctggcta tcacgagttg   19920
gccccttgga cacctgtaag agttgcctct gacattctct tttatattat accagagagg   19980
cgaggaacac tacttggtat gcgtctcatc aaagccctaa agcaatgggc tagtgataat   20040
gaatgctctg aggttcgcct gtctatcgcc tctggtatta tgaagaacg tgtcggacgt    20100 atgtataagc gacttggctt tgaaccgttt ggcactgtgt ataacctgaa gttctaagga   20160
gataacatgg gtgttgtaaa gaaagcattt aaggctatcg gtcttgctca agatgcacca   20220
cgtattgaag ccaaagtccc agcacagcag cttgagcgta agcctgagac tgaagctgaa   20280
gatattcaaa ttggtgcagg ggatgatgct actgcatctg caaaaggtaa gcgtggcctt   20340
gtccgtccgg tagcttctag cttgaaggtg taatatgaaa cagagcatag atttggagta   20400
tggaggtaag cggtctaaga tacctaagct atgggagaag ttctccaata aacgtagctc   20460
tttccttgat agggcgaagc attactccaa attaaccttg ccctatctga tgaatgacaa   20520
aggtgataac gagacttcgc agaatggatg gcaaggtgta ggtgctcagg caaccaacca   20580
tctagccaac aagctagcgc aagtactatt ccctgcacag cgttccttct ccgtgtaga   20640 cttaactgca caaggtgaga aggttcttaa tcagcgtggc ctgaagaaga cagagctagc   20700
taccatcttc gctcaagtgg aaacacgggc aatgaaagag ttagagcaac gtcaattccg   20760
gcctgctgta gtagaagcat ttaagcatct tattgttgct ggcagctgta tgctatacaa   20820
gccgagcaaa ggtgcaatca gtgctatccc aatgcatcac tacgtagtta accgtgatac   20880
caatggcgac ctgttagaca ttatcttgct acaagagaaa gccttacgta cctttgaccc   20940
agctacacgt gcggtagtag aggttggcct gaaaggtaag aagtgcaagg aagatgcag    21000 cgttaagctg tacacacatg ctaagtatct tggtgatgga ttttgggaac tcaagcaatc   21060
tgctgatgat atccctgtgg gtaaggtgag taaaatcaaa tcagaaaagc taccttcat    21120 cccattaact tggaagcgaa gctatggtga ggattgggt cgacctcttg cagaggatta   21180
ctccggtgat ttattcgtta tccaattctt atctgaagcg gttgcccgtg gtgctgcgct   21240
gatggcagat atcaagtacc tgattcgtcc tggtgctcaa actgatgttg accactttgt   21300
taactctggc actggtgagg ttgtcactgg tgtagaagaa gacatccata ttgtacagtt   21360
```

-continued

```
aggtaagtac gcagacctca cacctattag cgcggttcta gaggtataca ctcgccgtat    21420
cggtgttgtc ttcatgatgg agacaatgac acgccgtgac gccgaacgtg ttactgctgt    21480
agaaatccag cgagatgcgt tagagattga gcagaacatg ggtggtgtat actccctctt    21540
tgctactact atgcaatcgc cagtagcgat gtggggtctg ctggaggcag gggagtcctt    21600
cactagtgac ttagtggacc ctgtgattat cacaggtatt gaagctttag gacgcatggc    21660
tgagttggat aaactggcta actttgctca gtatatgtca ctgccattac aatggcctga    21720
gcctgtccta gctgctgtga atggcctga ctatatggat tgggtgcgtg gtcaaatctc    21780
tgctgaactg ccgttcctta aatcggctga agagatggca caagaacagg aagcacagat    21840
gcaagcacag caagcacaga tgcttgaaga aggtgtggct aaggccgtgc cgggtgtaat    21900
tcaacaagaa cttaaggagg cgtaatgtct ttctcattta ctgaaccgtc aaccactcac    21960
cctactgctg aagagggtcc ggtagaaacc aaggaggtaa caactgatgc tgctactact    22020
gatgctcctg ctgacgctgg cacttctgta caagatgaca atgctggtgc acaacctact    22080
gaagacaccg gaggagaagc ttctggacag ccttcagaaa aaggagacaa tggcggagag    22140
aatggtgaac ctaagccaga tgataccgcg accgacactg aggaagtgca atacttcttc    22200
ggagaacatg aagtaacagt agacatccca caggatgtaa ctgacagcct taaagagaaa    22260
ggcattgatg ccaagcaggt tgccaaggaa ctctattcca aggtggcaa gtttgaactg    22320 tcagatgcaa ccaagcagaa attgtatgat gcttttggca gtttgcggt agatgcttac    22380 ctatcaggtc taaaggctca aaatgaagcc ttcttcctga agaagccaa cgcagctaaa    22440 gagttggaag cagctaacac ccaacgcttc tctgatgttt ctaaggaaat tggtggcgaa    22500
gaaggttggt cccgtcttga ggagtgggca cttgaagcgc tgtctgatga cgaactaatg    22560
gcattcaatg cggtgatgga atctggcaac cagtacctgc aacaatatgc tgttcgtgaa    22620
ctggagggtc gtcgtaagca ggcacagggg gatgataagc catccctgat tgagccatca    22680
gcacctgcta aggctaatga agagaatggc ccactgacgc gagatcagta cgttcaagca    22740
atcgcaactc ttagccagaa gtacggcaat gaccgtaaag ctatggcaga agctcaggct    22800
aaactggacg cccgtcgccg tgctggcatg gctcgcggta tctaattcag tatttactgg    22860
acactataga agggagaaaa gttctcccta gttatcaatt tgatttataa ggagattata    22920
atacatgtct acaccgaata ctctgactaa cgttgctgta tctgcgtccg gtgaggttga    22980
cagccttctc attgagaagt ttaatggtaa ggtcaatgag cagtacctga aggtgagaa    23040 cattctgtcc tactttgatg tacaaactgt tactggcact aacacagtga gcaacaaata    23100
tttgggcgaa actgagttgc aggtgctagc accgggtcag tcccctaatg ccaccctac    23160 tcaggcggat aaaaccagt tggtaattga taccactgtc attgctcgta acactgtggc    23220
tcacatccac gatgtacaag gtgacatcga tagcctgaaa ccaaaactgg ctatgaacca    23280
agccaagcaa ctgaaacgtc tggaagacca tgggcaatt cagcagatgc tgttaggcgg    23340
tattgctaac accaaggccg aacgtaacaa gccgcgtgtt aaagggcatg gcttctctat    23400
caacgttaac gtaactgaga gtgaagcact ggctaaccct cagtatgtta tggctgcggt    23460
agagtatgct ctggagcaac agcttgagca ggaagtggac atctctgatg tagctatcat    23520
gatgccgtgg aagttcttca atgctttgcg tgatgcagac cgaattgtag ataagactta    23580
cactatcagc cagtctggtg caaccattaa tggcttcgtt ctctcttctt ataactgccc    23640
tgtgatcccg tctaaccgat tccctacctt cgctcaggat caggctcacc acctgttgtc    23700
taatgaagat aacggctatc gttatgaccc tatcgcagag atgaatggtg cagttgctgt    23760
```

```
tctgttcact tccgacgcac tgctggtggg tcgtaccatt gaagtgactg gtgacatctt    23820
ctatgagaag aaagagaaga cttattacat tgacaccttc atggctgagg gtgcaatccc    23880
tgaccgttgg gaagcagtgt ctgtagttac cactaaacgt gatgcaacta ctggtgatgc    23940
tggaggtcct ggtgatgatc acgcaaccgt actggctcgt gcacagcgta aggctgtata    24000
tgtcaaaacc gaaggtgctg cggctgcatt ctctgctgcc ccagcaggta tccaagcgga    24060
agaccttgta gcggcggtac gtgctgtaat ggcaaatgac attaagccga ctgcaatgaa    24120
acctactgag taacacctat gccctatcta ccttgcgtag gtagggttct ttttgttagg    24180
aggattcatg cctgtaatta gacaaaccag taaattagga catatgatgg aagatgtggc    24240
cttccagatt attgatagta agctggaagc ggtaaacttg tgtatgcgag ctattggtcg    24300
tgagggtgtg gattccctcg actcagggga cttggacgca gaagatgcaa gcaaaatgat    24360
cgacatcgta tcccagcggt tccagtacaa caaaggaggt ggctggtggt tcaatcgtga    24420 accaaaactgg caacttgcac cagacactaa cggtgaagtt aatttaccta caaactgcct    24480
agcagtattg cagtgttatg ctttaggtga aaagaaagta cctatgacta tgcgagcagg    24540
taagctctac tctacttgga gtcacaccct tgatatgcgt aagcatgtta atgctaatgg    24600
tatgattcgt cttaccttac tcaccttact accctacgag catctaccta caagtgtaat    24660
gcaggctatt gcctatcaag ctgctgtaga gtttattgtg tctaaggatg cagatcagac    24720
taagctagcc actgcgcagc agatagccac tcagcttctt atggatgtac aatctgagca    24780
aatgtcacag aagcgattaa acatgctggt acataaccct actcagcgtc agtttggtat    24840
catggctggt ggctctcaga atgtacctgc ttactctcat tcaccttatg agagttgggc    24900
gctccgtccg tgggaggatc gttaatgaa gtacaaggtt cattaggtag acaaatccaa    24960
gggattagcc agcagccgcc agcggtacgc ttggatggtc agtgcacagc tatggttaat    25020
atgatacctg atgtagtgaa tggtactcaa tcacgcatgg gtacaactca tattgcaaag    25080
atacttgatg cggggactga tgacatggct actcatcatt atcgcagagg tgatggtgat    25140
gaagagtatt tcttcacgtt gaagaaagga caagttcctg agatatttga taagtatggg    25200
cgcaaatgta atgtgacttc acaagatgca cctatgacct acctctctga ggttgttaat    25260
ccaagggaag atgtgcaatt catgacgata gctgatgtta ctttcatgct taatcgtagg    25320
aaagtagtta agctagtag caggaagtca cctaaagttg gaaacaaagc cattgtgttt    25380
tgtgcgtatg gtcaatatgg tacatcttat tccattgtaa ttaatgggc caacgctgct    25440 agttttaaaa caccggatgg tggaagtgca gaccatgttg aacaaattcg aactgaacgt    25500
atcacttctg aattgtactc taagttgcag caatggagcg gtgtgagtga ctatgaaata    25560
caaagagacg gtactagtat atttatcgag agacgggatg gtgctagctt tacaataaca    25620
accaccgatg gtgcaaaagg taaggactta gtggctatca agaataaagt tagctctact    25680
gacctactcc cttctcgtgc gcctgctggt tataaagtac aagtgtggcc tactggcagc    25740
aaacctgagt ctcgttactg gctgcaagct gagcctaaag agggaaacct tgtgtcttgg    25800
aaagaaacaa tagctgctga tgtattactt gggtttgata aaggcacaat gcccttacatt   25860 attgaacgta cagatatcat caacggcata gctcaattca agataagaca aggtgattgg    25920
gaagatcgta agtagggga tgacttgact aaccctatgc cctctttat tgatgaggaa    25980 gtaccccaga caataggtgg aatgttcatg gtgcagaacc gcctatgctt tacagcaggt    26040
gaagcggtta ttgcttctcg tacatcatac ttcttcgatt tctttcgtta tacggttatc    26100
```

```
tctgcattgg caactgaccc ctttgatatt ttctcagatg ctagtgaagt ctaccagcta    26160
aaacatgcag tgaccttaga tggcgctacc gtgttgttct ctgataagtc acaattcata    26220
ctgccaggcg ataagccttt agagaagtca aatgcactgc ttaagcctgt tacaacattt    26280
gaagtgaaca ataaagtgaa gccagtagta actggtgaat cggtaatgtt tgccactaat    26340
gatggttctt actctggtgt acgagagttc tatacagact cttatagtga cactaagaag    26400
gcacaagcaa tcacaagtca tgtgaataaa ctcatcgaag gtaacattac caacatggca    26460
gcaagcacca atgtcaacag gttacttgtc actaccgata agtatcgtaa cataatctac    26520
tgctacgatt ggtatatggca aggaacagac cgtgtacaat cagcatggca tgtatggaag    26580
tggcctatag gtacaaaggt gcgaggtatg ttttattctg gtgaattact ttacctgctc    26640
cttgagcgag gagatggcgt gtatctggag aagatggaca tgggtgatgc actaacctac    26700
ggtttgaatg accgcatcag aatggatagg caagcagagt tagtcttcaa gcatttcaaa    26760
gcagaagatg aatgggtatc tgagccgctc ccttgggttc ctactaaccc agaactttta    26820
gattgcatct taatcgaggg ttgggattca tatattggcg gctctttctt attcaagtac    26880
aaccctagtg acaatacttt gtctacaacc tttgatatgt atgatgacag ccatgtaaaa    26940
gcgaaggtta ttgttggtca gatttaccct caagagtttg aacctacgcc tgtggttatc    27000
agagacaatc aagaccgtgt atcctacatt gatgtaccag ttgtaggatt ggttcacctt    27060
aatcttgaca tgtaccccga tttctccgta gaagttaaga atgtgaagag tggtaaagta    27120
cgtagagtat tagcgtcaaa ccgtataggt ggtgctctca ataatacagt aggctatgtt    27180
gaaccgagag aaggtgtctt cagatttcca ctgagagcta agagcacgga tgttgtttat    27240
cgtattattg tagagtcacc tcacacattc cagcttcgtg atattgagtg ggaagggagc    27300
tacaatccaa ccaaaaggag ggtctaatgg ctataggttc agccgttatg ctggtatgt    27360 cttctattgg tagcatgttt gcaggcagtg gtgcagcagc cgctgctgga ggtgctgccg    27420
caggtggcgg aggtttgcta ggttcactag gtggattcct aagtggctct actgctggtt    27480
tctctaatgc tggccttctt ggtgctggcc ttcaagggtt aggcttgatt ggtgatctat    27540
ttggtggaag tgatgaagcc aaggcgatga gaaagcaca agaagagcaa tggcggcagc    27600
agcttattgc tacacaagag gcgtacaaga cagtggcaga cgcagaacgt tctgctgcta    27660
aacaatatca tgcagatgca atcagtaatc aggcttcact gctacagcag cgagcacagg    27720
ttgcattact tgctggggct actggtactg gtggtaattc tgtgtcctct atgcttaatg    27780
acttagcagc agatggcggc aggaaccaga gtactatcat tgataactat gagaatcaga    27840
agattaattt caccaaccag cttaagtcta tccaacgtgg tggtcagatg cagatgcgtg    27900
agtttaagaa gccttctgct atgaatacct tggttaaagg tattccaagt ctggcatctg    27960
cctatgtaac tggtagtaag tctggcaagg cattgggtaa agccttaact gattctcgca    28020
catattcatc tggaacaaga ggtatttaat ggcaattgag cgacaagcag tacaaggtct    28080
gccacaagtg caggccactt ctcctaatgt catgacctt gcacctcaac aagtgggagg    28140
tgtggaggct ggcgtggctt ctacctccgg tagtaggttt atcgaagacc ttattcgtgc    28200
agcaagcagc gtggctgatg ttaccactgg tatccttaat cagaagattg aggaagataa    28260
ggttgttcaa atggaacggg catataacgg attaatgcct tctgaggatg caactcgtgg    28320
tggcgctcgt gctaacatgc ttgtcaaagc tcaactgcta gctaatgatg aagcagcacg    28380
aatgaaagac atggctactc gtttccaagg aacggatgac gaatgacac aacttatggt    28440 tgactctcgt aatgagatgc agaataagct gttccagcaa taccctgagt tgcaaggtga    28500
```

```
caaagatact atgcgtatgg tcactaatgt cttccaagaa cagcagcctc agatttgggc   28560
tacacgaacc cagcataaac ttgaccgtga acaagcagac cgtgaggata cctttgacgg   28620
gcgagtggct tctacttggg attctaatat tgaccctgaa gcctctggct atgctttaca   28680
ggaacgaatc cgcgaaggtc ttactcaagg attactacct gaacagatgt acaagaagtt   28740
agtccagcga gcaatttcac ttgcacaagg cggtgatgtt agcatggctg aagccctgaa   28800
gtatgtgaag gacgataagg gtgtttctgt ttatgctaag aatccacagc ttatcacagc   28860
catcactagt ggtaatgcag tttgggctag gaataatgta gctgatgtaa ctcgtatgtc   28920
tttcgaagtt aaagaatcct accttgcagg tgatttaact gatgaagaat tgttggaacg   28980
agcacagcac attaataatc tgacaggtaa ctctgtcttc tctaatccag aactagaggc   29040
actgatgcgc caacgggcta agcagaatgc agagctaggt gcaatgcagg atatgcgacg   29100
tgagctttac tccgaccgcc tgactggctt ccaaggtaag actgataaag agaagaaggc   29160
ttacattgat gttatcaaac aggatagcca actttatgca gaccagcaaa tcaaacaacg   29220
tggcttggac ccttacagtc aagaggctga agctattcgt ggtgcagtgg aagtgcagcg   29280
cctgcaattc atgaactcca aaggcttagt ggatgatacc tttgagtctc gtatcaaagc   29340
catggaatct atgctatcgc ctgagcactt tgccaagggc gaaccacagg agttgatgac   29400
tattcgccag ttgtgggaac agttaccaga agagagccga ggtgtctttg gtgacacggt   29460
gaatggctac atggataact acaacactgc actacaaatg ggagagacac ctttgcaggc   29520
tgcaaggttt gcgcgtaaag cacagcagaa attctctcgt actgagaagg aaaccaagaa   29580
gttcaactca gctattggag atgcactgga tgaggtatct ggtgctggct ggtttgatgg   29640
taaaaccgaa gtgtcagact taggtaaagc tattgcggaa gaagagttac gagctaaggc   29700
caatatgttg tggtctagtg gtatgcgtaa catggattcc atcaagaagg ctttaattac   29760
ttggggcaat aaacgctaca ctcaatcaga ggatgcaaag acttccggtg gctatttcat   29820
taaaggtgat tacacttctg catctgatat gcttatgtca gttgggaaag gcgtaaaccc   29880
taccgatgta cctctggcgc ttggtaggta tgtagaaaca cagatgccag aattgaagaa   29940
ggagcttcaa gagggggaaa ctaaagatga tatatacatt gattacaatg aacagaaagg   30000
tactttcgtg attcgtgctg gtgcagcagg tcgccctctt tctggagtaa tccctgtaac   30060
ctctttagat accacttcac tactagattc tgcctatcag aagaaagtag aggaacgaga   30120
taaaggcgag tatgttcacc cgtatcgtac agatattggt gcacaagagc ctatgccagc   30180
taaaccaact gccaaagata ttggtaaatt tggactagct aacttcctca tgtcttctgc   30240
ttttgcttct ggtgagaatc tgccttctaa cttcgagatt aactatcgag gtaatatgca   30300
acaattctat gacaagctag ctatggatga gaataaagat aaagttggct taataaggc    30360 aactggaacc tttactccat ataaagacgc tcacggtgag tctatcggtt acggtcattt   30420
cttaacggaa gaagagaagc gaaacgggta tattaagatt ggcgatgaac tagttcccta   30480
tcgagggtct atgtctcagc ttacagagag caaggctcgc gctcttatgg agcaagatgc   30540
taagaagcat gtgcctccta ctcgtgactg gaagattccg tttgaccaga tgcaccctgc   30600
acagcaacgt ggcttgatgg atttaagcta caatttaggt aaaggtggaa tccagaactc   30660
accgcgtgct cttgctgcat tcaaagctgg taagcttacg gagggcttta tcgaaatgct   30720
gggcactgca tcaagtgaag gtaagcgtat tcctggccta ctgaagcgac gcgctgaggc   30780
atacaatatg gcatctgctg gtggtgtgcc taagattacc gaagtggaga ctcgtgaaga   30840
```

```
tggctccatg tgggttaggt ttggtggacc tatgccagca ggttctgtct cggcatggac    30900
tcataaacgt attggcgcgg atggttggta tcaggtttat gaggctgcac ctaccaagtt    30960
agctaaagat tctaaggtag gtaaagttaa gttgtagtac ctaactcaag gcttgtctca    31020
catgtgagac aggtctttat gataggcact atggaggaat tatggaacaa gacattaaga    31080
ctaattgggc tggatatgtc cagtctactc ctgagccgtt ttctattgag gcggctccgg    31140
tatcggctcc tacgatacgc cagcgtaatg agttacaaga gcaagttctt gaagctaaag    31200
ctgacgctga tatcttaggt gctgtaggtg ctgccttcca gaatgagtgg ttggcattcg    31260
gaggcaagcg gtggtatgac cgtgccactg ctgatttcac acctcaacca gactttgaga    31320
tacaacctga gcaacgtgaa gcactacgtt tcaaatatgg tacggatatg atgcagacaa    31380
tcactgaggg tgttcgttct gaggatgaat tgaacttccg tattcagaat gcggatgaag    31440
accttgagcg caataagcgc attgctcagg ctggctgggt tggctctgtg gcgacgattg    31500
gcgctgctgt gcttgaccct gtgggatggg ttgcctctat tccaaccggt ggtgccgcta    31560
aagttggact cgtaggccgt gctgtgcgtg gcgctatcgc cgctggcgtg agtaatgccg    31620
ctattgaatc cgtattggtc caaggtgaca tgactcgtga tttagatgac attatggtag    31680
cactgggttc cggtatggct atgggtggcg ttattggcgc tgtagcgcgt ggtagggcca    31740
ctaagctcag tgagcaaggt gatgacaggg ctgctagcat tgtgcgcagt gcagacgcag    31800
gggaccgcta tgttcgtgct gttgccgatg acagtatcgg tgcgatgcgt gttaagggcg    31860
cagaggttct cactgagggt gtattcgata tctccagtaa gagtgaagac ctactgaaaa    31920
ccttgcaacg agaaggtaat gcgattgata tgacacctcg ccgttgggct ggaactatgt    31980
ctgccctcgg tactgtcgtg cactcatcta aagatgcaag tatccgaggc cttggtgctc    32040
gtctgtttga atccccacaa ggtctaggta tgcagaaggc atctgctagt cttatgcaga    32100
atactaactt aaatcgcctg aaatctgctg atatgaaccg cttcaatgat gggtttgatt    32160
tgtggcttaa agaataataa atcaatccag tagcagggca taccaactct cattatgtac    32220
agcaatacaa tgaaaaggtg tgggaggcag tgcgtattgg catggatgag tctacaccta    32280
aatctatccg catggctgct gagggacaac aggctatgta cagagaggcg ctggctttac    32340
gtcaacgttc tggtgaagcg ggatttgaaa aggtaaaagc cgacaacaaa tatatgcctg    32400
atatctttga tagtatgaaa gccagacgtc aattcgatat gcacgataaa gaagacatca    32460
tcgaactttt ctctcgtgcc taccagaatg gcgctcgtaa gattccaaag gaagcagcag    32520
atgagattgc acgagcacag gtaaatcgcg ttgctgatgc taccttaact ggaaagctta    32580
gttttgaaaa ggcaatgtca ggtcagacta aggcagagta tgaagctatc atgcgtaagg    32640
caggcttcag tgatgaagaa attgaaaaga tgatagaagc tctggataac aaagaaacca    32700
gagataacat ctctaaccga gctaaaatga gtttaggatt agatgttact caagaataca    32760
atggcattcg tatgcgtgac ttcatgaata ccaacgtgga agagctaaca gataactata    32820
tgaaggaagc agcaggtggc gctgcattgg ctcgccaagg cttctctacc tatcaggctg    32880
cacttaatgc aattgacctt gtagagcgaa atgcacgaaa cgcggctaag gatagcaagg    32940
ctagtttggc attagatgaa gagattcgtc agatgcgaga aggtcttcgc ctgattatgg    33000
gcaagtcgat tgatgcagac ccacaggcta tatctactaa gatgatgcgt cgtggtcgtg    33060
atatcacagg tgtgcttcgc ttaggtcaaa tgggcttcgc acagctaggt gaacttgcca    33120
actttatggg tgaatttggt attgctgcaa ctactatggc tttaggtaag caattccgct    33180
tcacctctaa ggcgttgcgt aatggcgatg gcttcttccg agataagaac ttagctgagg    33240
```

```
ttgagagaat ggtggggtac attggtgagg ataactggct aacaactaag ggtgcacgtc    33300
ctgatgaatt tggtgatgta accacagtaa gagggatgat ggctcacttt gaccaatcca    33360
tgaactcaat acgtcgtgct caaaccaacc tatcactctt ccgcatggca cagggttctc    33420
tggagcgaat gactaatagg caaatagctt tgtctttcat tgaccacctt gaaggcaaga    33480
agattattcc tcagaagaaa ctggaggaac ttggtcttac tcaggagttc atgactaacc    33540
tacagaagca ctatgatgct aactctaaag gttctggctt gcttggcttt gatacaatgc    33600
cttatgccat gggtgaaact ttagctaatg ctattcgtcg taagtcaggt ctaatcatcc    33660
aacgtaactt cattggtgat gaaggtatct ggatgaacaa agcactaggt aagacatttg    33720
cacagcttaa gtcattctct cttgtatctg gtgagaagca atttggtcga gggattcgcc    33780
acgataaaat tggtcttgct aagaagacag cttacgggtt tgctttgggt tcaatagtgt    33840
atgcggcaaa agcctatgtg aactctattg ggcgagaaga ccaagatgaa tatttggaag    33900
agaagttatc gcctaaaggg ttggccttg gtgcaatggg tatgatgagt acaactgctg    33960
tatttagtct aggtggagat ttcttaggtg gcctaggtgt tctaccttcc gaactcattc    34020
aatcacgcta tgaagcaggt ttccaaagta agggtctgat tgaccaaata cctctggttg    34080
gcgttggtgc agatgcagta aatctggcta actcaatcaa gaagtatgca gaaggtgaca    34140
cagaaggtgt agatatcgct aagcgagcac tccgtcttgt gccacttacc aatataaatag    34200 gtgtccaaaa cgcattgcgt tatggcttag atgaactgga ggattgatga gttatacttt    34260
cacagaacat acagccaatg gtacgcaagt cacctatcct tttagctttg ctggtaggga    34320
taaaggttat cttcgtgcct cagatgtgat agtggagtct cttcaaggta acacttggat    34380
tgaagttaca tctggctggc aactaactgg cacgcaccag attacttttg atgtagcacc    34440
agttgcaggt ttgaagttcc gtattcgaag ggaagtacaa aaagaatatc catacgctga    34500
gtttgaccgt ggtgttacct tggatatgaa gtctttaaat ggttctttca ttcatatact    34560
ggagattaca caggagttac ttgacgggtt ttatccagaa ggatacttca ttaaacagaa    34620
tgtaagctgg ggcggcaata agattactga ttttggctgat ggcacaaatc cgggagatgc    34680
agtaaataaa gggcagcttg atgccatcga caagaagcat acagattgga acgccaaaca    34740
ggacattgag attgctggcc ttaaggctgg tatgacttct ggtattgcgc acagaactgt    34800
tccttggtac acgatagccc aaggtggtga gatttccgta aaaccacctt atgaatttca    34860
agatgcacta gtttttcctta atggggtatt gcagcaccaa attgtaggcg catactctat    34920
aagcaacaac actatcactt tcgcagagcc gcttgtggct ggtacagagg tgtatgtgct    34980
gattggtagt cgtgtggcta catctgaacc taatattcag ttggagttga actttgactt    35040
agtagaaggc caacaagtag tacagattgg ctctgcattt aagtacattg aggtctacct    35100
tgatggatta ttcaaaccta aacttgctta tcaggtagac ggtgacattg ttacttctc    35160 agaaagagta ccagaatgcc ggatgactgc taagattatc acagcataag gaggtgggat    35220
gattaactcc gaactggtag atagtggtgt gaagcttgcg ccacctgcac tcatatcagg    35280
tgggtacttc ctcggtatca gttgggataa ttggtgtta atagcaacat tcatttatac    35340
cgtgttgcaa attggggact ggttttataa taagttcaag atttggaggg agaagcgtga    35400
gcgtacacaa taaacatgca gctacagagg acgaggttgg cattctgcat ggtgctatta    35460
ccaaaatctt caataagaaa gcacaggcaa tactggacac tatagaagaa gaccctgatg    35520
cagcattaca tttagtgtct ggtaaggata ttggtgcgat gtgtaagtgg gttcttgata    35580
```

```
acggcattac cgccacacct gctgcacagc aggaagagtc caagttatct aagcgcctca   35640
aggctatccg agaggcatcc agtggtaaga taattcaatt cactaaggag gattgatggc   35700
taaggcaaga gaatcacaag cggaggctct tgccagatgg gagatgctac aggagttaca   35760
gcagaccttt ccttcaccg cggaaggttt gcttctcttt gcagatacag ttattcataa   35820
cttaattgca ggcaaccctc atctgattcg tatgcaggcg gatatcttga agttcctatt   35880
ttacggacac aagtaccgcc tcatcgaagc gcctcgtggt atcgctaaga caacactatc   35940
agcaatctat acggtattcc gtattattca tgaaccgcat aagcgtatca tggttgtgtc   36000
ccaaaacgcc aagcgagcag aggaaatcgc aggttgggta gttaaaatct tccgtggctt   36060
agactttctt gagtttatgc tgccggatat ctacgctggg gaccgtgcat ccgttaaggc   36120
gtttgagatt cattcaccc tacgtggtag tgataagtct ccttctgtat cctgttactc   36180
aatcgaagca ggtatgcagg gtgctcgtgc tgatattatt ctagcggatg acgtagagtc   36240
gatgcagaat gctcgtacgg cagcgggccg tgccttgctt gaggagctga ctaaggagtt   36300
tgaatctatc aaccagtttg gggatatcat ttaccttggt acacctcaga acgtaaactc   36360
tatctacaac aacctacctg ctcgtggtta ctctgttcgt atctggactg cgcgttaccc   36420
ttcagtagag caagagcaat gttatggcga cttccttgca cctatgattg ttcaagatat   36480
gaaggacaac ccagcacttc gctcagggta cgggttggat ggtaatagtg gtgcaccttg   36540
tgcccctgaa atgtatgatg atgaagtcct gattgagaag gaaatctctc agggtgctgc   36600
taagttccag cttcagttca tgcttaacac tcgcatgatg gatgctgaca gatacccatt   36660
acgcctgaac aatctaatct tcacctcgtt tggtacagag gaagtccctg tgatgcctac   36720
gtggagtaat gattccataa acatcattgg tgatgcacct aagtatggta acaagcctac   36780
ggatttcatg tacagacctg tagctcgccc atatgaatgg ggtgctgtct cccgcaagat   36840
tatgtatatt gaccctgcgg gtggtggtaa gaacggagat gagacgggtg tagccatcgt   36900
attcctgcac ggcacattca tttatgtgta tcagtgcttt ggtgtacctg gcggataccg   36960
agagtcgtcc ctgaatcgca ttgtgcaggc cgcaaagcag gcgggtgtta agaggtatt   37020 cattgagaag aactttggtc atggcgcgtt tgaggcggta attaagccgt actttgaacg   37080
agagtggcct gtaactctgg aagaggatta cgccaccgga cagaaagagt tgcgtatcat   37140
tgagacgctg gagccgctca tggcagccca taggcttatc ttcaatgcag agatggtgaa   37200
gtcagacttt gagtcggtac agcactatcc gcttgaacta cgcatgtcct acagtctttt   37260
caatcaaatg tcgaacataa cgattgagaa gaacagcctc cggcacgatg accgcctaga   37320
cgccctgtat ggcgctatac ggcaattaac ttctcagata gactatgacg aggttacacg   37380
gattaatcgc ctcagagcgc aggagatgcg cgattacatc catgctatga acacacctca   37440
tctacgcagg gcaatgctat atggagatta cggtactgag cgaagagtga ccaacacttc   37500
cgtagcgatg cagcagcgag tttacgggca gaactaccga aataaatcgg caagcagaaa   37560
tacactttct gcaaggattt caaggactta ttaattactg gacactatag aaggaaggcc   37620
cagataataa gagaaaataa taggtaatat atatataggt taacctaggt tatataggta   37680
tgccttagta tgggtgtact cctgtacacc ctattcctta ctaccttact atatttacat   37740
aataggagag agacaatggc taatgattat agtagtcaac cattaacagg taagtctaag   37800
agaaagcagg tacaacctgt aagtgaagaa ctaatgcttc cggtgctcaa aaaagaggaa   37860
gttagtaaga aaagcaatgt tattaatgat gccaccaaat caggtaaaca gaaagggccc   37920
atggtgtgcc ttgaagtgaa aggtggtgta ttgaagattg ctatcgcggt tgatggcaaa   37980
```

```
gaagattcag agtggaagtt agtaacagtg gaaccaactg ttaacccagt ttaagataag    38040
gaggaagatt acatggctaa atatggtact acaggttctg ttactggtca ggcttttcga    38100
gtaaaagcag tacaaactat tgcaacggca atcccgatgc ctgttgttaa agaagaagac    38160
cttaagagta aagaccaccc tatcaacatc aaacatttat caggtaaaca gaaaggtgca    38220
atggttgctc ttgagaaagg tgacacaacc ttacatattg ctgttgcacg tggtagtgaa    38280
cccacagacc cttgggatgt aactggtatg gaaaaggacg ctgttactcc agcaggggta    38340
taataatgct taataaatac ttcaagcgta aagagtttgc ttgccgttgt gggtgcggta    38400
catccactgt tgatgctgaa ttactacagg tagtcacaga tgtgcgtgag cactttggtt    38460
ctcctgtagt tatcacttcg ggtcatcgct gtgctaagca caatgccaat gtaggtggcg    38520
ctaagaactc catgcatctt actggtaagg ctgctgacat aaagtgtct ggcatattac     38580 cttctgaagt gcataagtat cttactagca ataccaagg caagtatggt ataggtaagt     38640
ataactcctt cactcacatc gatgtacggg atggttgtgc gcgatggtaa gatgtgttga    38700
atggtgtgag cgtatggttg cccaagctgc cgaggatggc aactatgatg actggaagaa    38760
ctactctgac ttgttagctc aatggaaagg gagatgcaat gaaaaagctg tttaagtcta    38820
agaaggttgt aggtgcactg gttgcacttg ttattgctct tgtttctgta ggtcttggtg    38880
tagaccttgg ctctggcacg gaatcctctg tgacagatgt ggtctgccaa gtgatcacct    38940
gtgaataagt ttctagaagt tctggcaggt cttattggcc tgcttgtctc tgctaagaag    39000
aaacaagaag agaaggaggc acaaagtgaa gcgaatcatg ttagtgacaa cccttctgat    39060
tggttcgctg accacttccg ggtgtcagca ggcgttacca gagaaagcaa tggtgaaacc    39120
tctgaggccg acgctgacgg cagtttacga ggtagacgat aaggtctgct ttagtaagcc    39180
tgacgctaca aaacttggtt tgtacattct ctcgctagaa cgcggataca attaatacat    39240
agctttatgt atcagtgtct tacgatttac tggacactat agaagaggta agatagcgcc    39300
gttcttttga gcggcctatt actagccaat cttcataggg agggttggaa agtaatagga    39360
gatagcatgg ctaaattaac caaacctaat actgaaggaa tcttgcataa aggacaatct    39420
ttgtatgagt accttgatgc gagagtttta acatcaaagc cgtttggtgc tgcaggtgac    39480
gccactactg atgatacgga ggttatagct gcttcattaa actctcagaa agctgtcaca    39540
gtctcagatg gtgtattctc tagctctggt attaacagta attactgtaa cttagacggc    39600
aggggtagtg gcgtgctaag tcaccgttca agtacaggta actacttagt atttaacaat    39660
ctacgtgcag gtcgcttaag taatattacg gtagaaagta ataaggcgac tgatacaact    39720
cagggacagc aggtatccct tgctggtgga agtgatgtta ctgtaagtga cgttaacttc    39780
tcaaacgtta aaggtactgg tttcagttta atcgcatacc ctaatgatgc gccacctgat    39840
ggacttatga ttaaaggcat tcgaggtagc tattccggct atgctactaa taggcagcc    39900 ggatgcgtac ttgctgattc ctcagttaac tccctcatag ataacgtcat tgctaagaac    39960
taccctcagt tcggagcagt agagttgaaa ggtacagcca gttacaacat agtcagtaat    40020
gttataggga cagattgcca gcatgtaact acaacggca ctgaagggcc aatagctcct     40080
tctaataacc ttatcaaggg ggtgatggct aataacccta gtatgcagc ggttgttgca     40140 ggcaaaggaa gtacgaactt aatctcagac gtgctcgtag attactcaac ttctgatgct    40200
aggcaggctc atggtgttac agtagagggt tctgataacg tcataaataa tgtgcttatg    40260
tcaggatgtg atggtactaa ctcttttagg caagggcaga ctgctacaat tgcacgcttt    40320
```

```
ataggtacag ctaataacaa ctatgcgtct gtatttccta gctacagtgc tacaggtgtt   40380
attactttcg aatccggctc tacccgtaac ttcgtagagg taaagcaccc tggcaggaga   40440
aacgaccttc tcagttctgc tagtactatt gacggtgcag ctactattga cggcactagt   40500
aatagtaacg tagtgcacgc acctgcctta gggcagtaca taggtagtat gtcaggtagg   40560
ttcgaatggc ggattaagtc catgtcactc ccttcaggcg ttcttacttc tgctgataag   40620
tacagaatgc ttggagatgg tgctgtgtca ttagctgtag gtgggggcac ttcttctcaa   40680
gttcgcctat ttacttctga tggtacttct cggacagtgt ccctcaccaa cggtaacgtg   40740
cgtctttcta ccagtagcac aggcttttg cagttaggtg ctgatgcaat gaccccagac    40800
agtactggta catacgcatt aggttccgcc agccgagcat ggtctggcgg ttttactcaa   40860
gcagcattca ctgttacctc agatgctcgg tgtaaaacag aacctcttac tatctcagat   40920
gccttactgg atgcttggtc tgaagttgac tttgtgcagt ttcagtattt ggatcgtgtt   40980
gaggagaagg gtgcagactc agctagatgg cacttcggta tcatcgctca gcgagctaag   41040
gaggctttcg aacgtcacgg tatagatgca catcgctatg gcttcttgtg cttcgacagt   41100
tgggatgatg tatacgagga agatgccaat ggctctcgta aactgattac accagcaggt   41160
tcccgctacg gtattcgtta cgaggaagta ctgatattag aggctgcgtt gatgcggcgg   41220
actattaagc gtatgcagga agcactagct tccctgccta agtaagcaac aggcagtgcg   41280
taagcactgc ttttagcgca acttttctta aaggttatca cggtggtagc ctttcagaaa   41340
aggaggttac atgattcaaa gactaggttc ttcattagtt aaattcaaga gtaaaatagc   41400
aggtgcaatc tggcgtaact tggatgacaa gctcaccgag gttgtatcgc ttaaagattt   41460
tggagccaaa ggtgatggta agacaaacga ccaagatgca gtaaatgcag cgatggcttc   41520
aggtaagaga attgacggtg ctggtgctac ttacaaagta tcatctttac ctgatatgga   41580
gcgattctat aacacccgct tcgtatggga acgtttagca ggtcaacctc tttactatgt   41640
gagtaaaggt tttatcaatg gtgaactata taaaatcacg gataaccctt attacaatgc   41700
ttggcctcaa gacaaagcgt ttgtatatga gaacgtgata tatgcacctt acatgggtag   41760
tgaccgtcat ggtgttagtc gtctgcatgt atcatgggtt aagtctggtg acgatggtca   41820
aacatggtct actccagagt ggttaactga tctgcatcca gattacccta cagtgaacta   41880
tcattgtatg agtatgggtg tatgtcgcaa ccgtctgttt gccatgattg aaacacgtac   41940
tttagccaag aacaaactaa ccaattgtgc attgtgggat cgccctatgt ctcgtagtct   42000
gcatcttact ggtggtatca ctaaggctgc aaatcagcaa tatgcaacaa tacatgtacc   42060
agatcacgga ctattcgtgg gcgattttgt taacttctct aattctgcgg taacaggtgt   42120
atcaggtgat atgactgttg caacggtaat agataaggac aacttcacgg ttcttacacc   42180
taaccagcag acttcagatt tgaataacgc tggaaagagt tggcacatgg gtacttcttt   42240
ccataagtct ccatggcgta agacagatct tggtctaatc cctagtgtca cagaggtgca   42300
tagctttgct actattgata acaatggctt tgttatgggc tatcatcaag gtgatgtagc   42360
tccacgagaa gttggtcttt tctacttccc tgatgctttc aatagcccat ctaattatgt   42420
tcgtcgtcag ataccatctg agtatgaacc agatgcgtca gagccatgca tcaagtacta   42480
tgacggtgta ttataccctt tcactcgtgg cactcttggt gacagacttg gaagctcttt   42540
gcatcgtagt agagatatag gtcagacttg ggagtcactg agatttccac ataatgttca   42600
tcatactacc ctacctttg ctaaagtagg agatgacctt attatgtttg gttcagaacg    42660
tgcagaaaat gaatgggaag caggtgcacc agatgatcgt tacaaggcat cttatcctcg   42720
```

```
taccttctat gcacgattga atgtaaacaa ttggaatgca gatgatattg aatgggttaa   42780
catcacagac caaatctatc aaggtgacat tgtgaactct agtgtaggtg taggttcggt   42840
agtagttaaa gacagctaca tttactatat ctttggtggc gaaaaccatt tcaacccaat   42900
gacttatggt gacaacaaag gtaaagaccc atttaaaggt catggacacc ctactgatat   42960
atactgctat aagatgcaga ttgcaaatga caatcgtgta tctcgtaagt ttacatatgg   43020
tgcaactccg ggtcaagcta tacctactt  catgggtact gatggaatac gaaatatccc   43080
tgcacctttg tatttctcag ataacattgt tacagaggat actaaagttg gacacttaac   43140
acttaaagca agcacaagtt ccaatatacg atctgaagtg cagatggaag gtgaatatgg   43200
ctttattggc aagtctgttc caaaggacaa cccaactggt caacgtttga ttatttgtgg   43260
tggagaagag acttcgtcct cttcaggtgc acagataact ttgcacggct ctaattcaag   43320
taaggctaat cgtatcactt ataacggaaa tgagcaccta ttccaaggtg caccaatcat   43380
gcctgctgta gataaccagt ttgctgctgg tggacctagt aaccgattca ctaccatcta   43440
cctaggtagt gaccctgtta caacttcaga tgctgaccac aagtacagta tctctagtat   43500
taataccaag gtgttaaagg cttggagcag ggttggtttt aaacagtatg gtttgaatag   43560
tgaagcagag agggaccttg atagcataca cttcggtgtc ttggctcagg atattgtagc   43620
tgcttttgaa gctgaagggt tggatgccat taagtatgga attgtgtcct tcgaagaagg   43680
taggtacggt gtgaggtata gtgaagttct aatactagag gctgcttata ctcgttatcg   43740
tttagacaag ttagaggaga tgtatgccac taataaaatc agttaagcaa gctgctgtac   43800
tccagaacac agaagagctt attcaatcag gacgtgaccc taagcaggct tatgccattg   43860
ccaaggatgt tcaacgtcgt gccatgaaga aaccttctgc atcttctgcg taagcaggtt   43920
aatatcttag tataaacaag ggcagactta ggtttgtcct tagtgtattc caaaggaggt   43980
aacatgctga agatggttg  ggtttcatat gaccctacag accctaagaa ttggctacag   44040
gttatcgcta tagcttgtgc aggtagccta ttggctgccc tgatgtattc attatggatg   44100
tacacaaagt aaccaaagtc aaaattttga tgtaggcgtg tgtcagctct ctcgccctcg   44160
ccctcgccgg gttgtcccca tagggtggcc tgagggaatc cgtcttcgac gggcagggct   44220
gatgtactcc ttgtctagta caagggaggc ggagggaacg cctagggagg cctaggaatg   44280
gcttagtggt ggacaaggtg attaccttag tgaagcctct tagtgcattc ctgaggccat   44340
tcagggcgtt tatgagggat tgacagggtg tgagggcgtg ggcta              44385
```

<210> SEQ ID NO 2
<211> LENGTH: 1309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
tgacagccac ggcatacaag gttacattaa gcatcaagac ggcgacgtct ttaaacatcc     60
cgctctttaa caatacggtt tgtgtcttga taggctaact aactaactaa ggtaattatc    120
atgaaagggt taatttgtgt agaacgtatg gtcaatggta aacttgaaat attaccactg    180
gaaaaccaat ctagcttcaa agagtggtat ggctgtttct cactgattta aggtaaaggc    240
tggcactagt cagcctatca aggcgcaaac caagctcttt aacaatttgg atggtagctt    300
cttagtctgg ataggttaaa cctaggagat tctcttgagt ctcctataat gtaacctaac    360
```

| | |
|---|---|
| taactaaatg aggattaaaa gaggagatat acaatggttt ttacgcttga ggacttcgtt | 420 |
| ggtgactggc gtcaaaccgc ggggtataat cttgatcagg tcctggagca gggcggagtt | 480 |
| tcgtccttat tccagaactt aggggtaagt gttacgccga ttcagcgcat cgtgctgagt | 540 |
| ggagagaatg gattgaaaat tgacattcac gttatcattc cgtatgaggg tttgagtgga | 600 |
| gaccagatgg gacagattga aaagattttc aaagtggtgt atcccgtcga tgaccatcac | 660 |
| tttaaagtaa ttctgcacta tgggacccct gtgatcgacg tgtaacgcc aaacatgatt | 720 |
| gactatttcg gtcgccctta cgaaggtatc gccgtcttcg acggaaaaaa aatcactgtc | 780 |
| acgggaacat tatggaacgg aaataaaatt atcgacgaac gtctgatcaa tcctgatgga | 840 |
| agcctgttat ttcgcgttac gatcaatgga gtgaccggat ggcgtttatg cgaacgtatt | 900 |
| ttggcttaaa gaggagatat acaatggaac gcaacgcaaa tgcatattat aatttattag | 960 |
| cagctacggt tgaagccttt aatgaacgca tccaattcga cgaaatccgt gagggcgacg | 1020 |
| actatagcga cgcccttcat gaggttgtag acagcaatgt tccagtttat tacagcgaaa | 1080 |
| tctttacagt gatggctgct gatggtattg atgttgattt tgaggatgct ggtttgattc | 1140 |
| ctgacacgaa ggatgtaacc aagattctac aagctcgcat ctatgaagct ctttataatg | 1200 |
| atgtaccaaa tgacagcgat gtagtttggt gtgaaggcga agaagaggaa gaataaggat | 1260 |
| ggaaaagcaa tataacttta tcttttcaga cggtgtaacc ctgaagtgt | 1309 |

<210> SEQ ID NO 3
<211> LENGTH: 1408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---|
| acgtccagcc tccttcctag atattcctga gattataaac cttggaaata aatatgtgga | 60 |
| agaggaagtc aaggttgtag cccaccactc agcctcatgg aatgcagaac aaagtgccat | 120 |
| aacctttgtg catctcttaa tagagaccca ccactcagcc tcatgaatg cagaacaaag | 180 |
| tgcacataac ctttgtgcat ctcttagtag agaagattta tccctatggg ttgctgtaga | 240 |
| tgaagggcag attgtagggt tcctgtgggc tggctatcac gagttggccc cttggacacc | 300 |
| tgtaagagtt gcctctgaca ttctctttta tattatacca gagagaaggg gaacactact | 360 |
| tggtatgcgc ttaattaagg cattgaaaca gtgggcatca gataatgaat gctctgaagt | 420 |
| gcgtttaagt attgcaagtg gcatcaacga ggagcgcgta gggcgcatgt acaaacggct | 480 |
| cggctttgaa ccgtttggca ctgtgtataa cctgaagttc taagaggag atatacaatg | 540 |
| gtttttacgc ttgaggactt cgttggtgac tggcgtcaaa ccgcggggta atcttgat | 600 |
| caggtcctgg agcagggcgg agtttcgtcc ttattccaga acttaggggt aagtgttacg | 660 |
| ccgattcagc gcatcgtgct gagtggagag aatggattga aaattgacat tcacgttatc | 720 |
| attccgtatg agggtttgag tggagaccag atgggacaga ttgaaaagat tttcaaagtg | 780 |
| gtgtatcccg tcgatgacca tcactttaaa gtaattctgc actatgggac ccttgtgatc | 840 |
| gacggtgtaa cgccaaacat gattgactat ttcggtcgcc cttacgaagg tatcgccgtc | 900 |
| ttcgacggaa aaaaatcac tgtcacggga acattatgga acggaaataa aattatcgac | 960 |
| gaacgtctga tcaatcctga tggaagcctg ttatttcgcg ttacgatcaa tggagtgacc | 1020 |
| ggatggcgtt tatgcgaacg tattttggct taaagaggag atatacaatg gtgttgtaa | 1080 |

```
agaaagcatt taaggctatc ggtcttgctc aagatgcacc acgtattgaa gccaaagtcc    1140
cagcacagca gcttgagcgt aagcctgaga ctgaagctga agatattcaa attggtgcag    1200
gggatgatgc tactgcatct gcaaaaggta agcgtggcct tgtccgtccg gtagcttcta    1260
gcttgaaggt gtaatatgaa acagagcata gatttggagt atggaggtaa gcggtctaag    1320
atacctaagc tatgggagaa gttctccaat aaacgtagct ctttccttga tagggcgaag    1380
cattactcca aattaacctt gccctatc                                       1408

<210> SEQ ID NO 4
<211> LENGTH: 44927
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
tcgccctcgc cctcgccggg ttgtccccat agggtggcct gagggaatcc gtcttcgacg      60
ggcagggctg atgtactcct tgtctagtac aagggaggcg gagggaacgc ctagggaggc     120
ctaggaatgg cttagtggtg gacaaggtga ttaccttagt gaagcctctt agtgcattcc     180
tgaggccatt cagggcgttt atgagggatt gacagggtgt gagggcgtgg gctatctgtt     240
cctttgctcc tcacttcgtt cgtcgctgcg gtagcctgat gtgtacctta ggttattcct     300
tgatggatag cttaggttag ccttagtgga ttaccttagt taaagcctta gtgcttcact     360
tagtatcagc ttagtagtgt accttagtaa gtcttagtgt cttctcttag tgattgcaca     420
tgcaagcatg taagatgcta ataggtcgcg gtcggcagac cgctaaagaa agagaatggt     480
aataagatgc agtaggagga acaccagaag cctagccaac ctaagctatc ctagctctat     540
atctattgct tttccttagt ctaacacgtt agacaaccta tcttattctt agtgatggta     600
acttagtgtt gacaagataa tcttagtgta atactatgca tcacgtaggc ggtgctgagg     660
cacctagtag ccagctagta aggcatacga agagactagc gcttacattg ctctttaaca     720
atttgcttag tgtaacctat gtatgccgtg gttaactact tattgaatga ggtattaact     780
atgacattaa ataaccgtga actgtccgtt ctcttcactc tgttgtgcta catgattcgt     840
aacaacgaat tacttacaga tgatgagtta gccttgtatc accgctttct taacgaaggt     900
tggaccgata cagttaatca ataccgtaac atgatagatg agttgaggga gggtaaataa     960
tgtatcaaca tgaggtattc tttgaatcag ctagcgaagc tattcgcttc cgtgatgata    1020
tgatgcaagc tggtgtaggc gttgatgtgt atcactattt gatagattac gacactgaat    1080
atcaccgagt taccttagta tctgagtatg acaaccaagt cattactgag tatctaggca    1140
gtgaagatta cgattacgat gaagtaatca cgacaaatct ctaaattaac tgttgacagc    1200
cacggcatac aaggttacat taagcatcaa gacggcgacg tctttaaaca tcccgctctt    1260
taacaatacg gtttgtgtct tgataggcta actaactaac taaggtaatt atcatgaaag    1320
ggttaatttg tgtagaacgt atggtcaatg gtaaacttga atattacca  ctggaaaacc    1380 aatctagctt caaagagtgg tatggctgtt tctcactgat ttaaggtaaa ggctggcact    1440
agtcagccta tcaaggcgca aaccaagctc tttaacaatt tggatggtag cttcttagtc    1500
tggataggtt aaacctagga gattctcttg agtctcctat aatgtaacct aactaactaa    1560
atgaggatta aaagaggaga tatacaatgg tttttacgct tgaggacttc gttggtgact    1620
ggcgtcaaac cgcggggtat aatcttgatc aggtcctgga gcagggcgga gtttcgtcct    1680
```

```
tattccagaa cttaggggta agtgttacgc cgattcagcg catcgtgctg agtggagaga    1740
atggattgaa aattgacatt cacgttatca ttccgtatga gggtttgagt ggagaccaga    1800
tgggacagat tgaaaagatt ttcaaagtgg tgtatcccgt cgatgaccat cactttaaag    1860
taattctgca ctatgggacc cttgtgatcg acggtgtaac gccaaacatg attgactatt    1920
tcggtcgccc ttacgaaggt atcgccgtct tcgacggaaa aaaaatcact gtcacgggaa    1980
cattatggaa cggaaataaa attatcgacg aacgtctgat caatcctgat ggaagcctgt    2040
tatttcgcgt tacgatcaat ggagtgaccg gatggcgttt atgcgaacgt attttggctt    2100
aaagaggaga tatacaatgg aacgcaacgc aaatgcatat tataatttat tagcagctac    2160
ggttgaagcc tttaatgaac gcatccaatt cgacgaaatc cgtgagggcg acgactatag    2220
cgacgccctt catgaggttg tagacagcaa tgttccagtt tattacagcg aaatctttac    2280
agtgatggct gctgatggta ttgatgttga ttttgaggat gctggtttga ttcctgacac    2340
gaaggatgta accaagattc tacaagctcg catctatgaa gctctttata atgatgtacc    2400
aaatgacagc gatgtagttt ggtgtgaagg cgaagaagag gaagaataag gatggaaaag    2460
caatataact ttatcttttc agacggtgta accctgaagt gttccctacg attcgcacaa    2520
attcgtgagg aagtactagg cactacatac aaactattta gctgacacta taagagaagg    2580
cttaacaagg cgttactaag gtagcgcctg attaaacttt cacttactag gagttgagat    2640
tatgaaaacc ttgattggat gcttcttgtt ggcttctctt gctctggcat ttaccgctaa    2700
agctggttat gacgcttata aagtagaaca agcccagcaa gactgggcca aaaaaaagtt    2760
caacttgtgc agcaagagca cacctacga gtactgcaac aaaacactaa gacacttatg    2820
gaaagagtaa ctagcctata gcccacctga gtgggctatg tgatatttac ttaacactat    2880
ataaggtgat tactatgact actgaaaaca ccctcgtgtc tgtccgtgaa gctgcaaccg    2940
ctgaaatcaa gcaacattta gacaatatcg gcacttctta catcaaagta ggggcttgtc    3000
tgaatgagtt acgcggagac tttgaaggtc aaaaagagtt tttagcctat gttgaagcag    3060
agtttgccat taagaaggca caatgttaca agctgatgag tgtagcccgt gtctttgaag    3120
gcgatgatcg ctttaaaggc gtggcgatgc gtgtaatgct ggcgcttgtt cctttcgctg    3180
atgaaaatat aatcatggag aaggccgcag aactcgccgc aaatggcaag ctggacacta    3240
atgccgtaaa cgccctgatt gaacctaaga aagagtcaaa ggccgaaacg gtacaatcta    3300
aggctgagac agtaaaaccg caggagaacg cgactgagtc cgcagaatca catgaaatgc    3360
aagcgccgca ggtagtgcca cccgcgagcg agcaggagtc cgacgaatca gcaccttggg    3420
aagaggaaag caaaccggaa gcgccaaagg cagctccgat ggataacacg gctaatactg    3480
agaatgccgc tattgctggt ctgctggcac aaattaaagc actgactgag caattacagg    3540
cagccaatga ccgcatcgcc tccttaagta gcgcacgcga aagcaagaag gcatccgcac    3600
ctatgctgcc gcagttcaaa tcttcctgct tctacgctcg cttaggcttg agcgcggagg    3660
aggcaacgaa gaaaacagca gttaacaagg cacgccgcga actggttaag ctgggatacg    3720
gtgaaggcca tgaggcatgg cccttaatct ctgaggcagt agaagagttg actaagtaac    3780
cttatcggtg gcatcttctt aggtgtcacc tattaaggtt tctttcacta ggagtaaaca    3840
agatgcaagg cctacacgct attcaacttc aacttgaaga agaaatgttt aacggcggta    3900
tccgtcgctt tgaagcggac caacaacgcc agattgcatc cggtaatgaa tcagacacgg    3960
catggaatcg ccgcttattg tccgagttaa tcgcgccaat ggctgaaggt attcaggcat    4020
```

```
acaaggaaga gtatgaaggt aaaagaggcc gtgcaccgcg tgcattagct ttcattaact    4080
gcgtagaaaa cgaagtggca gcatatatca cgatgaaaat cgttatggat atgctgaaca    4140
cggatgtaac cttgcaggct atagccatga atgtagctga ccgcattgag gaccaagtac    4200
gttttagcaa gctggaaggt cacgccgcca aatactttga aaaagttaag aagtcactta    4260
aggcaagtaa gactaaatca tatcgccatg cgcacaacgt agcggtagtg gctgagaagt    4320
cagtagctga ccgtgacgct gatttctccc gctgggaggc atggcctaaa gacaccttgc    4380
tgcaaattgg gatgaccttg cttgaaatct tagagaatag cgtattcttc aacgggcaac    4440
ctgtcttcct ccgcaccttg cgcactaatg gcggcaaaca tggtgtttac tacctacaga    4500
ctagtgaaca cgtaggtgag tggataactg cattcaaaga gcacgtagcg caactgagtc    4560
ctgcctatgc tccttgcgtc atccctccgc gtccgtgggt atcacctttt aacgcggtt    4620 tccacactga gaaagtagca agccgtattc gtctggtaaa aggaaaccgc gaacacgtcc    4680
gcaagctgac caaaaagcaa atgccagagg tttacaaggc tgttaacgcg ttgcaggcga    4740
ctaaatggca ggttaacaag gaagttttac aggttgtgga agacgtcatc cgtctagacc    4800
taggttatgg tgtaccttcc tttaaaccac tcattgaccg cgagaacaag ccagctaatc    4860
cagtgccgct agaatttcag cacctacggg gccgtgaact gaaagaaatg cttacgccgg    4920
aacaatggca agcctttatc aactggaaag gtgaatgtac taagctgtac accgctgaaa    4980
ctaagcgcgg aagcaaatcg gcggcaaccg ttcgcatggt tggtcaggcc cgtaaatata    5040
gccagttcga cgcaatctac ttcgtgtatg cactggacag ccgcagccgc gtctacgcgc    5100
aatctagcac actctcaccg caatcaaatg acttgggcaa ggccttgctc cgttttaccg    5160
aagggcagcg tcttgatagc gctgaggcgc ttaagtggtt tttggtgaac ggggctaata    5220 actgggggttg ggataagaaa acttttgacg tgcgcaccgc taacgtgctg atagtgaat    5280 ttcaagacat gtgccgcgac attgcagcgg atccgctgac cttcactcaa tgggtaaatg    5340
ccgactcccc ttacggcttc cttgcatggt gctttgaata tgcgcgttat ctggatgcac    5400
tggatgaagg cacgcaagac caattcatga cgcacctccc agtccatcaa gatggtagtt    5460
gttctggtat ccagcactac agtgctatgc tacgcgatgc agtaggtgcg aaagcagtaa    5520
accttaagcc ctctgactct cctcaagata tttatggtgc cgttgcgcag gtagtaattc    5580
agaagaatta tgcatacatg aatgcagagg atgcggaaac cttcacttct ggcagcgtga    5640
ctttaacagg tgcggagctg cgtagtatgg ctagtgcgtg ggatatgata ggaatcactc    5700
gcggcctgac caaaaagccc gtaatgcaca taccttatgg cagcacacgt ctaacctgcc    5760
gtgagtcagt gattgattat atcgttgatt tagaagaaaa agaggcccaa cgggctattg    5820
cggaagggcg taccgccaat cctgtacacc cttttgataa tgaccgtaaa gacagcctga    5880
cacctagcgc agcttataac tatatgacag ctttaatctg gccttctatt tcggaagtgg    5940
ttaaagcccc tatagtggca atgaaaatga ttcgtcagct tgcccgtttc gcagctaaaa    6000
ggaatgaagg cttagagtat accctgccta ctggcttcat cttgcaacaa aagattatgg    6060
ctactgatat gctccgcgta tctacttgct tgatgggaga aatcaagatg agtctacaga    6120
ttgaaacaga cgtagtggat gaaacggcaa tgatgggcgc tgctgctcct aactttgtgc    6180
atggtcatga tgccagccac cttatcttaa cagtctgcga ccttgttgat aaagggatta    6240
catctatcgc agttattcat gactcttttg gcactcatgc aggccgtaca gccgaccttc    6300
gtgatagctt aagggcagaa atggtgaaga tgtatcaagg ccgtaatgca ctgcaaagcc    6360
tgctagatga gcacgaagaa cgctggttag ttgataccgg aatacaagta ccagagcaag    6420
```

```
gggagtttga ccttaacgaa atcttagttt cagactattg cttcgcataa tattaatagg   6480
ccattccttc gggagtggcc tttcttttac ctactacctg taacatttca ttaacataaa   6540
agtgtctcac atgtgagact tatttaccgg acactatagg atagccgtcg gagacgggaa   6600
agaaagggaa gataaaggat ataaaggaag taataggtat taaaggttat ataggttatc   6660
taggaatacc tattaccttc ttccttcctc ttattaccac tcagaggaag gcagaccta    6720 ggttgtctca catgtgagac ttcgtattta ccggacagta tagataagat taactcactt   6780
tggagattta accatgcgca actttgagaa gatggcccgt aaagctaacc gttttgacat   6840
ggaagagggg cagaagaaag gcaagaagct gaataagcct gtccgtgacc gtgcatctaa   6900
acgcgctgcg tgggagttct aagttatggc tattattcag aatgtaccgt gtcctgcctg   6960
tcaaaagaat ggacatgata ttactggcaa ccatctcatg atatttgatg atggtgccgg   7020
ctactgtaat cgtggacact tcatgataa tggtagacct tactatcaca agccggaagg    7080
tggcatcgag ataaccgagt tatctattac tggcaatatc aaatatacac cttctcaatt   7140
caaagaaatg gagaaggaag ggaagataag cgaccctaaa ttacgtgcca tcgcacttgg   7200
tggtatgcgt atgaaagacc gttgggaggt catgaatgaa caagaaaggg cagagcaaga   7260
agcagagtgg aaacttgatg ttgaatggtt cctcacgctt aagcgtaaga accttgtttc   7320
caggcacatt cgcggcgaca tttgcgcatt gtatgatgta cgtgttgggc acgatgaaga   7380
gggtagagtc tcacggcatt actatccgcg cttcgaaaaa ggtgagctag taggcgctaa   7440
gtgtcgcaca ttacctaaag attttaagtt tggtcattta ggtaaactct ttggtatgca   7500
agatcttttc ggtatgaata ctttgtctca cgtgttagac aagggaagac gaaaggattg   7560
cttgctcatt gtccggcggcg aactggatgc actagcagcg cagcagatgc tccttgattc   7620
tgccaagggt actaagtggg aaggccagcc ataccatgta tggtctgtca acaaaggcga   7680
gtcttgcctt gaagagatag tgcagaaccg tgagcatatc gcccaattca agaagattat   7740
atggggtttt gatggagatg aggtagggca gaagcagaat cagcaagcgg ctcgcctgtt   7800
tcctggtaaa tcctatatcc ttgaatacc ctctggttgc aaagatgcta acaaggcatt    7860
gatggctggc aaggctaaag aatttgtaga tgcatggttt aatgccaagt catctgatga   7920
agtctttggt agccagatta aatctatcgc atctcaaagg gataagctca aggctgcacg   7980
tccagagcaa ggactgtcat ggccttggcc taagctgaac aaggtaacgc taggtattcg   8040
taagaaccag cttatcattg taggtgcagg gtctggtgta ggtaagactg agttccttcg   8100
tgaagtagtt aagcacctca ttgaagaaca cggtgaatct gtaggcatca tttctacaga   8160
agacccgatg gtcaaggtgt cccgtgcttt tatcggcaag tggattgata agcgtattga   8220
gttacctcca accaacgacc cgaaagaaga cggataccgt gaggtgttcg actataccga   8280
ggaagaagct aacgccgcca ttgattatgt agctgataca ggtaagctgt tgtagctga    8340 cctagagggt gactattcga tggaaaaggt agagcaaact tgcctagagt ttgaggctat   8400
gggtatttct aatatcatca ttgataactt aacggggatt aaattagatg agcgtgcttt   8460
tggtgggaag gttggtgcac ttgatgaatg cgtcaagcgg attggtacta tcaaagaccg   8520
acacccggtt actatattcc ttgtatcaca ccttacacgt cctccggcaa accgtaccca   8580
acacgaagaa ggtggcgaag ttatcctttc tgacttccga ggctcaggcg ctatcggatt   8640
ctgggcatct tacgccttgg ggattgagcg taatacaaga gctgaaacgc ttgacgaaag   8700
gactaccacg tacatctcat gtgtcaaaga ccgcgaccaa ggtatctaca ctggaaccaa   8760
```

-continued

```
ggtcatgctt aagggtgaca ttcaaaccgg acgtttaatg gaaccacaag cccgtactaa    8820
gtcatttgat acaggtgaag caaggcaaca agaagtacca gatttaccgg atactataga    8880
agagactacc ttcgatgaag aaagtgagtt ctgattagtg tatttatcag gcttgtctca    8940
catgtgagac aggctcttat taagtacatt aaataactgg agattgatta tgtataactt    9000
agtgttgaat gtaggtgact tgtacgcaa catcaagaaa gattcaagtc gctatctttg    9060
ccgtggtgtt gtaacctttg taggtgagaa cctgtattat gtagaatatc gcagtggtgt    9120
taagcaatat taccacaaga agacagcaca taaatatctt gaaaagattg tagagataaa    9180
caatcaatgt aagtgcatac atgatgaggt ttgcgataaa tgtgctcgcc agatgcttaa    9240
gaatttccta gctcctcttt attatggtgc tggtcctcaa acactagcag agtgcatggc    9300
agaaaagaaa accacactca agaaagagcg tcgcaatgta atcactggta agactcaaag    9360
tgagatgatt aagcaatgtg gcactgcatt aggtgttaca cagtttaata ctcgtgcatt    9420
gggtaaatcc acaggacaag ctatggtaaa gattggagaa gccatgatgc atccaaatgt    9480
acctgtgcga atcatggatg ttgaccatgc aatcacagaa caaggtacgc aacgacgtgt    9540
aattaataag cattttgccg acactataga aggcattatt cgtaagcaag ggttgaaagg    9600
tcttcacatc ttaaatggtg aagaattact gtacctacct atcgttactg aagaaacata    9660
cgtgaatatc taaggagtta atcatgacta aggtattaat ttatatgcgt ggacctcata    9720
aatgctatgc agttgtagca ccaaatggtg ttaagcctta tcgtacttca aaaagattgg    9780
cattaatagg tgctagtagt agtgcaagtt tccaaatgga acttttggt cattggactg    9840 aaaggcaatt ccgtgaggat tttaaagtca ttggcagctt catggtgaaa tatgcagaat    9900
aaacatagtc ttagaatgtt cgatggtcat gaaaacctgc aagccaagat tactaaccaa    9960
gccttcctgt tcgcacagtt aactatggct gaggctaaga agaatagtct cactcgtgaa    10020
caggttatca aggaggccac ttgggaacca caccaaggta aatatatggg ccacaaatta    10080
actgtaacac gcagtcgata agtcaagggt tgtccaacgt gttggacagc ctttcatcat    10140
attgattggg aggtattaaa tgactaagtt tactatgcaa gacctcatta aattacgtga    10200
tgaaatagaa tcaccggaag ttaatacaga gtttcactac attgatccac gagataaacg    10260
agagattcct gattatcaga ttgagacgga gttaatgtat gaagattatt gattggaaga    10320
aggaagcaga aggccgtatc ctagtgatgg atgcggaggc taaaggcctg ctgggtgcta    10380
tccgctacgg tcatcgtgaa gatgtacaca ttatttgctg catggacttg ctcaccactg    10440
aggagttcct cttcttcgac ccatatgaga tgcgtgaccc tgaagcaagg gaacacttga    10500
aagagtggga aggccatcaa gatgggacct tggttgatgg tgttaacttc ctaaagcact    10560
gtgaagccat cgtctcacag aacttcctag gctatgacgg gcttctcttt gagaaagcct    10620
tccctgacat ctggaaggga tttaactaca ccgagaggcg cggcaagggc agactacgtg    10680
ctgacttgtg tccggtacgc gtcatggata cgctggtcat gagtcgcctg ttaaacccag    10740
atagacgcct tcctccgcaa gcatatgcca aaggtatggg taacgttgcc cctcactcaa    10800
ttgaggcgca cggcattcgt ataggccgtt ataagccgga gaacgaggat tggtctaaac    10860
taactgacca catggtacat cgtgtacgcg aggacgtggc gataggccgt gacctattcc    10920
tctggctatt taacggagaa tggacggagc acaaacgccg tggcgtgaat aaacgcactg    10980
gcctaggtat tgagacagcc ttccacatgg agtccattgt gacgctggag atgagccgtc    11040
aggccgagcg tggattccgt ctggatatag ataaagcatt agcacgatgc gaggaattgg    11100
acgctaagat tgatgagaca gtcgcagcgt tccgtccgca catgcctatg cgtatcaagt    11160
```

```
ctaaaccttt taaaccggaa gaaaagaatg aagtatgcca acgcgcaaat gagtatggag   11220
ctagcaacaa tatacctact gtccttgacc cctctcactt tcttcacgca gagagacgag   11280
gagatcgcaa gacagtatgg agtgtcacta ctaagtctgg tgattggtcg gctagcgtca   11340
agaaagactt tcctcacctt agaggaaacc gtaatgacac gccaagtgtc aagtggattg   11400
gcgcttactc gcctgttact ttcgaagaga ttcccttggg taacagggat acagttaagc   11460
aagtgctcta tgattatgga tggaaaggtg ttgaatttaa cgataccgag caagcgcatc   11520
tcgatgagca tggcgtatta cccaagcctt ggagtgggaa gataaatgaa aagtcccttat  11580 ctttatggca agagagagcc gcacgtgaag gtaaaacagt ccctgattgg tgcttgggta   11640
tcgctgcatg gtacatactc gtatcccgtc gtggtcagat cctcaaccgt ggtgacgttg   11700
aagccttcga ccagaagggg gtgtggcctt cgcaagctgg tatacgaaag tgtcgcggcc   11760
ttgtacctgt agcatttaac aaggagttag gaatcaatgc gcagcaatac tacgaaaggt   11820
acggatgctg gcctacgtca gacaaggatg acggagaatg gcgtgtgcca gctattgcta   11880
ttagtattgg aacttctacg ttccgtatgc gtcatcgtaa cgtggttaat attcctgccc   11940
gtggcttgta tcctttacgt gatttattca tagcagggaa aggcaagcta atccttggtt   12000
gtgacggtgc aggtcttgaa ctgcgtgtcc tgtctcactt catgaatgac cctgagtacc   12060
aagagattgt actgcacggt gatattcata cgcataacca gatgaaggct ggtcttccta   12120
agcgtgatat ggcgaagaca tttatatatg ccttcctata tgggtctggt atagctaacc   12180
ttgcagcagt atgtggtgtt actgaggaag aaatggagga agttgtggca agatttgagg   12240
ttgaactacc atctcttgca cgtcttcgtg agaatgttat cgcacaaggt aacaagtttg   12300
gctacctaca agcacctgat ggtcattggg gtcgcatccg tatgtctggt ggtgaactta   12360
aagaacacac tatgcttaac gtactactcc agatgactgg ttctctgtgt atgaaatacg   12420
cattggtcag agcgttttca gtgatgcgca aggaaggtgt ggccttagat agcatgggaa   12480
acccttgcgg tatagctaac gtgcacgatg aaatccagat ggaagtccct gaagatgagg   12540
tcttgtatct caactacgac ttgcctttca ccttagaagg gttcgaaaca gagaaggctg   12600
ctgtgaaagc agtgttcgat gcagaggaga acgtgttca tgtggattct gaaggacgta   12660
tgtggtctgc tgcaaatctc gttagtgttg atgctggtgt acttcattgc cagcgtcgtt   12720
atcaccgtgc agggcatatc attgccgacg caatgacctg ggcgggtcag tacctgaaga   12780
tgcgttgtcc gatggcaggt gagtataaga ttggtgcaag ttggaaggaa acacactgat   12840
ggacaggttt gatattgttt gcctattctc taccttcttt cttatattcc ttatgcttgc   12900
ttgctatgga agtatgcgat tagatatacc tgatgaagag gagggttacg attgatgcag   12960
gcatctttta ttattcttgg agtcatatta tttatggtag tattctgggc tttctctggc   13020
attgacccag attgtgatgg taactacgac tgagttatac tcaaggtcac ttacgagtgg   13080
cctttatgaa taacttattc ctacttattt tgtctaacat gatttactgg acactataga   13140
aggaaagcat aggtaatcta ggtttataag gtagtatagg taattaagta aatataggag   13200
atataaatat gtctatggta actactctgg tattcgtggc tcaatacttt cgtggtcttg   13260
ctaataagtt caagtccaag gctatcaaag ctattgaggc tcgcatcgaa gcagtacagg   13320
cagagcaagt taaagttgaa gaacatcgta gttctcaaat gattgactgt cataaccgct   13380
actatgcatc tcgtgatgaa ctaaatgcac gtcaagtcaa agaggtagaa gatatgctgg   13440
cacgtcacca gcaagagcgt gacagcctga aagctgaatt tgaagagaac aaggcatcaa   13500
```

-continued

```
ttgctcttgt acatcaagct gcatctgaca gtctgaagaa agagattgtt atgctggaaa   13560
tcgaactgga taacctgacc aaataagggg gggttatgat ggaagaagta attcaagcta   13620
aacatgtagg tattatcttt cgcgatctag agcagcgtaa agttgcaggt catactcgtc   13680
tggctaaaga ggaagacacc gcaatcacta ctgtagaaca agcagatgcc tatcgtggac   13740
cagagttcac tcaaggtgaa acttgtcacc aattgagcct atcaatttgt gacactatgg   13800
ctattgtaaa tgtgcaagaa gtcgaagagg gtgagtgtgt cagttacatc taccctttag   13860
atactattgc acgcattaag gtaatccata agtaattact agacactata gaacaatagg   13920
tcggcttagt tcggcctatg attgtaaagt gttgttgatg ttgaaccatt gtgcatcttg   13980
cacaacccga taccgtatag ggcttttctag tgagtacatg cttgtgctca gtacaaagct   14040
aactgacaat aggagactaa ataaatggca cgtggtgatt ttgattttgg tgctcaggtt   14100
actaaatctg aaggtaaagt cttttaagaat ccagaagtag gtgatcatga agcagtaatc   14160
tctggcatca ttcatgttgg ttccttccaa gacatcttta agaaaggtaa taccactgaa   14220
gttaagaagc cagcaaactt tgttctggtt aagattgtcc tgatgggtga cgatgacaag   14280
aacgaagatg gttctcgcat ggaacaatgg atggctgtgc ctctgaagtc tggtgataag   14340
gcaacactga ctaagttcct gaatgcagtt gaccctaaag agttgctggg tggcttcgat   14400
gatttcattg gtgaatgcct gactgcaacg atggtcggtt ctggtgataa gaatgacgat   14460
ggctcattca gtatgttaa ctggaaggga tttggtggta tgccggacaa gctgaagaaa   14520
ctggtcattg ctcaggttga agaggaaggt ctgtctatga caggtcacat taccttcgac   14580
aagctgacca aagaaatcct tgatgacatc ccagccaact tggtgcgtca atacttcctg   14640
aacgagacgc ctcgtggtaa gaacctgtct gttgctggtt ctcacgtaga agcaatcatt   14700
aaagctgctc gtgaagaaga cccagaatgg aagaaggcta agaagaaaga cgaggaagat   14760
gctaccccag ctaatcgtaa atctctggat actggtgagt ctgttccaca ggaagtacct   14820
gaagcagaag atactcctgc accggagatg gatgaggacg cggaatatta aggagaaagg   14880
atgaaagtac aaatcgtaac cctgcactgc aagaaaggaa ttacaactct tggcggcaac   14940
acttttcact ccttctctga aggggacaca tatgccgacc tgcactacat ctggcgcgac   15000
ggacagcacg tggtgaacta cagcgaccca gctacgggga aacgccacgg cgtatcgctt   15060
ccggcgcatg acattgctca ggtgaacaca gttttataaa gtctcacgtg tgagacaaat   15120
cggtgtccgg tatttactgg acactataga agagaagaat tttaatcggc gataatgcca   15180
taaccaacaa aaggagaatt taatatgttc aagattgaaa ctatcgtaaa ccgtgttgtt   15240
aaaggtgctg ctctggtatc cgttgagtct ttcattatcg tcgatgaaac tgatcaactg   15300
gtagctggta ctaaggctta cgatacccgt gaagaagctc aggctaagat tgacagcatg   15360
ggtaacttcg ctgctggtct ggagttcgct cgtgcttgct tccctgagca ggctgacaaa   15420
gctcagattg gtaaggctaa tatcgtagct gaatatctgg attgggttgc tgctggtaaa   15480
ccagtgaaag aagttaaggc tgctgaagaa gctgaagctc agcagaaaga agtagctgca   15540
ccggaaactc cggtaagtga agaggaagaa ttttgataat agcaggtgtt gcctctgtta   15600
gtcctagctg actatcacgc tcacctcatc taatgccctg tctgccttag tgtaggcagg   15660
gtcttttgcg taatagttat tggagaatga attatgccga ctattgaatc tcgaattgaa   15720
ctggacatta gctacaatgc aatcaccaga cagtatattg gggttgccta tgattacaaa   15780
actggtgaga agctagtgga ggtgagacaa tgggatgact attggttaag acagaacctc   15840
catgatgcgg tgtcctcctt cctgaaggag tggcctacat gcgaccaaac ttcgacttcg   15900
```

```
gagctacagt atcggaagac aataacctgt tgctgtggcc aactgaaggt aatcgaatcg    15960
ctttaataga tgctgatatg ttaccttaca tcatagggta tacaatcagt gatatgactt    16020
atgtacgagc cacaactcgt gttaagtcag ggcaagtccc ctcaatcaaa gatacacctg    16080
agtgtaagca agcgtgtgac cgtgtgaact ccttgcttaa ctcttgggtg tatgcagcag    16140
aatgtgatgc agctaagttg ttcatgacga aatcagaagc taacttccgt gtccgcctag    16200
cattcaccaa gccttataaa ggtcaacgta agaccgagaa gcctccattc ttctatgaat    16260
tgcgagagca tctcttagag gttcacggtg caatcttggc agatggagag gaagcagatg    16320
acctcatgag tatcgcacaa tgggacagcc accgccgctt ccagcaagat acaggtaacg    16380
agttccctat cggtagtcca gagcataaag cattctctga tacttgcatc gtttccttgg    16440
ataaggattt gatgattgtt cccggttggc atctacagcc gggtcaagag aagaaatggg    16500
tagagcctat gggttggctt gagctacgcc gtaaggctaa tgggcaagtc aaagatctaa    16560
aaggtgctgg cctcatgttc cactatgcac agatgattat cggtgatgat attgataact    16620
atgctggcat accaggtcgt ggtgctaaat atgcctatga tcttctcaaa gattgtaaga    16680
cagagaaaga gttgtacatg gcagtgctgg gtgcttacaa ggctaagttc gggcatggac    16740
aagttaaaat taagaattac cgaggtggtt atcgtatcgg caaagccttt gacctaatgc    16800
ttgagtgtgg tcgcttatct cacatggcaa gattcaaggg tgatatatgg cgagccgata    16860
agaacccaat cttgtgggga gatgatgcgg aatggttagc aaattaaaat catcggaggt    16920
ggcagcttat aagaaggaat tgctagataa gcaaggatgg aaatgccctc tgtgtggcgg    16980
cagtctcaaa gctgtcacac ctgtaaaccg tgtacttgac catgaccatg agacaggatt    17040
ctgccgcgct gttgtatgcc gaggctgcaa tggtgcggaa gggaagatta agggtgttat    17100
ctctggttat ggtaaggctg gtaacaaccg ttacttccag cttcaatggt tagagcgact    17160
atatgaatac tggaagttac atagtacgcc tcagacagat aagttatatc acaaacatca    17220
aacggaggca gagaagcgcg aggctaagaa ccgtaaggca cgccttgctt atgcaagaaa    17280
gaaggaggtt aaagttgggt aagctgcgca gcttgtacaa agactccgag gtacttgatg    17340
caatcgagca agctaccgac gagaaaggta atgttaacta caatgagatg gcacgtgtat    17400
tatcgtgtca tactgtgggt aagaagatta cccgccagtt ggctcgatac tggcatggtc    17460
aattcaagaa gaccaagaag aatggtgatt actaccagac ccttctgcaa gaagataagc    17520
gtatcaaaga agagcgtaag ctcaggactc ctgaccgcta cgaggatttg gctattgtgc    17580
cattgcctga ctcgcctcat cgaagtgtac tggtgatccc tgatactcat gcaccttatg    17640
agcacccaga taccctagag ttccttgcag ccgtggcagc acgttaccgt ccagacacag    17700
tggtacacct aggagatgag gcagacaaac atgccctgtc attccacgat tcggacccaa    17760
atctggatag tgctggcatg gagttagaga aggctcgtat cttcatgcac aaattgcaca    17820
agatgttccc tgtgatgcgc ctgtgtcact ctaaccacgg ctctatgcac ttccgtaagg    17880
caagcgccaa aggcatccct gtgcaatacc tgcgcaccta tcgtgaagtc ttcttcccgc    17940
agggaggtgg cgaccagtgg gattggcaac atacgcacgt ccttgagttg ccgaatggtg    18000
aacaagtggc attcaagcat caacctgctg gctctgtcct agcagatgca gcgcatgagc    18060
gtatgaacct tgtgtgtggt cacttgcacg gtaagatgtc tgtggagtac gcacgtaata    18120
cacatgaaca gtattgggct gtgcaaggtg gctgcttaat tgatgagtca tcccgtgcat    18180
ttgcctatgg tcgtgagtct aaatacaagc cagcattagg ttgtgtggtc attctggagg    18240
```

```
gtgtgcctca cattgtcccg atgcaaacca atagcgacaa ccgttggatt ggcaagattt    18300
agttgacact atagaacaaa gggctaggta agactttatc ggctggcgta tccaaatgat    18360
attgcactag cccttgattg tatagtgaat ggaggattca atatgtcaca ctatgaatgt    18420
aagaagtgtc ataagcgtta tgattactgt acttgtggtc aagagaaaac atcttttaaa    18480
gttggagaca aggtatttcg taatgaaaaa gattcgattc cttggaatca atactgcaaa    18540
gaagctggta ttgaccctga tagccctgta accatagatg atattgatgg cattaacttg    18600
tgctttcgtg aggtgagggg tacaggttgg gattccaaaa aattcaaact tgcatctgat    18660
aagttagaca acaatatggt aattaagcct aagcactacg agttctttga tggcgtagag    18720
gcaatcacta tcattgcccg cagtatgacc gagaagcaat cgctggcta ttgcatgggt    18780 aatgctttga agtaccgtct acgtgcaggt aagaagttca acactgaaga agacctgaag    18840
aaagcagatt actacaaaga gttattccag aagcatcgtc acgaatgtat tgatgaggat    18900
atttgatatg aatatctttg agttcctagg tcttccagaa gaccaccgca atcacccatt    18960
catgctggtg aagcatcgcg gtgaagttcc tgagaagaaa ttaacttttc catgttatgc    19020
acaggtgaaa cgagatggta tcttttctgc tgttgttgtt cgcactgatg gtgtcgttgg    19080 cattttggt cgcactggta agaaattggc aaacactgaa ggactcgaac aagcctttgc    19140
tacctttccg gttggcattt atcttggtga gcttcagtct atggccattg atatctacct    19200
tgaggcaatc tctggggttg tgaaccccaa tcgcactgag ccacttgatt tcataggcca    19260
gcagattaaa gacaacctgt atatcgactt cttcgatatg ttaactatta aggcattcca    19320
tgatggattc actgatgttt cttatctcaa acgttacgat gctttacatc gtcgtatcgg    19380
cgctcatctt agcgggtgca acgctatcct tcctatcact ccttgccata atgagcgaga    19440
agttgaagcg tttgcgcaag agcaaataga tgcaggacgt gagggtgctg tattcaaact    19500
ggactgcgat tatgaagcag gacacaaagg ttatcgtcag actaagaag tccgtaaggt    19560 aacctatgac cttacttgta ttggctttga agaaggtaaa ggcaaataca aaggtaaggt    19620
agctaacctc atttttcaaat ggaaaggagg caagacaatc aaagctatgt taggtaaggg    19680
gtggactcat gcagatgcag agcagatgtt ccacgacatt aaacatggtg gacgattgaa    19740
tgtcattggt aaaatctttg aagtcaaagg tcttcaggat tcaagcaagg gcaacattcg    19800
tctgcccaaa gcgggagaat taagacatga caaagatgaa ccagatttct tttgatagca    19860
tgaaggcaac tcgtgcagtt gaggtagcag aagctatctt cgaaacttta tcctgtggca    19920
tggaagtgcc atatacttta cttgctgatg cagaagaact tggtcttct gtagaagcta    19980 tccaagagaa ggttgacgaa ttatatggta cagacgaaga agaaaccgac gatttcattt    20040
gaaggaatgg agatgcttga gatgattctc aagccttctt ctcctaaggt gactaagact    20100
catgaagagt taatcgttga tgaagttaag cgttacatca tggattgtgt cagagcacaa    20160
ctggtggtcc aatgatacgt ccagcctcct tcctagatat tcctgagatt ataaaccttg    20220
ggaataaata tgtggaagag gaagtcaagg ttgtagccca ccactcagcc tcatggaatg    20280
cagaacaaag tgccataacc tttgtgcatc tcttaataga gacccaccac tcagcctcat    20340
ggaatgcaga acaaagtgca cataaccttt gtgcatctct tagtagagaa gatttatccc    20400
tatgggttgc tgtagatgaa gggcagattg tagggttcct gtgggctggc tatcacgagt    20460
tggccccttg gacacctgta agagttgcct ctgacattct cttttatatt ataccagaga    20520
ggcgaggaac actacttggt atgcgtctca tcaaagccct aaagcaatgg gctagtgata    20580
atgaatgctc tgaggttcgc ctgtctatcg cctctggtat taatgaagaa cgtgtcggac    20640
```

```
gtatgtataa gcgacttggc tttgaaccgt ttggcactgt gtataacctg aagttctaag    20700
gagataacat gggtgttgta aagaaagcat ttaaggctat cggtcttgct caagatgcac    20760
cacgtattga agccaaagtc ccagcacagc agcttgagcg taagcctgag actgaagctg    20820
aagatattca aattggtgca ggggatgatg ctactgcatc tgcaaaaggt aagcgtggcc    20880
ttgtccgtcc ggtagcttct agcttgaagg tgtaatatga acagagcat agatttggag     20940 tatggaggta agcggtctaa gatacctaag ctatgggaga agttctccaa taaacgtagc    21000
tctttccttg ataggggaa gcattactcc aaattaacct tgccctatct gatgaatgac     21060
aaaggtgata cgagacttc gcagaatgga tggcaaggtg taggtgctca ggcaaccaac     21120
catctagcca acaagctagc gcaagtacta ttccctgcac agcgttcctt cttccgtgta    21180
gacttaactg cacaaggtga gaaggttctt aatcagcgtg gcctgaagaa gacagagcta    21240
gctaccatct tcgctcaagt ggaaacacgg gcaatgaaag agttagagca cgtcaattc     21300 cggcctgctg tagtagaagc atttaagcat cttattgttg ctggcagctg tatgctatac    21360
aagccgagca aggtgcaat cagtgctatc ccaatgcatc actacgtagt taaccgtgat     21420
accaatggcg acctgttaga cattatcttg ctacaagaga aagccttacg tacctttgac    21480
ccagctacac gtgcggtagt agaggttggc ctgaaaggta agaagtgcaa ggaagatgac    21540
agcgttaagc tgtacacaca tgctaagtat cttggtgatg gattttggga actcaagcaa    21600
tctgctgatg atatccctgt gggtaaggtg agtaaaatca aatcagaaaa gctaccttc     21660 atcccattaa cttggaagcg aagctatggt gaggattggg gtcgacctct tgcagaggat    21720
tactccggtg attattcgt tatccaattc ttatctgaag cggttgcccg tggtgctgcg    21780
ctgatggcag atatcaagta cctgattcgt cctggtgctc aaactgatgt tgaccacttt    21840
gttaactctg gcactggtga ggttgtcact ggtgtagaag aagacatcca tattgtacag    21900
ttaggtaagt acgcagacct cacacctatt agcgcggttc tagaggtata cactcgccgt    21960
atcggtgttg tcttcatgat ggagacaatg acacgccgtg acgccgaacg tgttactgct    22020
gtagaaatcc agcgagatgc gttagagatt gagcagaaca tgggtggtgt atactccctc    22080
tttgctacta ctatgcaatc gccagtagcg atgtggggtc tgctggaggc agggggagtcc   22140 ttcactagtg acttagtgga ccctgtgatt atcacaggta ttgaagcttt aggacgcatg    22200
gctgagttgg ataaactggc taactttgct cagtatatgt cactgccatt acaatggcct    22260
gagcctgtcc tagctgctgt gaaatggcct gactatatgg attgggtgcg tggtcaaatc    22320
tctgctgaac tgccgttcct taaatcggct gaagagatgg cacaagaaca ggaagcacag    22380
atgcaagcac agcaagcaca gatgcttgaa gaaggtgtgg ctaaggccgt gccgggtgta    22440
attcaacaag aacttaagga ggcgtaatgt ctttctcatt tactgaaccg tcaaccactc    22500
accctactgc tgaagagggt ccggtagaaa ccaaggaggt aacaactgat gctgctacta    22560
ctgatgctcc tgctgacgct ggcacttctg tacaagatga caatgctggt gcacaaccta    22620
ctgaagacac cggaggagaa gcttctggac agccttcaga aaaggagac aatggcggag     22680 agaatggtga acctaagcca gatgataccg cgaccgacac tgaggaagtg caatacttct    22740
tcggagaaca tgaagtaaca gtagacatcc cacaggatgt aactgacagc cttaaagaga    22800
aaggcattga tgccaagcag gttgccaagg aactctattc caaaggtggc aagtttgaac    22860
tgtcagatga aaccaagcag aaattgtatg atgcttttgg caagtttcgc gtagatgctt    22920
acctatcagg tctaaaggct caaaatgaag ccttcttcct gaaagaagcc aacgcagcta    22980
```

```
aagagttgga agcagctaac acccaacgct tctctgatgt ttctaaggaa attggtggcg    23040
aagaaggttg gtcccgtctt gaggagtggg cacttgaagc gctgtctgat gacgaactaa    23100
tggcattcaa tgcggtgatg gaatctggca accagtacct gcaacaatat gctgttcgtg    23160
aactggaggg tcgtcgtaag caggcacagg gggatgataa gccatccctg attgagccat    23220
cagcacctgc taaggctaat gaagagaatg gcccactgac gcgagatcag tacgttcaag    23280
caatcgcaac tcttagccag aagtacggca atgaccgtaa agctatggca gaagctcagg    23340
ctaaactgga cgcccgtcgc cgtgctggca tggctcgcgg tatctaattc agtatttact    23400
ggacactata gaagggagaa aagttctccc tagttatcaa tttgatttat aaggagatta    23460
taatacatgt ctacaccgaa tactctgact aacgttgctg tatctgcgtc cggtgaggtt    23520
gacagccttc tcattgagaa gtttaatggt aaggtcaatg agcagtacct gaaaggtgag    23580
aacattctgt cctactttga tgtacaaact gttactggca ctaacacagt gagcaacaaa    23640
tatttgggcg aaactgagtt gcaggtgcta gcaccgggtc agtcccctaa tgccaccct    23700 actcaggcgg ataaaaacca gttggtaatt gataccactg tcattgctcg taacactgtg    23760
gctcacatcc acgatgtaca aggtgacatc gatagcctga aaccaaaact ggctatgaac    23820
caagccaagc aactgaaacg tctggaagac cagatggcaa ttcagcagat gctgttaggc    23880
ggtattgcta acaccaaggc cgaacgtaac aagccgcgtg ttaaagggca tggcttctct    23940
atcaacgtta acgtaactga gagtgaagca ctggctaacc ctcagtatgt tatggctgcg    24000
gtagagtatg ctctggagca acagcttgag caggaagtgg acatctctga tgtagctatc    24060
atgatgccgt ggaagttctt caatgctttg cgtgatgcag accgaattgt agataagact    24120
tacactatca gccagtctgg tgcaaccatt aatggcttcg ttctctcttc ttataactgc    24180
cctgtgatcc cgtctaaccg attccctacc ttcgctcagg atcaggctca ccacctgttg    24240
tctaatgaag ataacggcta tcgttatgac cctatcgcag agatgaatgg tgcagttgct    24300
gttctgttca cttccgacgc actgctggtg ggtcgtacca ttgaagtgac tggtgacatc    24360
ttctatgaga agaaagagaa gacttattac attgacacct tcatggctga gggtgcaatc    24420
cctgaccgtt gggaagcagt gtctgtagtt accactaaac gtgatgcaac tactggtgat    24480
gctggaggtc ctggtgatga tcacgcaacc gtactggctc gtgcacagcg taaggctgta    24540
tatgtcaaaa ccgaaggtgc tgcggctgca ttctctgctg ccccagcagg tatccaagcg    24600
gaagaccttg tagcggcggt acgtgctgta atggcaaatg acattaagcc gactgcaatg    24660
aaacctactg agtaacacct atgccctatc taccttgcgt aggtagggtt cttttttgtta    24720 ggaggattca tgcctgtaat tagacaaacc agtaaattag gacatatgat ggaagatgtg    24780
gccttccaga ttattgatag taagctggaa gcggtaaact tgtgtatgcg agctattggt    24840
cgtgagggtg tggattccct cgactcaggg gacttggacg cagaagatgc aagcaaaatg    24900
atcgacatcg tatcccagcg gttccagtac aacaaaggag gtggctggtg gttcaatcgt    24960 gaaccaaaact ggcaacttgc accagacact aacggtgaag ttaatttacc taacaactgc    25020
ctagcagtat tgcagtgtta tgctttaggt gaaaagaaag tacctatgac tatgcgagca    25080
ggtaagctct actctacttg gagtcacacc tttgatatgc gtaagcatgt taatgctaat    25140
ggtatgattc gtcttacctt actcacctta ctaccctacg agcatctacc tacaagtgta    25200
atgcaggcta ttgcctatca agctgctgta gagtttattg tgtctaagga tgcagatcag    25260
actaagctag ccactgcgca gcagatagcc actcagcttc ttatgggatgt acaatctgag    25320 caaatgtcac agaagcgatt aaacatgctg gtacataacc ctactcagcg tcagtttggt    25380
```

```
atcatggctg gtggctctca gaatgtacct gcttactctc attcaccttg tgagagttgg    25440
gcgctccgtc cgtgggagga tcgttaatgg aagtacaagg ttcattaggt agacaaatcc    25500
aagggattag ccagcagccg ccagcggtac gcttggatgg tcagtgcaca gctatggtta    25560
atatgatacc tgatgtagtg aatggtactc aatcacgcat gggtacaact catattgcaa    25620
agatacttga tgcggggact gatgacatgg ctactcatca ttatcgcaga ggtgatggtg    25680
atgaagagta tttcttcacg ttgaagaaag gacaagttcc tgagatattt gataagtatg    25740
ggcgcaaatg taatgtgact tcacaagatg cacctatgac ctacctctct gaggttgtta    25800
atccaaggga agatgtgcaa ttcatgacga tagctgatgt tactttcatg cttaatcgta    25860
ggaaagtagt taaagctagt agcaggaagt cacctaaagt tggaaacaaa gccattgtgt    25920
tttgtgcgta tggtcaatat ggtacatctt attccattgt aattaatggg ccaacgctg    25980 ctagttttaa acaccggat ggtggaagtg cagaccatgt tgaacaaatt cgaactgaac    26040
gtatcacttc tgaattgtac tctaagttgc agcaatggag cggtgtgagt gactatgaaa    26100
tacaaagaga cggtactagt atatttatcg agagacggga tggtgctagc tttacaataa    26160
caaccaccga tggtgcaaaa ggtaaggact tagtggctat caagaataaa gttagctcta    26220
ctgacctact ccccttctcgt gcgcctgctg gttataaagt acaagtgtgg cctactggca    26280
gcaaacctga gtctcgttac tggctgcaag ctgagcctaa agagggaaac cttgtgtctt    26340
ggaaagaaac aatagctgct gatgtattac ttgggtttga taaggcaca atgccttaca    26400 ttattgaacg tacagatatc atcaacggca tagctcaatt caagataaga caaggtgatt    26460
gggaagatcg taaagtaggg gatgacttga ctaaccctat gccctctttt attgatgagg    26520 aagtaccca acaataggt ggaatgttca tggtgcagaa ccgcctatgc tttacagcag    26580
gtgaagcggt tattgcttct cgtacatcat acttcttcga tttctttcgt tatacggtta    26640
tctctgcatt ggcaactgac cccttttgata ttttctcaga tgctagtgaa gtctaccagc    26700
taaaacatgc agtgacctta gatggcgcta ccgtgttgtt ctctgataag tcacaattca    26760
tactgccagg cgataagcct ttagagaagt caaatgcact gcttaagcct gttacaacat    26820
ttgaagtgaa caataaagtg aagccagtag taactggtga atcggtaatg tttgccacta    26880
atgatggttc ttactctggt gtacgagagt tctatacaga ctcttatagt gacactaaga    26940
aggcacaagc aatcacaagt catgtgaata aactcatcga aggtaacatt accaacatgg    27000
cagcaagcac caatgtcaac aaggttacttg tcactaccga taagtatcgt aacataatct    27060
actgctacga ttggttatgg caaggaacag accgtgtaca atcagcatgg catgtatgga    27120
agtggcctat aggtacaaag gtgcgaggta tgttttattc tggtgaatta ctttacctgc    27180
tccttgagcg aggagatggc gtgtatctgg agaagatgga catgggtgat gcactaacct    27240
acggtttgaa tgaccgcatc agaatggata ggcaagcaga gttagtcttc aagcattca    27300 aagcagaaga tgaatgggta tctgagccgc tccctggggt tcctactaac ccagaacttt    27360
tagattgcat cttaatcgag ggttgggatt catatatttg cggctctttc ttattcaagt    27420
acaaccctag tgacaatact ttgtctacaa cctttgatat gtatgatgac agccatgtaa    27480
aagcgaaggt tattgttggt cagatttacc ctcaagagtt tgaacctacg cctgtggtta    27540
tcagagacaa tcaagaccgt gtatcctaca ttgatgtacc agttgtagga ttggttcacc    27600
ttaatcttga catgtacccc gatttctccg tagaagttaa gaatgtgaag agtggtaaag    27660
tacgtagagt attagcgtca aaccgtatag gtggtgctct caataataca gtaggctatg    27720
```

```
ttgaaccgag agaaggtgtc ttcagatttc cactgagagc taagagcacg gatgttgttt   27780
atcgtattat tgtagagtca cctcacacat tccagcttcg tgatattgag tgggaaggga   27840
gctacaatcc aaccaaaagg agggtctaat ggctataggt tcagccgtta tggctggtat   27900
gtcttctatt ggtagcatgt ttgcaggcag tggtgcagca gccgctgctg gaggtgctgc   27960
cgcaggtggc ggaggtttgc taggttcact aggtggattc ctaagtggct ctactgctgg   28020
tttctctaat gctggccttc ttggtgctgg ccttcaaggg ttaggcttga ttggtgatct   28080
atttggtgga agtgatgaag ccaaggcgat gaagaaagca caagaagagc aatggcggca   28140
gcagcttatt gctacacaag aggcgtacaa gacagtggca gacgcagaac gttctgctgc   28200
taaacaatat catgcagatg caatcagtaa tcaggcttca ctgctacagc agcgagcaca   28260
ggttgcatta cttgctgggg ctactggtac tggtggtaat tctgtgtcct ctatgcttaa   28320
tgacttagca gcagatggcg gcaggaacca gagtactatc attgataact atgagaatca   28380
gaagattaat ttcaccaacc agcttaagtc tatccaacgt ggtggtcaga tgcagatgcg   28440
tgagtttaag aagcccttctg ctatgaatac cttggttaaa ggtattccaa gtctggcatc   28500
tgcctatgta actggtagta agtctggcaa ggcattgggt aaagccttaa ctgattctcg   28560
cacatattca tctggaacaa gaggtattta atggcaattg agcgacaagc agtacaaggt   28620
ctgccacaag tgcaggccac ttctcctaat gtcatgacct tgcacctca acaagtggga   28680 ggtgtggagg ctggcgtggc ttctacctcc ggtagtaggt ttatcgaaga ccttattcgt   28740
gcagcaagca gcgtggctga tgttaccact ggtatcctta atcagaagat tgaggaagat   28800
aaggttgttc aaatgaacg ggcatataac ggattaatgc cttctgagga tgcaactcgt   28860
ggtggcgctc gtgctaacat gcttgtcaaa gctcaactgc tagctaatga tgaagcagca   28920
cgaatgaaag acatggctac tcgtttccaa ggaacggatg acgaatggac acaacttatg   28980
gttgactctc gtaatgagat gcagaataag ctgttccagc aatacctga gttgcaaggt   29040 gacaaagata ctatgcgtat ggtcactaat gtcttccaag aacagcagcc tcagatttgg   29100
gctacacgaa cccagcataa acttgaccgt gaacaagcag accgtgagga tacctttgac   29160
gggcgagtgg cttctacttg ggattctaat attgaccctg aagcctctgg ctatgcttta   29220
caggaacgaa tccgcgaagg tcttactcaa ggattactac ctgaacagat gtacaagaag   29280
ttagtccagc gagcaatttc acttgcacaa ggcggtgatg ttagcatggc tgaagccctg   29340
aagtatgtga aggacgataa gggtgtttct gtttatgcta agaatccaca gcttatcaca   29400
gccatcacta gtggtaatgc agtttgggct aggaataatg tagctgatgt aactcgtatg   29460 tcttttcgaag ttaaagaatc ctaccttgca ggtgatttaa ctgatgaaga attgttggaa   29520
cgagcacagc acattaataa tctgacaggt aactctgtct tctctaatcc agaactagag   29580
gcactgatgc gccaacgggc taagcagaat gcagagctag gtgcaatgca ggatatgcga   29640
cgtgagcttt actccgaccg cctgactggc ttccaaggta agactgataa agagaagaag   29700
gcttacattg atgttatcaa acaggatagc caactttatg cagaccagca aatcaaacaa   29760
cgtggcttgg acccttacag tcaagaggct gaagctattc gtggtgcagt ggaagtgcag   29820
cgcctgcaat tcatgaactc caaaggctta gtggatgata cctttgagtc tcgtatcaaa   29880
gccatggaat ctatgctatc gcctgagcac tttgccaagg gcgaaccaca ggagttgatg   29940
actattcgcc agttgtggga acagttacca aagagagcc gaggtgtctt tggtgacacg   30000
gtgaatggct acatggataa ctacaacact gcactacaaa tgggagagac acctttgcag   30060
gctgcaaggt ttgcgcgtaa agcacagcag aaattctctc gtactgagaa ggaaaccaag   30120
```

```
aagttcaact cagctattgg agatgcactg gatgaggtat ctggtgctgg ctggtttgat    30180
ggtaaaaccg aagtgtcaga cttaggtaaa gctattgcgg aagaagagtt acgagctaag    30240
gccaatatgt tgtggtctag tggtatgcgt aacatggatt ccatcaagaa ggctttaatt    30300
acttggggca ataaacgcta cactcaatca gaggatgcaa agacttccgg tggctatttc    30360
attaaaggtg attacacttc tgcatctgat atgcttatgt cagttgggaa aggcgtaaac    30420
cctaccgatg tacctctggc gcttggtagg tatgtagaaa cacagatgcc agaattgaag    30480
aaggagcttc aagaggggga aactaaagat gatatataca ttgattacaa tgaacagaaa    30540
ggtactttcg tgattcgtgc tggtgcagca ggtcgccctc tttctggagt aatccctgta    30600
acctctttag ataccacttc actactagat tctgcctatc agaagaaagt agaggaacga    30660
gataaaggcg agtatgttca cccgtatcgt acagatattg gtgcacaaga gcctatgcca    30720
gctaaaccaa ctgccaaaga tattggtaaa tttggactag ctaacttcct catgtcttct    30780
gcttttgctt ctggtgagaa tctgccttct aacttcgaga ttaactatcg aggtaatatg    30840
caacaattct atgacaagct agctatggat gagaataaag ataaagttgg ctttaataag    30900
gcaactggaa cctttactcc atataaagac gctcacggtg agtctatcgg ttacggtcat    30960
ttcttaacgg aagaagagaa gcgaaacggg tatattaaga ttggcgatga actagttccc    31020
tatcgagggt ctatgtctca gcttacagag agcaaggctc gcgctcttat ggagcaagat    31080
gctaagaagc atgtgcctcc tactcgtgac tggaagattc cgtttgacca gatgcaccct    31140
gcacagcaac gtggcttgat ggatttaagc tacaatttag gtaaaggtgg aatccagaac    31200
tcaccgcgtg ctcttgctgc attcaaagct ggtaagctta cggagggctt tatcgaaatg    31260
ctgggcactg catcaagtga aggtaagcgt attcctggcc tactgaagcg acgcgctgag    31320
gcatacaata tggcatctgc tggtggtgtg cctaagatta ccgaagtgga gactcgtgaa    31380
gatggctcca tgtgggttag gtttggtgga cctatgccag caggttctgt ctcggcatgg    31440
actcataaac gtattggcgc ggatggttgg tatcaggttt atgaggctgc acctaccaag    31500
ttagctaaag attctaaggt aggtaaagtt aagttgtagt acctaactca aggcttgtct    31560
cacatgtgag acaggtcttt atgataggca ctatggagga attatggaac aagacattaa    31620
gactaattgg gctggatatg tccagtctac tcctgagccg ttttctattg aggcggctcc    31680
ggtatcggct cctacgatac gccagcgtaa tgagttacaa gagcaagttc ttgaagctaa    31740
agctgacgct gatatcttag gtgctgtagg tgctgccttc cagaatgagt ggttggcatt    31800
cggaggcaag cggtggtatg accgtgccac tgctgatttc acacctcaac cagactttga    31860
gatacaacct gagcaacgtg aagcactacg tttcaaatat ggtacggata tgatgcagac    31920
aatcactgag ggtgttcgtt ctgaggatga attgaacttc cgtattcaga atgcggatga    31980
agaccttgag cgcaataagc gcattgctca ggctggctgg gttggctctg tggcgacgat    32040
tggcgctgct gtgcttgacc ctgtgggatg ggttgcctct attccaaccg gtggtgccgc    32100
taaagttgga ctcgtaggcc gtgctgtgcg tggcgctatc gccgctggcg tgagtaatgc    32160
cgctattgaa tccgtattgg tccaaggtga catgactcgt gatttagatg acattatggt    32220
agcactgggt tccggtatgg ctatggtgg cgttattggc gctgtagcgc gtggtagggc    32280
cactaagctc agtgagcaag gtgatgacag ggctgctagc attgtgcgca gtgcagacgc    32340
aggggaccgc tatgttcgtg ctgttgccga tgacagtatc ggtgcgatgc gtgttaaggg    32400
cgcagaggtt ctcactgagg gtgtattcga tatctccagt aagagtgaag acctactgaa    32460
```

```
aaccttgcaa cgagaaggta atgcgattga tatgcacct  cgccgttggg ctggaactat   32520
gtctgccctc ggtactgtcg tgcactcatc taaagatgca agtatccgag gccttggtgc   32580
tcgtctgttt gaatccccac aaggtctagg tatgcagaag gcatctgcta gtcttatgca   32640
gaatactaac ttaaatcgcc tgaaatctgc tgatatgaac cgcttcaatg atgggtttga   32700
tttgtggctt aaagagaata atatcaatcc agtagcaggg cataccaact ctcattatgt   32760
acagcaatac aatgaaaagg tgtgggaggc agtgcgtatt ggcatggatg agtctacacc   32820
taaatctatc cgcatggctg ctgagggaca acaggctatg tacagagagg cgctggcttt   32880
acgtcaacgt tctggtgaag cgggatttga aaaggtaaaa gccgacaaca aatatatgcc   32940
tgatatcttt gatagtatga aagccagacg tcaattcgat atgcacgata agaagacat    33000
catcgaactt ttctctcgtg cctaccagaa tggcgctcgt aagattccaa aggaagcagc   33060
agatgagatt gcacgagcac aggtaaatcg cgttgctgat gctaccttaa ctggaaagct   33120
tagttttgaa aaggcaatgt caggtcagac taaggcagag tatgaagcta tcatgcgtaa   33180
ggcaggcttc agtgatgaag aaattgaaaa gatgatagaa gctctggata caaagaaac    33240
cagagataac atctctaacc gagctaaaat gagtttagga ttagatgtta ctcaagaata   33300
caatggcatt cgtatgcgtg acttcatgaa taccaacgtg gaagagctaa cagataacta   33360
tatgaaggaa gcagcaggtg gcgctgcatt ggctcgccaa ggcttctcta cctatcaggc   33420
tgcacttaat gcaattgacc ttgtagagcg aaatgcacga aacgcggcta aggatagcaa   33480
ggctagtttg gcattagatg aagagattcg tcagatgcga gaaggtcttc gcctgattat   33540
gggcaagtcg attgatgcag acccacaggc tatatctact aagatgatgc gtcgtggtcg   33600
tgatatcaca ggtgtgcttc gcttaggtca atgggcttc gcacagctag gtgaacttgc   33660
caactttatg ggtgaatttg gtattgctgc aactactatg gctttaggta agcaattccg   33720
cttcacctct aaggcgttgc gtaatggcga tggcttcttc cgagataaga acttagctga   33780
ggttgagaga atggtggggt acattggtga ggataactgg ctaacaacta agggtgcacg   33840
tcctgatgaa tttggtgatg taaccacagt aagagggatg atggctcact ttgaccaatc   33900
catgaactca atacgtcgtg ctcaaaccaa cctatcactc ttccgcatgg cacagggttc   33960
tctggagcga atgactaata ggcaaatagc tttgtctttc attgaccacc ttgaaggcaa   34020
gaagattatt cctcagaaga aactggagga acttggtctt actcaggagt tcatgactaa   34080
cctacagaag cactatgatg ctaactctaa aggttctggc ttgcttggct tgatacaat    34140
gccttatgcc atgggtgaaa cttagctaa tgctattcgt cgtaagtcag gtctaatcat    34200
ccaacgtaac ttcattggtg atgaaggtat ctggatgaac aaagcactag gtaagacatt   34260
tgcacagctt aagtcattct ctcttgtatc tggtgagaag caatttggtc gagggattcg   34320
ccacgataaa attggtcttg ctaagaagac agcttacggg tttgctttgg gttcaatagt   34380
gtatgcggca aaagcctatg tgaactctat tgggcgagaa gaccaagatg aatatttgga   34440
agagaagtta tcgcctaaag ggttggcctt tggtgcaatg ggtatgatga gtacaactgc   34500
tgtatttagt ctaggtggag atttcttagg tggcctaggt gttctacctt ccgaactcat   34560
tcaatcacgc tatgaagcag gtttccaaag taagggtctg attgaccaaa tacctctggt   34620
tggcgttggt gcagatgcag taaatctggc taactcaatc aagaagtatg cagaaggtga   34680
cacagaaggt gtagatatcg ctaagcgagc actccgtctt gtgccactta ccaatataat   34740
aggtgtccaa aacgcattgc gttatggctt agatgaactg gaggattgat gagttatact   34800
ttcacagaac atacagccaa tggtacgcaa gtcacctatc ctttagctt  tgctggtagg   34860
```

```
gataaaggtt atcttcgtgc ctcagatgtg atagtggagt ctcttcaagg taacacttgg   34920
attgaagtta catctggctg gcaactaact ggcacgcacc agattacttt tgatgtagca   34980
ccagttgcag gtttgaagtt ccgtattcga agggaagtac aaaaagaata tccatacgct   35040
gagtttgacc gtggtgttac cttggatatg aagtctttaa atggttcttt cattcatata   35100
ctggagatta cacaggagtt acttgacggg ttttatccag aaggatactt cattaaacag   35160
aatgtaagct ggggcggcaa taagattact gatttggctg atggcacaaa tccgggagat   35220
gcagtaaata aagggcagct tgatgccatc gacaagaagc atacagattg gaacgccaaa   35280
caggacattg agattgctgg ccttaaggct ggtatgactt ctggtattgc gcacagaact   35340
gttccttggt acacgatagc ccaaggtggt gagatttccg taaaaccacc ttatgaattt   35400
caagatgcac tagttttcct taatggggta ttgcagcacc aaattgtagg cgcatactct   35460
ataagcaaca acactatcac tttcgcagag ccgcttgtgg ctggtacaga ggtgtatgtg   35520
ctgattggta gtcgtgtggc tacatctgaa cctaatattc agttggagtt gaactttgac   35580
ttagtagaag gccaacaagt agtacagatt ggctctgcat ttaagtacat tgaggtctac   35640
cttgatggat tattacaacc taaacttgct tatcaggtag acggtgacat tgttactttc   35700
tcagaaagag taccagaatg ccggatgact gctaagatta tcacagcata aggaggtggg   35760
atgattaact ccgaactggt agatagtggt gtgaagcttg cgccacctgc actcatatca   35820
ggtgggtact tcctcggtat cagttgggat aattgggtgt aatagcaac attcatttat   35880 accgtgttgc aaattgggga ctggttttat aataagttca agatttggag ggagaagcgt   35940
gagcgtacac aataaacatg cagctacaga ggacgaggtt ggcattctgc atggtgctat   36000
taccaaaatc ttcaataaga aagcacaggc aatactggac actatagaag aagaccctga   36060
tgcagcatta catttagtgt ctggtaagga tattggtgcg atgtgtaagt gggttcttga   36120
taacggcatt accgccacac ctgctgcaca gcaggaagag tccaagttat ctaagcgcct   36180
caaggctatc cgagaggcat ccagtggtaa gataattcaa ttcactaagg aggattgatg   36240
gctaaggcaa gagaatcaca agcggaggct cttgccagat gggagatgct acaggagtta   36300
cagcagacct ttccttacac cgcggaaggt ttgcttctct ttgcagatac agttattcat   36360
aacttaattg caggcaaccc tcatctgatt cgtatgcagg cggatatctt gaagttccta   36420
ttttacggac acaagtaccg cctcatcgaa gcgcctcgtg gtatcgctaa gacaacacta   36480
tcagcaatct atacggtatt ccgtattatt catgaaccgc ataagcgtat catggttgtg   36540
tcccaaaacg ccaagcgagc agaggaaatc gcaggttggg tagttaaaat cttccgtggc   36600
ttagactttc ttgagtttat gctgccggat atctacgctg ggaccgtgc atccgttaag   36660 gcgtttgaga ttcattacac cctacgtggt agtgataagt ctccttctgt atcctgttac   36720
tcaatcgaag caggtatgca gggtgctcgt gctgatatta ttctagcgga tgacgtagag   36780
tcgatgcaga atgctcgtac ggcagcgggc cgtgccttgc ttgaggagct gactaaggag   36840
tttgaatcta tcaaccagtt tggggatatc atttaccttg gtacacctca gaacgtaaac   36900
tctatctaca caaacctacc tgctcgtggt tactctgttc gtatctggac tgcgcgttac   36960
ccttcagtag agcaagagca atgttatggc gacttccttg cacctatgat tgttcaagat   37020
atgaaggaca acccagcact tcgctcaggg tacgggttgg atggtaatag tggtgcacct   37080
tgtgcccctg aaatgtatga tgatgaagtc ctgattgaga aggaaatctc tcagggtgct   37140
gctaagttcc agcttcagtt catgcttaac actcgcatga tggatgctga cagataccca   37200
```

```
ttacgcctga caatctaat cttcacctcg tttggtacag aggaagtccc tgtgatgcct    37260
acgtggagta atgattccat aaacatcatt ggtgatgcac ctaagtatgg taacaagcct    37320
acggatttca tgtacagacc tgtagctcgc ccatatgaat ggggtgctgt ctcccgcaag    37380
attatgtata ttgaccctgc gggtggtggt aagaacggag atgagacggg tgtagccatc    37440
gtattcctgc acggcacatt catttatgtg tatcagtgct ttggtgtacc tggcggatac    37500
cgagagtcgt ccctgaatcg cattgtgcag gccgcaaagc aggcgggtgt aaagaggta     37560 ttcattgaga agaactttgg tcatggcgcg tttgaggcgg taattaagcc gtactttgaa    37620
cgagagtggc ctgtaactct ggaagaggat tacgccaccg gacagaaaga gttgcgtatc    37680
attgagacgc tggagccgct catggcagcc cataggctta tcttcaatgc agagatggtg    37740
aagtcagact ttgagtcggt acagcactat ccgcttgaac tacgcatgtc ctacagtctt    37800
ttcaatcaaa tgtcgaacat aacgattgag aagaacagcc tccggcacga tgaccgccta    37860
gacgccctgt atggcgctat acggcaatta acttctcaga tagactatga cgaggttaca    37920
cggattaatc gcctcagagc gcaggagatg cgcgattaca tccatgctat gaacacacct    37980
catctacgca gggcaatgct atatggagat tacggtactg agcgaagagt gaccaacact    38040
tccgtagcga tgcagcagcg agtttacggg cagaactacc gaaataaatc ggcaagcaga    38100
aatacacttt ctgcaaggat ttcaaggact tattaattac tggacactat agaaggaagg    38160
cccagataat aagagaaaat aataggtaat atatatatag gttaacctag gttatatagg    38220
tatgccttag tatgggtgta ctcctgtaca ccctattcct tactacctta ctatatttac    38280
ataataggag agagacaatg gctaatgatt atagtagtca accattaaca ggtaagtcta    38340
agagaaagca ggtacaacct gtaagtgaag aactaatgct tccggtgctc aaaaaagagg    38400
aagttagtaa gaaaagcaat gttattaatg atgccaccaa atcaggtaaa cagaaagggg    38460
ccatggtgtg ccttgaagtg aaaggtggtg tattgaagat tgctatcgcg gttgatggca    38520
aagaagattc agagtggaag ttagtaacag tggaaccaac tgttaaccca gtttaagata    38580
aggaggaaga ttacatggct aaatatggta ctacaggttc tgttactggt caggcttttc    38640
gagtaaaagc agtacaaact attgcaacgg caatcccgat gcctgttgtt aaagaagaag    38700
accttaagag taaagaccac cctatcaaca tcaaacattt atcaggtaaa cagaaaggtg    38760
caatggttgc tcttgagaaa ggtgacacaa ccttacatat tgctgttgca cgtggtagtg    38820
aacccacaga cccttgggat gtaactggta tggaaaagga cgctgttact ccagcagggg    38880
tataataatg cttaataaat acttcaagcg taaagagttt gcttgccgtt gtgggtgcgg    38940
tacatccact gttgatgctg aattactaca ggtagtcaca gatgtgcgtg agcactttgg    39000
ttctcctgta gttatcactt cgggtcatcg ctgtgctaag cacaatgcca atgtaggtgg    39060
cgctaagaac tccatgcatc ttactggtaa ggctgctgac attaaagtgt ctggcatatt    39120
accttctgaa gtgcataagt atcttactag caaataccaa ggcaagtatg gtataggtaa    39180
gtataactcc ttcactcaca tcgatgtacg ggatggttgt gcgcgatggt aagatgtgtt    39240
gaatggtgtg agcgtatggt tgcccaagct gccgaggatg gcaactatga tgactggaag    39300
aactactctg acttgttagc tcaatggaaa gggagatgca atgaaaaagc tgtttaagtc    39360
taagaaggtt gtaggtgcac tggttgcact tgttattgct cttgtttctg taggtcttgg    39420
tgtagacctt ggctctggca cggaatcctc tgtgacagat gtggtctgcc aagtgatcac    39480
ctgtgaataa gtttctagaa gttctggcag gtccttattgg cctgcttgtc tctgctaaga    39540
agaaacaaga agagaaggag gcacaaagtg aagcgaatca tgttagtgac aacccttctg    39600
```

```
attggttcgc tgaccacttc cgggtgtcag caggcgttac cagagaaagc aatggtgaaa    39660
cctctgaggc cgacgctgac ggcagtttac gaggtagacg ataaggtctg ctttagtaag    39720
cctgacgcta caaaacttgg tttgtacatt ctctcgctag aacgcggata caattaatac    39780
atagctttat gtatcagtgt cttacgattt actggacact atagaagagg taagatagcc    39840 ccgttcttttt gagcggccta ttactagcca atcttcatag ggaggggttgg aaagtaatag   39900 gagatagcat ggctaaatta accaaaccta atactgaagg aatcttgcat aaaggacaat    39960
ctttgtatga gtaccttgat gcgagagttt taacatcaaa gccgtttggt gctgcaggtg    40020
acgccactac tgatgatacg gaggttatag ctgcttcatt aaactctcag aaagctgtca    40080
cagtctcaga tggtgtattc tctagctctg gtattaacag taattactgt aacttagacg    40140
gcaggggtag tggcgtgcta agtcaccgtt caagtacagg taactactta gtatttaaca    40200
atctacgtgc aggtcgctta agtaatatta cggtagaaag taataaggcg actgatacaa    40260 ctcaggaca gcaggtatcc cttgctggtg gaagtgatgt tactgtaagt gacgttaact    40320
tctcaaacgt taaaggtact ggtttcagtt taatcgcata ccctaatgat gcgccacctg    40380
atggacttat gattaaaggc attcgaggta gctattccgg ctatgctact aataaggcag    40440
ccggatgcgt acttgctgat tcctcagtta actccctcat agataacgtc attgctaaga    40500
actaccctca gttcggagca gtagagttga aaggtacagc cagttacaac atagtcagta    40560
atgttatagg gacagattgc cagcatgtaa cttacaacgg cactgaaggg ccaatagctc    40620
cttctaataa ccttatcaag ggggtgatgg ctaataaccc taagtatgca gcggttgttg    40680
caggcaaagg aagtacgaac ttaatctcag acgtgctcgt agattactca acttctgatg    40740
ctaggcaggc tcatggtgtt acagtagagg gttctgataa cgtcataaat aatgtgctta    40800
tgtcaggatg tgatggtact aactctttag gacaagggca gactgctaca attgcacgct    40860
ttataggtac agctaataac aactatgcgt ctgtatttcc tagctacagt gctacaggtg    40920
ttattacttt cgaatccggc tctacccgta acttcgtaga ggtaaagcac cctggcagga    40980
gaaacgacct tctcagttct gctagtacta ttgacggtgc agctactatt gacggcacta    41040
gtaatagtaa cgtagtgcac gcacctgcct tagggcagta catagggtagt atgtcaggta    41100 ggttcgaatg gcggattaag tccatgtcac tccccttcagg cgttcttact tctgctgata    41160
agtacagaat gcttggagat ggtgctgtgt cattagctgt aggtggggc acttcttctc    41220 aagttcgcct atttacttct gatggtactt ctcggacagt gtccctcacc aacggtaacg    41280
tgcgtctttc taccagtagc acaggctttt tgcagttagg tgctgatgca atgacccccag   41340 acagtactgg tacatacgca ttaggttccg ccagccgagc atggtctggc ggttttactc    41400
aagcagcatt cactgttacc tcagatgctc ggtgtaaaac agaacctctt actatctcag    41460
atgccttact ggatgcttgg tctgaagttg acttttgtgca gtttcagtat ttggatcgtg    41520
ttgaggagaa gggtgcagac tcagctagat ggcacttcgg tatcatcgct cagcgagcta    41580
aggaggcttt cgaacgtcac ggtatagatg cacatcgcta tggcttcttg tgcttcgaca    41640
gttgggatga tgtatacgag gaagatgcca atggctctcg taaactgatt acaccagcag    41700
gttcccgcta cggtattcgt tacgaggaag tactgatatt agaggctgcg ttgatgcggc    41760
ggactattaa gcgtatgcag gaagcactag cttccctgcc taagtaagca acaggcagtg    41820
cgtaagcact gcttttagcg caacttttct taaaggttat cacggtggta gcctttcaga    41880
aaaggaggtt acatgattca aagactaggt tcttcattag ttaaattcaa gagtaaaata    41940
```

```
gcaggtgcaa tctggcgtaa cttggatgac aagctcaccg aggttgtatc gcttaaagat    42000
tttggagcca aaggtgatgg taagacaaac gaccaagatg cagtaaatgc agcgatggct    42060
tcaggtaaga gaattgacgg tgctggtgct acttacaaag tatcatcttt acctgatatg    42120
gagcgattct ataacacccg cttcgtatgg gaacgtttag caggtcaacc tctttactat    42180
gtgagtaaag gttttatcaa tggtgaacta tataaaatca cggataaccc ttattacaat    42240
gcttggcctc aagacaaagc gtttgtatat gagaacgtga tatatgcacc ttacatgggt    42300
agtgaccgtc atggtgttag tcgtctgcat gtatcatggg ttaagtctgg tgacgatggt    42360
caaacatggt ctactccaga gtggttaact gatctgcatc cagattaccc tacagtgaac    42420
tatcattgta tgagtatggg tgtatgtcgc aaccgtctgt ttgccatgat tgaaacacgt    42480
actttagcca agaacaaact aaccaattgt gcattgtggg atcgccctat gtctcgtagt    42540
ctgcatctta ctggtggtat cactaaggct gcaaatcagc aatatgcaac aatacatgta    42600
ccagatcacg gactattcgt gggcgatttt gttaacttct ctaattctgc ggtaacaggt    42660
gtatcaggtg atatgactgt tgcaacggta atagataagg acaacttcac ggttcttaca    42720
cctaaccagc agacttcaga tttgaataac gctggaaaga gttggcacat gggtacttct    42780
ttccataagt ctccatggcg taagacagat cttggtctaa tccctagtgt cacagaggtg    42840
catagctttg ctactattga taacaatggc tttgttatgg gctatcatca aggtgatgta    42900
gctccacgag aagttggtct tttctacttc cctgatgctt tcaatagccc atctaattat    42960
gttcgtcgtc agataccatc tgagtatgaa ccagatgcgt cagagccatg catcaagtac    43020
tatgacggtg tattatacct tatcactcgt ggcactcttg gtgacagact tggaagctct    43080
ttgcatcgta gtagagatat aggtcagact tgggagtcac tgagatttcc acataatgtt    43140
catcatacta ccctaccttt tgctaaagta ggagatgacc ttattatgtt tggttcagaa    43200
cgtgcagaaa atgaatggga agcaggtgca ccagatgatc gttacaaggc atcttatcct    43260
cgtaccttct atgcacgatt gaatgtaaac aattggaatg cagatgatat tgaatggggt    43320
aacatcacag accaaatcta tcaaggtgac attgtgaact ctagtgtagg tgtaggttcg    43380
gtagtagtta aagacagcta catttactat atctttggtg gcgaaaacca tttcaaccca    43440
atgacttatg gtgacaacaa aggtaaagac ccatttaaag gtcatggaca ccctactgat    43500
atatactgct ataagatgca gattgcaaat gacaatcgtg tatctcgtaa gtttacatat    43560
ggtgcaactc cgggtcaagc tatacctact ttcatgggta ctgatggaat acgaaatatc    43620
cctgcacctt tgtatttctc agataacatt gttacagagg atactaaagt tggacactta    43680
acacttaaag caagcacaag ttccaatata cgatctgaag tgcagatgga aggtgaatat    43740
ggctttattg gcaagtctgt tccaaaggac aacccaactg gtcaacgttt gattatttgt    43800
ggtggagaag agacttcgtc ctcttcaggt gcacagataa cttttgcacgg ctctaattca    43860 agtaaggcta atcgtatcac ttataacgga aatgagcacc tattccaagg tgcaccaatc    43920
atgcctgctg tagataacca gtttgctgct ggtggaccta gtaaccgatt cactaccatc    43980
tacctaggta gtgaccctgt tacaacttca gatgctgacc acaagtacag tatctctagt    44040
attaatacca aggtgttaaa ggcttggagc agggttggtt ttaaacagta tggtttgaat    44100
agtgaagcag agagggacct tgatagcata cacttcggtg tcttggctca ggatattgta    44160
gctgcttttg aagctgaagg gttggatgcc attaagtatg gaattgtgtc cttcgaagaa    44220
ggtaggtacg gtgtgaggta tagtgaagtt ctaaatactag aggctgctta tactcgttat    44280
cgtttagaca agttagagga gatgtatgcc actaataaaa tcagttaagc aagctgctgt    44340
```

```
actccagaac acagaagagc ttattcaatc aggacgtgac cctaagcagg cttatgccat    44400
tgccaaggat gttcaacgtc gtgccatgaa gaaaccttct gcatcttctg cgtaagcagg    44460
ttaatatctt agtataaaca agggcagact taggtttgtc cttagtgtat tccaaaggag    44520
gtaacatgct gaaagatggt tgggtttcat atgaccctac agaccctaag aattggctac    44580
aggttatcgc tatagcttgt gcaggtagcc tattggctgc cctgatgtat tcattatgga    44640
tgtacacaaa gtaaccaaag tcaaaatttt gatgtaggcg tgtgtcagct ctctcgccct    44700
cgccctcgcc gggttgtccc catagggtgg cctgagggaa tccgtcttcg acgggcaggg    44760
ctgatgtact ccttgtctag tacaagggag gcggagggaa cgcctaggga ggcctaggaa    44820
tggcttagtg gtggacaagg tgattacctt agtgaagcct cttagtgcat tcctgaggcc    44880
attcagggcg tttatgaggg attgacaggg tgtgagggcg tgggcta                 44927
```

```
<210> SEQ ID NO 5
<211> LENGTH: 44920
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

```
tcgccctcgc cctcgccggg ttgtccccat agggtggcct gagggaatcc gtcttcgacg      60
ggcagggctg atgtactcct tgtctagtac aagggaggcg gagggaacgc ctagggaggc     120
ctaggaatgg cttagtggtg gacaaggtga ttaccttagt gaagcctctt agtgcattcc     180
tgaggccatt cagggcgttt atgagggatt gacagggtgt gagggcgtgg gctatctgtt     240
cctttgctcc tcacttcgtt cgtcgctgcg gtagcctgat gtgtacctta ggttattcct     300
tgatggatag cttaggttag ccttagtgga ttaccttagt taaagcctta gtgcttcact     360
tagtatcagc ttagtagtgt accttagtaa gtcttagtgt cttctcttag tgattgcaca     420
tgcaagcatg taagatgcta ataggtcgcg gtcggcagac cgctaaagaa agagaatggt     480
aataagatgc agtaggagga acaccagaag cctagccaac ctaagctatc ctagctctat     540
atctattgct tttccttagt ctaacacgtt agacaaccta tcttattctt agtgatggta     600
acttagtgtt gacaagataa tcttagtgta atactatgca tcacgtaggc ggtgctgagg     660
cacctagtag ccagctagta aggcatacga agagactagc gcttacattg ctctttaaca     720
atttgcttag tgtaacctat gtatgccgtg gttaactact tattgaatga ggtattaact     780
atgacattaa ataaccgtga actgtccgtt ctcttcactc tgttgtgcta catgattcgt     840
aacaacgaat tacttacaga tgatgagtta gccttgtatc accgctttct taacgaaggt     900
tggaccgata cagttaatca ataccgtaac atgatagatg agttgaggga gggtaaataa     960
tgtatcaaca tgaggtattc tttgaatcag ctagcgaagc tattcgcttc cgtgatgata    1020
tgatgcaagc tggtgtaggc gttgatgtgt atcactattt gatagattac gacactgaat    1080
atcaccgagt taccttagta tctgagtatg acaaccaagt cattactgag tatctaggca    1140
gtgaagatta cgattacgat gaagtaatca cgacaaatct ctaaattaac tgttgacagc    1200
cacggcatac aaggttacat taagcatcaa gacggcgacg tctttaaaca tcccgctctt    1260
taacaatacg gtttgtgtct tgataggcta actaactaac taaggtaatt atcatgaaag    1320
ggttaatttg tgtagaacgt atggtcaatg gtaaacttga aatattacca ctggaaaacc    1380
aatctagctt caaagagtgg tatggctgtt tctcactgat ttaaggtaaa ggctggcact    1440
```

```
agtcagccta tcaaggcgca aaccaagctc tttaacaatt tggatggtag cttcttagtc    1500
tggataggtt aaacctagga gattctcttg agtctcctat aatgtaacct aactaactaa    1560
atgaggatta aatcatggaa cgcaatgcta acgcttacta caaccttctg gctgcaactg    1620
ttgaagcatt caacgagcgt attcagtttg atgagattcg cgaaggtgat gattactctg    1680
atgcactaca tgaggttgta gacagcaatg ttccagttta ttacagcgaa atctttacag    1740
tgatggctgc tgatggtatt gatgttgatt ttgaggatgc tggtttgatt cctgacacga    1800
aggatgtaac caagattcta caagctcgca tctatgaagc tctttataat gatgtaccaa    1860
atgacagcga tgtagtttgg tgtgaaggcg aagaagagga agaataagga tggaaaagca    1920
atataacttt atcttttcag acggtgtaac cctgaagtgt tccctacgat tcgcacaaat    1980
tcgtgaggaa gtactaggca ctacatacaa actatttagc tgacactata agagaaggct    2040
taacaaggcg ttactaaggt agcgcctgat taaactttca cttactagga gttgagatta    2100
tgaaaacctt gattggatgc ttcttgttgg cttctcttgc tctggcattt accgctaaag    2160
ctggttatga cgcttataaa gtagaacaag cccagcaaga ctgggccaaa aaaaagttca    2220
acttgtgcag caagagcaac acctacgagt actgcaacaa acactaaga cacttatgga    2280 aagagtaact agcctatagc ccacctgagt gggctatgtg atatttactt aacactatat    2340
aaggtgatta ctatgactac tgaaaacacc ctcgtgtctg tccgtgaagc tgcaaccgct    2400
gaaatcaagc aacatttaga caatatcggc acttcttaca tcaaagtagg ggcttgtctg    2460
aatgagttac gcggagactt tgaaggtcaa aaagagtttt tagcctatgt tgaagcagag    2520
tttgccatta agaaggcaca atgttacaag ctgatgagtg tagcccgtgt ctttgaaggc    2580
gatgatcgct ttaaaggcgt ggcgatgcgt gtaatgctgg cgcttgttcc tttcgctgat    2640
gaaaatataa tcatggagaa ggccgcagaa ctcgccgcaa atggcaagct ggacactaat    2700
gccgtaaacg ccctgattga acctaagaaa gagtcaaagg ccgaaacggt acaatctaag    2760
gctgagacag taaaccgca ggagaacgcg actgagtccg cagaatcaca tgaaatgcaa    2820
gcgccgcagg tagtgccacc cgcgagcgag caggagtccg acgaatcagc accttgggaa    2880
gaggaaagca aaccggaagc gccaaaggca gctccgatgg ataacacggc taatactgag    2940
aatgccgcta ttgctggtct gctggcacaa attaaagcac tgactgagca attacaggca    3000
gccaatgacc gcatcgcctc cttaagtagc gcacgcgaaa gcaagaaggc atccgcacct    3060
atgctgccgc agttcaaatc ttcctgcttc tacgctcgct taggcttgag cgcggaggag    3120
gcaacgaaga aaacagcagt taacaaggca cgccgcgaac tggttaagct gggatacggt    3180
gaaggccatg aggcatggcc cttaatctct gaggcagtag aagagttgac taagtaacct    3240
tatcggtggc atcttcttag gtgtcaccta ttaaggtttc tttcactagg agtaaacaag    3300
atgcaaggcc tacacgctat tcaacttcaa cttgaagaag aaatgtttaa cggcggtatc    3360
cgtcgctttg aagcggacca acaacgccag attgcatccg gtaatgaatc agacacggca    3420
tggaatcgcc gcttattgtc cgagttaatc gcgccaatgg ctgaaggtat tcaggcatac    3480
aaggaagagt atgaaggtaa aagaggccgt gcaccgcgtg cattagcttt cattaactgc    3540
gtagaaaacg aagtggcagc atatatcacg atgaaaatcg ttatggatat gctgaacacg    3600
gatgtaacct tgcaggctat agccatgaat gtagctgacc gcattgagga ccaagtacgt    3660
tttagcaagc tggaaggtca cgccgccaaa tactttgaaa aagttaagaa gtcacttaag    3720
gcaagtaaga ctaaatcata tcgccatgcg cacaacgtag cggtagtggc tgagaagtca    3780
```

```
gtagctgacc gtgacgctga tttctcccgc tgggaggcat ggcctaaaga caccttgctg    3840
caaattggga tgaccttgct tgaaatctta gagaatagcg tattcttcaa cgggcaacct    3900
gtcttcctcc gcaccttgcg cactaatggc ggcaaacatg gtgtttacta cctacagact    3960
agtgaacacg taggtgagtg gataactgca ttcaaagagc acgtagcgca actgagtcct    4020
gcctatgctc cttgcgtcat ccctccgcgt ccgtgggtat cacctttttaa cggcggtttc    4080 cacactgaga aagtagcaag ccgtattcgt ctggtaaaag gaaaccgcga acacgtccgc    4140
aagctgacca aaaagcaaat gccagaggtt tacaaggctg ttaacgcgtt gcaggcgact    4200
aaatggcagg ttaacaagga agttttacag gttgtggaag acgtcatccg tctagaccta    4260
ggttatggtg taccttcctt taaaccactc attgaccgcg agaacaagcc agctaatcca    4320
gtgccgctag aatttcagca cctacggggc cgtgaactga agaaatgct tacgccggaa     4380 caatggcaag cctttatcaa ctggaaaggt gaatgtacta agctgtacac cgctgaaact    4440
aagcgcggaa gcaaatcggc ggcaaccgtt cgcatggttg gtcaggcccg taaatatagc    4500
cagttcgacg caatctactt cgtgtatgca ctggacagcc gcagccgcgt ctacgcgcaa    4560
tctagcacac tctcaccgca atcaaatgac ttgggcaagg ccttgctccg ttttaccgaa    4620
gggcagcgtc ttgatagcgc tgaggcgctt aagtggtttt tggtgaacgg ggctaataac    4680 tgggggttggg ataagaaaac ttttgacgtg cgcaccgcta acgtgctgga tagtgaattt    4740
caagacatgt gccgcgacat tgcagcggat ccgctgacct tcactcaatg ggtaaatgcc    4800
gactcccctt acggcttcct tgcatggtgc tttgaatatg cgcgttatct ggatgcactg    4860
gatgaaggca cgcaagacca attcatgacg cacctcccag tccatcaaga tggtagttgt    4920
tctggtatcc agcactacag tgctatgcta cgcgatgcag taggtgcgaa agcagtaaac    4980 cttaagcccct ctgactctcc tcaagatatt tatggtgccg ttgcgcaggt agtaattcag    5040
aagaattatg catacatgaa tgcagaggat gcggaaacct tcacttctgg cagcgtgact    5100
ttaacaggtg cggagctgcg tagtatggct agtgcgtggg atatgatagg aatcactcgc    5160
ggcctgacca aaaagcccgt aatgacacta cctttatggca gcacacgtct aacctgccgt    5220
gagtcagtga ttgattatat cgttgattta gaagaaaaag aggcccaacg ggctattgcg    5280
gaagggcgta ccgccaatcc tgtacaccct tttgataatg accgtaaaga cagcctgaca    5340
cctagcgcag cttataacta tatgacagct ttaatctggc cttctatttc ggaagtggtt    5400
aaagccccta tagtggcaat gaaaatgatt cgtcagcttg cccgtttcgc agctaaaagg    5460
aatgaaggct tagagtatac cctgcctact ggcttcatct tgcaacaaaa gattatggct    5520
actgatatgc tccgcgtatc tacttgcttg atgggagaaa tcaagatgag tctacagatt    5580
gaaacagacg tagtggatga acggcaatg atgggcgctg ctgctcctaa ctttgtgcat    5640
ggtcatgatg ccagccacct tatcttaaca gtctgcgacc ttgttgataa agggattaca    5700
tctatcgcag ttattcatga ctcttttggc actcatgcag gccgtacagc cgaccttcgt    5760
gatagcttaa gggcagaaat ggtgaagatg tatcaaggcc gtaatgcact gcaaagcctg    5820
ctagatgagc acgaagaacg ctggttagtt gataccggaa tacaagtacc agagcaaggg    5880
gagtttgacc ttaacgaaat cttagtttca gactattgct tcgcataata ttaataggcc    5940
attccttcgg gagtggcctt tcttttacct actacctgta acatttcatt aacataaaag    6000
tgtctcacat gtgagactta tttaccggac actataggat agccgtcgga gacgggaaag    6060
aaagggaaga taaggatat aaaggaagta ataggtatta aaggttatat aggttatcta    6120 ggaatacccta ttaccttctt ccttcctctt attaccactc agaggaaggg cagacctagg    6180
```

```
ttgtctcaca tgtgagactt cgtatttacc ggacagtata gataagatta actcactttg   6240
gagatttaac catgcgcaac tttgagaaga tggcccgtaa agctaaccgt tttgacatgg   6300
aagaggggca gaagaaaggc aagaagctga ataagcctgt ccgtgaccgt gcatctaaac   6360
gcgctgcgtg ggagttctaa gttatggcta ttattcagaa tgtaccgtgt cctgcctgtc   6420
aaaagaatgg acatgatatt actggcaacc atctcatgat atttgatgat ggtgccggct   6480
actgtaatcg tggacacttt catgataatg gtagacctta ctatcacaag ccggaaggtg   6540
gcatcgagat aaccgagtta tctattactg gcaatatcaa atatacacct tctcaattca   6600
aagaaatgga gaaggaaggg aagataagcg accctaaatt acgtgccatc gcacttggtg   6660
gtatgcgtat gaaagaccgt tgggaggtca tgaatgaaca agaaagggca gagcaagaag   6720
cagagtggaa acttgatgtt gaatggttcc tcacgcttaa gcgtaagaac cttgtttcca   6780
ggcacattcg cggcgacatt tgcgcattgt atgatgtacg tgttgggcac gatgaagagg   6840
gtagagtctc acggcattac tatccgcgct tcgaaaaagg tgagctagta ggcgctaagt   6900
gtcgcacatt acctaaagat tttaagtttg gtcatttagg taaactcttt ggtatgcaag   6960
atcttttcgg tatgaatact ttgtctcacg tgttagacaa gggaagacga aaggattgct   7020
tgctcattgt cggcggcgaa ctggatgcac tagcagcgca gcagatgctc cttgattctg   7080
ccaagggtac taagtgggaa ggccagccat accatgtatg gtctgtcaac aaaggcgagt   7140
cttgccttga agagatagtg cagaaccgtg agcatatcgc ccaattcaag aagattatat   7200
ggggttttga tggagatgag gtagggcaga agcagaatca gcaagcggct cgcctgtttc   7260
ctggtaaatc ctatatcctt gaataccct ctggttgcaa agatgctaac aaggcattga   7320
tggctggcaa ggctaaagaa tttgtagatg catggtttaa tgccaagtca tctgatgaag   7380
tctttggtag ccagattaaa tctatcgcat ctcaaaggga taagctcaag gctgcacgtc   7440
cagagcaagg actgtcatgg ccttggccta agctgaacaa ggtaacgcta ggtattcgta   7500
agaaccagct tatcattgta ggtgcagggt ctggtgtagg taagactgag ttccttcgtg   7560
aagtagttaa gcacctcatt gaagaacacg gtgaatctgt aggcatcatt tctacagaag   7620
acccgatggt caaggtgtcc cgtgcttta tcggcaagtg gattgataag cgtattgagt   7680
tacctccaac caacgacccg aaagaagacg gataccgtga ggtgttcgac tataccgagg   7740
aagaagctaa cgccgccatt gattatgtag ctgatacagg taagctgttt gtagctgacc   7800
tagagggtga ctattcgatg gaaaaggtag agcaaacttg cctagagttt gaggctatgg   7860
gtatttctaa tatcatcatt gataacttaa cggggattaa attagatgag cgtgcttttg   7920
gtgggaaggt tggtgcactt gatgaatgcg tcaagcggat tggtactatc aaagaccgac   7980
acccggttac tatattcctt gtatcacacc ttacacgtcc tccggcaaac cgtacccaac   8040
acgaagaagg tggcgaagtt atccttctg acttccgagg ctcaggcgct atcggattct   8100
gggcatctta cgccttgggg attgagcgta atacaagagc tgaaacgctt gacgaaagga   8160
ctaccacgta catctcatgt gtcaaagacc gcgaccaagg tatctacact ggaaccaagg   8220
tcatgcttaa gggtgacatt caaaccggac gtttaatgga accacaagcc cgtactaagt   8280
catttgatac aggtgaagca aggcaacaag aagtaccaga tttaccggat actatagaag   8340
agactacctt cgatgaagaa agtgagttct gattagtgta tttatcaggc ttgtctcaca   8400
tgtgagacag gctcttatta agtacattaa ataactggag attgattatg tataacttag   8460
tgttgaatgt aggtgacttt gtacgcaaca tcaagaaaga ttcaagtcgc tatctttgcc   8520
```

```
gtggtgttgt aacctttgta ggtgagaacc tgtattatgt agaatatcgc agtggtgtta    8580
agcaatatta ccacaagaag acagcacata aatatcttga aaagattgta gagataaaca    8640
atcaatgtaa gtgcatacat gatgaggttt gcgataaatg tgctcgccag atgcttaaga    8700
atttcctagc tcctctttat tatggtgctg gtcctcaaac actagcagag tgcatggcag    8760
aaaagaaaac cacactcaag aaagagcgtc gcaatgtaat cactggtaag actcaaagtg    8820
agatgattaa gcaatgtggc actgcattag gtgttacaca gtttaatact cgtgcattgg    8880
gtaaatccac aggacaagct atggtaaaga ttggagaagc catgatgcat ccaaatgtac    8940
ctgtgcgaat catggatgtt gaccatgcaa tcacagaaca aggtacgcaa cgacgtgtaa    9000
ttaataagca ttttgccgac actatagaag gcattattcg taagcaaggg ttgaaaggtc    9060
ttcacatctt aaatggtgaa gaattactgt acctacctat cgttactgaa gaaacatacg    9120
tgaatatcta aggagttaat catgactaag gtattaattt atatgcgtgg acctcataaa    9180
tgctatgcag ttgtagcacc aaatggtgtt aagccttatc gtacttcaaa agattggca    9240 ttaataggtg ctagtagtag tgcaagtttc caaatggaac tttttggtca ttggactgaa    9300
aggcaattcc gtgaggattt taaagtcatt ggcagcttca tggtgaaata tgcagaataa    9360
acatagtctt agaatgttcg atggtcatga aaacctgcaa gccaagatta ctaaccaagc    9420
cttcctgttc gcacagttaa ctatggctga ggctaagaag aatagtctca ctcgtgaaca    9480
ggttatcaag gaggccactt gggaaccaca ccaaggtaaa tatatgggcc acaaattaac    9540
tgtaacacgc agtcgataag tcaagggttg tccaacgtgt tggacagcct ttcatcatat    9600
tgattgggag gtattaaatg actaagttta ctatgcaaga cctcattaaa ttacgtgatg    9660
aaatagaatc accggaagtt aatacagagt ttcactacat tgatccacga gataaacgag    9720
agattcctga ttatcagatt gagacggagt taatgtatga agattattga ttggaagaag    9780
gaagcagaag gccgtatcct agtgatggat gcggaggcta aaggcctgct gggtgctatc    9840
cgctacggtc atcgtgaaga tgtacacatt atttgctgca tggacttgct caccactgag    9900
gagttcctct tcttcgaccc atatgagatg cgtgaccctg aagcaaggga acacttgaaa    9960
gagtgggaag gccatcaaga tgggaccttg gttgatggtg ttaacttcct aaagcactgt   10020
gaagccatcg tctcacagaa cttcctaggc tatgacgggc ttctctttga gaaagccttc   10080
cctgacatct ggaagggatt taactacacc gagaggcgcg gcaagggcag actacgtgct   10140
gacttgtgtc cggtacgcgt catggatacg ctggtcatga gtcgcctgtt aaacccagat   10200
agacgccttc ctccgcaagc atatgccaaa ggtatgggta acgttgcccc tcactcaatt   10260
gaggcgcacg gcattcgtat aggccgttat aagccggaga acgaggattg gtctaaacta   10320
actgaccaca tggtacatcg tgtacgcgag gacgtggcga taggccgtga cctattcctc   10380 tggctatttta acggagaatg gacggagcac aaacgccgtg gcgtgaataa acgcactggc   10440
ctaggtattg agacagcctt ccacatggag tccattgtga cgctggagat gagccgtcag   10500
gccgagcgtg gattccgtct ggatatagat aaagcattag cacgatgcga ggaattggac   10560
gctaagattg atgagacagt cgcagcgttc cgtccgcaca tgcctatgcg tatcaagtct   10620 aaaccttttta aaccggaaga aaagaatgaa gtatgccaac gcgcaaatga gtatggagct   10680
agcaacaata tacctactgt ccttgacccc tctcactttc ttcacgcaga gagacgagga   10740
gatcgcaaga cagtatggag tgtcactact aagtctggtg attggtcggc tagcgtcaag   10800
aaagactttc ctcaccttag aggaaaccgt aatgacacgc caagtgtcaa gtggattggc   10860
gcttactcgc ctgttacttt cgaagagatt cccttgggta acagggatac agttaagcaa   10920
```

-continued

```
gtgctctatg attatggatg gaaaggtgtt gaatttaacg ataccgagca agcgcatctc   10980
gatgagcatg gcgtattacc caagccttgg agtgggaaga taaatgaaaa gtcccttact   11040
ttatggcaag agagagccgc acgtgaaggt aaaacagtcc ctgattggtg cttgggtatc   11100
gctgcatggt acatactcgt atcccgtcgt ggtcagatcc tcaaccgtgg tgacgttgaa   11160
gccttcgacc agaagggggt gtggccttcg caagctggta tacgaaagtg tcgcggcctt   11220
gtacctgtag catttaacaa ggagttagga atcaatgcgc agcaatacta cgaaaggtac   11280
ggatgctggc ctacgtcaga caaggatgac ggagaatggc gtgtgccagc tattgctatt   11340
agtattggaa cttctacgtt ccgtatgcgt catcgtaacg tggttaatat tcctgcccgt   11400
ggcttgtatc ctttacgtga tttattcata gcagggaaag gcaagctaat ccttggttgt   11460
gacggtgcag gtcttgaact gcgtgtcctg tctcacttca tgaatgaccc tgagtaccaa   11520
gagattgtac tgcacggtga tattcatacg cataaccaga tgaaggctgg tcttcctaag   11580
cgtgatatgg cgaagacatt tatatatgcc ttcctatatg ggtctggtat agctaacctt   11640
gcagcagtat gtggtgttac tgaggaagaa atggaggaag ttgtggcaag atttgaggtt   11700
gaactaccat ctccttgcacg tcttcgtgag aatgttatcg cacaaggtaa caagtttggc   11760
tacctacaag cacctgatgg tcattggggt cgcatccgta tgtctggtgg tgaacttaaa   11820
gaacacacta tgcttaacgt actactccag atgactggtt ctctgtgtat gaaatacgca   11880
ttggtcagag cgttttgcagt gatgcgcaag gaaggtgtgg ccttagatag catgggaaac   11940
ccttgcggta tagctaacgt gcacgatgaa atccagatgg aagtccctga agatgaggtc   12000
ttgtatctca actacgactt gcctttcacc ttagaagggt tcgaaacaga gaaggctgct   12060
gtgaaagcag tgttcgatgc agaggagaaa cgtgttcatg tggattctga aggacgtatg   12120
tggtctgctg caaatctcgt tagtgttgat gctggtgtac ttcattgcca gcgtcgttat   12180
caccgtgcag ggcatatcat tgccgacgca atgacctggg cgggtcagta cctgaagatg   12240
cgttgtccga tggcaggtga gtataagatt ggtgcaagtt ggaaggaaac acactgatgg   12300
acaggtttga tattgtttgc ctattctcta ccttctttct tatattcctt atgcttgctt   12360
gctatggaag tatgcgatta gatataccctg atgaagagga gggttacgat tgatgcaggc   12420
atcttttatt attcttggag tcatattatt tatggtagta ttctgggctt tctctggcat   12480
tgacccagat tgtgatggta actacgactg agttatactc aaggtcactt acgagtggcc   12540
tttatgaata acttattcct acttattttg tctaacatga tttactggac actatagaag   12600
gaaagcatag gtaatctagg tttataaggt agtataggta attaagtaaa tataggagat   12660
ataaatatgt ctatggtaac tactctggta ttcgtggctc aatactttcg tggtcttgct   12720
aataagttca gtccaaggc tatcaaagct attgaggctc gcatcgaagc agtacaggca   12780
gagcaagtta agttgaaga acatcgtagt tctcaaatga ttgactgtca taaccgctac   12840
tatgcatctc gtgatgaact aaatgcacgt caagtcaaag aggtagaaga tatgctggca   12900
cgtcaccagc aagagcgtga cagcctgaaa gctgaatttg aagagaacaa ggcatcaatt   12960
gctcttgtac atcaagctgc atctgacagt ctgaagaaag agattgttat gctggaaatc   13020
gaactggata acctgaccaa ataagggggg gttatgatga agaagtaat tcaagctaaa   13080 catgtaggta ttatctttcg cgatctagag cagcgtaaag ttgcaggtca tactcgtctg   13140
gctaaagagg aagacaccgc aatcactact gtagaacaag cagatgccta tcgtggacca   13200
gagttcactc aaggtgaaac ttgtcaccaa ttgagcctat caatttgtga cactatggct   13260
```

```
attgtaaatg tgcaagaagt cgaagagggt gagtgtgtca gttacatcta ccctttagat   13320
actattgcac gcattaaggt aatccataag taattactag acactataga acaataggtc   13380
ggcttagttc ggcctatgat tgtaaagtgt tgttgatgtt gaaccattgt gcatcttgca   13440
caacccgata ccgtatagggcttttctagtg agtacatgct tgtgctcagt acaaagctaa   13500
ctgacaatag gagactaaat aaatggcacg tggtgatttt gattttggtg ctcaggttac   13560
taaatctgaa ggtaaagtct ttaagaatcc agaagtaggt gatcatgaag cagtaatctc   13620
tggcatcatt catgttggtt ccttccaaga catctttaag aaaggtaata ccactgaagt   13680
taagaagcca gcaaactttg ttctggttaa gattgtcctg atgggtgacg atgacaagaa   13740
cgaagatggt tctcgcatgg aacaatggat ggctgtgcct ctgaagtctg gtgataaggc   13800
aacactgact aagttcctga atgcagttga ccctaaagag ttgctgggtg gcttcgatga   13860
tttcattggt gaatgcctga ctgcaacgat ggtcggttct ggtgataaga atgacgatgg   13920
ctcattcaag tatgttaact ggaagggatt tggtggtatg ccggacaagc tgaagaaact   13980
ggtcattgct caggttgaag aggaaggtct gtctatgaca ggtcacatta ccttcgacaa   14040
gctgaccaaa gaaatccttg atgacatccc agccaacttg gtgcgtcaat acttcctgaa   14100
cgagacgcct cgtggtaaga acctgtctgt tgctggttct cacgtagaag caatcattaa   14160
agctgctcgt gaagaagacc cagaatggaa gaaggctaag aagaaagacg aggaagatgc   14220 tacccccagct aatcgtaaat ctctggatac tggtgagtct gttccacagg aagtacctga   14280
agcagaagat actcctgcac cggagatgga tgaggacgcg gaatattaag gagaaaggat   14340
gaaagtacaa atcgtaaccc tgcactgcaa gaaaggaatt acaactcttg gcggcaacac   14400
ttttcactcc ttctctgaag gggacacata tgccgacctg cactacatct ggcgcgacgg   14460
acagcacgtg gtgaactaca gcgacccagc tacggggaaa cgccacggcg tatcgcttcc   14520
ggcgcatgac attgctcagg tgaacacagt tttataaagt ctcacgtgtg agacaaatcg   14580
gtgtccggta tttactggac actatagaag agaagaattt taatcggcga taatgccata   14640
accaacaaaa ggagaattta atatgttcaa gattgaaact atcgtaaacc gtgttgttaa   14700
aggtgctgct ctggtatccg ttgagtcttt cattatcgtc gatgaaactg atcaactggt   14760
agctggtact aaggcttacg atacccgtga agaagctcag gctaagattg acagcatggg   14820
taacttcgct gctggtctgg agttcgctcg tgcttgcttc cctgagcagg ctgacaaagc   14880
tcagattggt aaggctaata tcgtagctga atatctggat tgggttgctg ctggtaaacc   14940
agtgaaagaa gttaaggctg ctgaagaagc tgaagctcca gcagaagaag tagctgcacc   15000
ggaaactccg gtaagtgaag aggaagaatt ttgataatag caggtgttgc ctctgttagt   15060
cctagctgac tatcacgctc acctcatcta atgccctgtc tgccttagtg taggcaggggt   15120 cttttgcgta atagttattg gagaatgaat tatgccgact attgaatctc gaattgaact   15180
ggacattagc tacaatgcaa tcaccagaca gtatattggg gttgcctatg attacaaaac   15240
tggtgagaag ctagtggagg tgagacaatg ggatgactat tggttaagac agaacctcca   15300
tgatgcggtg tcctccttcc tgaaggagtg gcctacatgc gaccaaactt cgacttcgga   15360
gctacagtat cggaagacaa taacctgttg ctgtggccaa ctgaaggtaa tcgaatcgct   15420
ttaatagatg ctgatatgtt accttacatc atagggtata caatcagtga tatgacttat   15480
gtacagccca caactcgtgt taagtcaggg caagtcccct caatcaaaga tacacctgag   15540
tgtaagcaag cgtgtgaccg tgtgaactcc ttgcttaact cttgggtgta tgcagcgaaa   15600
tgtgatgcag ctaagttgtt catgacgaaa tcagaagcta acttccgtgt ccgcctagca   15660
```

```
ttcaccaagc cttataaagg tcaacgtaag accgagaagc ctccattctt ctatgaattg    15720
cgagagcatc tcttagaggt tcacggtgca atcttggcag atggagagga agcagatgac    15780
ctcatgagta tcgcacaatg ggacagccac cgccgcttcc agcaagatac aggtaacgag    15840
ttccctatcg gtagtccaga gcataaagca ttctctgata cttgcatcgt ttccttggat    15900
aaggatttga tgattgttcc cggttggcat ctacagccgg gtcaagagaa gaaatgggta    15960
gagcctatgg gttggcttga gctacgccgt aaggctaatg ggcaagtcaa agatctaaaa    16020
ggtgctggcc tcatgttcca ctatgcacag atgattatcg gtgatgatat tgataactat    16080
gctggcatac caggtcgtgg tgctaaatat gcctatgatc ttctcaaaga ttgtaagaca    16140
gagaaagagt tgtacatggc agtgctgggt gcttacaagg ctaagttcgg gcatggacaa    16200
gttaaaatta agaattaccg aggtggttat cgtatcggca aagcctttga cctaatgctt    16260
gagtgtggtc gcttatctca catggcaaga ttcaagggtg atatatggcg agccgataag    16320
aacccaatct tgtggggaga tgatgcgaa tggttagcaa attaaaatca tcggaggtgg    16380
cagcttataa gaaggaattg ctagataagc aaggatggaa atgccctctg tgtggcggca    16440
gtctcaaagc tgtcacacct gtaaaccgtg tacttgacca tgaccatgag acaggattct    16500
gccgcgctgt tgtatgccga ggctgcaatg gtgcggaagg gaagattaag ggtgttatct    16560
ctggttatgg taaggctggt aacaaccgtt acttccagct tcaatggtta gagcgactat    16620
atgaatactg gaagttacat agtacgcctc agacagataa gttatatcac aaacatcaaa    16680
cggaggcaga gaagcgcgag gctaagaacc gtaaggcacg ccttgcttat gcaagaaaga    16740
aggaggttaa agttgggtaa gctgcgcagc ttgtacaaag actccgaggt acttgatgca    16800
atcgagcaag ctaccgacga gaaaggtaat gttaactaca atgagatggc acgtgtatta    16860
tcgtgtcata ctgtgggtaa gaagattacc cgccagttgg ctcgatactg gcatggtcaa    16920
ttcaagaaga ccaagaagaa tggtgattac taccagaccc ttctgcaaga agataagcgt    16980
atcaaagaag agcgtaagct caggactcct gaccgctacg aggatttggc tattgtgcca    17040
ttgcctgact cgcctcatcg aagtgtactg gtgatccctg atactcatgc accttatgag    17100
cacccagata ccctagagtt ccttgcagcc gtggcagcac gttaccgtcc agacacagtg    17160
gtacacctag gagatgaggc agacaaaacat gccctgtcat tccacgattc ggacccaaat    17220
ctggatagtc ctggcatgga gttagagaag gctcgtatct tcatgcacaa attgcacaag    17280
atgttccctg tgatgcgcct gtgtcactct aaccacggct ctatgcactt ccgtaaggca    17340
agcgccaaag gcatccctgt gcaatacctg cgcacctatc gtgaagtctt cttcccgcag    17400
ggaggtggcg accagtggga ttggcaacat acgcacgtcc ttgagttgcc gaatggtgaa    17460
caagtggcat tcaagcatca acctgctggc tctgtcctag cagatgcagc gcatgagcgt    17520
atgaaccttg tgtgtggtca cttgcacggt aagatgtctg tggagtacgc acgtaataca    17580
catgaacagt attgggctgt gcaaggtggc tgcttaattg atgagtcatc ccgtgcatttt    17640 gcctatggtc gtgagtctaa atacaagcca gcattaggtt gtgtggtcat tctggagggt    17700
gtgcctcaca ttgtcccgat gcaaaccaat agcgacaacc gttggattgg caagatttag    17760
ttgacactat agaacaaagg gctaggtaag actttatcgg ctggcgtatc caaatgatat    17820
tgcactagcc cttgattgta tagtgaatgg aggattcaat atgtcacact atgaatgtaa    17880
gaagtgtcat aagcgttatg attactgtac ttgtggtcaa gagaaaacat cttttaaagt    17940
tggagacaag gtatttcgta atgaaaaaga ttcgattcct tggaatcaat actgcaaaga    18000
```

```
agctggtatt gaccctgata gccctgtaac catagatgat attgatggca ttaacttgtg   18060
ctttcgtgag gtgagggta caggttggga ttccaaaaaa ttcaaacttg catctgataa    18120
gttagacaac aatatggtaa ttaagcctaa gcactacgag ttctttgatg gcgtagaggc   18180
aatcactatc attgcccgca gtatgaccga gaagcaattc gctggctatt gcatgggtaa   18240
tgctttgaag taccgtctac gtgcaggtaa gaagttcaac actgaagaag acctgaagaa   18300
agcagattac tacaaagagt tattccagaa gcatcgtcac gaatgtattg atgaggatat   18360
ttgatatgaa tatctttgag ttcctaggtc ttccagaaga ccaccgcaat cacccattca   18420
tgctggtgaa gcatcgcggt gaagttcctg agaagaaatt aacttttcca tgttatgcac   18480
aggtgaaacg agatggtatc ttttctgctg ttgttgttcg cactgatggt gtcgttggca   18540 ttttggtcg cactggtaag aaattggcaa acactgaagg actcgaacaa gcctttgcta   18600
cctttccggt tggcatttat cttggtgagc ttcagtctat ggccattgat atctaccttg   18660
aggcaatctc tggggttgtg aaccccaatc gcactgagcc acttgatttc ataggccagc   18720
agattaaaga caacctgtat atcgacttct tcgatatgtt aactattaag gcattccatg   18780
atggattcac tgatgtttct tatctcaaac gttacgatgc tttacatcgt cgtatcggcg   18840
ctcatcttag cgggtgcaac gctatccttc ctatcactcc ttgccataat gagcgagaag   18900
ttgaagcgtt tgcgcaagag caaatagatg caggacgtga gggtgctgta ttcaaactgg   18960
actgcgatta tgaagcagga cacaaaggtt atcgtcagac taaagaagtc cgtaaggtaa   19020
cctatgacct tacttgtatt ggctttgaag aaggtaaagg caaatacaaa ggtaaggtag   19080
ctaacctcat tttcaaatgg aaaggaggca agacaatcaa agctatgtta ggtaagggt    19140 ggactcatgc agatgcagag cagatgttcc acgacattaa acatggtgga cgattgaatg   19200
tcattggtaa aatctttgaa gtcaaaggtc ttcaggattc aagcaagggc aacattcgtc   19260
tgcccaaagc gggagaatta agacatgaca aagatgaacc agatttcttt tgatagcatg   19320
aaggcaactc gtgcagttga ggtagcagaa gctatcttcg aaactttatc ctgtggcatg   19380
gaagtgccat atactttact tgctgatgca gaagaacttg gtctttctgt agaagctatc   19440
caagagaagg ttgacgaatt atatggtaca gacgaagaag aaaccgacga tttcatttga   19500
aggaatggag atgcttgaga tgattctcaa gccttcttct cctaaggtga ctaagactca   19560
tgaagagtta atcgttgatg aagttaagcg ttacatcatg gattgtgtca gagcacaact   19620
ggtggtccaa tgatacgtcc agcctccttc ctagatattc ctgagattat aaaccttggg   19680
aataaatatg tggaagagga agtcaaggtt gtagcccacc actcagcctc atggaatgca   19740
gaacaaagtg ccataacctt tgtgcatctc ttaatagaga cccaccactc agcctcatgg   19800
aatgcagaac aaagtgcaca taacctttgt gcatctctta gtagagaaga tttatcccta   19860
tgggttgctg tagatgaagg gcagattgta gggttcctgt gggctggcta tcacgagttg   19920
gccccttgga cacctgtaag agttgcctct gacattctct tttatattat accagagaga   19980
aggggaacac tacttggtat gcgcttaatt aaggcattga aacagtgggc atcagataat   20040
gaatgctctg aagtgcgttt aagtattgca gtggcatca acgaggagcg cgtagggcgc    20100
atgtacaaac ggctcggctt tgaaccgttt ggcactgtgt ataacctgaa gttctaaaga   20160
ggagatatac aatggttttt acgcttgagg acttcgttgg tgactggcgt caaaccgcgg   20220
ggtataatct tgatcaggtc ctggagcagg gcggagtttc gtccttattc cagaacttag   20280
gggtaagtgt tacgccgatt cagcgcatcg tgctgagtgg agagaatgga ttgaaaattg   20340
acattcacgt tatcattccg tatgagggtt tgagtggaga ccagatggga cagattgaaa   20400
```

```
agattttcaa agtggtgtat cccgtcgatg accatcactt taaagtaatt ctgcactatg   20460
ggacccttgt gatcgacggt gtaacgccaa acatgattga ctatttcggt cgcccttacg   20520
aaggtatcgc cgtcttcgac ggaaaaaaaa tcactgtcac gggaacatta tggaacggaa   20580
ataaaattat cgacgaacgt ctgatcaatc ctgatgaaag cctgttattt cgcgttacga   20640
tcaatggagt gaccggatgg cgtttatgcg aacgtatttt ggcttaaaga ggagatatac   20700
aatgggtgtt gtaaagaaag catttaaggc tatcggtctt gctcaagatg caccacgtat   20760
tgaagccaaa gtcccagcac agcagcttga gcgtaagcct gagactgaag ctgaagatat   20820
tcaaattggt gcaggggatg atgctactgc atctgcaaaa ggtaagcgtg ccttgtccg    20880 tccggtagct tctagcttga aggtgtaata tgaaacagag catagatttg gagtatggag   20940
gtaagcggtc taagatacct aagctatggg agaagttctc caataaacgt agctctttcc   21000
ttgatagggc gaagcattac tccaaattaa ccttgcccta tctgatgaat gacaaaggtg   21060
ataacgagac ttcgcagaat ggatggcaag gtgtaggtgc tcaggcaacc aaccatctag   21120
ccaacaagct agcgcaagta ctattccctg cacagcgttc cttcttccgt gtagacttaa   21180
ctgcacaagg tgagaaggtt cttaatcagc gtggcctgaa gagacagag ctagctacca    21240 tcttcgctca agtggaaaca cgggcaatga aagagttaga gcaacgtcaa ttccggcctg   21300
ctgtagtaga agcatttaag catcttattg ttgctggcag ctgtatgcta tacaagccga   21360
gcaaaggtgc aatcagtgct atcccaatgc atcactacgt agttaaccgt gataccaatg   21420
gcgacctgtt agacattatc ttgctacaag agaaagcctt acgtaccttt gacccagcta   21480
cacgtgcggt agtagaggtt ggcctgaaag gtaagaagtg caaggaagat gacagcgtta   21540
agctgtacac acatgctaag tatcttggtg atggattttg ggaactcaag caatctgctg   21600
atgatatccc tgtgggtaag gtgagtaaaa tcaaatcaga aaagctacct ttcatcccat   21660
taacttggaa gcgaagctat ggtgaggatt gggtcgacc tcttgcagag gattactccg    21720
gtgatttatt cgttatccaa ttcttatctg aagcggttgc ccgtggtgct gcgctgatgg   21780
cagatatcaa gtacctgatt cgtcctggtg ctcaaactga tgttgaccac tttgttaact   21840
ctggcactgg tgaggttgtc actggtgtag aagaagacat ccatattgta cagttaggta   21900
agtacgcaga cctcacacct attagcgcgg ttctagaggt atacactcgc cgtatcggtg   21960
ttgtcttcat gatggagaca atgacacgcc gtgacgccga acgtgttact gctgtagaaa   22020
tccagcgaga tgcgttagag attgagcaga acatgggtgg tgtatactcc ctctttgcta   22080
ctactatgca atcgccagta gcgatgtggg gtctgctgga ggcaggggag tccttcacta   22140
gtgacttagt ggaccctgtg attatcacag gtattgaagc tttaggacgc atggctgagt   22200
tggataaact ggctaacttt gctcagtata tgtcactgcc attacaatgg cctgagcctg   22260
tcctagctgc tgtgaaatgg cctgactata tggattgggt gcgtggtcaa atctctgctg   22320
aactgccgtt ccttaaatcg gctgaagaga tggcacaaga acaggaagca cagatgcaag   22380
cacagcaagc acagatgctt gaagaaggtg tggctaaggc cgtgccgggt gtaattcaac   22440
aagaacttaa ggaggcgtaa tgtctttctc atttactgaa ccgtcaacca ctcaccctac   22500
tgctgaagag ggtccggtag aaaccaagga ggtaacaact gatgctgcta ctactgatgc   22560
tcctgctgac gctggcactt ctgtacaaga tgacaatgct ggtgcacaac ctactgaaga   22620
caccggagga gaagcttctg gacagccttc agaaaaagga gacaatggcg gagagaatgg   22680
tgaacctaag ccagatgata ccgcgaccga cactgaggaa gtgcaatact tcttcggaga   22740
```

```
acatgaagta acagtagaca tcccacagga tgtaactgac agccttaaag agaaaggcat   22800
tgatgccaag caggttgcca aggaactcta ttccaaaggt ggcaagtttg aactgtcaga   22860
tgcaaccaag cagaaattgt atgatgcttt tggcaagttt gcggtagatg cttacctatc   22920
aggtctaaag gctcaaaatg aagccttctt cctgaaagaa gccaacgcag ctaaagagtt   22980
ggaagcagct aacacccaac gcttctctga tgtttctaag gaaattggtg gcgaagaagg   23040
ttggtcccgt cttgaggagt gggcacttga agcgctgtct gatgacgaac taatggcatt   23100
caatgcggtg atggaatctg caaccagta cctgcaacaa tatgctgttc gtgaactgga   23160
gggtcgtcgt aagcaggcac agggggatga taagccatcc ctgattgagc catcagcacc   23220
tgctaaggct aatgaagaga atggcccact gacgcgagat cagtacgttc aagcaatcgc   23280
aactcttagc cagaagtacg gcaatgaccg taaagctatg gcagaagctc aggctaaact   23340
ggacgcccgt cgccgtgctg gcatggctcg cggtatctaa ttcagtattt actggacact   23400
atagaaggga gaaagttct ccctagttat caatttgatt tataaggaga ttataataca   23460
tgtctacacc gaatactctg actaacgttg ctgtatctgc gtccggtgag gttgacagcc   23520
ttctcattga gaagtttaat ggtaaggtca atgagcagta cctgaaaggt gagaacattc   23580
tgtcctactt tgatgtacaa actgttactg gcactaacac agtgagcaac aaatatttgg   23640
gcgaaactga gttgcaggtg ctagcaccgg tcagtcccc taatgccacc cctactcagg   23700
cggataaaaa ccagttggta attgatacca ctgtcattgc tcgtaacact gtggctcaca   23760
tccacgatgt acaaggtgac atcgatagcc tgaaaccaaa actggctatg aaccaagcca   23820
agcaactgaa acgtctggaa gaccagatgg caattcagca gatgctgtta ggcggtatg   23880 ctaacaccaa ggccgaacgt aacaagccgc gtgttaaagg gcatggcttc tctatcaacg   23940
ttaacgtaac tgagagtgaa gcactggcta accctcagta tgttatggct gcggtagagt   24000
atgctctgga gcaacagctt gagcaggaag tggacatctc tgatgtagct atcatgatgc   24060
cgtggaagtt cttcaatgct ttgcgtgatg cagaccgaat tgtagataag acttacacta   24120
tcagccagtc tggtgcaacc attaatggct tcgttctctc ttcttataac tgccctgtga   24180
tcccgtctaa ccgattccct accttcgctc aggatcaggc tcaccacctg ttgtctaatg   24240
aagataacgg ctatcgttat gaccctatcg cagagatgaa tggtgcagtt gctgttctgt   24300
tcacttccga cgcactgctg gtgggtcgta ccattgaagt gactggtgac atcttctatg   24360
agaagaaaga gaagacttat tacattgaca ccttcatggc tgagggtgca atccctgacc   24420
gttgggaagc agtgtctgta gttaccacta aacgtgatgc aactactggt gatgctggag   24480
gtcctggtga tgatcacgca accgtactgg ctcgtgcaca gcgtaaggct gtatatgtca   24540
aaaccgaagg tgctgcggct gcattctctg ctgccccagc aggtatccaa gcggaagacc   24600
ttgtagcggc ggtacgtgct gtaatggcaa atgacattaa gccgactgca atgaaaccta   24660
ctgagtaaca cctatgccct atctaccttg cgtaggtagg gttcttttg ttaggaggat   24720 tcatgcctgt aattagacaa accagtaaat taggacatat gatggaagat gtggccttcc   24780
agattattga tagtaagctg gaagcggtaa acttgtgtat gcgagctatt ggtcgtgagg   24840
gtgtggattc cctcgactca ggggacttgg acgcagaaga tgcaagcaaa atgatcgaca   24900
tcgtatccca gcggttccag tacaacaaag gaggtggctg gtggttcaat cgtgaaccaa   24960
actggcaact tgcaccagac actaacggtg aagttaattt acctaacaac tgcctagcag   25020
tattgcagtg ttatgcttta ggtgaaaaga agtacctat gactatgcga gcaggtaagc   25080
tctactctac ttggagtcac accttgata tgcgtaagca tgttaatgct aatggtatga   25140
```

```
ttcgtcttac cttactcacc ttactaccct acgagcatct acctacaagt gtaatgcagg   25200
ctattgccta tcaagctgct gtagagttta ttgtgtctaa ggatgcagat cagactaagc   25260
tagccactgc gcagcagata gccactcagc ttcttatgga tgtacaatct gagcaaatgt   25320
cacagaagcg attaaacatg ctggtacata accctactca gcgtcagttt ggtatcatgg   25380
ctggtggctc tcagaatgta cctgcttact ctcattcacc ttatgagagt tgggcgctcc   25440
gtccgtggga ggatcgttaa tggaagtaca aggttcatta ggtagacaaa tccaagggat   25500
tagccagcag ccgccagcgg tacgcttgga tggtcagtgc acagctatgg ttaatatgat   25560
acctgatgta gtgaatggta ctcaatcacg catgggtaca actcatattg caaagatact   25620
tgatgcgggg actgatgaca tggctactca tcattatcgc agaggtgatg gtgatgaaga   25680
gtatttcttc acgttgaaga aaggacaagt tcctgagata tttgataagt atgggcgcaa   25740
atgtaatgtg acttcacaag atgcacctat gacctacctc tctgaggttg ttaatccaag   25800
ggaagatgtg caattcatga cgatagctga tgttactttc atgcttaatc gtaggaaagt   25860
agttaaagct agtagcagga agtcacctaa agttggaaac aaagccattg tgttttgtgc   25920
gtatggtcaa tatggtacat cttattccat tgtaattaat ggggccaacg ctgctagttt   25980
taaaacaccg gatggtggaa gtgcagacca tgttgaacaa attcgaactg aacgtatcac   26040
ttctgaattg tactctaagt tgcagcaatg gagcggtgtg agtgactatg aaatacaaag   26100
agacggtact agtatattta tcgagagacg ggatggtgct agctttacaa taacaaccac   26160
cgatggtgca aaaggtaagg acttagtggc tatcaagaat aaagttagct ctactgacct   26220
actcccttct cgtgcgcctg ctggttataa agtacaagtg tggcctactg gcagcaaacc   26280
tgagtctcgt tactggctgc aagctgagcc taaagaggga aaccttgtgt cttggaaaga   26340
aacaatagct gctgatgtat tacttgggtt tgataaaggc acaatgcctt acattattga   26400
acgtacagat atcatcaacg gcatagctca attcaagata agacaaggtg attgggaaga   26460
tcgtaaagta ggggatgact tgactaaccc tatgccctct tttattgatg aggaagtacc   26520
ccagacaata ggtggaatgt tcatggtgca gaaccgccta tgctttacag caggtgaagc   26580
ggttattgct tctcgtacat catacttctt cgatttcttt cgttatacgg ttatctctgc   26640
attggcaact gaccccttg atattttctc agatgctagt gaagtctacc agctaaaaca   26700
tgcagtgacc ttagatggcg ctaccgtgtt gttctctgat aagtcacaat tcatactgcc   26760
aggcgataag cctttagaga agtcaaatgc actgcttaag cctgttacaa catttgaagt   26820
gaacaataaa gtgaagccag tagtaactgg tgaatcggta atgtttgcca ctaatgatgg   26880
ttcttactct ggtgtacgag agttctatac agactcttat agtgacacta agaaggcaca   26940
agcaatcaca agtcatgtga ataaactcat cgaaggtaac attaccaaca tggcagcaag   27000
caccaatgtc aacaggttac ttgtcactac cgataagtat cgtaacataa tctactgcta   27060
cgattggtta tggcaaggaa cagaccgtgt acaatcagca tggcatgtat ggaagtggcc   27120
tataggtaca aaggtgcgag gtatgttta ttctggtgaa ttactttacc tgctccttga   27180
gcgaggagat ggcgtgtatc tggagaagat ggacatgggt gatgcactaa cctacggttt   27240
gaatgaccgc atcagaatgg ataggcaagc agagttagtc ttcaagcatt tcaaagcaga   27300
agatgaatgg gtatctgagc cgctcccttg ggttcctact aacccagaac ttttagattg   27360
catcttaatc gagggttggg attcatatat tggcggctct ttcttattca gtcaacccc   27420 tagtgacaat actttgtcta caacctttga tatgtatgat gacagccatg taaaagcgaa   27480
```

```
ggttattgtt ggtcagattt accctcaaga gtttgaacct acgcctgtgg ttatcagaga   27540
caatcaagac cgtgtatcct acattgatgt accagttgta ggattggttc accttaatct   27600
tgacatgtac cccgatttct ccgtagaagt taagaatgtg aagagtggta agtacgtag    27660 agtattagcg tcaaaccgta taggtggtgc tctcaataat acagtaggct atgttgaacc   27720
gagagaaggt gtcttcagat ttccactgag agctaagagc acggatgttg tttatcgtat   27780
tattgtagag tcacctcaca cattccagct tcgtgatatt gagtgggaag ggagctacaa   27840
tccaaccaaa aggagggtct aatggctata ggttcagccg ttatggctgg tatgtcttct   27900
attggtagca tgtttgcagg cagtggtgca gcagccgctg ctggaggtgc tgccgcaggt   27960
ggcggaggtt tgctaggttc actaggtgga ttcctaagtg gctctactgc tggtttctct   28020
aatgctggcc ttcttggtgc tggccttcaa gggttaggct tgattggtga tctatttggt   28080
ggaagtgatg aagccaaggc gatgaagaaa gcacaagaag agcaatggcg gcagcagctt   28140
attgctacac aagaggcgta caagacagtg gcagacgcag aacgttctgc tgctaaacaa   28200 tatcatcag atgcaatcag taatcaggct tcactgctac agcagcgagc acaggttgca   28260
ttacttgctg ggctactgg tactggtggt aattctgtgt cctctatgct taatgactta   28320
gcagcagatg gcggcaggaa ccagagtact atcattgata actatgagaa tcagaagatt   28380
aatttcacca accagcttaa gtctatccaa cgtggtggtc agatgcagat gcgtgagttt   28440
aagaagcctt ctgctatgaa taccttggtt aaaggtattc caagtctggc atctgcctat   28500
gtaactggta gtaagtctgg caaggcattg ggtaaagcct taactgattc tcgcacatat   28560
tcatctggaa caagaggtat ttaatggcaa ttgagcgaca agcagtacaa ggtctgccac   28620
aagtgcaggc cacttctcct aatgtcatga cctttgcacc tcaacaagtg ggaggtgtgg   28680
aggctggcgt ggcttctacc tccggtagta ggtttatcga agaccttatt cgtgcagcaa   28740
gcagcgtggc tgatgttacc actggtatcc ttaatcagaa gattgaggaa gataaggttg   28800
ttcaaatgga acgggcatat aacgattaa tgccttctga ggatgcaact cgtggtggcg   28860
ctcgtgctaa catgcttgtc aaagctcaac tgctagctaa tgatgaagca gcacgaatga   28920
aagacatggc tactcgtttc caaggaacgg atgacgaatg gacacaactt atggttgact   28980
ctcgtaatga gatgcagaat aagctgttcc agcaataccc tgagttgcaa ggtgacaaag   29040
atactatgcg tatggtcact aatgtcttcc aagaacagca gcctcagatt tgggctacac   29100
gaacccagca taaacttgac cgtgaacaag cagaccgtga ggatacctt gacgggcgag    29160 tggcttctac ttgggattct aatattgacc ctgaagcctc tggctatgct ttacaggaac   29220
gaatccgcga aggtcttact caaggattac tacctgaaca gatgtacaag aagttagtcc   29280
agcgagcaat ttcacttgca caaggcggtg atgttagcat ggctgaagcc ctgaagtatg   29340
tgaaggacga taagggtgtt tctgtttatg ctaagaatcc acagcttatc acagccatca   29400
ctagtggtaa tgcagtttgg gctaggaata atgtagctga tgtaactcgt atgtctttcg   29460
aagttaaaga atcctacctt gcaggtgatt taactgatga agaattgttg gaacgagcac   29520
agcacattaa taatctgaca ggtaactctg tcttctctaa tccagaacta gaggcactga   29580
tgcgccaacg ggctaagcag aatgcagagc taggtcaat gcaggatatg cgacgtgagc    29640
tttactccga ccgcctgact ggcttccaag gtaagactga taagagaag aaggcttaca    29700 ttgatgttat caaacaggat agccaacttt atgcagacca gcaaatcaaa caacgtggct   29760 tggacccta cagtcaagag gctgaagcta ttcgtggtgc agtggaagtg cagcgcctgc    29820
aattcatgaa ctccaaaggc ttagtggatg atacctttga gtctcgtatc aaagccatgg   29880
```

```
aatctatgct atcgcctgag cactttgcca agggcgaacc acaggagttg atgactattc   29940
gccagttgtg ggaacagtta ccagaagaga gccgaggtgt ctttggtgac acggtgaatg   30000
gctacatgga taactacaac actgcactac aaatgggaga gacacctttg caggctgcaa   30060
ggtttgcgcg taaagcacag cagaaattct ctcgtactga aaggaaacc  aagaagttca   30120
actcagctat tggagatgca ctggatgagg tatctggtgc tggctggttt gatggtaaaa   30180
ccgaagtgtc agacttaggt aaagctattg cggaagaaga gttacgagct aaggccaata   30240
tgttgtggtc tagtggtatg cgtaacatgg attccatcaa gaaggcttta attacttggg   30300
gcaataaacg ctacactcaa tcagaggatg caaagacttc cggtggctat ttcattaaag   30360
gtgattacac ttctgcatct gatatgctta tgtcagttgg gaaaggcgta aaccctaccg   30420
atgtacctct ggcgcttggt aggtatgtag aaacacagat gccagaattg aagaaggagc   30480
ttcaagaggg ggaaactaaa gatgatatat acattgatta caatgaacag aaaggtactt   30540
tcgtgattcg tgctggtgca gcaggtcgcc ctctttctgg agtaatccct gtaacctctt   30600
tagataccac ttcactacta gattctgcct atcagaagaa agtagaggaa cgagataaag   30660
gcgagtatgt tcacccgtat cgtacagata ttggtgcaca agagcctatg ccagctaaac   30720
caactgccaa agatattggt aaatttggac tagctaactt cctcatgtct tctgcttttg   30780
cttctggtga gaatctgcct tctaacttcg agattaacta tcgaggtaat atgcaacaat   30840
tctatgacaa gctagctatg gatgagaata agataaagt  tggctttaat aaggcaactg   30900
gaacctttac tccatataaa gacgctcacg gtgagtctat cggttacggt catttcttaa   30960
cggaagaaga gaagcgaaac gggtatatta agattggcga tgaactagtt ccctatcgag   31020
ggctctatgtc tcagcttaca gagagcaagg ctcgcgctct tatggagcaa gatgctaaga   31080
agcatgtgcc tcctactcgt gactggaaga ttccgtttga ccagatgcac cctgcacagc   31140
aacgtggctt gatggattta agctacaatt taggtaaagg tggaatccag aactcaccgc   31200
gtgctcttgc tgcattcaaa gctggtaagc ttacggaggg ctttatcgaa atgctgggca   31260
ctgcatcaag tgaaggtaag cgtattcctg gcctactgaa gcgacgcgct gaggcataca   31320
atatggcatc tgctggtggt gtgcctaaga ttaccgaagt ggagactcgt gaagatggct   31380
ccatgtgggt taggtttggt ggacctatgc cagcaggttc tgtctcggca tggactcata   31440
aacgtattgg cgcggatggt tggtatcagg tttatgaggc tgcacctacc aagttagcta   31500
aagattctaa ggtaggtaaa gttaagttgt agtacctaac tcaaggcttg tctcacatgt   31560
gagacaggtc tttatgatag gcactatgga ggaattatgg aacaagacat taagactaat   31620
tgggctggat atgtccagtc tactcctgag ccgttttcta ttgaggcggc tccggtatcg   31680
gctcctacga tacgccagcg taatgagtta caagagcaag ttcttgaagc taaagctgac   31740
gctgatatct taggtgctgt aggtgctgcc ttccagaatg agtggttggc attcggaggc   31800
aagcggtggt atgaccgtgc cactgctgat ttcacacctc aaccagactt tgagatacaa   31860
cctgagcaac gtgaagcact acgtttcaaa tatggtacgg atatgatgca gacaatcact   31920
gagggtgttc gttctgagga tgaattgaac ttccgtattc agaatgcgga tgaagacctt   31980
gagcgcaata agcgcattgc tcaggctggc tgggttggct ctgtgcgac  gattggcgct   32040
gctgtgcttg accctgtggg atgggttgcc tctattccaa ccggtggtgc cgctaaagtt   32100
ggactcgtag gccgtgctgt gcgtggcgct atcgccgctg gcgtgagtaa tgccgctatt   32160
gaatccgtat tggtccaagg tgacatgact cgtgatttag atgacattat ggtagcactg   32220
```

```
ggttccggta tggctatggg tggcgttatt ggcgctgtag cgcgtggtag ggccactaag    32280
ctcagtgagc aaggtgatga cagggctgct agcattgtgc gcagtgcaga cgcagggac     32340 cgctatgttc gtgctgttgc cgatgacagt atcggtgcga tgcgtgttaa gggcgcagag    32400
gttctcactg agggtgtatt cgatatctcc agtaagagtg aagacctact gaaaaccttg    32460
caacgagaag gtaatgcgat tgatatgaca cctcgccgtt gggctggaac tatgtctgcc    32520
ctcggtactg tcgtgcactc atctaaagat gcaagtatcc gaggccttgg tgctcgtctg    32580
tttgaatccc cacaaggtct aggtatgcag aaggcatctg ctagtcttat gcagaatact    32640
aacttaaatc gcctgaaatc tgctgatatg aaccgcttca atgatgggtt tgatttgtgg    32700
cttaaagaga ataatatcaa tccagtagca gggcatacca actctcatta tgtacagcaa    32760
tacaatgaaa aggtgtggga ggcagtgcgt attggcatgg atgagtctac acctaaatct    32820
atccgcatgg ctgctgaggg acaacaggct atgtacagag aggcgctggc tttacgtcaa    32880
cgttctggtg aagcgggatt tgaaaaggta aaagccgaca acaaatatat gcctgatatc    32940
tttgatagta tgaaagccag acgtcaattc gatatgcacg ataaagaaga catcatcgaa    33000
cttttctctc gtgcctacca gaatggcgct cgtaagattc aaaggaagc agcagatgag     33060 attgcacgag cacaggtaaa tcgcgttgct gatgctacct taactggaaa gcttagtttt    33120
gaaaaggcaa tgtcaggtca gactaaggca gagtatgaag ctatcatgcg taaggcaggc    33180
ttcagtgatg aagaaattga aaagatgata gaagctctgg ataacaaaga aaccagagat    33240
aacatctcta accgagctaa aatgagttta ggattagatg ttactcaaga atacaatggc    33300
attcgtatgc gtgacttcat gaataccaac gtggaagagc taacagataa ctatatgaag    33360
gaagcagcag gtggcgctgc attggctcgc caaggcttct ctacctatca ggctgcactt    33420
aatgcaattg accttgtaga gcgaaatgca cgaaacgcgg ctaaggatag caaggctagt    33480
ttggcattag atgaagagat tcgtcagatg cgagaaggtc ttcgcctgat tatgggcaag    33540
tcgattgatg cagacccaca ggctatatct actaagatga tgcgtcgtgg tcgtgatatc    33600
acaggtgtgc ttcgcttagg tcaaatgggc ttcgcacagc taggtgaact tgccaacttt    33660
atgggtgaat ttggtattgc tgcaactact atggctttag gtaagcaatt ccgcttcacc    33720
tctaaggcgt tgcgtaatgg cgatggcttc ttccgagata agaacttagc tgaggttgag    33780
agaatggtgg ggtacattgg tgaggataac tggctaacaa ctaagggtgc acgtcctgat    33840
gaatttggtg atgtaaccac agtaagaggg atgatggctc actttgacca atccatgaac    33900
tcaatacgtc gtgctcaaac caacctatca ctcttccgca tggcacaggg ttctctggag    33960
cgaatgacta ataggcaaat agctttgtct ttcattgacc accttgaagg caagaagatt    34020
attcctcaga agaaactgga ggaacttggt cttactcagg agttcatgac taacctacag    34080
aagcactatg atgctaactc taaaggttct ggcttgcttg gctttgatac aatgccttat    34140
gccatgggtg aaactttagc taatgctatt cgtcgtaagt caggtctaat catccaacgt    34200
aacttcattg gtgatgaagg tatctggatg aacaaagcac taggtaagac atttgcacag    34260
cttaagtcat tctctcttgt atctggtgag aagcaatttg gtcgagggat tcgccacgat    34320
aaaattggtc ttgctaagaa gacagcttac gggtttgctt tgggttcaat agtgtatgcg    34380
gcaaaagcct atgtgaactc tattgggcga gaagaccaag atgaatattt ggaagagaag    34440
ttatcgccta aagggttggc ctttggtgca atgggtatga tgagtacaac tgctgtatt    34500 agtctaggtg gagatttctt aggtggccta ggtgttctac cttccgaact cattcaatca    34560
cgctatgaag caggtttcca agtaagggt ctgattgacc aaataccctct ggttggcgtt    34620
```

```
ggtgcagatg cagtaaatct ggctaactca atcaagaagt atgcagaagg tgacacagaa   34680
ggtgtagata tcgctaagcg agcactccgt cttgtgccac ttaccaatat aataggtgtc   34740
caaaacgcat tgcgttatgg cttagatgaa ctggaggatt gatgagttat actttcacag   34800
aacatacagc caatggtacg caagtcacct atccttttag ctttgctggt agggataaag   34860
gttatcttcg tgcctcagat gtgatagtgg agtctcttca aggtaacact tggattgaag   34920
ttacatctgg ctggcaacta actggcacgc accagattac ttttgatgta gcaccagttg   34980
caggtttgaa gttccgtatt cgaagggaag tacaaaaaga atatccatac gctgagtttg   35040
accgtggtgt taccttggat atgaagtctt taaatggttc tttcattcat atactggaga   35100
ttacacagga gttacttgac gggttttatc cagaaggata cttcattaaa cagaatgtaa   35160
gctggggcgg caataagatt actgatttgg ctgatggcac aaatccggga gatgcagtaa   35220
ataaagggca gcttgatgcc atcgacaaga agcatacaga ttggaacgcc aaacaggaca   35280
ttgagattgc tggccttaag gctggtatga cttctggtat tgcgcacaga actgttcctt   35340
ggtacacgat agcccaaggt ggtgagattt ccgtaaaacc accttatgaa tttcaagatg   35400
cactagtttt ccttaatggg gtattgcagc accaaattgt aggcgcatac tctataagca   35460
acaacactat cactttcgca gagccgcttg tggctggtac agaggtgtat gtgctgattg   35520
gtagtcgtgt ggctacatct gaacctaata ttcagttgga gttgaacttt gacttagtag   35580
aaggccaaca agtagtacag attggctctg catttaagta cattgaggtc taccttgatg   35640
gattattaca acctaaactt gcttatcagg tagacggtga cattgttact ttctcagaaa   35700
gagtaccaga atgccggatg actgctaaga ttatcacagc ataaggaggt gggatgatta   35760
actccgaact ggtagatagt ggtgtgaagc ttgcgccacc tgcactcata tcaggtgggt   35820
acttcctcgg tatcagttgg gataattggg tgttaatagc aacattcatt tataccgtgt   35880
tgcaaattgg ggactggttt tataataagt tcaagatttg gagggagaag cgtgagcgta   35940
cacaataaac atgcagctac agaggacgag gttggcattc tgcatggtgc tattaccaaa   36000
atcttcaata agaaagcaca ggcaatactg gacactatag aagaagaccc tgatgcagca   36060
ttacatttag tgtctggtaa ggatattggt gcgatgtgta agtgggttct tgataacggc   36120
attaccgcca cacctgctgc acagcaggaa gagtccaagt tatctaagcg cctcaaggct   36180
atccgagagg catccagtgg taagataatt caattcacta aggaggattg atggctaagg   36240
caagagaatc acaagcggag gctcttgcca gatgggagat gctacaggag ttacagcaga   36300
cctttcctta caccgcggaa ggtttgcttc tctttgcaga tacagttatt cataacttaa   36360
ttgcaggcaa ccctcatctg attcgtatgc aggcggatat cttgaagttc ctattttacg   36420
gacacaagta ccgcctcatc gaagcgcctc gtggtatcgc taagacaaca ctatcagcaa   36480
tctatacggt attccgtatt attcatgaac cgcataagcg tatcatggtt gtgtcccaaa   36540
acgccaagcg agcagaggaa atcgcaggtt gggtagttaa atcttccgt ggcttagact   36600
ttcttgagtt tatgctgccg gatatctacg ctggggaccg tgcatccgtt aaggcgtttg   36660
agattcatta caccctacgt ggtagtgata agtctccttc tgtatcctgt tactcaatcg   36720
aagcaggtat gcagggtgct cgtgctgata ttattctagc ggatgacgta gagtcgatgc   36780
agaatgctcg tacggcagcg ggccgtgcct tgcttgagga gctgactaag gagtttgaat   36840
ctatcaacca gtttggggat atcatttacc ttggtacacc tcagaacgta aactctatct   36900
acaacaacct acctgctcgt ggttactctg ttcgtatctg gactgcgcgt tacccttcag   36960
```

-continued

```
tagagcaaga gcaatgttat ggcgacttcc ttgcacctat gattgttcaa gatatgaagg    37020
acaacccagc acttcgctca gggtacgggt tggatggtaa tagtggtgca ccttgtgccc    37080
ctgaaatgta tgatgatgaa gtcctgattg agaaggaaat ctctcagggt gctgctaagt    37140
tccagcttca gttcatgctt aacactcgca tgatggatgc tgacagatac ccattacgcc    37200
tgaacaatct aatcttcacc tcgtttggta cagaggaagt ccctgtgatg cctacgtgga    37260
gtaatgattc cataaacatc attggtgatg cacctaagta tggtaacaag cctacggatt    37320
tcatgtacag acctgtagct cgcccatatg aatggggtgc tgtctcccgc aagattatgt    37380
atattgaccc tgcgggtggt ggtaagaacg gagatgagac gggtgtagcc atcgtattcc    37440
tgcacggcac attcatttat gtgtatcagt gctttggtgt acctggcgga taccgagagt    37500
cgtccctgaa tcgcattgtg caggccgcaa agcaggcggg tgttaaagag gtattcattg    37560
agaagaactt tggtcatggc gcgtttgagg cggtaattaa gccgtacttt gaacgagagt    37620
ggcctgtaac tctggaagag gattacgcca ccggacagaa agagttgcgt atcattgaga    37680
cgctggagcc gctcatggca gcccataggc ttatcttcaa tgcagagatg gtgaagtcag    37740
actttgagtc ggtacagcac tatccgcttg aactacgcat gtcctacagt cttttcaatc    37800 aaaatgtcgaa cataacgatt gagaagaaca gcctccggca cgatgaccgc ctagacgccc    37860
tgtatggcgc tatacggcaa ttaacttctc agatagacta tgacgaggtt acacggatta    37920
atcgcctcag agcgcaggag atgcgcgatt acatccatgc tatgaacaca cctcatctac    37980
gcagggcaat gctatatgga gattacggta ctgagcgaag agtgaccaac acttccgtag    38040
cgatgcagca gcgagtttac gggcagaact accgaaataa atcggcaagc agaaatacac    38100
tttctgcaag gatttcaagg acttattaat tactggacac tatagaagga aggcccagat    38160
aataagagaa aataataggt aatatatata taggttaacc taggttatat aggtatgcct    38220
tagtatgggt gtactcctgt acaccctatt ccttactacc ttactatatt tacataatag    38280
gagagagaca atggctaatg attatagtag tcaaccatta acaggtaagt ctaagagaaa    38340
gcaggtacaa cctgtaagtg aagaactaat gcttccggtg ctcaaaaaag aggaagttag    38400
taagaaaagc aatgttatta atgatgccac caaatcaggt aaacagaaag gggccatggt    38460
gtgccttgaa gtgaaaggtg gtgtattgaa gattgctatc gcggttgatg gcaaagaaga    38520
ttcagagtgg aagttagtaa cagtggaacc aactgttaac ccagtttaag ataaggagga    38580
agattacatg gctaaatatg gtactacagg ttctgttact ggtcaggctt ttcgagtaaa    38640
agcagtacaa actattgcaa cggcaatccc gatgcctgtt gttaaagaag aagacccttaa    38700 gagtaaagac caccctatca acatcaaaca tttatcaggt aaacagaaag gtgcaatggt    38760
tgctcttgag aaaggtgaca caaccttaca tattgctgtt gcacgtggta gtgaacccac    38820
agacccttgg gatgtaactg gtatggaaaa ggacgctgtt actccagcag gggtataata    38880
atgcttaata aatacttcaa gcgtaaagag tttgcttgcc gttgtgggtg cggtacatcc    38940
actgttgatg ctgaattact acaggtagtc acagatgtgc gtgagcactt tggttctcct    39000
gtagttatca cttcgggtca tcgctgtgct aagcacaatg ccaatgtagg tggcgctaag    39060
aactccatgc atcttactgg taaggctgct gacattaaag tgtctggcat attaccttct    39120
gaagtgcata agtatcttac tagcaaatac caaggcaagt atggtatagg taagtataac    39180
tccttcactc acatcgatgt acgggatggt tgtgcgcgat ggtaagatgt gttgaatggt    39240
gtgagcgtat ggttgcccaa gctgccgagg atggcaacta tgatgactgg aagaactact    39300
ctgacttgtt agctcaatgg aaagggagat gcaatgaaaa agctgtttaa gtctaagaag    39360
```

```
gttgtaggtg cactggttgc acttgttatt gctcttgttt ctgtaggtct tggtgtagac   39420
cttggctctg gcacggaatc ctctgtgaca gatgtggtct gccaagtgat cacctgtgaa   39480
taagtttcta gaagttctgg caggtcttat tggcctgctt gtctctgcta agaagaaaca   39540
agaagagaag gaggcacaaa gtgaagcgaa tcatgttagt gacaaccctt ctgattggtt   39600
cgctgaccac ttccgggtgt cagcaggcgt taccagagaa agcaatggtg aaacctctga   39660
ggccgacgct gacggcagtt tacgaggtag acgataaggt ctgctttagt aagcctgacg   39720
ctacaaaact tggtttgtac attctctcgc tagaacgcgg atacaattaa tacatagctt   39780
tatgtatcag tgtcttacga tttactggac actatagaag aggtaagata gcgccgttct   39840
tttgagcggc ctattactag ccaatcttca tagggagggt tggaaagtaa taggagatag   39900
catggctaaa ttaaccaaac ctaatactga aggaatcttg cataaaggac aatctttgta   39960
tgagtacctt gatgcgagag ttttaacatc aaagccgttt ggtgctgcag gtgacgccac   40020
tactgatgat acggaggtta tagctgcttc attaaactct cagaaagctg tcacagtctc   40080
agatggtgta ttctctagct ctggtattaa cagtaattac tgtaacttag acggcagggg   40140
tagtggcgtg ctaagtcacc gttcaagtac aggtaactac ttagtattta acaatctacg   40200
tgcaggtcgc ttaagtaata ttacggtaga aagtaataag gcgactgata caactcaggg   40260
acagcaggta tcccttgctg gtggaagtga tgttactgta agtgacgtta acttctcaaa   40320
cgttaaaggt actggtttca gtttaatcgc atacectaat gatgcgccac ctgatggact   40380
tatgattaaa ggcattcgag gtagctattc cggctatgct actaataagg cagccggatg   40440
cgtacttgct gattcctcag ttaactccct catagataac gtcattgcta agaactaccc   40500
tcagttcgga gcagtagagt tgaaaggtac agccagttac aacatagtca gtaatgttat   40560
agggacagat tgccagcatg taacttacaa cggcactgaa gggccaatag ctccttctaa   40620
taaccttatc aagggggtga tggctaataa ccctaagtat gcagcggttg ttgcaggcaa   40680
aggaagtacg aacttaatct cagacgtgct cgtagattac tcaacttctg atgctaggca   40740
ggctcatggt gttacagtag agggttctga taacgtcata aataatgtgc ttatgtcagg   40800
atgtgatggt actaactctt taggacaagg cagactgct acaattgcac gctttatagg   40860
tacagctaat aacaactatg cgtctgtatt tcctagctac agtgctacag gtgttattac   40920
tttcgaatcc ggctctaccc gtaacttcgt agaggtaaag caccctggca ggagaaacga   40980
ccttctcagt tctgctagta ctattgacgg tgcagctact attgacggca ctagtaatag   41040
taacgtagtg cacgcacctg ccttagggca gtacataggt agtatgtcag gtaggttcga   41100
atggcggatt aagtccatgt cactccctc aggcgttctt acttctgctg ataagtacag   41160
aatgcttgga gatggtgctg tgtcattagc tgtaggtggg ggcacttctt ctcaagttcg   41220
cctatttact tctgatggta cttctcggac agtgtccctc accaacggta acgtgcgtct   41280
ttctaccagt agcacaggct ttttgcagtt aggtgctgat gcaatgaccc agacagtac   41340 tggtacatac gcattaggtt ccgccagccg agcatggtct ggcggtttta ctcaagcagc   41400
attcactgtt acctcagatg ctcggtgtaa aacagaacct cttactatct cagatgcctt   41460
actggatgct tggtctgaag ttgactttgt gcagtttcag tatttggatc gtgttgagga   41520
gaagggtgca gactcagcta gatggcactt cggtatcatc gctcagcgag ctaaggaggc   41580
tttcgaacgt cacggtatag atgcacatcg ctatggcttc ttgtgcttcg acagttggga   41640
tgatgtatac gaggaagatg ccaatggctc tcgtaaactg attacaccag caggttcccg   41700
```

```
ctacggtatt cgttacgagg aagtactgat attagaggct gcgttgatgc ggcggactat    41760
taagcgtatg caggaagcac tagcttccct gcctaagtaa gcaacaggca gtgcgtaagc    41820
actgctttta gcgcaacttt tcttaaaggt tatcacggtg gtagcctttc agaaaaggag    41880
gttacatgat tcaaagacta ggttcttcat tagttaaatt caagagtaaa atagcaggtg    41940
caatctggcg taacttggat gacaagctca ccgaggttgt atcgcttaaa gattttggag    42000
ccaaaggtga tggtaagaca aacgaccaag atgcagtaaa tgcagcgatg gcttcaggta    42060
agagaattga cggtgctggt gctacttaca aagtatcatc tttacctgat atggagcgat    42120
tctataacac ccgcttcgta tgggaacgtt tagcaggtca acctctttac tatgtgagta    42180
aaggttttat caatggtgaa ctatataaaa tcacggataa cccttattac aatgcttggc    42240
ctcaagacaa agcgtttgta tatgagaacg tgatatatgc accttacatg ggtagtgacc    42300
gtcatggtgt tagtcgtctg catgtatcat gggttaagtc tggtgacgat ggtcaaacat    42360
ggtctactcc agagtggtta actgatctgc atccagatta ccctacagtg aactatcatt    42420
gtatgagtat gggtgtatgt cgcaaccgtc tgtttgccat gattgaaaca cgtactttag    42480
ccaagaacaa actaaccaat tgtgcattgt gggatcgccc tatgtctcgt agtctgcatc    42540
ttactggtgg tatcactaag gctgcaaatc agcaatatgc aacaatacat gtaccagatc    42600
acggactatt cgtgggcgat tttgttaact tctctaattc tgcggtaaca ggtgtatcag    42660
gtgatatgac tgttgcaacg gtaatagata aggacaactt cacggttctt acacctaacc    42720
agcagacttc agatttgaat aacgctggaa agagttggca catgggtact tctttccata    42780
agtctccatg gcgtaagaca gatcttggtc taatccctag tgtcacagag gtgcatagct    42840
ttgctactat tgataacaat ggctttgtta tgggctatca tcaaggtgat gtagctccac    42900
gagaagttgg tcttttctac ttccctgatg ctttcaatag cccatctaat tatgttcgtc    42960
gtcagatacc atctgagtat gaaccagatg cgtcagagcc atgcatcaag tactatgacg    43020
gtgtattata ccttatcact cgtggcactc ttggtgacag acttggaagc tctttgcatc    43080
gtagtagaga tataggtcag acttgggagt cactgagatt tccacataat gttcatcata    43140
ctaccctacc ttttgctaaa gtaggagatg accttattat gtttggttca gaacgtgcag    43200
aaaatgaatg ggaagcaggt gcaccagatg atcgttacaa ggcatcttat cctcgtacct    43260
tctatgcacg attgaatgta aacaattgga atgcagatga tattgaatgg gttaacatca    43320
cagaccaaat ctatcaaggt gacattgtga actctagtgt aggtgtaggt tcggtagtag    43380
ttaaagacag ctacatttac tatatctttg gtggcgaaaa ccatttcaac ccaatgactt    43440
atggtgacaa caaaggtaaa gacccattta aaggtcatgg acaccctact gatatatact    43500
gctataagat gcagattgca aatgacaatc gtgtatctcg taagtttaca tatggtgcaa    43560
ctccgggtca agctatacct acttcatgg gtactgatgg aatacgaaat atccctgcac     43620
ctttgtattt ctcagataac attgttacag aggatactaa agttggacac ttaacactta    43680
aagcaagcac aagttccaat atacgatctg aagtgcagat ggaaggtgaa tatggctta    43740 ttggcaagtc tgttccaaag gacaacccaa ctggtcaacg tttgattatt gtggtggag    43800 aagagacttc gtcctcttca ggtgcacaga taacttgca cggctctaat tcaagtaagg    43860
ctaatcgtat cacttataac ggaaatgagc acctattcca aggtgcacca atcatgcctg    43920
ctgtagataa ccagttttgct gctggtggac ctagtaaccg attcactacc atctacctag    43980
gtagtgaccc tgttacaact tcagatgctg accacaagta cagtatctct agtattaata    44040
ccaaggtgtt aaaggcttgg agcagggttg gttttaaaca gtatggtttg aatagtgaag    44100
```

```
cagagaggga ccttgatagc atacacttcg gtgtcttggc tcaggatatt gtagctgctt    44160
ttgaagctga agggttggat gccattaagt atgaattgt  gtccttcgaa gaaggtaggt    44220
acggtgtgag gtatagtgaa gttctaatac tagaggctgc ttatactcgt tatcgtttag    44280
acaagttaga ggagatgtat gccactaata aaatcagtta agcaagctgc tgtactccag    44340
aacacagaag agcttattca atcaggacgt gaccctaagc aggcttatgc cattgccaag    44400
gatgttcaac gtcgtgccat gaagaaacct tctgcatctt ctgcgtaagc aggttaatat    44460
cttagtataa acaagggcag acttaggttt gtccttagtg tattccaaag gaggtaacat    44520
gctgaaagat ggttgggttt catatgaccc tacagaccct aagaattggc tacaggttat    44580
cgctatagct tgtgcaggta gcctattggc tgccctgatg tattcattat ggatgtacac    44640
aaagtaacca aagtcaaaat tttgatgtag gcgtgtgtca gctctctcgc cctcgccctc    44700
gccgggttgt ccccataggg tggcctgagg gaatccgtct tcgacgggca gggctgatgt    44760
actccttgtc tagtacaagg gaggcggagg gaacgcctag ggaggcctag gaatggctta    44820
gtggtggaca aggtgattac cttagtgaag cctcttagtg cattcctgag gccattcagg    44880
gcgtttatga gggattgaca gggtgtgagg gcgtgggcta                          44920
```

```
<210> SEQ ID NO 6
<211> LENGTH: 20
<212> TYPE: DNA
<213> ORGANISM: Escherichia virus K1-5

<400> SEQUENCE: 6
actaaatgag gattaaatca                                                   20

<210> SEQ ID NO 7
<211> LENGTH: 20
<212> TYPE: DNA
<213> ORGANISM: Escherichia virus K1-5

<400> SEQUENCE: 7
ttactctgat gcactacatg                                                   20

<210> SEQ ID NO 8
<211> LENGTH: 20
<212> TYPE: DNA
<213> ORGANISM: Escherichia virus K1-5

<400> SEQUENCE: 8
tatattatac cagagaggcg                                                   20

<210> SEQ ID NO 9
<211> LENGTH: 20
<212> TYPE: DNA
<213> ORGANISM: Escherichia virus K1-5

<400> SEQUENCE: 9
gaagttctaa ggagataaca                                                   20

<210> SEQ ID NO 10
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
```

```
aacctaacta actaaatgag gattaaaaga ggagatatac aatggttttt acgcttgagg    60
acttcgtt                                                             68
```

<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
tgtataacct gaagttctaa agaggagata tacaatggtt tttacgcttg aggac          55
```

<210> SEQ ID NO 12
<211> LENGTH: 23
<212> TYPE: DNA
<213> ORGANISM: Escherichia virus K1-5

<400> SEQUENCE: 12

```
actaaatgag gattaaatca tgg                                             23
```

<210> SEQ ID NO 13
<211> LENGTH: 23
<212> TYPE: DNA
<213> ORGANISM: Escherichia virus K1-5

<400> SEQUENCE: 13

```
ttactctgat gcactacatg agg                                             23
```

<210> SEQ ID NO 14
<211> LENGTH: 23
<212> TYPE: DNA
<213> ORGANISM: Escherichia virus K1-5

<400> SEQUENCE: 14

```
tatattatac cagagaggcg agg                                             23
```

<210> SEQ ID NO 15
<211> LENGTH: 23
<212> TYPE: DNA
<213> ORGANISM: Escherichia virus K1-5

<400> SEQUENCE: 15

```
gaagttctaa ggagataaca tgg                                             23
```

<210> SEQ ID NO 16
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 16

```
acuaaaugag gauuaaauca guuuuagagc uagaaauagc aaguuaaaau aaggcuaguc    60
cguuaucaac uugaaaaagu ggcaccgagu cggugcuuuu uuu                      103
```

<210> SEQ ID NO 17
<211> LENGTH: 103
<212> TYPE: RNA
<213> ORGANISM: Artificial Sequence
<220> FEATURE:

<223> OTHER INFORMATION: Description of Artificial Sequence: Synthetic
      polynucleotide

<400> SEQUENCE: 17
uuacucugau gcacuacaug guuuuagagc uagaaauagc aaguuaaaau aaggcuaguc    60
cguuaucaac uugaaaaagu ggcaccgagu cggugcuuuu uuu                    103

<210> SEQ ID NO 18
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 18
uauauuauac cagagaggcg guuuuagagc uagaaauagc aaguuaaaau aaggcuaguc    60
cguuaucaac uugaaaaagu ggcaccgagu cggugcuuuu uuu                    103

<210> SEQ ID NO 19
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 19
gaaguucuaa ggagauaaca guuuuagagc uagaaauagc aaguuaaaau aaggcuaguc    60
cguuaucaac uugaaaaagu ggcaccgagu cggugcuuuu uuu                    103

<210> SEQ ID NO 20
<211> LENGTH: 33
<212> TYPE: DNA
<213> ORGANISM: Escherichia virus K1-5
<220> FEATURE:
<221> NAME/KEY: CDS
<222> LOCATION: (1)..(33)

<400> SEQUENCE: 20 gat gat tac tct gat gca cta cat gag gtt gta                         33
Asp Asp Tyr Ser Asp Ala Leu His Glu Val Val
1               5                  10

<210> SEQ ID NO 21
<211> LENGTH: 11
<212> TYPE: PRT
<213> ORGANISM: Escherichia virus K1-5

<400> SEQUENCE: 21

Asp Asp Tyr Ser Asp Ala Leu His Glu Val Val
1               5                  10

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 22

```
gac gac tat agc gac gcc ctt cat gag gtt gta                                33
Asp Asp Tyr Ser Asp Ala Leu His Glu Val Val
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<400> SEQUENCE: 23

Asp Asp Tyr Ser Asp Ala Leu His Glu Val Val
1               5                   10
```